(12) United States Patent
Qi

(10) Patent No.: US 12,286,633 B2
(45) Date of Patent: Apr. 29, 2025

(54) COMPOSITIONS AND METHODS FOR GENOME EDITING IN PLANTS

(71) Applicant: University of Maryland, College Park, College Park, MD (US)

(72) Inventor: Yiping Qi, Potomac, MD (US)

(73) Assignee: University of Maryland, College Park, College Park, MD (US)

( * ) Notice: Subject to any disclaimer, the term of this patent is extended or adjusted under 35 U.S.C. 154(b) by 130 days.

(21) Appl. No.: 17/247,582

(22) Filed: Dec. 17, 2020

(65) Prior Publication Data

US 2021/0180076 A1 Jun. 17, 2021

Related U.S. Application Data

(60) Provisional application No. 62/949,230, filed on Dec. 17, 2019.

(51) Int. Cl.
*C12N 15/82* (2006.01)
*C12N 9/22* (2006.01)

(52) U.S. Cl.
CPC ........... *C12N 15/8213* (2013.01); *C12N 9/22* (2013.01); *C12N 15/8216* (2013.01); *C12N 2310/20* (2017.05); *C12N 2800/80* (2013.01)

(58) Field of Classification Search
None
See application file for complete search history.

(56) References Cited

U.S. PATENT DOCUMENTS

| 2019/0292553 A1 | 9/2019 | Gao et al. |
| 2021/0095271 A1* | 4/2021 | Li .......................... A61P 25/30 |
| 2021/0130838 A1 | 5/2021 | Qi et al. |

FOREIGN PATENT DOCUMENTS

| WO | WO-2016205749 A1 * | 12/2016 | ........... C12N 15/102 |
| WO | 2017141173 A2 | 8/2017 | |
| WO | 2019126709 A1 | 6/2019 | |
| WO | 2020191248 A1 | 9/2020 | |

OTHER PUBLICATIONS

Lowder et al. "A CRISPR/Cas9 Toolbox for Multiplexed Plant Genome Editing and Transcriptional Regulation" 2015 Plant Phys. 169:971-985. (Year: 2015).*

(Continued)

*Primary Examiner* — Matthew R Keogh
*Assistant Examiner* — Rebecca Stephens
(74) *Attorney, Agent, or Firm* — McKee, Voorhees & Sease, PLC

(57) ABSTRACT

Compositions and methods for modifying genomic DNA sequences of a plant cell are provided. The methods produce double stranded breaks at target sites in a genomic DNA sequence, resulting in mutation, insertion, and/or deletion of DNA sequences at the target site(s) in a genome. The compositions comprise DNA constructs comprising nucleotide sequences that encode a Cas12b protein. The DNA constructs can be used to direct the modification of genomic DNA at a target site. Methods to use these DNA constructs to modify genomic DNA sequences are described herein. Additionally, compositions and methods for modulating the expression of genes are provided.

9 Claims, 28 Drawing Sheets

Specification includes a Sequence Listing.

(56) References Cited

OTHER PUBLICATIONS

ADDGENE summary page for the pYPQ292 plasmid (citing Ming et al. 2020 Nature Plants 10.1038/s41477-020-0614-6, summary available at https://www.addgene.org/129672/; last accessed Aug. 11, 2022). (Year: 2020).*
Xu et al. "Generation of inheritable and "transgene clean" targeted genome-modified rice in later generations using the CRISPR/Cas9" Nature Scientific Reports 5: 11491 (10 pages) DOI: 10.1038/srep11491. (Year: 2015).*
Mikami et al. "Comparison of CRISPR/Cas9 expression constructs for efficient targeted mutagenesis in rice" 2015 Plant Mol Biol 88:561-572. (Year: 2015).*
Teng et al. "Repurposing CRISPR-Cas12b for mammalian genome engineering" 2018 Cell Discovery 4(63): DOI 10.1038/s41421-018-0069-3, 15 total pages; (Year: 2018).*
Endo et al. "Efficient targeted mutagenesis of rice and tobacco genomes using Cpf1 from Francisella novicida" 2016 Scientific Reports 6:38169 (9 total pages) DOI:10.1038/srep38169 (Year: 2016).*
Ma et al. "A robust CRISPR/Cas9 System for Convenient, High-Efficiency Multiplex Genome Editing in Monocot and Dicot Plants" 2015 Molecular Plant 8:1274-1284 (11 total pages). (Year: 2015).*
Ming et al. "CRISPR-Cas12b enables efficient plant genome engineering" epub Mar. 9, 2020 Nature Plants 6(3):202-208, doi: 10.1038/s41477-020-0614-6 (9 total pages). (Year: 2020).*
Wada et al. "Expanding the plant genome editing toolbox with recently developed CRISPR-Cas systems" 2022 Plant Physiology 188:1825-1837 (13 total pages). (Year: 2022).*
UniProtKB Accession ID C6L686_ORYSJ version 30 published Nov. 7, 2018, 2 total pages. (Year: 2018).*
Mahammed et al. "Rice plants overexpressing OsEPF1 show reduced stomatal density and increased root cortical aerenchyma formation" published online Apr. 3, 2019 Scientific Reports 9:5584 (https://doi.org/10.1038/s41598-019-41922-7 (13 total pages). (Year: 2019).*
Takano-Kai et al. "Evolutionary History of GS3, a Gene Conferring Grain Length in Rice" 2009 Genetics 182:1323-1334. (Year: 2009).*
Anzalone et al., "Search-and-replace genome editing without double-strand breaks or donor DNA", Nature, vol. 576 (7785), pp. 149-157, Dec. 2019.
Bae et al., "Cas-OFFinder: a fast and versatile algorithm that searches for potential off-target sites of Cas9 RNA-guided endonucleases", Bioinformatics, vol. 30, No. 10, pp. 1473-1475, 2014.
Chavez et al., "Highly-efficient Cas9-mediated transcriptional programming", Nat. Methods, vol. 12(4), pp. 326-328, Apr. 2015.
Fu et al., "Improving CRISPR-Cas nuclease specificity using truncated guide RNAs", Nature Biotechnology, vol. 32, No. 3, pp. 279-286, Mar. 2014.
Jain et al., "Defining the seed sequence of the Cas12b CRISPR-Cas effector complex", RNA Biology, vol. 16, No. 4, pp. 413-422, 2019.
Jinek et al., "A Programmable Dual-RNA-Guided DNA Endonuclease in Adaptive Bacterial Immunity", Science, vol. 337, pp. 816-821, Aug. 17, 2012.

Kuscu et al., "Genome-wide analysis reveals characteristics of off-target sites bound by the Cas9 endonuclease", Nature Biotechnology, vol. 32, No. 7, pp. 677-685, Jul. 2014.
Li et al., "A potent Cas9-derived gene activator for plant and mammalian cells", Nat. Plants, vol. 3(12), pp. 930-936, Dec. 2017.
Liu et al., "C2c1-sgRNA Complex Structure Reveals RNA-Guided DNA Cleavage Mechanism", Molecular Cell, vol. 65, pp. 310-322, Jan. 19, 2017.
Liu et al., "DSDecode: A Web-Based Tool for Decoding of Sequencing Chromatograms for Genotyping of Targeted Mutations", Molecular Plant, vol. 8, pp. 1431-1433, Sep. 2015.
Lowder et al., "A CRISPR/Cas9 Toolbox for Multiplexed Plant Genome Editing and Transcriptional Regulation", Plant Physiology, vol. 169, pp. 971-985, Oct. 2015.
Lowder et al., "Robust Transcriptional Activation in Plants Using Multiplexed CRISPR-Act2.0 and mTALE-Act Systems", Molecular Plant, vol. 11, pp. 245-256, Feb. 2018.
Malzahn et al., "Application of CRISPR-Cas12a temperature sensitivity for improved genome editing in rice, maize, and *Arabidopsis*", BMC Biology, vol. 17:9, 14 pages, 2019.
Paul et al., "CRISPR/Cas9 for plant genome editing: accomplishments, problems and prospects", Plant Cell Rep., vol. 35, pp. 1417-1427, Apr. 12, 2016.
Shmakov et al., "Discovery and functional characterization of diverse Class 2 CRISPR-Cas systems", Mol. Cell, vol. 60(3), pp. 385-397, Nov. 5, 2015.
Strecker et al., "Engineering of CRISPR-Cas12b for human genome editing", Nature Communications, vol. 10, 9 pages, 2019.
Tang et al., "A CRISPR-Cpf1 system for efficient genome editing and transcriptional repression in plants", Nature Plants, vol. 3, 22 pages, Feb. 17, 2017.
Tang et al., "A Single Transcript CRISPR-Cas9 System for Efficient Genome Editing in Plants", Molecular Plant, vol. 9, pp. 1088-1091, Jul. 2016.
Teng et al., "Repurposing CRISPR-Cs12b for mammalian genome engineering", Cell Discovery, vol. 4:63, 15 pages, 2018.
Teng et al., "Artificial sgRNAs engineered for genome editing with new Cas12b orthologs", Cell Discovery, vol. 5:23, 4 pages, 2019.
Wu et al., "Structural basis of stringent PAM recognition by CRISPR-C2c1 in complex with sgRNA", Cell Research, vol. 27, pp. 705-708, May 2017.
Yang et al., "PAM-dependent Target DNA Recognition and Cleavage by C2c1 CRISPR-Cas Endonuclease", Cell, vol. 167(7), pp. 1814-1828, Dec. 15, 2016.
You et al., "CRISPRMatch: An Automatic Calculation and Visualization Tool for High-throughput CRISPR Genome-editing Data Analysis", Int. J. Biol. Sci., vol. 14, pp. 858-862, May 22, 2018.
Zetsche et al., "Cpf1 Is a Single RNA-Guided Endonuclease of a Class 2 CRISPR-Cas System", Cell, vol. 163, pp. 759-771, Oct. 22, 2015.
Zhang et al., "The Emerging and uncultivated potential of CRISPR technology in plant science", Nature Plants, 17 pages, 2019.
Zhong et al., "Plane Genome Editing Using FnCpf1 and LbCpf1 Nucleases at Redefined and Altered PAM Sites", Molecular Plant, vol. 11, pp. 999-1002, Jul. 2018.

* cited by examiner

| AacCas12b reagents | Tested T0 lines | Mutated T0 lines (number; percentage of total) | Biallelic mutation lines (number; percentage of total) |
|---|---|---|---|
| OsEPFL9-sgRNA02-L10 (pLR1380) | 22 | 8; 36.4% | 0; 0% |

```
pLR1380: AacCas12b+OsEPFL9-sgRNA02-L10
         GCTC****CAATCAAGGCACCATGGCACCAGCAGCATCTCAGGTACCCCT WT (osepfl9)

pLR1380-01
  Allele 1: GCTC****CAATCAAGGCACCATGGCACCAGCAGCATCTCAGGTACCCCT WT
  Allele 2: GCTC****CAATCAAGGGCACCA--------CTCAGGTACCCCT -8bp
pLR1380-03
  Allele 1: GCTC****CAATCAAGGGCACCATGGCACCAGCAGCATCTCAGGTACCCCT WT
  Allele 2: GCTC****CAATCAAGGGCACCAT----------CAGGTACCCCT -10bp
pLR1380-09
  Allele 1: GCTC****CAATCAAGGCACCATGGCACCAGCAGCATCTCAGGTACCCCT WT
  Allele 2: GCTC****CAATC-------------------CTCAGGTACCCCT -19bp
pLR1380-12
  Allele 1: GCTC****CAATCAAGGCACCATGGCACCAGCAGCATCTCAGGTACCCCT WT
  Allele 2: GCTC****CAATCAAGGGCACCA--GCAGCATCTCAGGTACCCCT -2bp
pLR1380-13
  Allele 1: GCTC****CAATCAAGGCACCATGGCACCAGCAGCATCTCAGGTACCCCT WT
  Allele 2: GCTC****CAATCAAGGGCACCA--GCAGCATCTCAGGTACCCCT -2bp
```

*FIG. 10A*

| AaCas12b reagents | Tested T0 lines | Mutated T0 lines (number; percentage of total) | Biallelic mutation lines (number; percentage of total) |
|---|---|---|---|
| OsEPFL9-sgRNA02-L10 (pLR1687) | 24 | 13; 54.2% | 6; 25.0% |

```
pLR1687: AaCas12b+OsEPFL9-sgRNA02-L10
         GCTCCnnnnCAATCAAGGGCACnnnnnnnnnnnnnnGCATCTCAGGTACCCCCT  WT (osEPFL9)
pLR1687-03
Allele 1: GCTCCnnnnCAATCAAGGGCAC-------------TCAGGTACCCCCT      -12bp
Allele 2: GCTCCnnnnCAATCAAGGGCACCAT----------GGTACCCCCT         -12bp
pLR1687-06
Allele 1: GCTCCnnnnCAATC-----------------------TCAGGTACCCCCT    -20bp
Allele 2: GCTCCnnnnCAATCAAGGGCAC--------------CATCTCAGGTACCCCCT -8bp
pLR1687-09
Allele 1: GCTCCnnnnCAATCAAGGGC-----------------CTCAGGTACCCCCT   -13bp
Allele 2: GCTCCnnnnCAATCAAGGGCAC--------------CATCTCAGGTACCCCCT -8bp
pLR1687-16
Allele 1: GCTCCnnnnCAATCAAGGGCACC---------CATCTCAGGTACCCCCT     -7bp
Allele 2: GCTCCnnnnCAATCAAGGGCACCCA--GCAGCATCTCAGGTACCCCCT      -2bp
pLR1687-21
Allele 1: GCTCCnnnnCAATCAAGGGCACCACCATGGCCAGCa----TCTCAGGTACCCCCT -12bp
Allele 2: GCTCCnnnnCAATCAAGGGCACCACCATGGCAGCa----------------     -14bp
```

FIG. 10B

| AaCas12b reagents | Tested T0 lines | Mutated T0 lines (number; percentage of total) | Biallelic mutation lines (number; percentage of total) |
|---|---|---|---|
| OsROC5-sgRNA02-L4 (pLR1811) | 24 | 0; 0% | 0; 0% |
| OsEPFL9-sgRNA02-L10 (pLR1811) | 24 | 16; 66.7% | 7; 29.2% |
| OsGS3-sgRNA02-L12 (pLR1811) | 24 | 17; 70.8% | 11; 45.8% |

FIG. 12B

COMPOSITIONS AND METHODS FOR GENOME EDITING IN PLANTS

CROSS REFERENCE TO RELATED APPLICATIONS

This application claims priority to provisional application U.S. Ser. No. 62/949,230, filed Dec. 17, 2019, which is incorporated herein by reference in its entirety.

GOVERNMENT SUPPORT

This invention was made with government support under IOS1758745 awarded by National Science Foundation and 20183352228789 awarded by USDA National Institute of Food and Agriculture. The government has certain rights in the invention.

SEQUENCE LISTING

The instant application contains a Sequence Listing which has been submitted in ASCII format via EFS-Web and is hereby incorporated by reference in its entirety. Said ASCII copy, created on Dec. 15, 2020, is named 2020-12-15QI_P13394US01_SEQLISTING_ST25.txt and is 436,494 bytes in size.

TECHNICAL FIELD

The present invention relates to compositions and methods for editing genomic sequences and for modulating gene expression in plants.

BACKGROUND

Methodologies for specific gene targeting or precise genome editing are of great importance to functional characterization of plant genes and genetic improvement of agricultural crops. Plants with stably modified genomic DNA can have new traits such as herbicide tolerance, insect resistance, or accumulation of valuable proteins including pharmaceutical proteins and industrial enzymes imparted to them. The expression of native plant genes may be up- or down-regulated or otherwise altered, their expression may be abolished entirely, DNA sequences may be altered (e.g., through point mutations, insertions, or deletions), or new non-native genes may be inserted into a plant genome to impart new traits to the plant.

The most common methods for modifying plant genomic DNA tend to modify the DNA at random sites within the genome. In many cases, however, it is desirable to modify the genomic DNA at a pre-determined target site in the plant genome of interest, e.g., to avoid disruption of native plant genes or to insert a transgene cassette at a genomic locus that is known to provide robust gene expression. Only recently have technologies for targeted modification of plant genomic DNA become available. CRISPR-Cas9 and Cas12a, as RNA-guided endonuclease systems, have become leading sequence-specific nucleases (SSNs) in plant genome engineering. Cas12b (formerly C2c1), a class 2 type V-B CRISPR system, was recently demonstrated as a new SSN for mammalian genome editing. Similar to Cas12a (formerly Cpf1, a class 2 type V-A system), Cas12b prefers T-rich PAMs (protospacer adjacent motifs) and generates staggered ends of DNA double-strand breaks (DSBs). Similar to Cas9 (a class 2 type II system), Cas12b requires a CRISPR RNA (crRNA) and a trans-activating crRNA (tracrRNA), which can be combined as a single guide RNA (sgRNA), for DNA targeting. By contrast, Cas12a only requires a crRNA. Hence, Cas12b is more amendable than Cas12a with versatile guide RNA engineering. In addition, Cas12b is significantly smaller than Cas9 and Cas12a in protein size. In human and mouse cells, AaCas12b can barely tolerate single base pair mismatches in the protospacer, suggesting it has high targeting specificity.

It is an objective of the present disclosure to provide Cas12b systems for plant genome engineering. Additional objectives, features, and advantages will become apparent based on the disclosure contained herein.

SUMMARY

The presently disclosed subject matter relates generally to genome engineering. In certain embodiments, the disclosed subject matter relates to compositions and methods for editing genome sequences in a cell. The cell may be a prokaryotic cell or a eukaryotic cell. The cell may be a non-mammalian cell. Preferably, the cell is a plant cell.

In certain embodiments, the compositions relate to CRISPR Cas12b nucleases, for example, *Alicyclobacillus acidoterrestris* Cas12b (AacCas12b), *Alicyclobacillus acidiphilus* Cas12b (AaCas12b), *Bacillus thermoamylovorans* Cas12b (BthCas12b), and *Bacillus hisashii* Cas12b (BhCas12b). Applicants have surprisingly found that Cas12b from *Alicyclobacillus acidiphilus* provides superior editing efficiency in plant cells. The methods produce double-stranded breaks (DSBs) at a target site in a genomic DNA sequence, resulting in mutation, insertion, and/or deletion of DNA sequences at the target site in a genome. In certain embodiments, the methods may include multiplexed genome editing.

Compositions comprise DNA constructs comprising nucleotide sequences that encode a Cas12b protein operably linked to a promoter that is operable in the cells of interest. Particular Cas12b protein sequences are set forth in SEQ ID NOs: 5-8; particular Cas12b protein-encoding polynucleotide sequences are set forth in SEQ ID NOs: 1-4. The DNA constructs comprising polynucleotide sequences that encode the Cas12b proteins of the invention, or the Cas12b proteins of the invention themselves, can be used to direct the modification of genomic DNA at genomic loci. Methods to use these DNA constructs to modify genomic DNA sequences are described herein. In certain embodiments, the DNA constructs are vectors for delivery of Cas12b to plant cells. Modified plants and plant cells, including *Oryza sativa* and *Oryza sativa* cells, are also encompassed.

Compositions and methods for modulating the expression of genes are also provided. The methods target protein(s) to sites in a genome to effect an up- or down-regulation of a gene or genes whose expression is regulated by the targeted site in the genome. Compositions comprise DNA constructs comprising nucleotide sequences that encode a modified Cas12b protein with diminished or abolished nuclease activity, optionally fused to a transcriptional activation or repression domain. Methods to use these DNA constructs to modify gene expression are described herein.

While multiple embodiments are disclosed, still other embodiments of the inventions will become apparent to those skilled in the art from the following detailed description, which shows and describes illustrative embodiments of the invention. Accordingly, the figures and detailed description are to be regarded as illustrative in nature and not restrictive.

BRIEF DESCRIPTION OF THE FIGURES

The following drawings form part of the specification and are included to further demonstrate certain embodiments or various aspects of the invention. In some instances, embodiments of the invention can be best understood by referring to the accompanying figures in combination with the detailed description presented herein. The description and accompanying figures may highlight a certain specific example, or a certain aspect of the invention. However, one skilled in the art will understand that portions of the example or aspect may be used in combination with other examples or aspects of the invention.

FIG. 10A and FIG. 10B show a summary of the genotyping results on stable transgenic T0 lines at the OsEPFL9-crRNA02 site by AacCas12b and AaCas12b. Genotypes of five example mutants are shown for each Cas12b (SEQ ID NOs: 77-89). The PAM sequence (GTTG) and the target sequence are in grey. The NcoI enzyme site used in RFLP analysis is underlined.

FIG. 12A and FIG. 12B are a summary of the genotyping results on multiplexed stable transgenic T0 lines by AacCas12b and AaCas12b at three sites: OsROC5-sgRNA02 (L4), OsEPFL9-sgRNA02 (L10) and OsGS3-sgRNA02 (L12). RFLP analysis of independent T0 lines (shown below) and Sanger sequencing were both used for genotyping. The plus sign '+' indicates heterozygous or homozygous mutants confirmed by both methods.

DETAILED DESCRIPTION

Figure 1:
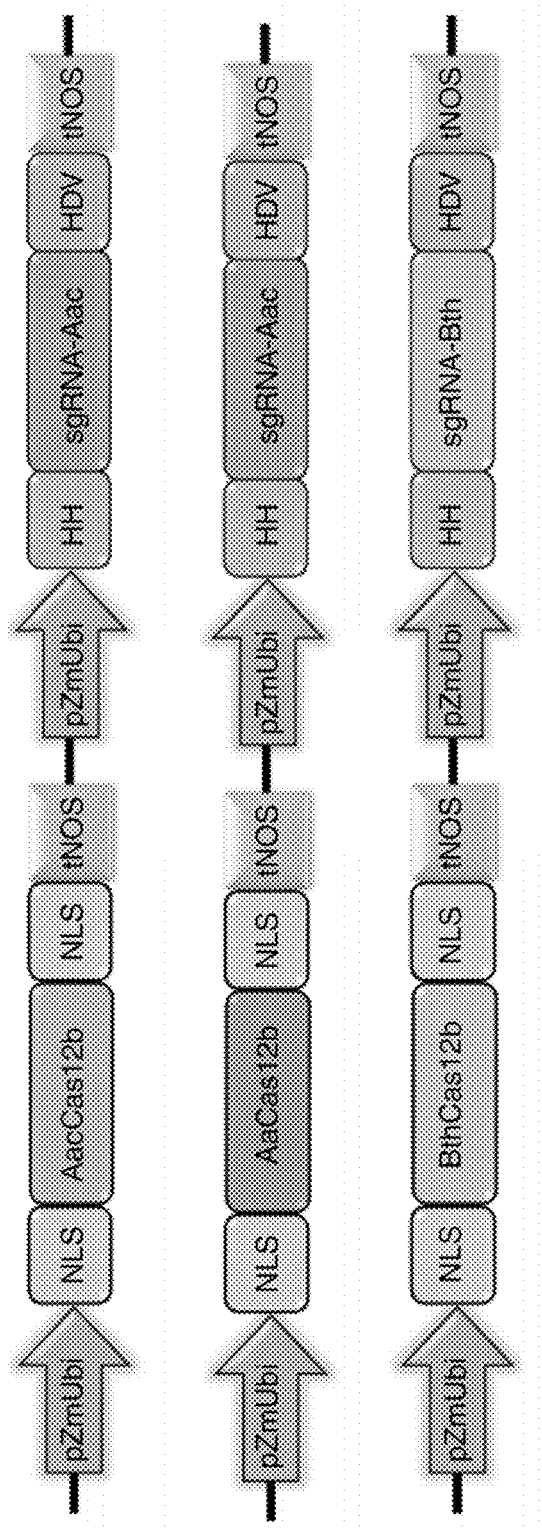
FIG. 1 is an illustration of the dual Pol II promoter system for expression of Cas12b and sgRNA. Note the sgRNA is flanked by HH and HDV ribozymes for precise processing.

The present disclosure relates to Cas12b-mediated genome editing in plants. Methods and compositions are provided herein for the control of gene expression involving sequence targeting, such as genome perturbation or gene-editing, that relate to the CRISPR-Cas12b system and components thereof. The CRISPR enzymes of the invention are selected from a Cas12b enzyme. The methods and compositions include nucleic acids to bind target DNA sequences. Also provided are nucleic acids encoding the Cas12b polypeptides, as well as methods of using Cas12b polypeptides to modify chromosomal (i.e., genomic) or organellar DNA sequences of host cells including plant cells. The Cas12b polypeptides interact with specific guide RNAs (gRNAs), which direct the Cas12b endonuclease to a specific target site, at which site the Cas12b endonuclease introduces a double-stranded break that can be repaired by a DNA repair process such that the DNA sequence is modified. The methods disclosed herein can be used to target and modify specific chromosomal sequences and/or introduce exogenous sequences at targeted locations in the genome of plant cells. The methods can further be used to introduce sequences or modify regions within organelles (e.g., chloroplasts and/or mitochondria). Furthermore, the targeting is specific with limited off target effects.

So that the present invention may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation, the preferred materials and methods are described herein. In describing and claiming the embodiments of the present invention, the following terminology will be used in accordance with the definitions set out below.

It is to be understood that all terminology used herein is for the purpose of describing particular embodiments only, and is not intended to be limiting in any manner or scope. For example, as used in this specification and the appended claims, the singular forms "a," "an" and "the" can include plural referents unless the content clearly indicates otherwise. Similarly, the word "or" is intended to include "and" unless the context clearly indicate otherwise. The word "or" means any one member of a particular list and also includes any combination of members of that list. Further, all units, prefixes, and symbols may be denoted in its SI accepted form.

Numeric ranges recited within the specification are inclusive of the numbers defining the range and include each integer within the defined range. Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges, fractions, and individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6, and decimals and fractions, for example, 1.2, 3.8, 1½, and 4¾ This applies regardless of the breadth of the range.

The term "about," as used herein, refers to variation in the numerical quantity that can occur, for example, through typical measuring techniques and equipment, with respect to any quantifiable variable, including, but not limited to, mass, volume, time, and temperature. Further, given solid and liquid handling procedures used in the real world, there is certain inadvertent error and variation that is likely through differences in the manufacture, source, or purity of the ingredients used to make the compositions or carry out the methods and the like. The term "about" also encompasses these variations. Whether or not modified by the term "about," the claims include equivalents to the quantities.

The methods and compositions of the present invention may comprise, consist essentially of, or consist of the components and ingredients of the present invention as well as other ingredients described herein. As used herein, "consisting essentially of" means that the methods, systems, apparatuses and compositions may include additional steps, components or ingredients, but only if the additional steps, components or ingredients do not materially alter the basic and novel characteristics of the claimed methods, systems, apparatuses, and compositions.

Cas12b Endonucleases

The terms "CRISPR-Cas protein", "CRISPR protein", "Cas protein", "Cas effector protein", "CRISPR enzyme", and "Cas enzyme" may be used interchangeably herein. Provided herein are Cas12b proteins, and fragments and variants thereof, for use in modifying genomes including plant genomes. The present disclosure encompasses the use of a Cas12b effector protein, derived from a Cas12b locus denoted as subtype V-B. Such effector proteins are also referred to as C2c1. Cas12b is a large protein (about 1100-1300 amino acids) that contains a RuvC-like nuclease domain homologous to the corresponding domain of Cas9 along with a counterpart to the characteristic arginine-rich cluster of Cas9. However, Cas12b lacks the HNH nuclease domain that is present in all Cas9 proteins, and the RuvC-like domain is contiguous in the Cas12b sequence, in contrast to Cas9 where it contains long inserts including the HNH domain. Accordingly, in particular embodiments, the CRISPR-Cas enzyme comprises only a RuvC-like nuclease domain.

Cas12b creates a staggered cut at the target locus, with a 5' overhang, or a "sticky end" at the PAM distal side of the target sequence. In some embodiments, the 5' overhang is 7 nt. See Lewis and Ke, Mol Cell. 2017 Feb. 2; 65(3):377-379. Cas12b creates double strand breaks at the distal end of PAM, in contrast to cleavage at the proximal end of PAM created by Cas9. Cas12a and Cas12b are both Type V CRISPR-Cas proteins that share structure similarity. Unlike Cas9, which generates blunt cuts at the proximal end of PAM, Cas12a and Cas12b generate staggered cuts at the distal end of PAM.

Cas12b polypeptides can be wild type Cas12b polypeptides, modified Cas12b polypeptides, or a fragment of a wild type or modified Cas12b polypeptide. The Cas12b polypeptide can be modified to increase nucleic acid binding affinity and/or specificity, alter an enzymatic activity, and/or change another property of the protein. For example, nuclease (i.e., DNase, RNase) domains of the Cas12b polypeptide can be modified, deleted, or inactivated. Alternatively, the Cas12b polypeptide can be truncated to remove domains that are not essential for the function of the protein.

In some embodiments, the Cas12b polypeptide can be derived from a wild type Cas12b polypeptide or fragment thereof. In other embodiments, the Cas12b polypeptide can be derived from a modified Cas12b polypeptide. For example, the amino acid sequence of the Cas12b polypeptide can be modified to alter one or more properties (e.g., nuclease activity, affinity, stability, etc.) of the protein. Alternatively, domains of the Cas12b polypeptide not involved in RNA-guided cleavage can be eliminated from the protein such that the modified Cas12b polypeptide is smaller than the wild type Cas12b polypeptide.

In some embodiments, the Cas12b polypeptide can be modified to inactivate the nuclease domain so that it is no longer functional. In some embodiments in which one of the nuclease domains is inactive, the Cas12b polypeptide does not cleave double-stranded DNA. In specific embodiments, the mutated Cas12b polypeptide comprises one or more mutations in a position corresponding to amino acid positions D570, E848, or D977 in *Alicyclobacillus acidiphilus* Cas12b when aligned for maximum identity that reduces or eliminates the nuclease activity.

The nuclease domain can be modified using well-known methods, such as site-directed mutagenesis, PCR-mediated mutagenesis, and total gene synthesis, as well as other methods known in the art. Cas12b proteins with inactivated nuclease domains (dCas12b proteins) can be used to modulate gene expression without modifying DNA sequences. In certain embodiments, a dCas12b protein may be targeted to particular regions of a genome such as promoters for a gene or genes of interest through the use of appropriate gRNAs. The dCas12b protein can bind to the desired region of DNA and may interfere with RNA polymerase binding to this region of DNA and/or with the binding of transcription factors to this region of DNA. This technique may be used to up- or down-regulate the expression of one or more genes of interest. In certain other embodiments, the dCas12b protein may be fused to a repressor domain to further downregulate the expression of a gene or genes whose expression is regulated by interactions of RNA polymerase, transcription factors, or other transcriptional regulators with the region of chromosomal DNA targeted by the gRNA. In certain other embodiments, the dCas12b protein may be fused to an activation domain to effect an upregulation of a gene or genes whose expression is regulated by interactions of RNA polymerase, transcription factors, or other transcriptional regulators with the region of chromosomal DNA targeted by the gRNA.

The Cas12b polypeptides disclosed herein can further comprise at least one nuclear localization signal (NLS). In general, an NLS comprises a stretch of basic amino acids. Nuclear localization signals are known in the art (see, e.g., Lange et al., *J. Biol. Chem.* (2007) 282:5101-5105). The NLS can be located at the N-terminus, the C-terminus, or in an internal location of the Cas12b polypeptide.

The Cas12b polypeptide disclosed herein can further comprise at least one plastid targeting signal peptide, at least one mitochondrial targeting signal peptide, or a signal peptide targeting the Cas12b polypeptide to both plastids and mitochondria. Plastid, mitochondrial, and dual-targeting signal peptide localization signals are known in the art (see, e.g., Nassoury and Morse (2005) *Biochim Biophys Acta* 1743:5-19; Kunze and Berger (2015) *Front Physiol* 6:259; Herrmann and Neupert (2003) *IUBMB Life* 55:219-225; Soll (2002) *Curr Opin Plant Biol* 5:529-535; Carrie and Small (2013) *Biochim Biophys Acta* 1833:253-259; Carrie et al. (2009) *FEBS J* 276:1187-1195; Silva-Filho (2003) *Curr Opin Plant Biol* 6:589-595; Peeters and Small (2001) *Biochim Biophys Acta* 1541:54-63; Murcha et al. (2014) *J Exp Bot* 65:6301-6335; Mackenzie (2005) *Trends Cell Biol* 15:548-554; Glaser et al. (1998) *Plant Mol Biol* 38:311-338). The plastid, mitochondrial, or dual-targeting signal peptide can be located at the N-terminus, the C-terminus, or in an internal location of the Cas12b polypeptide.

In still other embodiments, the Cas12b polypeptide can also comprise at least one marker domain. Non-limiting examples of marker domains include fluorescent proteins, purification tags, and epitope tags. In certain embodiments, the marker domain can be a fluorescent protein. Non limiting examples of suitable fluorescent proteins include green fluorescent proteins (e.g., GFP, GFP-2, tagGFP, turboGFP, EGFP, Emerald, Azami Green, Monomeric Azami Green, CopGFP, AceGFP, ZsGreen1), yellow fluorescent proteins (e.g. YFP, EYFP, Citrine, Venus, YPet, PhiYFP, ZsYellow1), blue fluorescent proteins (e.g. EBFP, EBFP2, Azurite, mKalama1, GFPuv, Sapphire, T-sapphire), cyan fluorescent proteins (e.g. ECFP, Cerulean, CyPet, AmCyan1, Midoriishi-Cyan), red fluorescent proteins (mKate, mKate2, mPlum, DsRed monomer, mCherry, mRFP1, DsRed-Express, DsRed2, DsRed-Monomer, HcRed-Tandem, HcRed1, AsRed2, eqFP611, mRasberry, mStrawberry, Jred), and orange fluorescent proteins (mOrange, mKO, Kusabira-Orange, Monomeric Kusabira-Orange, mTangerine, tdTomato) or any other suitable fluorescent protein. In other embodiments, the marker domain can be a purification tag and/or an epitope tag. Exemplary tags include, but are not limited to, glutathione-S-transferase (GST), chitin binding protein (CBP), maltose binding protein, thioredoxin (TRX), poly(NANP), tandem affinity purification (TAP) tag, myc, AcV5, AU1, AUS, E, ECS, E2, FLAG, HA, nus, Softag 1, Softag 3, Strep, SBP, Glu-Glu, HSV, KT3, S, 51, T7, V5, VSV-G, 6×His, biotin carboxyl carrier protein (BCCP), and calmodulin.

In certain embodiments, the Cas12b polypeptide may be part of a protein-RNA complex comprising a guide RNA. The guide RNA interacts with the Cas12b polypeptide to direct the Cas12b polypeptide to a specific target site, wherein the 5' end of the guide RNA can base pair with a specific protospacer sequence of the nucleotide sequence of interest in the plant genome, whether part of the nuclear, plastid, and/or mitochondrial genome. As used herein, the term "DNA-targeting RNA" refers to a guide RNA that interacts with the Cas12b polypeptide and the target site of the nucleotide sequence of interest in the genome of a cell. A DNA-targeting RNA, or a DNA polynucleotide encoding a DNA-targeting RNA, can comprise: a first segment comprising a nucleotide sequence that is complementary to a sequence in the target DNA, and a second segment that interacts with a Cas12b polypeptide.

The polynucleotides encoding Cas12b polypeptides disclosed herein can be used to isolate corresponding sequences from other prokaryotic or eukaryotic organisms, or from metagenomically-derived sequences whose native host organism is unclear or unknown. In this manner, methods such as PCR, hybridization, and the like can be used to identify such sequences based on their sequence homology or identity to the sequences set forth herein. Sequences isolated based on their sequence identity to the entire Cas12b sequences set forth herein or to variants and fragments thereof are encompassed by the present invention. Such sequences include sequences that are orthologs of the disclosed Cas12b sequences. "Orthologs" is intended to mean genes derived from a common ancestral gene and which are found in different species as a result of speciation. Genes found in different species are considered orthologs when their nucleotide sequences and/or their encoded protein sequences share at least about 75%, about 80%, about 85%, about 90%, about 91%, about 92%, about 93%, about 94%, about 95%, about 96%, about 97%, about 98%, about 99%, or greater sequence identity. Functions of orthologs are often highly conserved among species. Thus, isolated polynucleotides that encode polypeptides having Cas12b endonuclease activity and which share at least about 75% or more sequence identity to the sequences disclosed herein, are encompassed by the present invention.

In particular embodiments, the Cas12b protein from an organism from a genus comprising *Alicyclobacillus, Desulfovibrio, Desulfonatronum, Opitutaceae, Tuberibacillus, Bacillus, Brevibacillus, Candidatus, Desulfatirhabdium, Citrobacter, Elusimicrobia, Methylobacterium, Omnitrophica, Phycisphaerae, Planctomycetes, Spirochaetes,* and *Verrucomicrobiaceae.*

In further particular embodiments, the Cas12b protein is from a species selected from *Alicyclobacillus acidoterrestris* (e.g., ATCC 49025), *Alicyclobacillus contaminans* (e.g., DSM 17975), *Alicyclobacillus macrosporangiidus* (e.g. DSM 17980), *Bacillus hisashii* strain C4, *Candidatus Lindowbacteria* bacterium RIFCSPLOW02, *Desulfovibrio inopinatus* (e.g., DSM 10711), *Desulfonatronum thiodismutans* (e.g., strain MLF-1), *Elusimicrobia bacterium* RIFOXYA12, Omnitrophica WOR 2 bacterium RIFCSPHIGH02, *Opitutaceae* bacterium TAV5, *Phycisphaerae bacterium* ST-NAGAB-D1, *Planctomycetes bacterium* RBG 13 46 10, *Spirochaetes bacterium* GWB1 27 13, *Verrucomicrobiaceae bacterium* UBA2429, *Tuberibacillus calidus* (e.g., DSM 17572), *Bacillus thermoamylovorans* (e.g., strain B4166), *Brevibacillus* sp. CF112, *Bacillus* sp. NSP2.1, *Desulfatirhabdium butyrativorans* (e.g., DSM 18734), *Alicyclobacillus herbarius* (e.g., DSM 13609), *Citrobacter freundii* (e.g., ATCC 8090), *Brevibacillus agri* (e.g., BAB-2500), *Methylobacterium nodulans*(e.g., ORS 2060).

In some embodiments, the Cas12b from *Alicyclobacillus acidoterrestris, Alicyclobacillus acidiphilus, Bacillus thermoamylovorans,* or *Bacillus hisashii.* In a preferred embodiment, the Cas12b from *Alicyclobacillus acidiphilus.* Applicants have surprisingly found that Cas12b from *Alicyclobacillus acidiphilus* provides superior editing efficiency in plant cells.

As used herein, Cas12b endonuclease activity refers to CRISPR endonuclease activity wherein, a guide RNA (gRNA) associated with a Cas12b polypeptide causes the Cas12b-gRNA complex to bind to a pre-determined nucleotide sequence that is complementary to the gRNA; and wherein Cas12b activity can introduce a double-stranded break at or near the site targeted by the gRNA. In certain embodiments, this double-stranded break may be a staggered DNA double-stranded break. As used herein a "staggered DNA double-stranded break" can result in a double strand break with about 1, about 2, about 3, about 4, about 5, about 6, about 7, about 8, about 9, or about 10 nucleotides of overhang on either the 3' or 5' ends following cleavage. In specific embodiments, the Cas12b polypeptide introduces a staggered DNA double-stranded break with a 5' overhang. The double strand break can occur at or near the sequence to which the DNA-targeting RNA (e.g., guide RNA) sequence is targeted.

Fragments and variants of the Cas12b polynucleotides and Cas12b amino acid sequences encoded thereby that retain Cas12b nuclease activity are encompassed herein. By "Cas12b nuclease activity" is intended the binding of a pre-determined DNA sequence as mediated by a guide RNA. In embodiments wherein the Cas12b nuclease retains a functional RuvC domain, Cas12b nuclease activity can further comprise double-strand break induction. By "fragment" is intended a portion of the polynucleotide or a portion of the amino acid sequence. "Variants" is intended to mean substantially similar sequences. For polynucleotides, a variant comprises a polynucleotide having deletions (i.e., truncations) at the 5' and/or 3' end; deletion and/or addition of one or more nucleotides at one or more internal sites in the native polynucleotide; and/or substitution of one or more nucleotides at one or more sites in the native polynucleotide. As used herein, a "native" polynucleotide or polypeptide comprises a naturally occurring nucleotide sequence or amino acid sequence, respectively. Generally, variants of a particular polynucleotide of the invention will have at least about 75%, 80%, 85%, 90%, 91%, 92%, 93%, 94%, 95%, 96%, 97%, 98%, 99% or more sequence identity to that particular polynucleotide as determined by sequence alignment programs and parameters as described elsewhere herein.

"Variant" amino acid or protein is intended to mean an amino acid or protein derived from the native amino acid or protein by deletion (so-called truncation) of one or more amino acids at the N-terminal and/or C-terminal end of the native protein; deletion and/or addition of one or more amino acids at one or more internal sites in the native protein; or substitution of one or more amino acids at one or more sites in the native protein. Variant proteins encompassed by the present invention are biologically active, that is they continue to possess the desired biological activity of the native protein. Biologically active variants of a native polypeptide will have at least about 80%, 85%, 90%, 91%, 92%, 93%, 94%, 95%, 96%, 97%, 98%, 99% or more sequence identity to the amino acid sequence for the native sequence as determined by sequence alignment programs and parameters described herein. A biologically active variant of a protein of the invention may differ from that protein by as few as 1-15 amino acid residues, as few as 1-10, such as 6-10, as few as 5, as few as 4, 3, 2, or even 1 amino acid residue.

Variant sequences may also be identified by analysis of existing databases of sequenced genomes. In this manner, corresponding sequences can be identified and used in the methods of the invention.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11-17; the local alignment algorithm of Smith et al. (1981) *Adv. Appl. Math.* 2:482; the global alignment algorithm of Needleman and Wunsch (1970) *J Mol. Biol.* 48:443-453; the search-for-local alignment method of Pearson and Lipman (1988) *Proc. Natl. Acad. Sci.* 85:2444-2448; the algorithm of Karlin and Altschul (1990) *Proc. Natl. Acad. Sci. USA* 87:2264-2268, modified as in Karlin and Altschul (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA). Alignments using these programs can be performed using the default parameters. The CLUSTAL program is well described by Higgins et al. (1988) *Gene* 73:237-244; Higgins et al. (1989) *CABIOS* 5:151-153; Corpet et al. (1988) *Nucleic Acids Res.* 16:10881-90; Huang et al. (1992) *CABIOS* 8:155-65; and Pearson et al. (1994) *Meth. Mol. Biol.* 24:307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The MUSCLE algorithm for multiple sequence alignment may be used for comparisons of multiple nucleic acid or protein sequences (Edgar (2004) *Nucleic Acids Research* 32:1792-1797). The BLAST programs of Altschul et al (1990) *J Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See the website at www.ncbi.nlm.nih.gov. Alignment may also be performed manually by inspection.

The nucleic acid molecules encoding Cas12b polypeptides, or fragments or variants thereof, can be codon optimized for expression in a plant of interest or other cell or organism of interest. A "codon-optimized gene" is a gene having its frequency of codon usage designed to mimic the frequency of preferred codon usage of the host cell. Nucleic acid molecules can be codon optimized, either wholly or in part. Because any one amino acid (except for methionine and tryptophan) is encoded by a number of codons, the sequence of the nucleic acid molecule may be changed without changing the encoded amino acid. Codon optimization is when one or more codons are altered at the nucleic acid level such that the amino acids are not changed but expression in a particular host organism is increased. Those having ordinary skill in the art will recognize that codon tables and other references providing preference information for a wide range of organisms are available in the art (see, e.g., Zhang et al. (1991) *Gene* 105:61-72; Murray et al. (1989) *Nucl. Acids Res.* 17:477-508). Methodology for optimizing a nucleotide sequence for expression in a plant is provided, for example, in U.S. Pat. No. 6,015,891, and the references cited therein.

Fusion Proteins

Fusion proteins are provided herein comprising a Cas12b polypeptide, or a fragment or variant thereof, and an effector domain. The Cas12b polypeptide can be directed to a target site by a guide RNA, at which site the effector domain can modify or effect the targeted nucleic acid sequence. The effector domain can be a cleavage domain, an epigenetic modification domain, a transcriptional activation domain, a transcriptional repressor domain, a deaminase domain, or a reverse transcriptase. The fusion protein can further comprise at least one additional domain chosen from a nuclear localization signal, plastid signal peptide, mitochondrial signal peptide, signal peptide capable of protein trafficking to multiple subcellular locations, a cell-penetrating domain, or a marker domain, any of which can be located at the N-terminus, C-terminus, or an internal location of the fusion protein. The Cas12b polypeptide can be located at the N-terminus, the C-terminus, or in an internal location of the fusion protein. The Cas12b polypeptide can be directly fused to the effector domain, or can be fused with a linker. In specific embodiments, the linker sequence fusing the Cas12b polypeptide with the effector domain can be at least 1, 2, 3, 4, 5, 6, 7, 8, 9, 10, 15, 20, 25, 30, 40, or 50 amino acids in length. For example, the linker can range from 1-5, 1-10, 1-20, 1-50, 2-3, 3-10, 3-20, 5-20, or 10-50 amino acids in length.

In some embodiments, the Cas12b polypeptide of the fusion protein can be derived from a wild type Cas12b protein. The Cas12b-derived protein can be a modified variant or a fragment. In some embodiments, the Cas12b polypeptide can be modified to contain a nuclease domain (e.g. a RuvC or RuvC-like domain) with reduced or eliminated nuclease activity. For example, the Cas12b-derived polypeptide can be modified such that the nuclease domain is deleted or mutated such that it is no longer functional (i.e., the nuclease activity is absent). Particularly, a Cas12b polypeptide can have polypeptide comprises one or more mutations in a position corresponding to amino acid positions D570, E848, or D977 in *Alicyclobacillus acidiphilus* Cas12b (SEQ ID NO: 7) when aligned for maximum identity that reduces or eliminates the nuclease activity.

The nuclease domain can be inactivated by one or more deletion mutations, insertion mutations, and/or substitution mutations using known methods, such as site-directed mutagenesis, PCR-mediated mutagenesis, and total gene synthesis, as well as other methods known in the art. In an exemplary embodiment, the Cas12b polypeptide of the fusion protein is modified by mutating the RuvC-like domain such that the Cas12b polypeptide has no nuclease activity.

The fusion protein also comprises an effector domain located at the N-terminus, the C-terminus, or in an internal location of the fusion protein. In some embodiments, the effector domain is a cleavage domain. As used herein, a "cleavage domain" refers to a domain that cleaves DNA. The cleavage domain can be obtained from any endonuclease or exonuclease. Non-limiting examples of endonucleases from which a cleavage domain can be derived include, but are not limited to, restriction endonucleases and homing endonucleases. See, for example, New England Biolabs Catalog or Belfort et al. (1997) *Nucleic Acids Res.* 25:3379-3388. Additional enzymes that cleave DNA are known (e.g., 51 Nuclease; mung bean nuclease; pancreatic DNase I; micrococcal nuclease; yeast HO endonuclease). See also Linn et al. (eds.) Nucleases, Cold Spring Harbor Laboratory Press, 1993. One or more of these enzymes (or functional fragments thereof) can be used as a source of cleavage domains.

In some embodiments, the cleavage domain can be derived from a type II-S endonuclease. Type II-S endonucleases cleave DNA at sites that are typically several base pairs away from the recognition site and, as such, have separable recognition and cleavage domains. These enzymes generally are monomers that transiently associate to form dimers to cleave each strand of DNA at staggered locations. Non-limiting examples of suitable type II-S endonucleases include BfiI, BpmI, BsaI, BsgI, BsmBI, BsmI, BspMI, FokI, MboII, and SapI.

In certain embodiments, the type II-S cleavage can be modified to facilitate dimerization of two different cleavage domains (each of which is attached to a Cas12b polypeptide or fragment thereof). In embodiments wherein the effector domain is a cleavage domain the Cas12b polypeptide can be modified as discussed herein such that its endonuclease activity is eliminated. For example, the Cas12b polypeptide can be modified by mutating the RuvC-like domain such that the polypeptide no longer exhibits endonuclease activity.

In other embodiments, the effector domain of the fusion protein can be an epigenetic modification domain. In general, epigenetic modification domains alter histone structure and/or chromosomal structure without altering the DNA sequence. Changes in histone and/or chromatin structure can lead to changes in gene expression. Examples of epigenetic modification include, without limit, acetylation or methylation of lysine residues in histone proteins, and methylation of cytosine residues in DNA. Non-limiting examples of suitable epigenetic modification domains include histone acetyltansferase domains, histone deacetylase domains, histone methyltransferase domains, histone demethylase domains, DNA methyltransferase domains, and DNA demethylase domains.

In embodiments in which the effector domain is a histone acetyltansferase (HAT) domain, the HAT domain can be derived from EP300 (i.e., E1A binding protein p300), CRE-BBP (i.e., CREB-binding protein), CDY1, CDY2, CDYL1, CLOCK, ELP3, ESA1, GCNS (KAT2A), HAT1, KAT2B, KAT5, MYST1, MYST2, MYST3, MYST4, NCOA1, NCOA2, NCOA3, NCOAT, P/CAF, Tip60, TAFII250, or TF3C4. In embodiments wherein the effector domain is an epigenetic modification domain, the Cas12b polypeptide can be modified as discussed herein such that its endonuclease activity is eliminated. For example, the Cas12b polypeptide can be modified by mutating the RuvC-like domain such that the polypeptide no longer possesses nuclease activity.

In some embodiments, the effector domain of the fusion protein can be a transcriptional activation domain. In general, a transcriptional activation domain interacts with transcriptional control elements and/or transcriptional regulatory proteins (i.e., transcription factors, RNA polymerases, etc.) to increase and/or activate transcription of one or more genes. In some embodiments, the transcriptional activation domain can be, without limit, a herpes simplex virus VP16 activation domain, VP64 (which is a tetrameric derivative of VP16), a NFκKB p65 activation domain, p53 activation domains 1 and 2, a CREB (cAMP response element binding protein) activation domain, an E2A activation domain, and an NFAT (nuclear factor of activated T-cells) activation domain. In other embodiments, the transcriptional activation domain can be Gal4, Gcn4, MLL, Rtg3, Gln3, Oaf1, Pip2, Pdr1, Pdr3, Pho4, and Leu3. The transcriptional activation domain may be wild type, or it may be a modified version of the original transcriptional activation domain. In some embodiments, the effector domain of the fusion protein is a VP16 or VP64 transcriptional activation domain. In an exemplary embodiment, the transcriptional activation domain is TV or VPR. In embodiments wherein the effector domain is a transcriptional activation domain, the Cas12b polypeptide can be modified as discussed herein such that its endonuclease activity is eliminated. For example, the Cas12b polypeptide can be modified by mutating the RuvC-like domain such that the polypeptide no longer possesses nuclease activity.

In still other embodiments, the effector domain of the fusion protein can be a transcriptional repressor domain. In general, a transcriptional repressor domain interacts with transcriptional control elements and/or transcriptional regulatory proteins (i.e., transcription factors, RNA polymerases, etc.) to decrease and/or terminate transcription of one or more genes. Non-limiting examples of suitable transcriptional repressor domains include inducible cAMP early repressor (ICER) domains, Kruppel-associated box A (KRAB-A) repressor domains, YY1 glycine rich repressor domains, Sp1-like repressors, E(spl) repressors, IκB repressor, and MeCP2. In an exemplary embodiment, the transcriptional repressor domain is an SRDX repressor domain.

In embodiments wherein the effector domain is a transcriptional repressor domain, the Cas12b polypeptide can be modified as discussed herein such that its endonuclease activity is eliminated. For example, the Cas12b polypeptide can be modified by mutating the RuvC-like domain such that the polypeptide no longer possesses nuclease activity.

In some embodiments, the effector domain of the fusion protein can be a nucleotide deaminase or a catalytic domain thereof. The nucleotide deaminase may be an adenosine deaminase or a cytidine deaminase. In general, a Cas12b fused with a deaminase domain can target a sequence in the genome of a plant through the direction of a guide RNA to perform base editing, including the introduction of C to T or A to G substitutions. In some embodiments, the adenosine deaminase can be, without limit, a member of the enzyme family known as adenosine deaminases that act on RNA (ADARs), a member of the enzyme family known as adenosine deaminases that act on tRNA (ADATs), or an adenosine deaminase domain-containing (ADAD) family member. In some embodiments, the cytidine deaminase can be, without limit, a member of the enzyme family known as apolipoprotein B mRNA-editing complex (APOBEC) family deaminase, an activation-induced deaminase (AID), or a cytidine deaminase 1 (CDA1).

In embodiments wherein the effector domain is a deaminase domain, the Cas12b polypeptide can be modified as discussed herein such that its endonuclease activity is eliminated. For example, the Cas12b polypeptide can be modified by mutating the RuvC-like domain such that the polypeptide no longer possesses nuclease activity. In some embodiments, the Cas12b polypeptide has nickase activity.

In some embodiments, the effector domain of the fusion protein can be a reverse transcriptase for prime editing. Prime editing of a target sequence enables the incorporation of a nucleotide change including a single-nucleotide change (e.g., any transition or any transversion), an insertion of one or more nucleotides, or a deletion of one or more nucleotides. A Cas12b fused with a reverse transcriptase is guided to a specific DNA sequence by a modified guide RNA, named a pegRNA. The pegRNA is altered (relative to a standard guide RNA) to comprise an extended portion that provides a DNA synthesis template sequence which encodes a single strand DNA flap, which is homologous to a strand of the targeted endogenous DNA sequence to be edited, but which contains the desired one or more nucleotide changes and which, following synthesis by the reverse transcriptase, becomes incorporated into the target DNA molecule. Prime editing is disclosed in, for example, PCT Publication WO/2020/191248, the entire contents of which is hereby incorporated by reference.

In embodiments wherein the effector domain is a reverse transcriptase, the Cas12b polypeptide can be modified as discussed herein such that its endonuclease activity is eliminated. For example, the Cas12b polypeptide can be modified by mutating the RuvC-like domain such that the polypeptide no longer possesses nuclease activity. In some embodiments, the Cas12b polypeptide has nickase activity.

In some embodiments, the fusion protein further comprises at least one additional domain. Non-limiting examples of suitable additional domains include nuclear localization signals, cell-penetrating or translocation domains, and marker domains.

When the effector domain of the fusion protein is a cleavage domain, a dimer comprising at least one fusion protein can form. The dimer can be a homodimer or a heterodimer. In some embodiments, the heterodimer comprises two different fusion proteins. In other embodiments, the heterodimer comprises one fusion protein and an additional protein.

The dimer can be a homodimer in which the two fusion protein monomers are identical with respect to the primary amino acid sequence. In one embodiment where the dimer is a homodimer, the Cas12b polypeptide can be modified such that the endonuclease activity is eliminated. In certain embodiments wherein the Cas12b polypeptide is modified such that endonuclease activity is eliminated, each fusion protein monomer can comprise an identical Cas12b polypeptide and an identical cleavage domain. The cleavage domain can be any cleavage domain, such as any of the exemplary cleavage domains provided herein. In such embodiments, specific guide RNAs would direct the fusion protein monomers to different but closely adjacent sites such that, upon dimer formation, the nuclease domains of the two monomers would create a double stranded break in the target DNA.

The dimer can also be a heterodimer of two different fusion proteins. For example, the Cas12b polypeptide of each fusion protein can be derived from a different Cas12b polypeptide or from an orthologous Cas12b polypeptide. For example, each fusion protein can comprise a Cas12b polypeptide derived from a different source. In these embodiments, each fusion protein would recognize a different target site (i.e., specified by the protospacer and/or PAM sequence). For example, the guide RNAs could position the heterodimer to different but closely adjacent sites such that their nuclease domains produce an effective double stranded break in the target DNA.

Alternatively, two fusion proteins of a heterodimer can have different effector domains. In embodiments in which the effector domain is a cleavage domain, each fusion protein can contain a different modified cleavage domain. In these embodiments, the Cas12b polypeptide(s) can be modified such that their endonuclease activities are eliminated. The two fusion proteins forming a heterodimer can differ in both the Cas12b polypeptide domain and the effector domain.

In any of the above-described embodiments, the homodimer or heterodimer can comprise at least one additional domain chosen from nuclear localization signals (NLSs), plastid signal peptides, mitochondrial signal peptides, signal peptides capable of trafficking proteins to multiple subcellular locations, cell-penetrating, translocation domains and marker domains, as detailed above. In any of the above-described embodiments, one or both of the Cas12b polypeptides can be modified such that endonuclease activity of the polypeptide is eliminated or modified.

The heterodimer can also comprise one fusion protein and an additional protein. For example, the additional protein can be a nuclease. In one embodiment, the nuclease is a zinc finger nuclease. A zinc finger nuclease comprises a zinc finger DNA binding domain and a cleavage domain. A zinc finger recognizes and binds three (3) nucleotides. A zinc finger DNA binding domain can comprise from about three zinc fingers to about seven zinc fingers. The zinc finger DNA binding domain can be derived from a naturally occurring protein or it can be engineered. See, for example, Beerli et al. (2002) *Nat. Biotechnol.* 20:135-141; Pabo et al. (2001) *Ann. Rev. Biochem.* 70:313-340; Isalan et al. (2001) *Nat. Biotechnol.* 19:656-660; Segal et al. (2001) *Curr. Opin. Biotechnol.* 12:632-637; Choo et al. (2000) *Curr. Opin. Struct. Biol.* 10:411-416; Zhang et al. (2000) *J. Biol. Chem.* 275(43):33850-33860; Doyon et al. (2008) *Nat. Biotechnol.* 26:702-708; and Santiago et al. (2008) *Proc. Natl. Acad. Sci. USA* 105:5809-5814. The cleavage domain of the zinc finger nuclease can be any cleavage domain detailed herein. In some embodiments, the zinc finger nuclease can comprise at least one additional domain chosen from nuclear localization signals, plastid signal peptides, mitochondrial signal peptides, signal peptides capable of trafficking proteins to multiple subcellular locations, cell-penetrating or translocation domains, which are detailed herein.

In certain embodiments, any of the fusion proteins detailed above or a dimer comprising at least one fusion protein may be part of a protein-RNA complex comprising at least one guide RNA. A guide RNA interacts with the Cas12b polypeptide of the fusion protein to direct the fusion protein to a specific target site, wherein the 5' end of the guide RNA base pairs with a specific protospacer sequence.

Nucleic Acids Encoding Cas12b Polypeptides or Fusion Proteins

Nucleic acids encoding any of the Cas12b polypeptides or fusion proteins described herein are provided. The nucleic acid can be RNA or DNA. Examples of polynucleotides that encode Cas12b polypeptides are set forth in SEQ ID NOs: 1-4. In one embodiment, the nucleic acid encoding the Cas12b polypeptide or fusion protein is mRNA. The mRNA can be 5' capped and/or 3' polyadenylated. In another embodiment, the nucleic acid encoding the Cas12b polypeptide or fusion protein is DNA. The DNA can be present in a vector.

Nucleic acids encoding the Cas12b polypeptide or fusion proteins can be codon optimized for efficient translation into protein in the plant cell of interest. Programs for codon optimization are available in the art (e.g., OPTIMIZER at genomes.urv.es/OPTIMIZER; OptimumGene™ from GenScript at genscript.com/codon_opt.html).

In certain embodiments, DNA encoding the Cas12b polypeptide or fusion protein can be operably linked to at least one promoter sequence. The DNA coding sequence can be operably linked to a promoter control sequence for expression in a host cell of interest. In some embodiments, the host cell is a plant cell. "Operably linked" is intended to mean a functional linkage between two or more elements. For example, an operable linkage between a promoter and a coding region of interest (e.g., region coding for a Cas12b polypeptide or guide RNA) is a functional link that allows for expression of the coding region of interest. Operably linked elements may be contiguous or non-contiguous. When used to refer to the joining of two protein coding regions, by operably linked is intended that the coding regions are in the same reading frame.

The promoter sequence can be constitutive, regulated, growth stage-specific, or tissue-specific. It is recognized that different applications can be enhanced by the use of different promoters in the nucleic acid molecules to modulate the timing, location and/or level of expression of the Cas12b polypeptide and/or guide RNA. Such nucleic acid molecules may also contain, if desired, a promoter regulatory region (e.g., one conferring inducible, constitutive, environmentally- or developmentally-regulated, or cell- or tissue-specific/selective expression), a transcription initiation start site, a ribosome binding site, an RNA processing signal, a transcription termination site, and/or a polyadenylation signal.

In some embodiments, the nucleic acid molecules provided herein can be combined with constitutive, tissue-preferred, developmentally-preferred or other promoters for expression in plants. Examples of constitutive promoters functional in plant cells include the cauliflower mosaic virus (CaMV) 35S transcription initiation region, the 1'- or 2'-promoter derived from T-DNA of *Agrobacterium tumefaciens*, the ubiquitin 1 promoter, the Smas promoter, the cinnamyl alcohol dehydrogenase promoter (U.S. Pat. No. 5,683,439), the Nos promoter, the pEmu promoter, the rubisco promoter, the GRP1-8 promoter and other transcription initiation regions from various plant genes known to those of skill. If low level expression is desired, weak promoter(s) may be used. Weak constitutive promoters include, for example, the core promoter of the Rsyn7 promoter (WO 99/43838 and U.S. Pat. No. 6,072,050), the core 35S CaMV promoter, and the like. Other constitutive promoters include, for example, U.S. Pat. Nos. 5,608,149; 5,608,144; 5,604,121; 5,569,597; 5,466,785; 5,399,680; 5,268,463; and 5,608,142. See also, U.S. Pat. No. 6,177,611, herein incorporated by reference.

Examples of inducible promoters are the Adh1 promoter which is inducible by hypoxia or cold stress, the Hsp70 promoter which is inducible by heat stress, the PPDK promoter and the pepcarboxylase promoter which are both inducible by light. Also useful are promoters which are chemically inducible, such as the In2-2 promoter which is safener induced (U.S. Pat. No. 5,364,780), the ERE promoter which is estrogen induced, and the Axigl promoter which is auxin induced and tapetum specific but also active in callus (PCT US01/22169).

Examples of promoters under developmental control in plants include promoters that initiate transcription preferentially in certain tissues, such as leaves, roots, fruit, seeds, or flowers. A "tissue specific" promoter is a promoter that initiates transcription only in certain tissues. Unlike constitutive expression of genes, tissue-specific expression is the result of several interacting levels of gene regulation. As such, promoters from homologous or closely related plant species can be preferable to use to achieve efficient and reliable expression of transgenes in particular tissues. In some embodiments, the expression comprises a tissue-preferred promoter. A "tissue preferred" promoter is a promoter that initiates transcription preferentially, but not necessarily entirely or solely in certain tissues.

In some embodiments, the nucleic acid molecules encoding a Cas12b polypeptide and/or guide RNA comprise a cell type specific promoter. A "cell type specific" promoter is a promoter that primarily drives expression in certain cell types in one or more organs. Some examples of plant cells in which cell type specific promoters functional in plants may be primarily active include, for example, BETL cells, vascular cells in roots, leaves, stalk cells, and stem cells. The nucleic acid molecules can also include cell type preferred promoters. A "cell type preferred" promoter is a promoter that primarily drives expression mostly, but not necessarily entirely or solely in certain cell types in one or more organs. Some examples of plant cells in which cell type preferred promoters functional in plants may be preferentially active include, for example, BETL cells, vascular cells in roots, leaves, stalk cells, and stem cells. The nucleic acid molecules described herein can also comprise seed-preferred promoters. In some embodiments, the seed-preferred promoters have expression in embryo sac, early embryo, early endosperm, aleurone, and/or basal endosperm transfer cell layer (BETL).

Examples of seed-preferred promoters include, but are not limited to, 27 kD gamma zein promoter and waxy promoter, Boronat, A. et al. (1986) *Plant Sci.* 47:95-102; Reina, M. et al. *Nucl. Acids Res.* 18(21):6426; and Kloesgen, R. B. et al. (1986) *Mol. Gen. Genet.* 203:237-244. Promoters that express in the embryo, pericarp, and endosperm are disclosed in U.S. Pat. No. 6,225,529 and PCT publication WO 00/12733. The disclosures for each of these are incorporated herein by reference in their entirety.

Promoters that can drive gene expression in a plant seed-preferred manner with expression in the embryo sac, early embryo, early endosperm, aleurone and/or basal endosperm transfer cell layer (BETL) can be used in the compositions and methods disclosed herein. Such promoters include, but are not limited to, promoters that are naturally linked to *Zea mays* early endosperm 5 gene, *Zea mays* early endosperm 1 gene, *Zea mays* early endosperm 2 gene, GRMZM2G124663, GRMZM2G006585, GRMZM2G120008, GRMZM2G157806, GRMZM2G176390, GRMZM2G472234, GRMZM2G138727, *Zea mays* CLAVATA1, *Zea may-sMRP1*, *Oryza sativa* PR602, *Oryza sativa* PR9a, *Zea mays* BET1, *Zea mays* BETL-2, *Zea mays* BETL-3, *Zea mays* BETL-4, *Zea mays* BETL-9, *Zea mays* BETL-10, *Zea mays* MEG1, *Zea mays* TCCR1, *Zea mays* ASP1, *Oryza sativa* ASP1, *Triticum durum* PR60, *Triticum durum* PR91, *Triticum durum* GL7, AT3G10590, AT4G18870, AT4G21080, AT5G23650, AT3G05860, AT5G42910, AT2G26320, AT3G03260, AT5G26630, AtIPT4, AtIPT8, AtLEC2, LFAH12. Additional such promoters are described in U.S. Pat. Nos. 7,803,990, 8,049,000, 7,745,697, 7,119,251, 7,964,770, 7,847,160, 7,700,836, U.S. Patent Application Publication Nos. 20100313301, 20090049571, 20090089897, 20100281569, 20100281570, 20120066795, 20040003427; PCT Publication Nos. WO/1999/050427, WO/2010/129999, WO/2009/094704, WO/2010/019996 and WO/2010/147825, each of which is herein incorporated by reference in its entirety for all purposes. Functional variants or functional fragments of the promoters described herein can also be operably linked to the nucleic acids disclosed herein.

Chemical-regulated promoters can be used to modulate the expression of a gene through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421-10425 and McNellis et al. (1998) *Plant* 14(2):247-257) and tetracycline-inducible and tetracycline-repressible promoters (see, for example, Gatz et al. (1991) *Mol. Gen. Genet.* 227:229-237, and U.S. Pat. Nos. 5,814,618 and 5,789,156), herein incorporated by reference.

Tissue-preferred promoters can be utilized to target enhanced expression of an expression construct within a particular tissue. In certain embodiments, the tissue-preferred promoters may be active in plant tissue. Tissue-preferred promoters are known in the art. See, for example, Yamamoto et al. (1997) *Plant* 12(2):255-265; Kawamata et al. (1997) *Plant Cell Physiol.* 38(7):792-803; Hansen et al. (1997) *Mol. Gen Genet.* 254(3):337-343; Russell et al. (1997) *Transgenic Res.* 6(2): 157-168; Rinehart et al. (1996) *Plant Physiol.* 112(3): 1331-1341; Van Camp et al. (1996) *Plant Physiol.* 112(2):525-535; Canevascini et al. (1996) *Plant Physiol.* 112(2):513-524; Yamamoto et al. (1994) *Plant Cell Physiol.* 35(5):773-778; Lam (1994) *Results Probl. Cell Differ.* 20:181-196; Orozco et al. (1993) *Plant Mol Biol.* 23(6):1129-1138; Matsuoka et al. (1993) *Proc Natl. Acad. Sci. USA* 90(20):9586-9590; and Guevara-Garcia et al. (1993) *Plant J.* 4(3):495-505. Such promoters can be modified, if necessary, for weak expression.

Leaf-preferred promoters are known in the art. See, for example, Yamamoto et al. (1997) *Plant J.* 12(2):255-265; Kwon et al. (1994) *Plant Physiol.* 105:357-67; Yamamoto et al. (1994) *Plant Cell Physiol.* 35(5):773-778; Gotor et al. (1993) *Plant J.* 3:509-18; Orozco et al. (1993) *Plant Mol. Biol.* 23(6):1129-1138; and Matsuoka et al. (1993) *Proc. Natl. Acad. Sci. USA* 90(20):9586-9590. In addition, the promoters of cab and rubisco can also be used. See, for example, Simpson et al. (1958) *EMBO J* 4:2723-2729 and Timko et al. (1988) *Nature* 318:57-58.

Root-preferred promoters are known and can be selected from the many available from the literature or isolated de novo from various compatible species. See, for example, Hire et al. (1992) *Plant Mol. Biol.* 20(2):207-218 (soybean root-specific glutamine synthetase gene); Keller and Baumgartner (1991) *Plant Cell* 3(10):1051-1061 (root-specific control element in the GRP 1.8 gene of French bean); Sanger et al. (1990) *Plant Mol. Biol.* 14(3):433-443 (root-specific promoter of the mannopine synthase (MAS) gene of *Agrobacterium tumefaciens*); and Miao et al. (1991) *Plant Cell* 3(1):11-22 (full-length cDNA clone encoding cytosolic glutamine synthetase (GS), which is expressed in roots and root nodules of soybean). See also Bogusz et al. (1990) *Plant Cell* 2(7):633-641, where two root-specific promoters isolated from hemoglobin genes from the nitrogen-fixing nonlegume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-specific promoter activity was preserved. Leach and Aoyagi (1991) describe their analysis of the promoters of the highly expressed roIC and roID root-inducing genes of *Agrobacterium rhizogenes* (see Plant Science (Limerick) 79(1):69-76). They concluded that enhancer and tissue-preferred DNA determinants are dissociated in those promoters. Teen et al. (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see *EMBO J.* 8(2): 343-350). The TRY gene, fused to nptII (neomycin phosphotransferase II) showed similar characteristics. Additional root-preferred promoters include the VfENOD-GRP3 gene promoter (Kuster et al. (1995) *Plant Mol. Biol.* 29(4):759-772); and roM promoter (Capana et al. (1994) *Plant Mol. Biol.* 25(4):681-691. See also U.S. Pat. Nos. 5,837,876; 5,750,386; 5,633,363; 5,459,252; 5,401,836; 5,110,732; and 5,023,179. The phaseolin gene (Murai et al. (1983) *Science* 23:476-482 and Sengopta-Gopalen et al. (1988) *PNAS* 82:3320-3324. The promoter sequence can be wild type or it can be modified for more efficient or efficacious expression.

The nucleic acid sequences encoding the Cas12b polypeptide or fusion protein can be operably linked to a promoter sequence that is recognized by a phage RNA polymerase for in vitro mRNA synthesis. In such embodiments, the in vitro-transcribed RNA can be purified for use in the methods of genome modification described herein. For example, the promoter sequence can be a T7, T3, or SP6 promoter sequence or a variation of a T7, T3, or SP6 promoter sequence. In some embodiments, the sequence encoding the Cas12b polypeptide or fusion protein can be operably linked to a promoter sequence for in vitro expression of the Cas12b polypeptide or fusion protein in plant cells. In such embodiments, the expressed protein can be purified for use in the methods of genome modification described herein.

In certain embodiments, the DNA encoding the Cas12b polypeptide or fusion protein also can be linked to a polyadenylation signal (e.g., SV40 polyA signal and other signals functional in the cells of interest) and/or at least one transcriptional termination sequence. Additionally, the sequence encoding the Cas12b polypeptide or fusion protein also can be linked to a sequence encoding at least one nuclear localization signal, at least one plastid signal peptide, at least one mitochondrial signal peptide, at least one signal peptide capable of trafficking proteins to multiple subcellular locations, at least one cell-penetrating domain, and/or at least one marker domain, described elsewhere herein. The DNA encoding the Cas12b polypeptide or fusion protein can be present in a vector. Suitable vectors include plasmid vectors, phagemids, cosmids, artificial/mini-chromosomes, transposons, and viral vectors (e.g., lentiviral vectors, adeno-associated viral vectors, etc.). In one embodiment, the DNA encoding the Cas12b polypeptide or fusion protein is present in a plasmid vector. Non-limiting examples of suitable plasmid vectors include pUC, pBR322, pET, pBluescript, pCAMBIA, and variants thereof. The vector can comprise additional expression control sequences (e.g., enhancer sequences, Kozak sequences, polyadenylation sequences, transcriptional termination sequences, etc.), selectable marker sequences (e.g., antibiotic resistance genes), origins of replication, and the like. Additional information can be found in "Current Protocols in Molecular Biology" Ausubel et al., John Wiley & Sons, New York, 2003 or "Molecular Cloning: A Laboratory Manual" Sambrook & Russell, Cold Spring Harbor Press, Cold Spring Harbor, N.Y., 3rd edition, 2001. In some embodiments, the vector comprising the sequence encoding the Cas12b polypeptide or fusion protein is selected from SEQ ID NOs: 27-46.

In some embodiments, the expression vector comprising the sequence encoding the Cas12b polypeptide or fusion protein can further comprise a sequence encoding a guide RNA. The sequence encoding the guide RNA can be operably linked to at least one transcriptional control sequence for expression of the guide RNA in the plant or plant cell of interest. For example, DNA encoding the guide RNA can be operably linked to a promoter sequence that is recognized by RNA polymerase III (Pol III). Examples of suitable Pol III promoters include, but are not limited to, mammalian U6, U3, H1, and 7SL RNA promoters and rice U6 and U3 promoters.

Methods for Modifying a Nucleotide Sequence in a Genome

Methods are provided herein for modifying a nucleotide sequence of a genome. Non-limiting examples of genomes include cellular, nuclear, organellar, and plasmid genomes. The methods comprise introducing into a genome host (e.g., a cell or organelle) one or more DNA-targeting polynucleotides such as a DNA-targeting RNA ("guide RNA," "gRNA," "CRISPR RNA," or "crRNA") or a DNA polynucleotide encoding a DNA-targeting RNA, wherein the DNA-targeting polynucleotide comprises: (a) a first segment comprising a nucleotide sequence that is complementary to a sequence in the target DNA; and (b) a second segment that interacts with a Cas12b polypeptide and also introducing to the genome host a Cas12b polypeptide, or a polynucleotide encoding a Cas12b polypeptide, wherein the a Cas12b polypeptide comprises: (a) a polynucleotide-binding portion that interacts with the gRNA or other DNA-targeting polynucleotide; and (b) an activity portion that exhibits site-directed enzymatic activity. The genome host can then be cultured under conditions in which the Cas12b polypeptide is expressed and cleaves the nucleotide sequence that is targeted by the gRNA. Finally, a genome host comprising the modified nucleotide sequence can be selected.

The methods disclosed herein comprise introducing into a genome host at least one Cas12b polypeptide or a nucleic acid encoding at least one Cas12b polypeptide, as described herein. In some embodiments, the Cas12b polypeptide can be introduced into the genome host as an isolated protein. In such embodiments, the Cas12b polypeptide can further comprise at least one cell-penetrating domain, which facilitates cellular uptake of the protein. In some embodiments, the Cas12b polypeptide can be introduced into the genome host as a nucleoprotein in complex with a guide polynucleotide (for instance, as a ribonucleoprotein in complex with a guide RNA). In other embodiments, the Cas12b polypeptide can be introduced into the genome host as an mRNA molecule that encodes the Cas12b polypeptide. In still other embodiments, the Cas12b polypeptide can be introduced into the genome host as a DNA molecule comprising an open reading frame that encodes the Cas12b polypeptide. In general, DNA sequences encoding the Cas12b polypeptide or fusion protein described herein are operably linked to a promoter sequence that will function in the genome host. The DNA sequence can be linear, or the DNA sequence can be part of a vector. In still other embodiments, the Cas12b polypeptide or fusion protein can be introduced into the genome host as an RNA-protein complex comprising the guide RNA or a fusion protein and the guide RNA.

In certain embodiments, mRNA encoding the Cas12b polypeptide may be targeted to an organelle (e.g., plastid or mitochondria). In certain embodiments, mRNA encoding one or more guide RNAs may be targeted to an organelle (e.g., plastid or mitochondria). In certain embodiments, mRNA encoding the Cas12b polypeptide and one or more guide RNAs may be targeted to an organelle (e.g., plastid or mitochondria). Methods for targeting mRNA to organelles are known in the art (see, e.g., U.S. Patent Application 2011/0296551; U.S. Patent Application No. 2011/0321187; Gomez and Pallas (2010) PLoS One 5:e12269), and are incorporated herein by reference.

In certain embodiments, DNA encoding the Cas12b polypeptide can further comprise a sequence encoding a guide RNA. In general, each of the sequences encoding the Cas12b polypeptide and the guide RNA is operably linked to one or more appropriate promoter control sequences that allow expression of the Cas12b polypeptide and the guide RNA, respectively, in the genome host. The DNA sequence encoding the Cas12b polypeptide and the guide RNA can further comprise additional expression control, regulatory, and/or processing sequence(s). The DNA sequence encoding the Cas12b polypeptide and the guide RNA can be linear or can be part of a vector.

Methods described herein further can also comprise introducing into a genome host at least one guide RNA or DNA encoding at least one polynucleotide such as a guide RNA. A guide RNA interacts with the Cas12b polypeptide to direct the Cas12b polypeptide to a specific target site, at which site the guide RNA base pairs with a specific DNA sequence in the targeted site. Guide RNAs can comprise three regions: a first region that is complementary to the target site in the targeted DNA sequence, a second region that forms a stem loop structure, and a third region that remains essentially single-stranded. The first region of each guide RNA is different such that each guide RNA guides a Cas12b polypeptide to a specific target site. The second and third regions of each guide RNA can be the same in all guide RNAs.

One region of the guide RNA is complementary to a sequence (i.e., protospacer sequence) at the target site in the targeted DNA such that the first region of the guide RNA can base pair with the target site. In various embodiments, the first region of the guide RNA can comprise from about 8 nucleotides to more than about 30 nucleotides. For example, the region of base pairing between the first region of the guide RNA and the target site in the nucleotide sequence can be about 8, about 9, about 10, about 11, about 12, about 13, about 14, about 15, about 16, about 17, about 18, about 19, about 20, about 22, about 23, about 24, about 25, about 27, about 30 or more than 30 nucleotides in length. In an exemplary embodiment, the first region of the guide RNA is about 23, 24, or 25 nucleotides in length. The guide RNA also can comprise a second region that forms a secondary structure. In some embodiments, the secondary structure comprises a stem or hairpin. The length of the stem can vary. For example, the stem can range from about 5, to about 6, to about 10, to about 15, to about 20, to about 25 base pairs in length. The stem can comprise one or more bulges of 1 to about 10 nucleotides. The overall length of the second region can range from about 14 to about 25 nucleotides in length. In certain embodiments, the loop is about 3, 4, or 5 nucleotides in length and the stem comprises about 5, 6, 7, 8, 9, or 10 base pairs.

The guide RNA can also comprise a third region that remains essentially single-stranded. Thus, the third region has no complementarity to any nucleotide sequence in the cell of interest and has no complementarity to the rest of the guide RNA. The length of the third region can vary. In general, the third region is more than about 4 nucleotides in length. For example, the length of the third region can range from about 5 to about 60 nucleotides in length. The combined length of the second and third regions (also called the universal or scaffold region) of the guide RNA can range from about 30 to about 120 nucleotides in length. In one aspect, the combined length of the second and third regions of the guide RNA range from about 40 to about 45 nucleotides in length.

In some embodiments, the guide RNA comprises a single molecule comprising all three regions. In other embodiments, the guide RNA can comprise two separate molecules. The first RNA molecule can comprise the first region of the guide RNA and one half of the "stem" of the second region of the guide RNA. The second RNA molecule can comprise the other half of the "stem" of the second region of the guide RNA and the third region of the guide RNA. Thus, in this embodiment, the first and second RNA molecules each contain a sequence of nucleotides that are complementary to one another. For example, in one embodiment, the first and second RNA molecules each comprise a sequence (of about 6 to about 25 nucleotides) that base pairs to the other sequence to form a functional guide RNA.

In certain embodiments, the guide RNA can be introduced into the genome host as an RNA molecule. The RNA molecule can be transcribed in vitro. Alternatively, the RNA molecule can be chemically synthesized. In other embodiments, the guide RNA can be introduced into the genome host as a DNA molecule. In such cases, the DNA encoding the guide RNA can be operably linked to one or more promoter sequences for expression of the guide RNA in the genome host. For example, the RNA coding sequence can be operably linked to a promoter sequence that is recognized by RNA polymerase III (Pol III).

The DNA molecule encoding the guide RNA can be linear or circular. In some embodiments, the DNA sequence encoding the guide RNA can be part of a vector. Suitable vectors include plasmid vectors, phagemids, cosmids, artificial/mini-chromosomes, transposons, and viral vectors. In an exemplary embodiment, the DNA encoding the guide RNA is present in a plasmid vector. Non-limiting examples of suitable plasmid vectors include pUC, pBR322, pET, pBluescript, pCAMBIA, and variants thereof. The vector can comprise additional expression control sequences (e.g., enhancer sequences, Kozak sequences, polyadenylation sequences, transcriptional termination sequences, etc.), selectable marker sequences (e.g., antibiotic resistance genes), origins of replication, and the like. In some embodiments, the vector comprising sequence encoding the guide RNA is selected from SEQ ID NOs: 47-55.

In embodiments in which both the Cas12b polypeptide and the guide RNA are introduced into the genome host as DNA molecules, each can be part of a separate molecule (e.g., one vector containing Cas12b polypeptide or fusion protein coding sequence and a second vector containing guide RNA coding sequence) or both can be part of the same molecule (e.g., one vector containing coding (and regulatory) sequence for both the Cas12b polypeptide or fusion protein and the guide RNA).

Cas12b proteins are RNA guided nucleases. Its cleavage relies on a tracr RNA to recruit a guide RNA comprising a guide sequence and a direct repeat, where the guide sequence hybridizes with the target nucleotide sequence to form a DNA/RNA heteroduplex. A Cas12b polypeptide in conjunction with a guide RNA is directed to a target site in a genome host, wherein the Cas12b polypeptide introduces a double-stranded break in the targeted DNA. The target site has no sequence limitation except that the sequence is immediately preceded (upstream) by a consensus sequence. This consensus sequence is also known as a protospacer adjacent motif (PAM). It is well-known in the art that a suitable PAM sequence must be located at the correct location relative to the targeted DNA sequence to allow the Cas12b nuclease to produce the desired double-stranded break. Cas12b PAM sequences are T-rich sequences. In some embodiments, the PAM sequence is 5' VTTV 3', wherein V is A, C, or G. In a particular embodiment, the PAM sequence is 5' ATTV 3' or 5' GTTG 3'. As detailed herein, the first region of the guide RNA is complementary to the protospacer of the target sequence. Typically, the first region of the guide RNA is about 19 to 21 nucleotides in length.

The target site can be in the coding region of a gene, in an intron of a gene, in a control region of a gene, in a non-coding region between genes, etc. The gene can be a protein coding gene or an RNA coding gene. The gene can be any gene of interest as described herein.

In some embodiments, the methods disclosed herein further comprise introducing at least one donor polynucleotide into a genome host. A donor polynucleotide comprises at least one donor sequence. In some aspects, a donor sequence of the donor polynucleotide corresponds to an endogenous or native sequence found in the targeted DNA. For example, the donor sequence can be essentially identical to a portion of the DNA sequence at or near the targeted site, but which comprises at least one nucleotide change. Thus, the donor sequence can comprise a modified version of the wild type sequence at the targeted site such that, upon integration or exchange with the native sequence, the sequence at the targeted location comprises at least one nucleotide change. For example, the change can be an insertion of one or more nucleotides, a deletion of one or more nucleotides, a substitution of one or more nucleotides, or combinations thereof. As a consequence of the integration of the modified sequence, the genome host can produce a modified gene product from the targeted chromosomal sequence.

The donor sequence of the donor polynucleotide can alternatively correspond to an exogenous sequence. As used herein, an "exogenous" sequence refers to a sequence that is not native to the genome host, or a sequence whose native location in the genome host is in a different location. For example, the exogenous sequence can comprise a protein coding sequence, which can be operably linked to an exogenous promoter control sequence such that, upon integration into the genome, the genome host is able to express the protein coded by the integrated sequence. For example, the donor sequence can be any gene of interest, such as those encoding agronomically important traits as described elsewhere herein. Alternatively, the exogenous sequence can be integrated into the targeted DNA sequence such that its expression is regulated by an endogenous promoter control sequence. In other iterations, the exogenous sequence can be a transcriptional control sequence, another expression control sequence, or an RNA coding sequence. Integration of an exogenous sequence into a targeted DNA sequence is termed a "knock in." The donor sequence can vary in length from several nucleotides to hundreds of nucleotides to hundreds of thousands of nucleotides.

In some embodiments, the donor sequence in the donor polynucleotide is flanked by an upstream sequence and a downstream sequence, which have substantial sequence identity to sequences located upstream and downstream, respectively, of the targeted site. Because of these sequence similarities, the upstream and downstream sequences of the donor polynucleotide permit homologous recombination between the donor polynucleotide and the targeted sequence such that the donor sequence can be integrated into (or exchanged with) the targeted DNA sequence.

The upstream sequence, as used herein, refers to a nucleic acid sequence that shares substantial sequence identity with a DNA sequence upstream of the targeted site. Similarly, the downstream sequence refers to a nucleic acid sequence that shares substantial sequence identity with a DNA sequence downstream of the targeted site. As used herein, the phrase "substantial sequence identity" refers to sequences having at least about 75% sequence identity. Thus, the upstream and downstream sequences in the donor polynucleotide can have about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity with sequence upstream or downstream to the targeted site. In an exemplary embodiment, the upstream and downstream sequences in the donor polynucleotide can have about 95% or 100% sequence identity with nucleotide sequences upstream or downstream to the targeted site. In one embodiment, the upstream sequence shares substantial sequence identity with a nucleotide sequence located immediately upstream of the targeted site (i.e., adjacent to the targeted site). In other embodiments, the upstream sequence shares substantial sequence identity with a nucleotide sequence that is located within about one hundred (100) nucleotides upstream from the targeted site. Thus, for example, the upstream sequence can share substantial sequence identity with a nucleotide sequence that is located about 1 to about 20, about 21 to about 40, about 41 to about 60, about 61 to about 80, or about 81 to about 100 nucleotides upstream from the targeted site. In one embodiment, the downstream sequence shares substantial sequence identity with a nucleotide sequence located immediately downstream of the targeted site (i.e., adjacent to the targeted site). In other embodiments, the downstream sequence shares substantial sequence identity with a nucleotide sequence that is located within about one hundred (100) nucleotides downstream from the targeted site. Thus, for example, the downstream sequence can share substantial sequence identity with a nucleotide sequence that is located about 1 to about 20, about 21 to about 40, about 41 to about 60, about 61 to about 80, or about 81 to about 100 nucleotides downstream from the targeted site.

Each upstream or downstream sequence can range in length from about 20 nucleotides to about 5000 nucleotides. In some embodiments, upstream and downstream sequences can comprise about 50, 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2800, 3000, 3200, 3400, 3600, 3800, 4000, 4200, 4400, 4600, 4800, or 5000 nucleotides. In exemplary embodiments, upstream and downstream sequences can range in length from about 50 to about 1500 nucleotides.

Donor polynucleotides comprising the upstream and downstream sequences with sequence similarity to the targeted nucleotide sequence can be linear or circular. In embodiments in which the donor polynucleotide is circular, it can be part of a vector. For example, the vector can be a plasmid vector.

In certain embodiments, the donor polynucleotide can additionally comprise at least one targeted cleavage site that is recognized by the Cas12b polypeptide. The targeted cleavage site added to the donor polynucleotide can be placed upstream or downstream or both upstream and downstream of the donor sequence. For example, the donor sequence can be flanked by targeted cleavage sites such that, upon cleavage by the Cas12b polypeptide, the donor sequence is flanked by overhangs that are compatible with those in the nucleotide sequence generated upon cleavage by the Cas12b polypeptide. Accordingly, the donor sequence can be ligated with the cleaved nucleotide sequence during repair of the double stranded break by a non-homologous repair process. Generally, donor polynucleotides comprising the targeted cleavage site(s) will be circular (e.g., can be part of a plasmid vector).

The donor polynucleotide can be a linear molecule comprising a short donor sequence with optional short overhangs that are compatible with the overhangs generated by the Cas12b polypeptide. In such embodiments, the donor sequence can be ligated directly with the cleaved chromosomal sequence during repair of the double-stranded break. In some instances, the donor sequence can be less than about 1,000, less than about 500, less than about 250, or less than about 100 nucleotides. In certain cases, the donor polynucleotide can be a linear molecule comprising a short donor sequence with blunt ends. In other iterations, the donor polynucleotide can be a linear molecule comprising a short donor sequence with 5' and/or 3' overhangs. The overhangs can comprise 1, 2, 3, 4, or 5 nucleotides.

In some embodiments, the donor polynucleotide will be DNA. The DNA may be single-stranded or double-stranded and/or linear or circular. The donor polynucleotide may be a DNA plasmid, a bacterial artificial chromosome (BAC), a yeast artificial chromosome (YAC), a viral vector, a linear piece of DNA, a PCR fragment, a naked nucleic acid, or a nucleic acid complexed with a delivery vehicle such as a liposome or poloxamer. In certain embodiments, the donor polynucleotide comprising the donor sequence can be part of a plasmid vector. In any of these situations, the donor polynucleotide comprising the donor sequence can further comprise at least one additional sequence.

In some embodiments, the method can comprise introducing one Cas12b polypeptide (or encoding nucleic acid) and one guide RNA (or encoding DNA) into a genome host, wherein the Cas12b polypeptide introduces one double-stranded break in the targeted DNA. In embodiments in which an optional donor polynucleotide is not present, the double-stranded break in the nucleotide sequence can be repaired by a non-homologous end-joining (NHEJ) repair process. Because NHEJ is error-prone, deletions of at least one nucleotide, insertions of at least one nucleotide, substitutions of at least one nucleotide, or combinations thereof can occur during the repair of the break. Accordingly, the targeted nucleotide sequence can be modified or inactivated. For example, a single nucleotide change (SNP) can give rise to an altered protein product, or a shift in the reading frame of a coding sequence can inactivate or "knock out" the sequence such that no protein product is made. In embodiments in which the optional donor polynucleotide is present, the donor sequence in the donor polynucleotide can be exchanged with or integrated into the nucleotide sequence at the targeted site during repair of the double-stranded break. For example, in embodiments in which the donor sequence is flanked by upstream and downstream sequences having substantial sequence identity with upstream and downstream sequences, respectively, of the targeted site in the nucleotide sequence, the donor sequence can be exchanged with or integrated into the nucleotide sequence at the targeted site during repair mediated by homology-directed repair process. Alternatively, in embodiments in which the donor sequence is flanked by compatible overhangs (or the compatible overhangs are generated in situ by the Cas12b polypeptide) the donor sequence can be ligated directly with the cleaved nucleotide sequence by a non-homologous repair process during repair of the double-stranded break. Exchange or integration of the donor sequence into the nucleotide sequence modifies the targeted nucleotide sequence or introduces an exogenous sequence into the targeted nucleotide sequence.

The methods disclosed herein can also comprise introducing one or more Cas12b polypeptides (or encoding nucleic acids) and two guide polynucleotides (or encoding DNAs) into a genome host, wherein the Cas12b polypeptides introduce two double-stranded breaks in the targeted nucleotide sequence. The two breaks can be within several base pairs, within tens of base pairs, or can be separated by many thousands of base pairs. In embodiments in which an optional donor polynucleotide is not present, the resultant double-stranded breaks can be repaired by a non-homologous repair process such that the sequence between the two cleavage sites is lost and/or deletions of at least one nucleotide, insertions of at least one nucleotide, substitutions of at least one nucleotide, or combinations thereof can occur during the repair of the break(s). In embodiments in which an optional donor polynucleotide is present, the donor sequence in the donor polynucleotide can be exchanged with or integrated into the targeted nucleotide sequence during repair of the double-stranded breaks by either a homology-based repair process (e.g., in embodiments in which the donor sequence is flanked by upstream and downstream sequences having substantial sequence identity with upstream and downstream sequences, respectively, of the targeted sites in the nucleotide sequence) or a non-homologous repair process (e.g., in embodiments in which the donor sequence is flanked by compatible overhangs).

Methods for Modifying a Nucleotide Sequence in a Plant Genome

Plant cells possess nuclear, plastid, and mitochondrial genomes. The compositions and methods of the present invention may be used to modify the sequence of the nuclear, plastid, and/or mitochondrial genome, or may be used to modulate the expression of a gene or genes encoded by the nuclear, plastid, and/or mitochondrial genome. Accordingly, by "chromosome" or "chromosomal" is intended the nuclear, plastid, or mitochondrial genomic DNA. "Genome" as it applies to plant cells encompasses not only chromosomal DNA found within the nucleus, but organelle DNA found within subcellular components (e.g., mitochondria or plastids) of the cell. Any nucleotide sequence of interest in a plant cell, organelle, or embryo can be modified using the methods described herein. In specific embodiments, the methods disclosed herein are used to modify a nucleotide sequence encoding an agronomically important trait, such as a plant hormone, plant defense protein, a nutrient transport protein, a biotic association protein, a desirable input trait, a desirable output trait, a stress resistance gene, a disease/pathogen resistance gene, a male sterility, a developmental gene, a regulatory gene, a gene involved in photosynthesis, a DNA repair gene, a transcriptional regulatory gene or any other polynucleotide and/or polypeptide of interest. Agronomically important traits such as oil, starch, and protein content can also be modified. Modifications include increasing content of oleic acid, saturated and unsaturated oils, increasing levels of lysine and sulfur, providing essential amino acids, and also modification of starch. Hordothionin protein modifications are described in U.S. Pat. Nos. 5,703,049, 5,885,801, 5,885, 802, and 5,990,389, herein incorporated by reference. Another example is lysine and/or sulfur rich seed protein encoded by the soybean 2S albumin described in U.S. Pat. No. 5,850,016, and the chymotrypsin inhibitor from barley, described in Williamson et al. (1987) *Eur. J. Biochem.* 165:99-106, the disclosures of which are herein incorporated by reference.

The Cas12b polypeptide (or encoding nucleic acid), the guide RNA(s) (or encoding DNA), and the optional donor polynucleotide(s) can be introduced into a plant cell, organelle, or plant embryo by a variety of means, including transformation. Transformation protocols as well as protocols for introducing polypeptides or polynucleotide sequences into plants may vary depending on the type of plant or plant cell, i.e., monocot or dicot, targeted for transformation. Suitable methods of introducing polypeptides and polynucleotides into plant cells include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (U.S. Pat. Nos. 5,563,055 and 5,981,840), direct gene transfer (Paszkowski et al. (1984) *EMBO* 13:2717-2722), and ballistic particle acceleration (see, for example, U.S. Pat. Nos. 4,945,050; 5,879,918; 5,886,244; and, 5,932,782; Tomes et al. (1995) in Plant Cell, Tissue, and Organ Culture: Fundamental Methods, ed. Gamborg and Phillips (Springer-Verlag, Berlin); McCabe et al. (1988) *Biotechnology* 6:923-926); and Led transformation (WO 00/28058). Also see Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); U.S. Pat. Nos. 5,240,855; 5,322,783; and, 5,324,646; Klein et al. (1988) *Plant Physiol.* 91:440-444 (maize); Fromm et al. (1990) *Biotechnology* 8:833-839 (maize); Hooykaas-Van Slogteren et al. (1984) *Nature* (London) 311:763-764; U.S. Pat. No. 5,736,369 (cereals); Bytebier et al. (1987) *Proc. Natl. Acad. Sci. USA* 84:5345-5349 (Liliaceae); De Wet et al. (1985) in The Experimental Manipulation of Ovule Tissues, ed. Chapman et al. (Longman, New York), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference. Site-specific genome editing of plant cells by biolistic introduction of a ribonucleoprotein comprising a nuclease and suitable guide RNA has been demonstrated (Svitashev et al (2016) *Nat Commun* 7:13274); these methods are herein incorporated by reference. "Stable transformation" is intended to mean that the nucleotide construct introduced into a plant integrates into the genome of the plant and is capable of being inherited by the progeny thereof. The nucleotide construct may be integrated into the nuclear, plastid, or mitochondrial genome of the plant. Methods for plastid transformation are known in the art (see, e.g., *Chloroplast Biotechnology: Methods and Protocols* (2014) Pal Maliga, ed. and U.S. Patent Application No. 2011/0321187), and methods for plant mitochondrial transformation have been described in the art (see, e.g., U.S. Patent Application No. 2011/0296551), herein incorporated by reference.

The cells that have been transformed may be grown into plants (i.e., cultured) in accordance with conventional ways. See, for example, McCormick et al. (1986) *Plant Cell Reports* 5:81-84. In this manner, the present invention provides transformed seed having a nucleic acid modification stably incorporated into their genome.

"Introduced" in the context of inserting a nucleic acid fragment (e.g., a recombinant DNA construct) into a cell, means "transfection" or "transformation" or "transduction" and includes reference to the incorporation of a nucleic acid fragment into a plant cell where the nucleic acid fragment may be incorporated into the genome of the cell (e.g., nuclear chromosome, plasmid, plastid chromosome or mitochondrial chromosome), converted into an autonomous replicon, or transiently expressed (e.g., transfected mRNA).

The present invention may be used for transformation of any plant species, including, but not limited to, monocots and dicots (i.e., monocotyledonous and dicotyledonous, respectively). Examples of plant species of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), camelina (*Camelina sativa*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), quinoa (*Chenopodium quinoa*), chicory (*Cichorium intybus*), lettuce (*Lactuca sativa*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oil palm (*Elaeis guineensis*), poplar (*Populus* spp.), eucalyptus (*Eucalyptus* spp.), oats (*Avena sativa*), barley (*Hordeum vulgare*), vegetables, ornamentals, and conifers. In some embodiments, the plant is rice (*Oryza sativa*).

The Cas12b polypeptides (or encoding nucleic acid), the guide RNA(s) (or DNAs encoding the guide RNA), and the optional donor polynucleotide(s) can be introduced into the plant cell, organelle, or plant embryo simultaneously or sequentially. The ratio of the Cas12b polypeptides (or encoding nucleic acid) to the guide RNA(s) (or encoding DNA) generally will be about stoichiometric such that the two components can form an RNA-protein complex with the target DNA. In one embodiment, DNA encoding a Cas12b polypeptide and DNA encoding a guide RNA are delivered together within the plasmid vector.

The compositions and methods disclosed herein can be used to alter expression of genes of interest in a plant, such as genes involved in grain weight. Therefore, the expression of a gene encoding a protein involved in grain weight may be modulated as compared to a control plant.

A "subject plant or plant cell" is one in which genetic alteration, such as a mutation, has been effected as to a gene of interest, or is a plant or plant cell which is descended from a plant or cell so altered and which comprises the alteration. A "control" or "control plant" or "control plant cell" provides a reference point for measuring changes in phenotype of the subject plant or plant cell. Thus, the expression levels are higher or lower than those in the control plant depending on the methods of the invention.

A control plant or plant cell may comprise, for example: (a) a wild-type plant or cell, i.e., of the same genotype as the starting material for the genetic alteration which resulted in the subject plant or cell; (b) a plant or plant cell of the same genotype as the starting material but which has been transformed with a null construct (i.e. with a construct which has no known effect on the trait of interest, such as a construct comprising a marker gene); (c) a plant or plant cell which is a non-transformed segregant among progeny of a subject plant or plant cell; (d) a plant or plant cell genetically identical to the subject plant or plant cell but which is not exposed to conditions or stimuli that would induce expression of the gene of interest; or (e) the subject plant or plant cell itself, under conditions in which the gene of interest is not expressed.

While the invention is described in terms of transformed plants, it is recognized that transformed organisms of the invention also include plant cells, plant protoplasts, plant cell tissue cultures from which plants can be regenerated, plant calli, plant clumps, and plant cells that are intact in plants or parts of plants such as embryos, pollen, ovules, flowers, glumes, panicles, leaves, stems, roots, root tips, anthers, pistils and the like. Grain is intended to mean the mature seed produced by commercial growers for purposes other than growing or reproducing the species. Progeny, variants, and mutants of the regenerated plants are also included within the scope of the invention, provided that these parts comprise the introduced polynucleotides.

Derivatives of coding sequences can be made using the methods disclosed herein to increase the level of preselected amino acids in the encoded polypeptide. For example, the gene encoding the barley high lysine polypeptide (BHL) is derived from barley chymotrypsin inhibitor, U.S. application Ser. No. 08/740,682, filed Nov. 1, 1996, and WO 98/20133, the disclosures of which are herein incorporated by reference. Other proteins include methionine-rich plant proteins such as from sunflower seed (Lilley et al. (1989) *Proceedings of the World Congress on Vegetable Protein Utilization in Human Foods and Animal Feedstuffs*, ed. Applewhite (American Oil Chemists Society, Champaign, Ill.), pp. 497-502; herein incorporated by reference); corn (Pedersen et al. (1986) *J. Biol. Chem.* 261:6279; Kirihara et al. (1988) *Gene* 71:359; both of which are herein incorporated by reference); and rice (Musumura et al. (1989) *Plant Mol. Biol.* 12:123, herein incorporated by reference). Other agronomically important genes encode latex, Floury 2, growth factors, seed storage factors, and transcription factors.

The methods disclosed herein can be used to modify herbicide resistance traits including genes coding for resistance to herbicides that act to inhibit the action of acetolactate synthase (ALS), in particular the sulfonylurea-type herbicides (e.g., the acetolactate synthase (ALS) gene containing mutations leading to such resistance, in particular the S4 and/or Hra mutations), genes coding for resistance to herbicides that act to inhibit action of glutamine synthase, such as phosphinothricin or basta (e.g., the bar gene); glyphosate (e.g., the EPSPS gene and the GAT gene; see, for example, U.S. Publication No. 20040082770 and WO 03/092360); or other such genes known in the art. The bar gene encodes resistance to the herbicide basta, the nptII gene encodes resistance to the antibiotics kanamycin and geneticin, and the ALS-gene mutants encode resistance to the herbicide chlorsulfuron. Additional herbicide resistance traits are described for example in U.S. patent application Ser. No. 2016/0208243, herein incorporated by reference.

Sterility genes can also be modified and provide an alternative to physical detasseling. Examples of genes used in such ways include male tissue-preferred genes and genes with male sterility phenotypes such as QM, described in U.S. Pat. No. 5,583,210. Other genes include kinases and those encoding compounds toxic to either male or female gametophytic development. Additional sterility traits are described for example in U.S. Patent Application 2016/0208243, herein incorporated by reference.

The quality of grain can be altered by modifying genes encoding traits such as levels and types of oils, saturated and unsaturated, quality and quantity of essential amino acids, and levels of cellulose. In corn, modified hordothionin proteins are described in U.S. Pat. Nos. 5,703,049, 5,885,801, 5,885,802, and 5,990,389.

Commercial traits can also be altered by modifying a gene or that could increase for example, starch for ethanol production, or provide expression of proteins. Another important commercial use of modified plants is the production of polymers and bioplastics such as described in U.S. Pat. No. 5,602,321. Genes such as β-Ketothiolase, PHBase (polyhydroxyburyrate synthase), and acetoacetyl-CoA reductase (see Schubert et al. (1988) *J. Bacteriol.* 170:5837-5847) facilitate expression of polyhyroxyalkanoates (PHAs).

Exogenous products include plant enzymes and products as well as those from other sources including prokaryotes and other eukaryotes. Such products include enzymes, cofactors, hormones, and the like. The level of proteins, particularly modified proteins having improved amino acid distribution to improve the nutrient value of the plant, can be increased. This is achieved by the expression of such proteins having enhanced amino acid content.

The methods disclosed herein can also be used for insertion of heterologous genes and/or modification of native plant gene expression to achieve desirable plant traits. Such traits include, for example, disease resistance, herbicide tolerance, drought tolerance, salt tolerance, insect resistance, resistance against parasitic weeds, improved plant nutritional value, improved forage digestibility, increased grain yield, cytoplasmic male sterility, altered fruit ripening, increased storage life of plants or plant parts, reduced allergen production, and increased or decreased lignin content. Genes capable of conferring these desirable traits are disclosed in U.S. Patent Application 2016/0208243, herein incorporated by reference.

Methods for Modulating Gene Expression

The methods disclosed herein further encompass modification of a nucleotide sequence or regulating expression of a nucleotide sequence in a genome host. The methods can comprise introducing into the genome host at least one fusion protein or nucleic acid encoding at least one fusion protein, wherein the fusion protein comprises a Cas12b polypeptide or a fragment or variant thereof and an effector domain, and (b) at least one guide RNA or DNA encoding the guide RNA, wherein the guide RNA guides the Cas12b polypeptide of the fusion protein to a target site in the targeted DNA and the effector domain of the fusion protein modifies the chromosomal sequence or regulates expression of one or more genes in near the targeted DNA sequence.

Fusion proteins comprising a Cas12b polypeptide or a fragment or variant thereof and an effector domain are described herein. In general, the fusion proteins disclosed herein can further comprise at least one nuclear localization signal, plastid signal peptide, mitochondrial signal peptide, or signal peptide capable of trafficking proteins to multiple subcellular locations. Nucleic acids encoding fusion proteins are described herein. In some embodiments, the fusion protein can be introduced into the genome host as an isolated protein (which can further comprise a cell-penetrating domain). Furthermore, the isolated fusion protein can be part of a protein-RNA complex comprising the guide RNA. In other embodiments, the fusion protein can be introduced into the genome host as a RNA molecule (which can be capped and/or polyadenylated). In still other embodiments, the fusion protein can be introduced into the genome host as a DNA molecule. For example, the fusion protein and the guide RNA can be introduced into the genome host as discrete DNA molecules or as part of the same DNA molecule. Such DNA molecules can be plasmid vectors.

In some embodiments, the method further comprises introducing into the genome host at least one donor polynucleotide as described elsewhere herein. Means for introducing molecules into genome hosts such as cells, as well as means for culturing cells (including cells comprising organelles) are described herein.

In certain embodiments in which the effector domain of the fusion protein is a cleavage domain, the method can comprise introducing into the genome host one fusion protein (or nucleic acid encoding one fusion protein) and two guide RNAs (or DNA encoding two guide RNAs). The two guide RNAs direct the fusion protein to two different target sites in the chromosomal sequence, wherein the fusion protein dimerizes (e.g., forms a homodimer) such that the two cleavage domains can introduce a double stranded break into the targeted DNA sequence. In embodiments in which the optional donor polynucleotide is not present, the double-stranded break in the targeted DNA sequence can be repaired by a non-homologous end-joining (NHEJ) repair process. Because NHEJ is error-prone, deletions of at least one nucleotide, insertions of at least one nucleotide, substitutions of at least one nucleotide, or combinations thereof can occur during the repair of the break. Accordingly, the targeted chromosomal sequence can be modified or inactivated. For example, a single nucleotide change (SNP) can give rise to an altered protein product, or a shift in the reading frame of a coding sequence can inactivate or "knock out" the sequence such that no protein product is made. In embodiments in which the optional donor polynucleotide is present, the donor sequence in the donor polynucleotide can be exchanged with or integrated into the targeted DNA sequence at the targeted site during repair of the double-stranded break. For example, in embodiments in which the donor sequence is flanked by upstream and downstream sequences having substantial sequence identity with upstream and downstream sequences, respectively, of the targeted site in the targeted DNA sequence, the donor sequence can be exchanged with or integrated into the targeted DNA sequence at the targeted site during repair mediated by homology-directed repair process. Alternatively, in embodiments in which the donor sequence is flanked by compatible overhangs (or the compatible overhangs are generated in situ by the Cas12b polypeptide) the donor sequence can be ligated directly with the cleaved targeted DNA sequence by a non-homologous repair process during repair of the double-stranded break. Exchange or integration of the donor sequence into the targeted DNA sequence modifies the targeted DNA sequence or introduces an exogenous sequence into the targeted DNA sequence.

In other embodiments in which the effector domain of the fusion protein is a cleavage domain, the method can comprise introducing into the genome host two different fusion proteins (or nucleic acid encoding two different fusion proteins) and two guide RNAs (or DNA encoding two guide RNAs). The fusion proteins can differ as detailed elsewhere herein. Each guide RNA directs a fusion protein to a specific target site in the targeted DNA sequence, wherein the fusion proteins can dimerize (e.g., form a heterodimer) such that the two cleavage domains can introduce a double stranded break into the targeted DNA sequence. In embodiments in which the optional donor polynucleotide is not present, the resultant double-stranded breaks can be repaired by a non-homologous repair process such that deletions of at least one nucleotide, insertions of at least one nucleotide, substitutions of at least one nucleotide, or combinations thereof can occur during the repair of the break. In embodiments in which the optional donor polynucleotide is present, the donor sequence in the donor polynucleotide can be exchanged with or integrated into the chromosomal sequence during repair of the double-stranded break by either a homology-based repair process (e.g., in embodiments in which the donor sequence is flanked by upstream and downstream sequences having substantial sequence identity with upstream and downstream sequences, respectively, of the targeted sites in the chromosomal sequence) or a non-homologous repair process (e.g., in embodiments in which the donor sequence is flanked by compatible overhangs).

In certain embodiments in which the effector domain of the fusion protein is a transcriptional activation domain or a transcriptional repressor domain, the method can comprise introducing into the genome host one fusion protein (or nucleic acid encoding one fusion protein) and one guide RNA (or DNA encoding one guide RNA). The guide RNA directs the fusion protein to a specific targeted DNA sequence, wherein the transcriptional activation domain or a transcriptional repressor domain activates or represses expression, respectively, of a gene or genes located near the targeted DNA sequence. That is, transcription may be affected for genes in close proximity to the targeted DNA sequence or may be affected for genes located at further distance from the targeted DNA sequence. It is well-known in the art that gene transcription can be regulated by distantly located sequences that may be located thousands of bases away from the transcription start site or even on a separate chromosome (Harmston and Lenhard (2013) *Nucleic Acids Res* 41:7185-7199).

In alternate embodiments in which the effector domain of the fusion protein is an epigenetic modification domain, the method can comprise introducing into the genome host one fusion protein (or nucleic acid encoding one fusion protein) and one guide RNA (or DNA encoding one guide RNA). The guide RNA directs the fusion protein to a specific targeted DNA sequence, wherein the epigenetic modification domain modifies the structure of the targeted DNA sequence. Epigenetic modifications include acetylation, methylation of histone proteins and/or nucleotide methylation. In some instances, structural modification of the chromosomal sequence leads to changes in expression of the chromosomal sequence.

Plants Comprising a Genetic Modification

Provided herein are plants, plant cells, plant organelles, and plant embryos comprising at least one nucleotide sequence that has been modified using a Cas12b polypeptide-mediated or fusion protein-mediated process as described herein. Also provided are plants, plant cells, plant organelles, and plant embryos comprising at least one DNA or RNA molecule encoding Cas12b polypeptide or fusion protein targeted to a chromosomal sequence of interest or a fusion protein, at least one guide RNA, and optionally one or more donor polynucleotide(s). The genetically modified plants disclosed herein can be heterozygous for the modified nucleotide sequence or homozygous for the modified nucleotide sequence. Plant cells comprising one or more genetic modifications in organellar DNA may be heteroplasmic or homoplasmic.

The modified chromosomal sequence of the plants, plant cells, plant organelles, and plant embryos may be modified such that it is inactivated, has up-regulated or down-regulated expression, or produces an altered protein product, or comprises an integrated sequence. The modified chromosomal sequence may be inactivated such that the sequence is not transcribed and/or a functional protein product is not produced. Thus, a genetically modified plant comprising an inactivated chromosomal sequence may be termed a "knock out" or a "conditional knock out." The inactivated chromosomal sequence can include a deletion mutation (i.e., deletion of one or more nucleotides), an insertion mutation (i.e., insertion of one or more nucleotides), or a nonsense mutation (i.e., substitution of a single nucleotide for another nucleotide such that a stop codon is introduced). As a consequence of the mutation, the targeted chromosomal sequence is inactivated and a functional protein is not produced. The inactivated chromosomal sequence comprises no exogenously introduced sequence. Also included herein are genetically modified plants in which two, three, four, five, six, seven, eight, nine, or ten or more chromosomal sequences are inactivated.

The modified chromosomal sequence can also be altered such that it codes for a variant protein product. For example, a genetically modified plant comprising a modified chromosomal sequence can comprise a targeted point mutation(s) or other modification such that an altered protein product is produced. In one embodiment, the chromosomal sequence can be modified such that at least one nucleotide is changed and the expressed protein comprises one changed amino acid residue (missense mutation). In another embodiment, the chromosomal sequence can be modified to comprise more than one missense mutation such that more than one amino acid is changed. Additionally, the chromosomal sequence can be modified to have a three nucleotide deletion or insertion such that the expressed protein comprises a single amino acid deletion or insertion. The altered or variant protein can have altered properties or activities compared to the wild type protein, such as altered substrate specificity, altered enzyme activity, altered kinetic rates, etc.

In some embodiments, the genetically modified plant can comprise at least one chromosomally integrated nucleotide sequence. A genetically modified eukaryote comprising an integrated sequence may be termed a "knock in" or a "conditional knock in." The nucleotide sequence that is integrated sequence can, for example, encode an orthologous protein, an endogenous protein, or combinations of both. In one embodiment, a sequence encoding an orthologous protein or an endogenous protein can be integrated into a nuclear or organellar chromosomal sequence encoding a protein such that the chromosomal sequence is inactivated, but the exogenous sequence is expressed. In such a case, the sequence encoding the orthologous protein or endogenous protein may be operably linked to a promoter control sequence. Alternatively, a sequence encoding an orthologous protein or an endogenous protein may be integrated into a nuclear or organellar chromosomal sequence without affecting expression of a chromosomal sequence. The present disclosure also encompasses genetically modified plants in which two, three, four, five, six, seven, eight, nine, or ten or more sequences, including sequences encoding protein(s), are integrated into the genome. Any gene of interest as disclosed herein can be introduced integrated into the chromosomal sequence of the plant nucleus or organelle. In particular embodiments, genes that increase plant growth or yield are integrated into the chromosome. The chromosomally integrated sequence encoding a protein can encode the wild type form of a protein of interest or can encode a protein comprising at least one modification such that an altered version of the protein is produced.

In certain embodiments, the genetically modified plant can comprise at least one modified chromosomal sequence encoding a protein such that the expression pattern of the protein is altered. For example, regulatory regions controlling the expression of the protein, such as a promoter or a transcription factor binding site, can be altered such that the protein is over-expressed, or the tissue-specific or temporal expression of the protein is altered, or a combination thereof. Alternatively, the expression pattern of the protein can be altered using a conditional knockout system. A non-limiting example of a conditional knockout system includes a Cre-lox recombination system. A Cre-lox recombination system comprises a Cre recombinase enzyme, a site-specific DNA recombinase that can catalyze the recombination of a nucleic acid sequence between specific sites (lox sites) in a nucleic acid molecule. Methods of using this system to produce temporal and tissue specific expression are known in the art.

The following numbered paragraphs also form part of the present disclosure:

1. A method of modifying a nucleotide sequence at a target site in the genome of a plant cell, the method comprising: introducing into the plant cell (i) a DNA-targeting RNA, or a DNA polynucleotide encoding a DNA-targeting RNA; and (ii) a Cas12b polypeptide, or a polynucleotide encoding a Cas12b polypeptide, wherein the method modifies the nucleotide sequence at the target site.

2. The method of numbered paragraph 1, further comprising: culturing the plant cell to produce a plant under conditions in which the Cas12b polypeptide is expressed and cleaves the nucleotide sequence at the target site to produce a modified nucleotide sequence; and selecting a plant comprising said modified nucleotide sequence.

3. The method of numbered paragraph 2, wherein the cleaving of the nucleotide sequence at the target site comprises a staggered double strand break.

4. The method of any of numbered paragraphs 1-3, wherein said modified nucleotide sequence comprises insertion of heterologous DNA into the genome of the plant cell, deletion of a nucleotide sequence from the genome of the plant cell, or mutation of at least one nucleotide in the genome of the plant cell.

5. The method of any of numbered paragraphs 1-4, wherein the polynucleotide encoding the Cas12b polypeptide is selected from SEQ ID NOs: 1-4, or a sequence having at least 90% identity thereto.

6. The method of any of numbered paragraphs 1-5, wherein the Cas12b polypeptide is selected from SEQ ID NOs: 5-8, or a sequence having at least 90% identity thereto.

7. The method of any of numbered paragraphs 1-6, wherein the Cas12b polypeptide is from *Alicyclobacillus acidoterrestris*, *Bacillus thermoamylovorans*, *Alicyclobacillus acidiphilus*, or *Bacillus hisashii*.

8. The method of numbered paragraph 7, wherein the Cas12b polypeptide is from *Alicyclobacillus acidiphilus*.

9. The method of any of numbered paragraphs 1-8, wherein said plant cell is from a monocotyledonous or a dicotyledonous species.

10. The method of any of numbered paragraphs 1-9, wherein said plant cell is an *Oryza sativa* cell.

11. The method of any of numbered paragraphs 1-10, wherein said DNA-targeting RNA is a guide RNA.

12. The method of any of numbered paragraphs 1-11, wherein the DNA-targeting RNA comprises: (a) a first segment comprising a nucleotide sequence that is complementary to a sequence in the target DNA; and (b) a second segment that interacts with a Cas12b polypeptide.

13. The method of any of numbered paragraphs 1-12, wherein the expression of the Cas12b polypeptide is under the control of an inducible promoter, a constitutive promoter, a cell type-specific promoter, or a developmentally-preferred promoter.

14. The method of any of numbered paragraphs 1-13, wherein the target site is located immediately 3' of a PAM site in the genome of the plant cell.

15. The method of numbered paragraph 14, wherein the PAM site comprises VTTV.

16. The method of any of numbered paragraphs 1-15, wherein the polynucleotide sequence encoding the Cas12b polypeptide is codon-optimized for expression in a plant cell.

17. The method of any of numbered paragraphs 1-16, wherein polynucleotide encoding the Cas12b polypeptide is present in a vector.

18. The method of numbered paragraph 17, wherein the vector is a polynucleotide sequence selected from SEQ ID NOs: 27-30.

19. The method of any of numbered paragraphs 1-18, wherein the Cas12b polypeptide comprises: (a) an RNA-binding portion that interacts with the DNA-targeting RNA; and (b) an activity portion that exhibits site-directed enzymatic activity.

20. The method of any of numbered paragraphs 1-19, wherein the Cas12b polypeptide is fused to a deaminase domain.

21. The method of numbered paragraph 20, wherein the modified nucleotide sequence comprises a base edit at the target site.

22. The method of any of numbered paragraphs 1-21, wherein the Cas12b polypeptide is fused to a reverse transcriptase.

23. The method of any of numbered paragraphs 20-22, wherein the Cas12b polypeptide comprises one or more mutations that reduce or eliminate the nuclease activity of the Cas12b polypeptide.

24. The method of any of numbered paragraphs 20-23, wherein the Cas12b polypeptide has nickase activity.

25. The method of any of numbered paragraphs 20-24, wherein the polynucleotide encoding the Cas12b polypeptide is selected from SEQ ID NOs: 9-17, or a sequence having at least 90% identity thereto.

26. The method of any of numbered paragraphs 20-25, wherein the Cas12b polypeptide is selected from SEQ ID NOs: 18-26, or a sequence having at least 90% identity thereto.

27. The method of any of numbered paragraphs 20-26, wherein the Cas12b polypeptide comprises one or more mutations in a position corresponding to amino acid positions D570, E848, or D977 in *Alicyclobacillus acidiphilus* Cas12b that reduce or eliminate the nuclease activity.

28. A method of modulating the expression of a target gene in a plant cell, the method comprising: introducing into the plant cell (i) a DNA-targeting RNA, or a DNA polynucleotide encoding a DNA-targeting RNA; and (ii) a mutated Cas12b polypeptide, or a polynucleotide encoding a mutated Cas12b polypeptide, wherein the mutated Cas12b polypeptide comprises one or more mutations that reduce or eliminate the nuclease activity of the Cas12b polypeptide, wherein the method modulates the expression of the target gene.

29. The method of numbered paragraph 28, wherein the target gene is upregulated or downregulated.

30. The method of numbered paragraphs 28 or 29, wherein the polynucleotide encoding the mutated Cas12b polypeptide is selected from SEQ ID NOs: 9-17, or a sequence having at least 90% identity thereto.

31. The method of any of numbered paragraphs 28-30, wherein the mutated Cas polypeptide is selected from SEQ ID NOs: 18-26, or a sequence having at least 90% identity thereto.

32. The method of any of numbered paragraphs 28-31, wherein the mutated Cas polypeptide comprises one or more mutations in a position corresponding to amino acid positions D570, E848, or D977 in *Alicyclobacillus acidiphilus* Cas12b that reduce or eliminate the nuclease activity.

33. The method of any of numbered paragraphs 28-32, wherein the mutated Cas12b polypeptide is fused to a transcriptional activation domain or a transcriptional repression domain.

34. The method of any of numbered paragraphs 28-33, wherein said plant cell is from a monocotyledonous or a dicotyledonous species.

35. The method of any of numbered paragraphs 28-34, wherein said plant cell is an *Oryza sativa* cell.

36. The method of any of numbered paragraphs 28-35, wherein said DNA-targeting RNA is a guide RNA.

37. The method of any of numbered paragraphs 28-36, wherein the expression of the Cas12b polypeptide is under the control of an inducible promoter, a constitutive promoter, a cell type-specific promoter, or a developmentally-preferred promoter.

38. The method of any of numbered paragraphs 28-37, wherein the polynucleotide sequence encoding the Cas12b polypeptide is codon-optimized for expression in a plant cell.

39. The method of any of numbered paragraphs 28-38, wherein polynucleotide encoding the mutated Cas12b polypeptide is present in a vector.

40. The method of numbered paragraph 39, wherein the vector is a polynucleotide sequence selected from SEQ ID NOs: 31-46.

41. A plant cell produced by the method of any of numbered paragraphs 1-40.

42. A plant comprising the plant cell of numbered paragraph 41.

43. A nucleic acid molecule comprising a polynucleotide sequence encoding a Cas12b polypeptide, wherein the polynucleotide sequence has at least 90% identity with a sequence selected from SEQ ID NOs: 1-4 and 9-17.

44. A nucleic acid molecule comprising a polynucleotide sequence encoding an Cas12b polypeptide operably linked to a heterologous promoter that is operable in a plant cell, wherein the Cas12b polypeptide has at least 90% identity with SEQ ID NO: 7, and wherein the Cas12b polypeptide provides increased editing efficiency in a plant cell relative to AacCas12b, BthCas12b, and BhCas12b.

45. A nucleic acid molecule comprising a polynucleotide sequence encoding a Cas12b polypeptide, wherein the Cas12b polypeptide has at least 90% identity with a sequence selected from SEQ ID NOs: 5-8 and 18-26, and wherein the polynucleotide comprises at least one base change so as not to be a naturally occurring sequence.

46. The nucleic acid molecule of any of numbered paragraphs 43-45, wherein the nucleic acid molecule is a vector.

47. The nucleic acid molecule of numbered paragraph 46, wherein the vector is a polynucleotide sequence selected from SEQ ID NOs: 27-46.

48. A plant or a plant cell comprising the nucleic acid molecule of any of numbered paragraphs 43-47.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

The following examples are offered by way of illustration and not by way of limitation.

EXAMPLES

Example 1: Characterization of Cas12b

Figure 2:
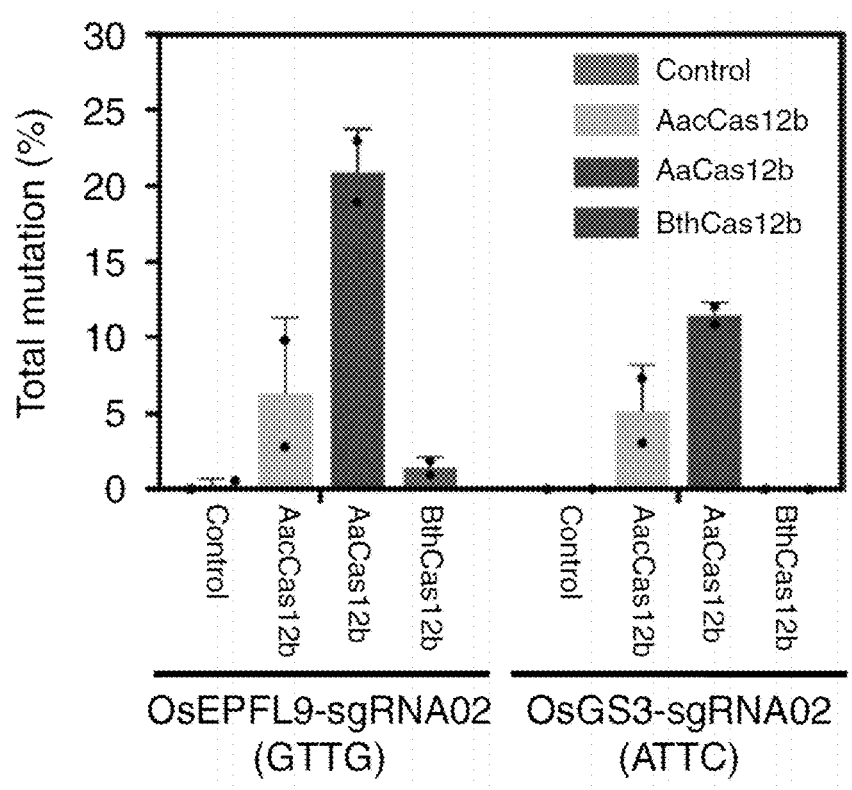
FIG. 2 shows a comparison of mutation frequencies by AacCas12b, AaCas12b and BthCas12b at two target sites. Data were generated from high-throughput sequencing. Error bars represent standard deviations of two or three biological replicates.
Figure 3A:
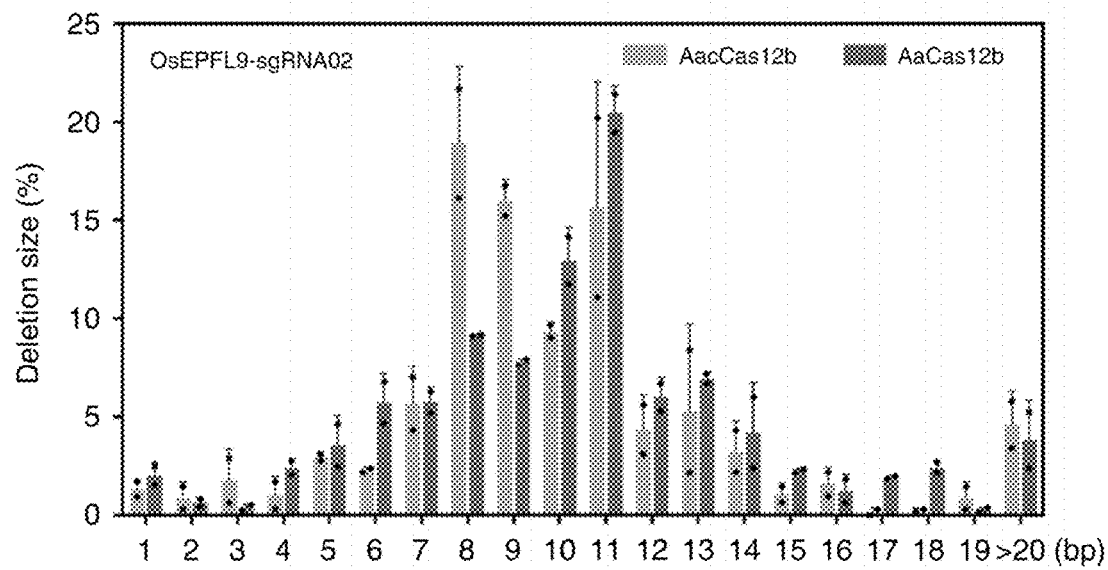
FIG. 3A and FIG. 3B show a comparison of deletion sizes by AacCas12b and AaCas12b at the OsEPFL9-sgRNA02 site and the OsGS3-sgRNA02 site. Data were generated from high-throughput sequencing. Error bars represent standard deviations of two or three biological replicates.
Figure 3B:
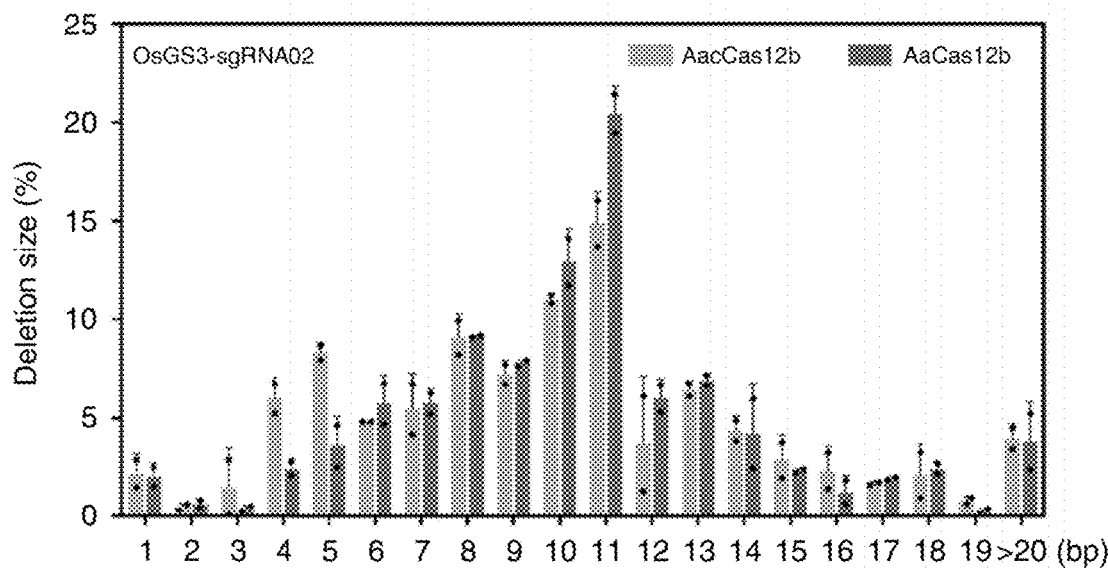
Figure 3C:
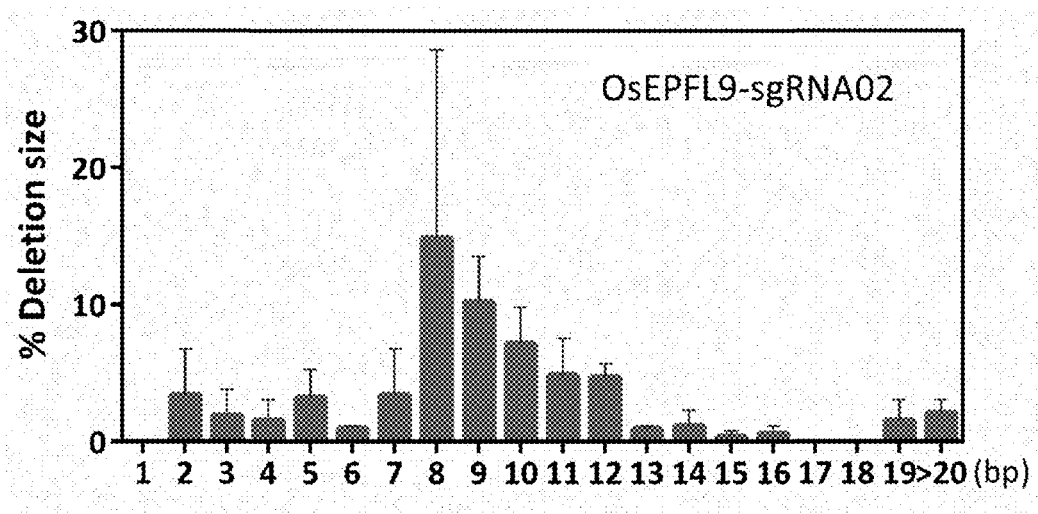
FIG. 3C shows deletion sizes at OsEPFL9-sgRNA02 by BthCas12b. Error bars represent standard deviations of two biological replicates.
Figure 4A:
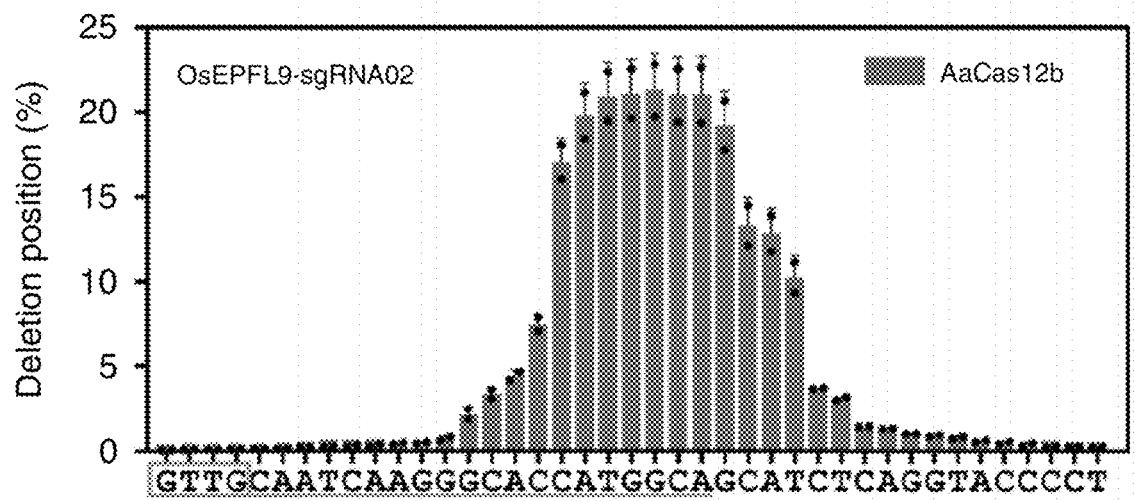
FIG. 4A and FIG. 4B show a comparison of deletion position by AaCas12b at the OsEPFL9-sgRNA02 site and OsGS3-sgRNA02 site (SEQ ID NOs: 56-57). PAM and protospacer sequences are circled and underlined, respectively. Data were generated from high-throughput sequencing. Error bars represent standard deviations of two or three biological replicates.
Figure 4B:
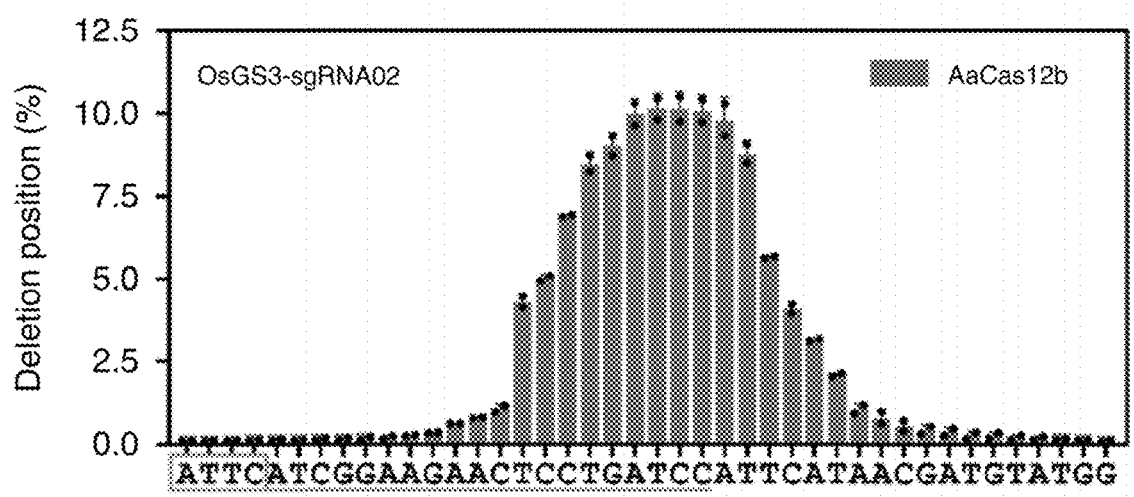
Figure 4C:
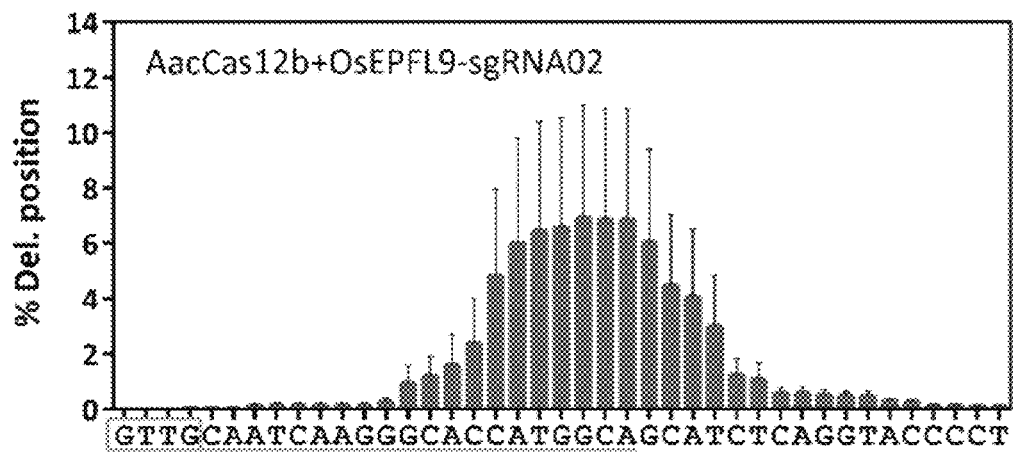
FIG. 4C and FIG. 4D show deletion position at OsEPFL9-sgRNA02 and OsGS3-sgRNA02 sites by AacCas12b (SEQ ID NOs: 56-57). Error bars represent standard deviations of two biological replicates.
Figure 4D:
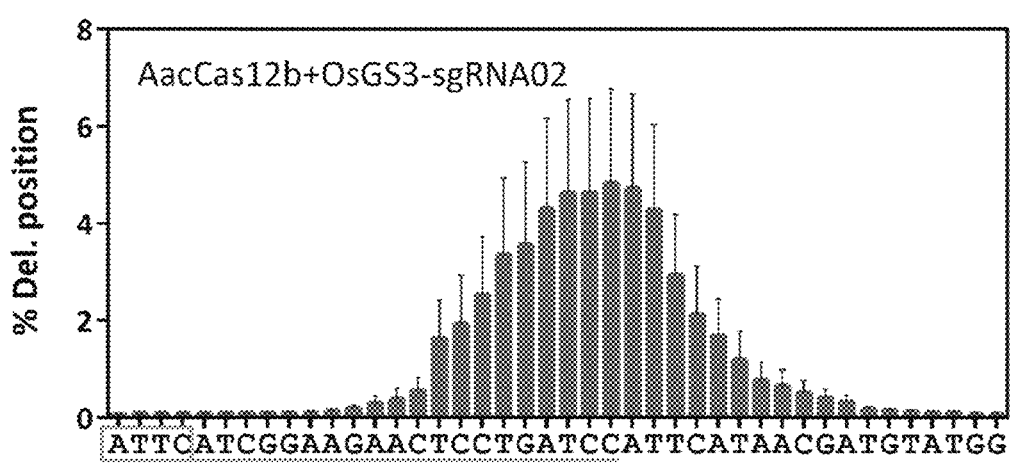
Figure 4E:
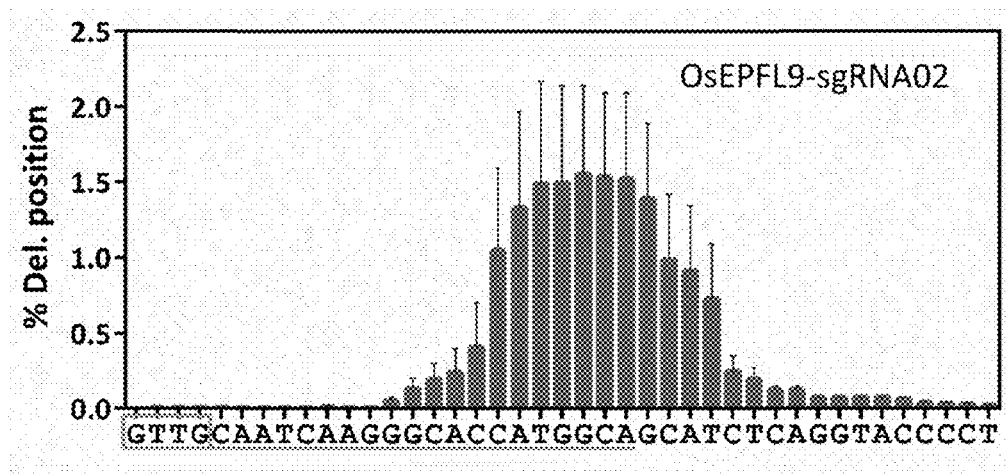
FIG. 4E shows deletion position at OsEPFL9-sgRNA02 by BthCas12b (SEQ ID NO: 56). Error bars represent standard deviations of two biological replicates.
Figure 5A:
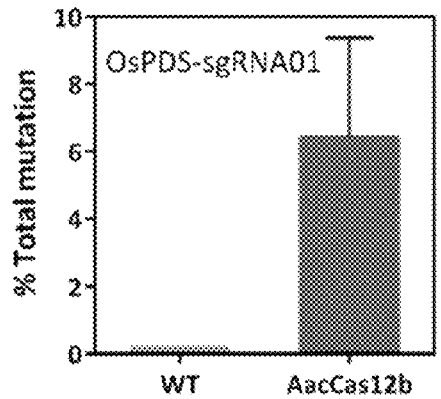
FIG. 5A and FIG. 5B show mutation frequency and deletion sizes at OsPDS-sgRNA01 by AacCas12b in rice protoplasts. Error bars represent standard deviations of two biological replicates.
Figure 5B:
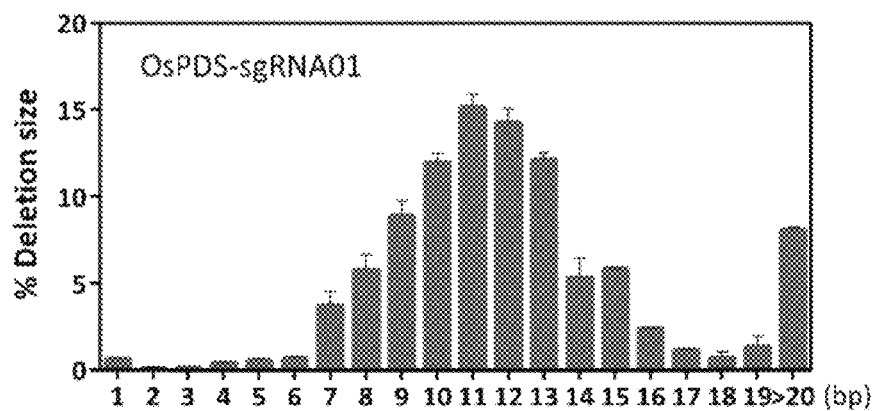

Structures for DNA targeting complexes of AacCas12b and BthCas12b have been recently resolved. We decided to test AacCas12b, AaCas12b and BthCas12b for their capability in plant genome editing. Since AaCas12b shares high sequence identity to AacCas12b, the AacCas12b sgRNA scaffold was used for both AacCas12b and AaCas12b. Similarly, a BthCas12b sgRNA scaffold was used for BthCas12b. These Cas12b DNA coding sequences were codon-optimized for rice, a major crop and test platform in this study. We adopted the dual Polymerase II (Pol II) promoter expression system and HH-HDV (hammerhead virus-hepatitis delta virus) dual ribozyme guide RNA processing system that we established for CRISPR-Cas12a (FIG. 1). Previous in vitro assays established PAMs as TTN (N=A, T, G, C) for AacCas12b and ATTN for BthCas12b. We targeted two sites in OsEPFL9 and OsGS3 with GTTG and ATTC PAMs, respectively. To quantify the editing efficiencies of Cas12b nucleases, expression vectors were transfected into rice protoplasts. AacCas12b resulted in editing efficiency over 10% at both sites, higher than AacCas12b (~5%) (FIG. 2). BthCas12b displayed very low editing efficiency (FIG. 2). AaCas12b, AacCas12b and BthCas12b mainly generated 4-14 bp deletions (FIG. 3A-3C), which are larger than those induced by Cas9 (1-3 bp). These deletions occurred about 12-24 nucleotides distal to the PAM sites (FIG. 4A-4E), consistent with the staggered DSBs generated in this region. Targeting an additional site in OsPDS with AacCas12b further confirmed this editing pattern (FIG. 5A, 5B).

Figure 6:
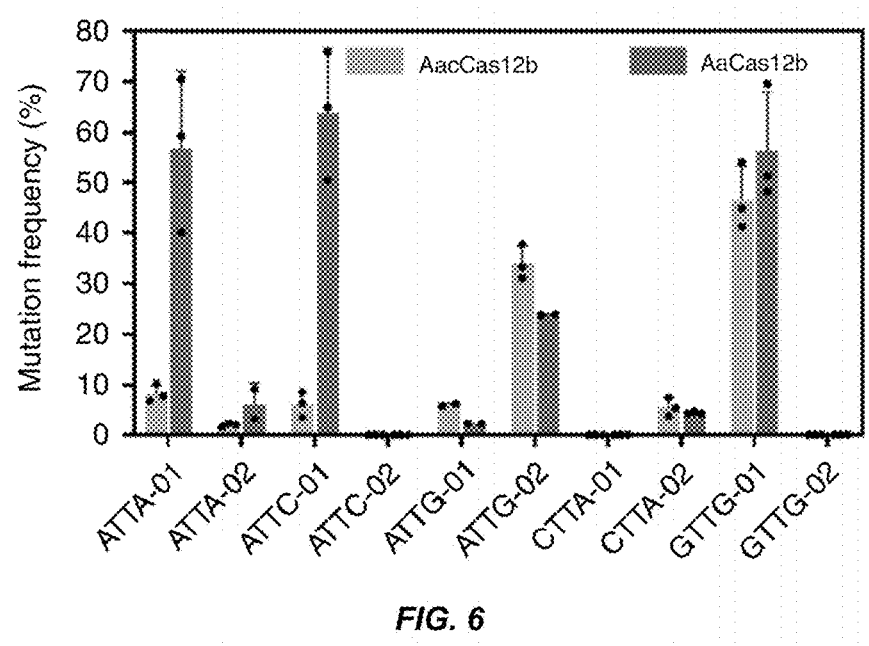
FIG. 6 shows a comparison of mutation frequencies by AacCas12b and AaCas12b at 10 sites with ATTV, CTTA and GTTG PAMs. Data were generated from high-throughput sequencing. Error bars represent standard deviations of two or three biological replicates.
Figure 7A:
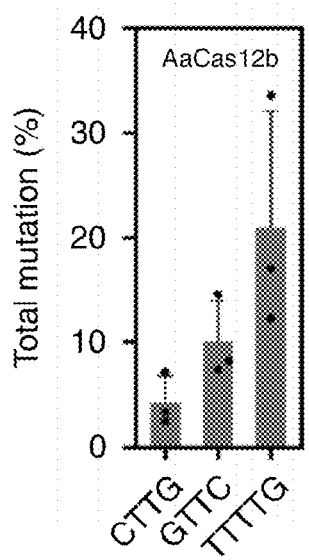
FIG. 7A shows targeted mutagenesis by AaCas12b at additional three PAM sites. Data were generated from high-throughput sequencing. Error bars represent standard deviations of two or three biological replicates.
Figure 7B:
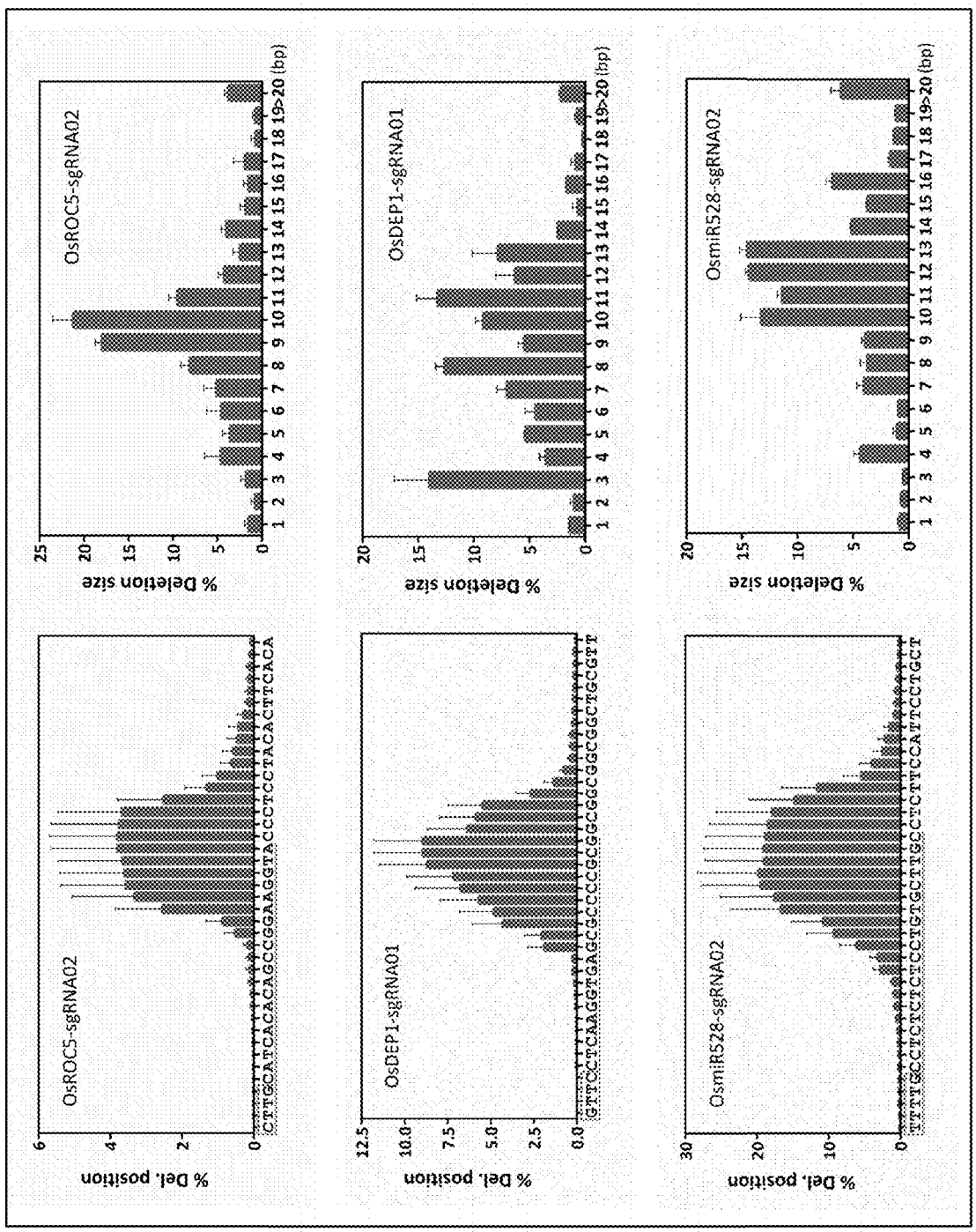
FIG. 7B shows deletion sizes and position at OsROC5-sgRNA02, OsDEP1-sgRNA01 and OsmiR528-sgRNA02 sites by AaCas12b in rice protoplasts (SEQ ID NOs: 90-92). Error bars represent standard deviations of two biological replicates.

To further investigate the PAM requirements for AacCas12b and AaCas12b in planta, we targeted a series of VTTV (V=A, C, G) PAM sites and assessed editing activity in rice protoplasts. While both AacCas12b and AaCas12b showed editing activity at five out of six ATTV sites, AaCas12b is generally more efficient and it resulted in over 50% mutation frequencies at ATTA-01 and ATTC-01 sites (FIG. 6). Among two additional GTTG PAM sites, both AacCas12b and AaCas12b resulted in high editing efficiency (50%-60%) at one site (GTTG-01) but failed at the other site (GTTG-02) (FIG. 6). Further testing suggested AaCas12b could edit CTTG and GTTC PAM sites (FIG. 7A, 7B). However, both Cas12b variants largely failed at an additional three CTTG and two GTTC PAM sites, as well as three CTTC and two GTTA PAM sites. Unlike Cas12a, AacCas12b and AaCas12b could barely edit six VTTTV PAM sites tested. Interestingly, AaCas12b could edit a TTTTV PAM site with ~20% mutation frequency (FIG. 7A, 7B). Together, our data demonstrates AaCas12b and AacCas12b are potent SSNs for targeted mutagenesis in rice and they generally recognize VTTV PAMs, with more preference for ATTV and GTTG PAMs. Our observation is largely consistent with the observations of PAM requirements for Cas12b orthologs in human cells.

Figure 8A:
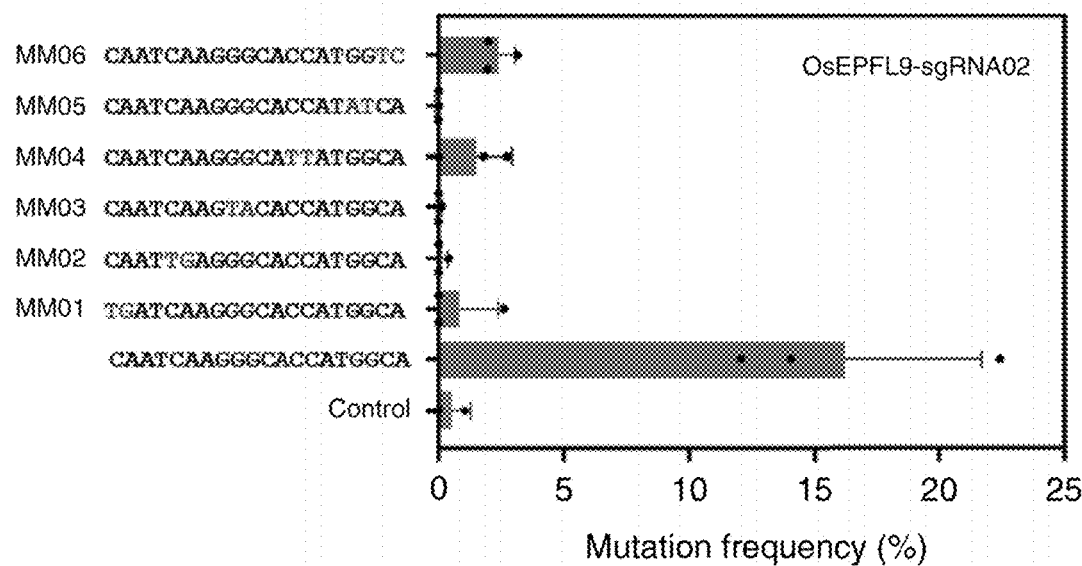
FIG. 8A and FIG. 8B show off-targeting analysis with mismatch (MM) sgRNAs at the OsEPFL9-sgRNA02 site and the Os12g24050-sgRNA01 site by AaCas12b (SEQ ID NOs: 58-71). Data were generated from RFLP analysis. Error bars represent standard deviations of two or three biological replicates.
Figure 8B:
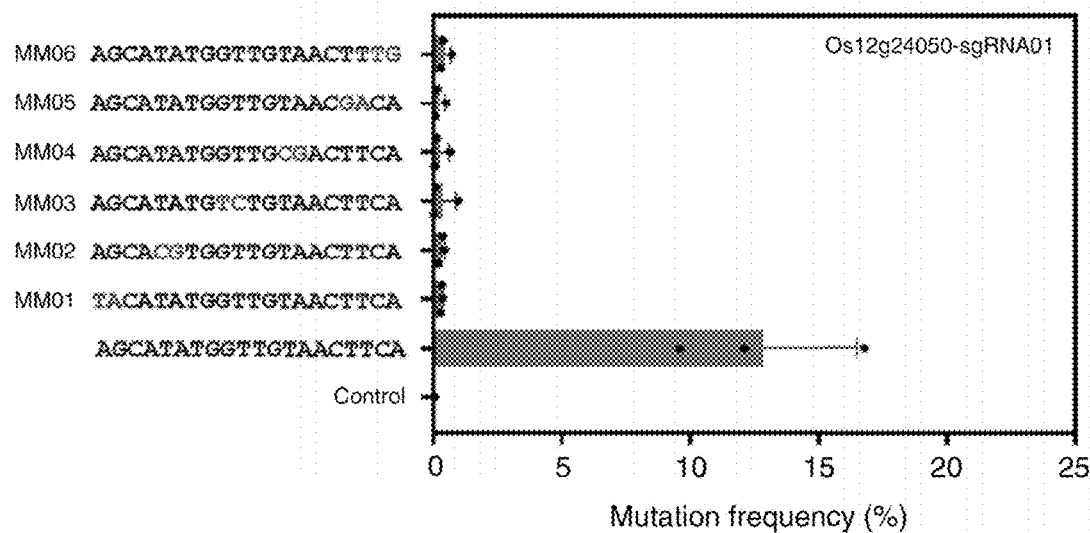
Figure 9:
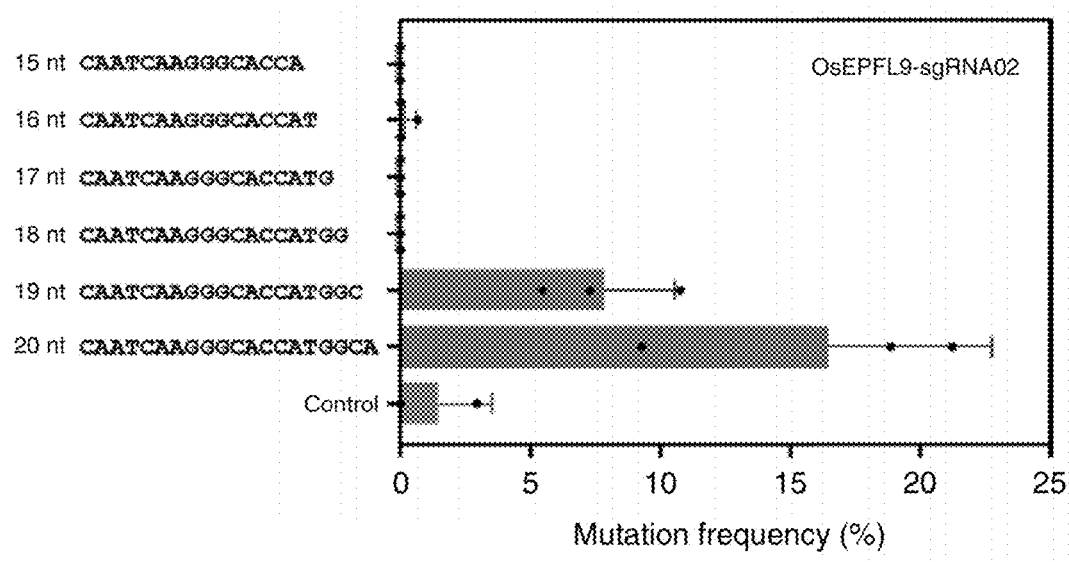
FIG. 9 shows a comparison of protospacer length for targeted mutagenesis at the OsEPFL9-sgRNA02 site by AaCas12b (SEQ ID NOs: 64 and 72-76). Data were generated from RFLP analysis. Error bars represent standard deviations of two or three biological replicates.

Initial comparison of three Cas12b orthologs suggested AaCas12b is superior to AacCas12b and BthCas12b for targeted mutagenesis in rice. We assessed targeting specificity of AaCas12b by using six crRNA protospacer sequences of OsEPFL9-sgRNA02 that carry double mismatch nucleotides (at positions 1-2, 5-6, 9-10, 13-14, 17-18 and 19-20). These six constructs were compared with the on-target control construct in rice protoplasts. The mutation frequency data suggest all these mismatch nucleotides had completely abolished editing activity at the target site (FIG. 8A). Similar results were obtained by targeting an independent site with Os12g24050-sgRNA01 (FIG. 8B), suggesting AaCas12b is a highly specific SSN in rice cells. Interestingly, a recent study in human and mouse cells suggests AaCas12b, unlike Cas9 and Cas12a, could barely tolerant single base mismatches at nearly every position of the protospacer, supporting its high specificity. We further shortened the length of the protospacer of OsEPFL9-sgRNA02 and found AaCas12b completely lost editing activity with protospacers of 18 nucleotides and shorter (FIG. 9). While more study is warranted, this result is in sharp contrast to Cas9 and Cas12a, which generally still possess nuclease activity with 17-18-nucleotide protospacers. Together, our data suggest AaCas12b is a highly specific SSN for plant genome editing.

Example 2: CRISPR-Cas12b Plant Genome Editing

We next sought to generate rice mutants by Cas12b. Both AacCas12b and AaCas12b constructs targeting the OsEPFL9-sgRNA02 site were transformed into rice calli by *Agrobacterium*. Analysis of 22 individual T0 transgenic lines for AacCas12b revealed eight lines carried monoallelic mutations at the target site, representing a 36.4% mutation rate (FIG. 10A). Consistent with the protoplast data, AaCas12b had a higher mutation rate of 54.2% as 13 out of 24 T0 lines were mutants and six lines carried biallelic mutations (FIG. 10B). The mutations in these edited lines were predominantly large deletions (FIG. 10A, 10B). These results demonstrated that both AacCas12b and AaCas12b can effectively generate stable mutants in rice.

Figure 11:
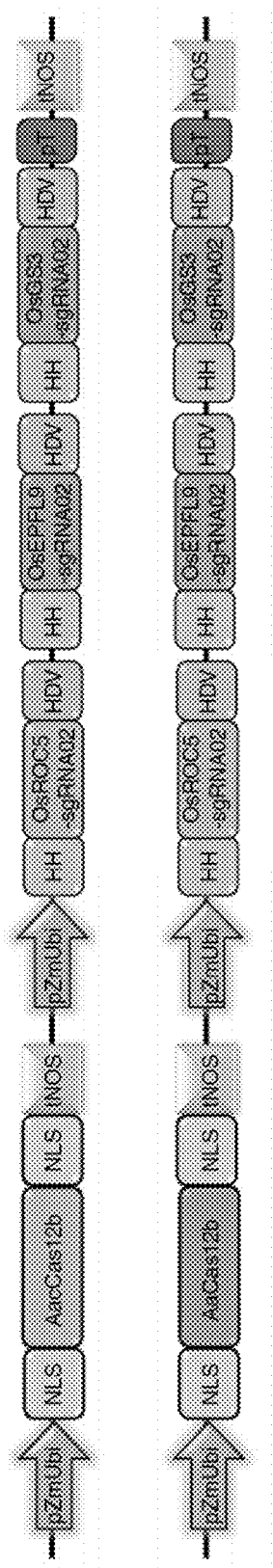
FIG. 11 is an illustration of the dual Pol II promoter based multiplexed Cas12b systems for AacCas12b and AaCas12b.
Figure 12A:
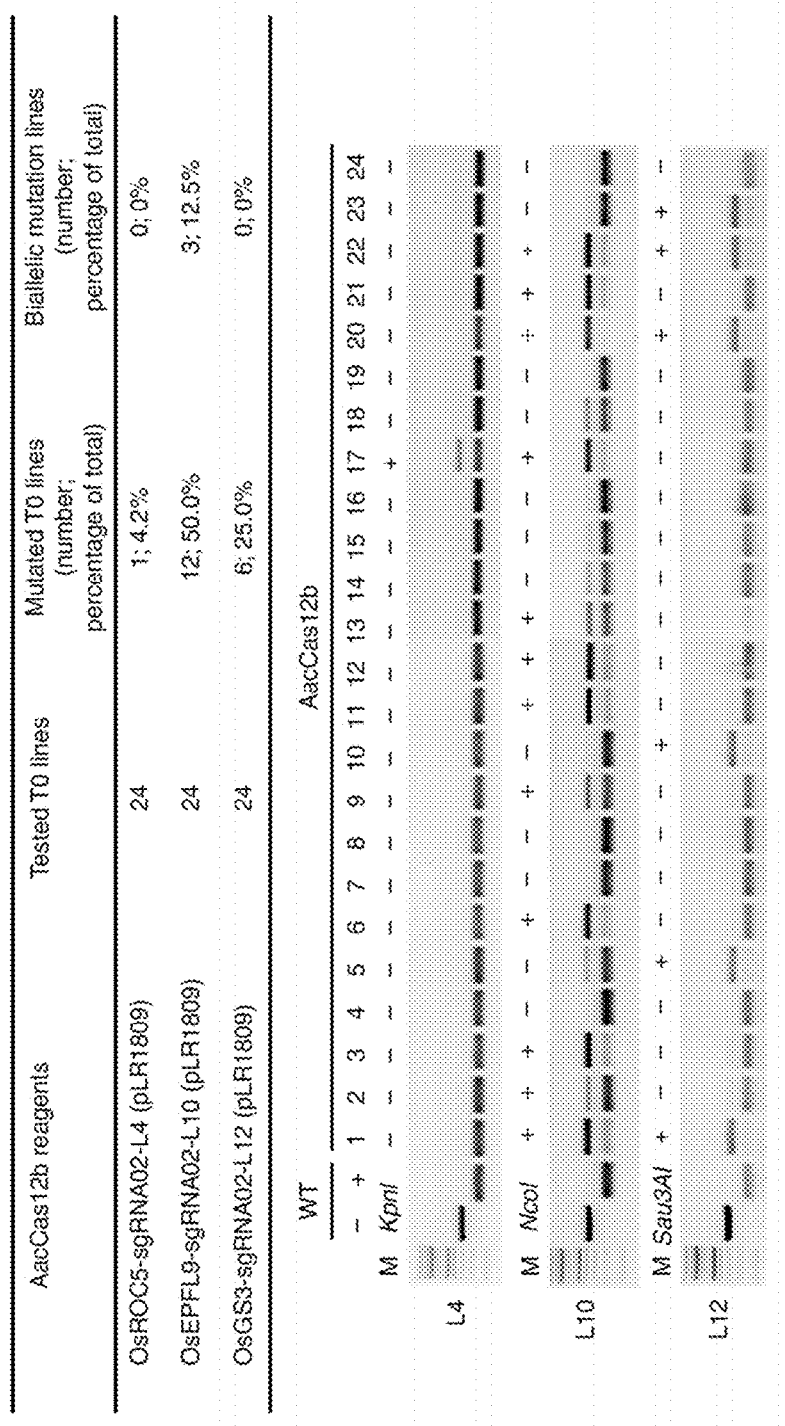

A major advantage of the CRISPR system is its flexibility of multiplexing. We constructed a multiplexed Cas12b system based on dual Pol II promoters and an HH-sgRNA-HDV array (FIG. 11). We decided to simultaneously target three rice genes with three sgRNAs: OsROC5-sgRNA02, OsEPFL9-sgRNA02 and OsGS3-sgRNA02. Two multiplexing constructs based on AacCas12b and AaCas12b were made for rice stable transformation. For each construct, we analyzed 24 independent T0 lines. For AacCas12b, one line (Line 17) carried a monoallelic mutation at the OsROC5-sgRNA02 site; 12 (50%) lines had mutations at the OsEPFL9-sgRNA02 site and three lines had biallelic mutations; six (25%) lines had mutations at the OsGS3-sgRNA02 site and none carried biallelic mutations (FIG. 12A). Among them, four (Lines 1, 17, 20 and 22) are double mutants (FIG. 12A). These mutations were first identified by Restriction Fragment Length Polymorphism (RFLP) assays and later confirmed by Sanger sequencing. For AaCas12b, none of the 24 T0 plants assayed carried mutations at the OsROC5-sgRNA02 site, consistent with the low editing activity for this sgRNA in protoplasts (FIG. 7). However, AaCas12b resulted in very high mutation rates at both OsEPFL9 and OsGS3 genes: at the OsEPFL9-sgRNA02 site, 16 (66.7%) T0 lines were mutants and seven lines had biallelic mutations; At the OsGS3-sgRNA02 site, 17 (70.85%) T0 lines were mutants and 11 lines had biallelic mutations (FIG. 12B). Impressively, 16 lines were double mutants and seven were biallelic double mutants (FIG. 12B). These mutations, including a 118 bp large deletion, have been further validated by Sanger sequencing. To assess off-target effects in T0 lines, we randomly selected two double mutants each generated by AacCas12b and AaCas12b. In both cases, sequencing of 7-8 top putative off-target sites of OsEPFL9-sgRNA02 and OsGS3-sgRNA02 revealed no off-target mutations. Taken together, we have successfully demonstrated multiplexed genome editing by generating combinational mutants with highly specific AacCas12b and AaCas12b.

Example 3: Cas12b CRISPR Interference Systems

Figure 13:
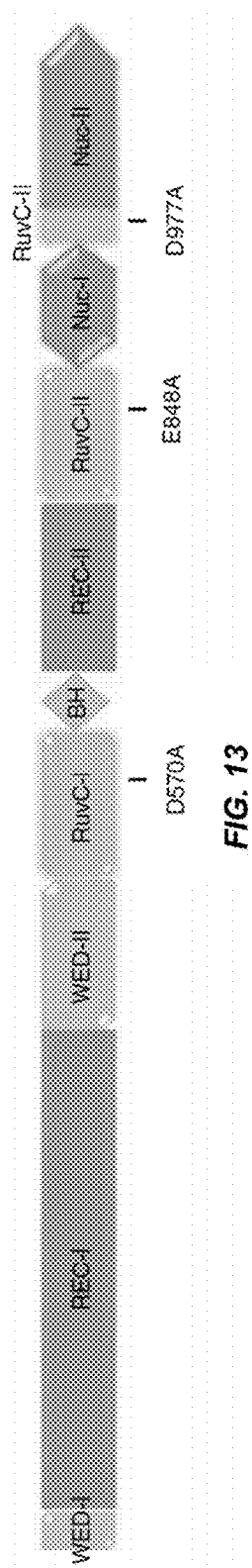
FIG. 13 is an illustration of protein domains of AacCas12b. The three amino acid mutations used to inactivate Cas12b nuclease activity are indicated.
Figure 14A:
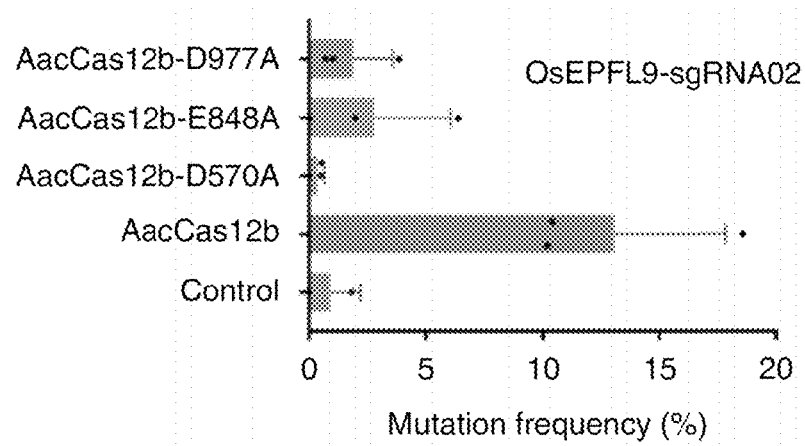
FIG. 14A and FIG. 14B shows RFLP analysis of nuclease activity for protein variants of AacCas12b and AaCas12b in rice protoplasts.
Figure 14B:
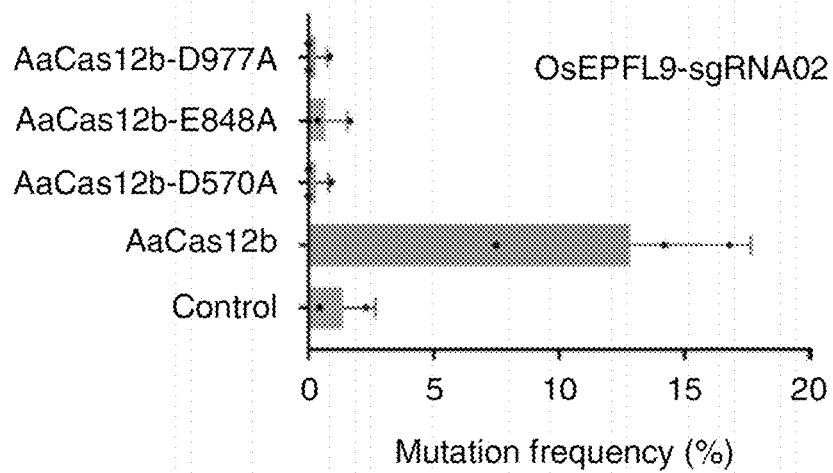
Figure 15:
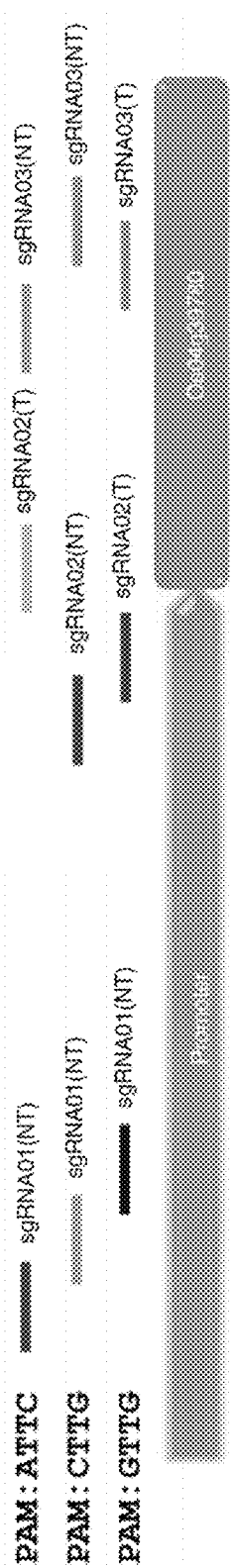
FIG. 15 is an illustration of nine sgRNAs that direct targeted transcriptional repression at Os04g39780. Relative targeting positions and PAM sites are indicated. These sgRNAs target either the non-template strand (NT) or the template strand (T) of the DNA.
Figure 16A:
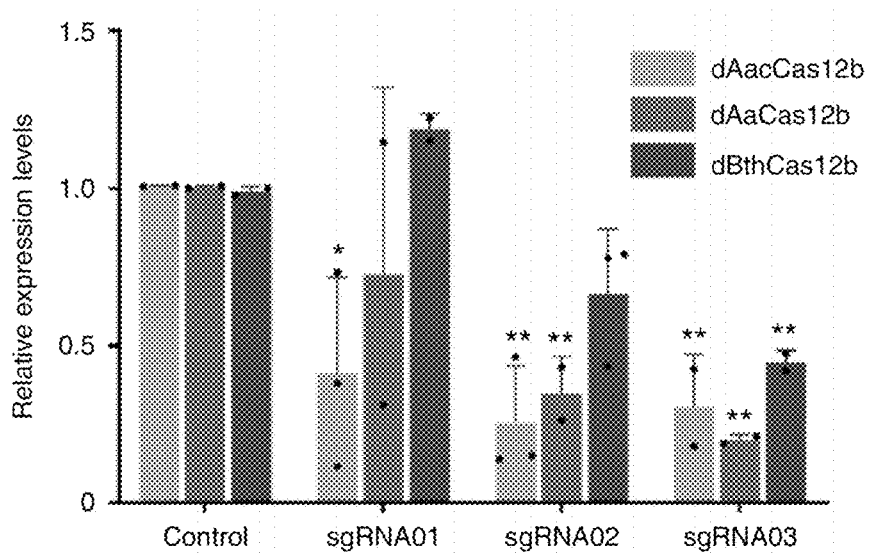
FIG. 16A, FIG. 16B, and FIG. 16C show qRT-PCR data showing targeted repression of Os04g39780 in rice protoplasts. dAacCas12b, dAaCas12b and dBthCas12b were compared at three different PAMs at different target positions. Student's t-test: *$P<0.05$, $P<0.01$, *$P<0.001$, compared to the control.
Figure 16B:
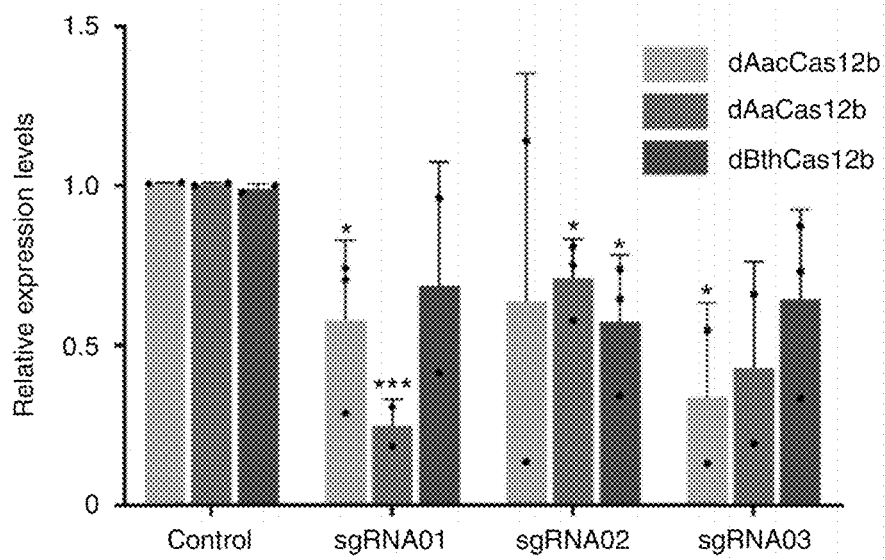
Figure 16C:
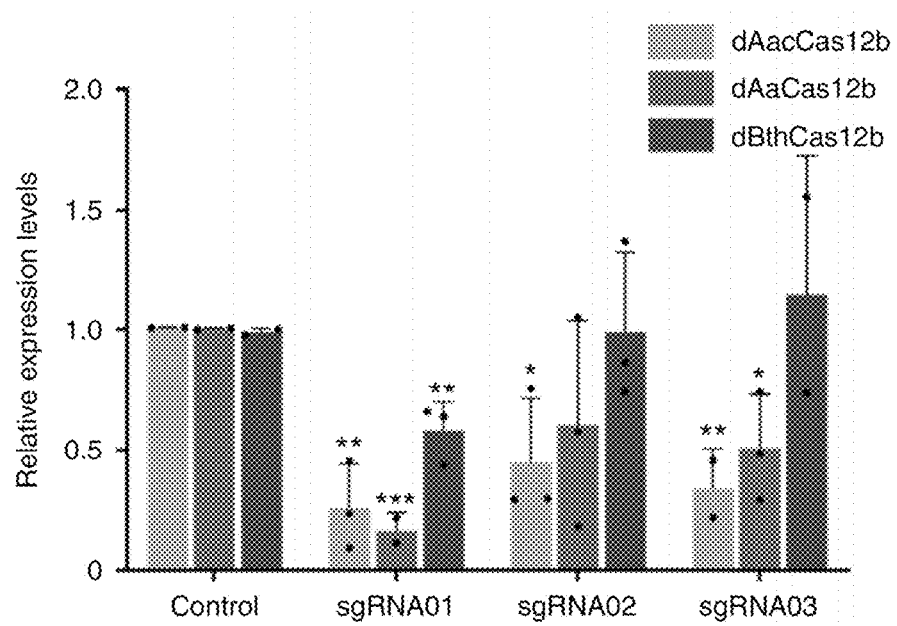
Figure 17A:
FIG. 17A shows illustrations of three synthetic transcriptional repressors based on AacCas12b, AaCas12b and BthCas12b.
Figure 17B:
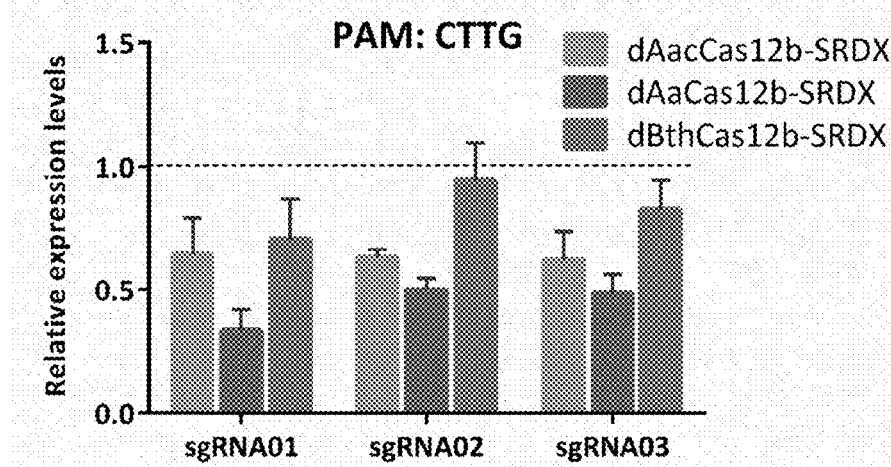
FIG. 17B is qRT-PCR data showing targeted repression by dCas12b-SRDX repressors in rice protoplasts. OsTubulin was used as the endogenous control gene. The gene expression level of the wild type was normalized as 1. Error bars represent standard deviations of two biological replicates.

We previously established CRISPR interference (CRISPRi) systems in plants based on Cas9 and Cas12a, which recognize NGG (for SpCas9) and TTTV (for AsCas12a and LbCas12a) PAMs, respectively. As Cas12b orthologs have different PAM requirements, repurposing them for CRISPRi will greatly expand the targeting range for plant transcriptional repression. We introduced single amino acid mutations at RuvC-I (D570A), RuvC-II (E848A) and RuvC-III (D977A) in AacCas12b and the corresponding mutations in AaCas12b and BthCas12b (FIG. 13). Assessment of these protein variants of AacCas12b and AaCas12b in rice protoplasts revealed that they indeed lost nuclease activity (FIG. 14A, 14B). We chose three of these deactivated Cas12b (dCas12b) proteins, AacCas12b-D570A, AaCas12b-D570A and BthCas12b-D573A, to test CRISPRi in rice cells. We targeted the rice gene Os04g39780 by focusing on three PAMs: ATTC, CTTG and GTTG. For each PAM, we designed three sgRNAs that target either the promoter or the coding sequence (FIG. 15). The resulting 27 CRISPRi constructs were tested in rice protoplasts and the target gene expression was quantified by qRT-PCR. Three out of nine dBthCas12b constructs resulted in transcriptional repression (FIG. 16A-16C), indicating BthCas12b was able to bind well to some target sites. Both dAacCas12b and dAaCas12b induced transcriptional repression at nearly every target site with variable repression levels (25%-75%) (FIG. 16A-16C). Interestingly, targeted binding of dCas12b to the promoter region and the coding sequence can both robustly repress the target gene expression (FIG. 16A-16C). We further fused three copies of SRDX repressor domain to the C-termini of the dCas12b proteins and generated three synthetic transcriptional repressors (FIG. 17A). By targeting the CTTG PAM sites with the same sgRNAs, we found these dCas12b-SRDX repressors resulted in comparable levels of gene repression to dCas12b (FIG. 17B). The data suggest the CRISPRi effects are predominantly contributed by transcription interference through dCas12b binding, rather than through chromatin modifications by the SRDX repressor.

Example 4: Cas12b Transcriptional Activation Systems

Figure 18:
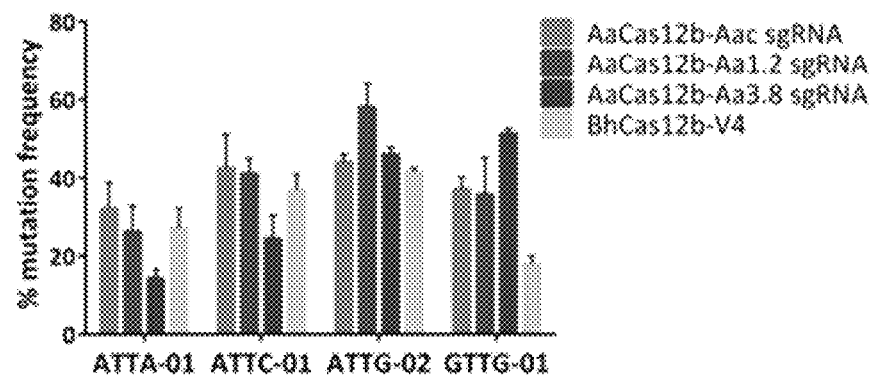
FIG. 18 shows a comparison of AaCas12b (with three sgRNA scaffolds) and BhCas12b systems at ATTA-01, ATTC-01, ATTG-02 and GTTG-01 sites in rice protoplasts.
Figure 19:
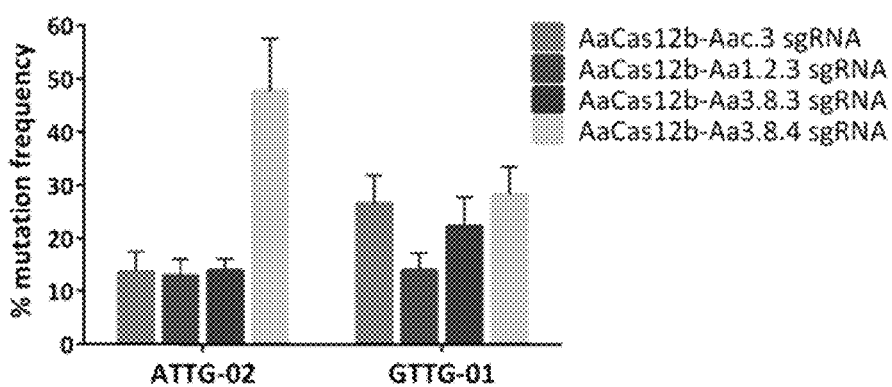
FIG. 19 shows a comparison of four MS2-containing Aac sgRNA scaffolds at ATTG-02 and GTTG-01 sites in rice protoplasts.
Figure 20:
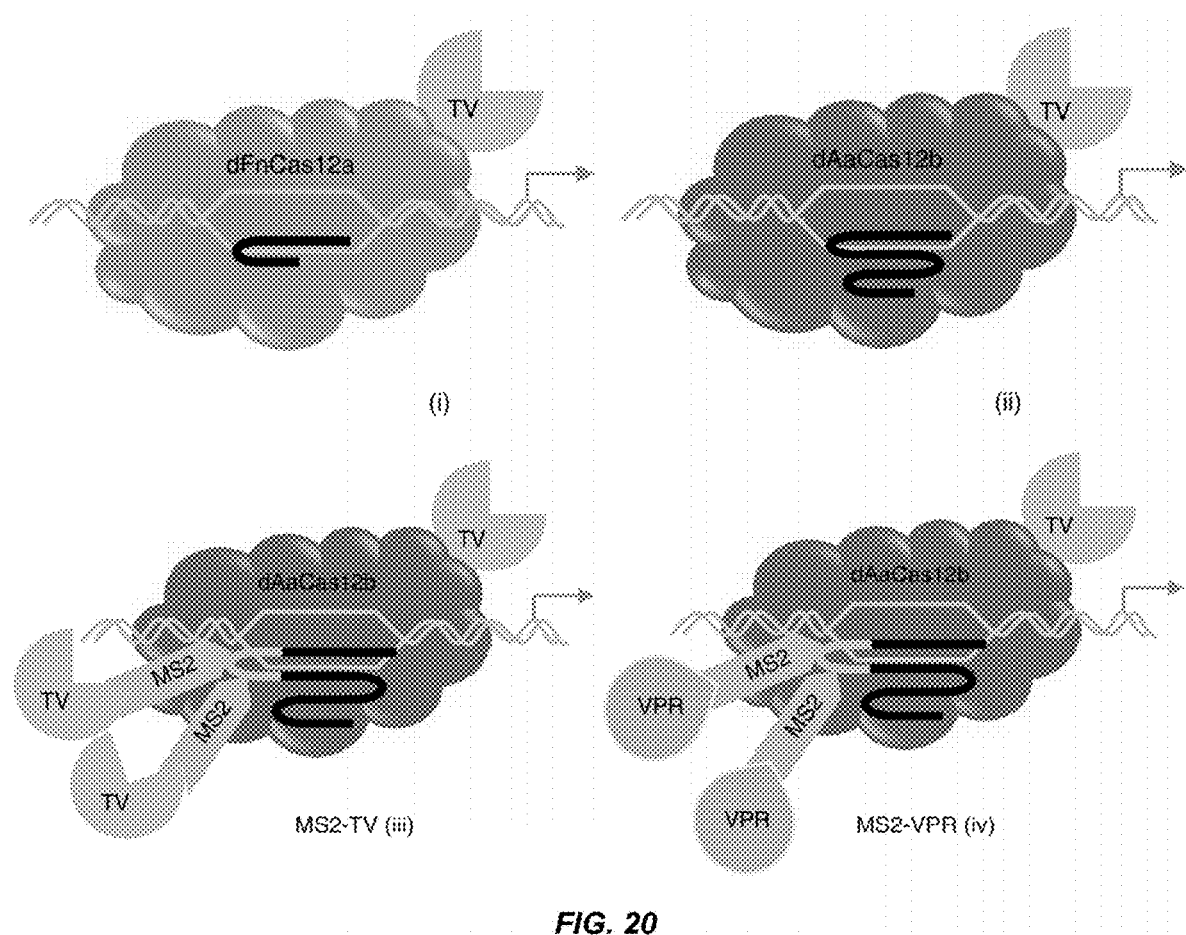
FIG. 20 shows schematics of four activation systems tested, including dFnCas12a-TV (I), dAaCas12b-TV with three different sgRNA scaffolds (II), dAaCas12b-TV with four different sgRNA scaffolds containing an MS2 aptamer to recruit MS2-TV (III), and dAaCas12b-TV with four different sgRNA scaffolds containing an MS2 aptamer to recruit MS2-VPR (IV).
Figure 21A:
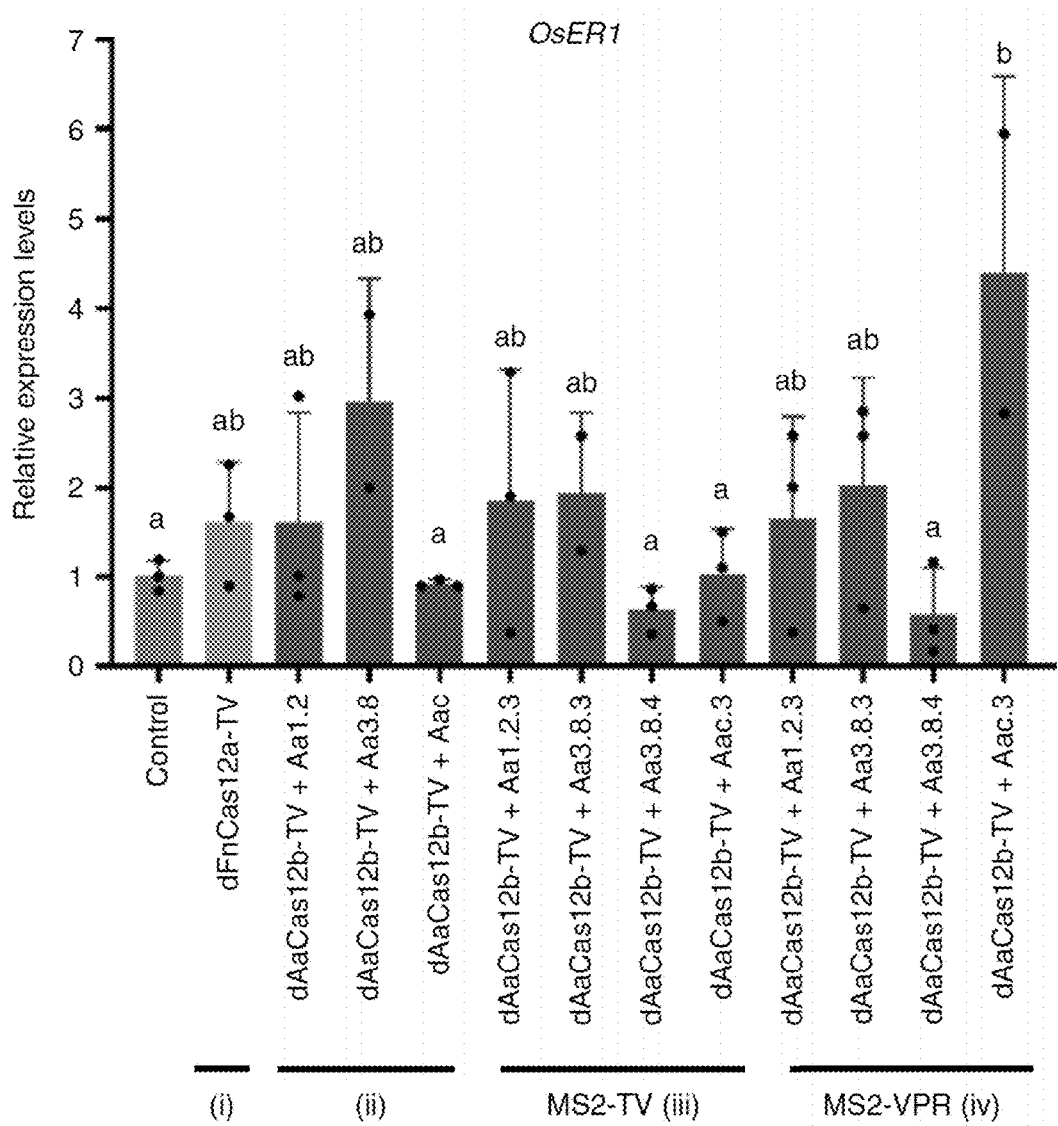
FIG. 21A and FIG. 21B show qRT-PCR data showing targeted activation of OsER1 and OsGW7 in rice protoplasts. A total of 12 activations systems were tested. A sgRNA was used to direct each Cas12 activation system to the promoter of interest. OsTubulin was used as the endogenous control gene. The gene expression level of the wild type was normalized as 1. Student's t test: *$P<0.1$, **$P<0.02$, compared to the control. Error bars represent standard deviations of three biological replicates.
Figure 21B:
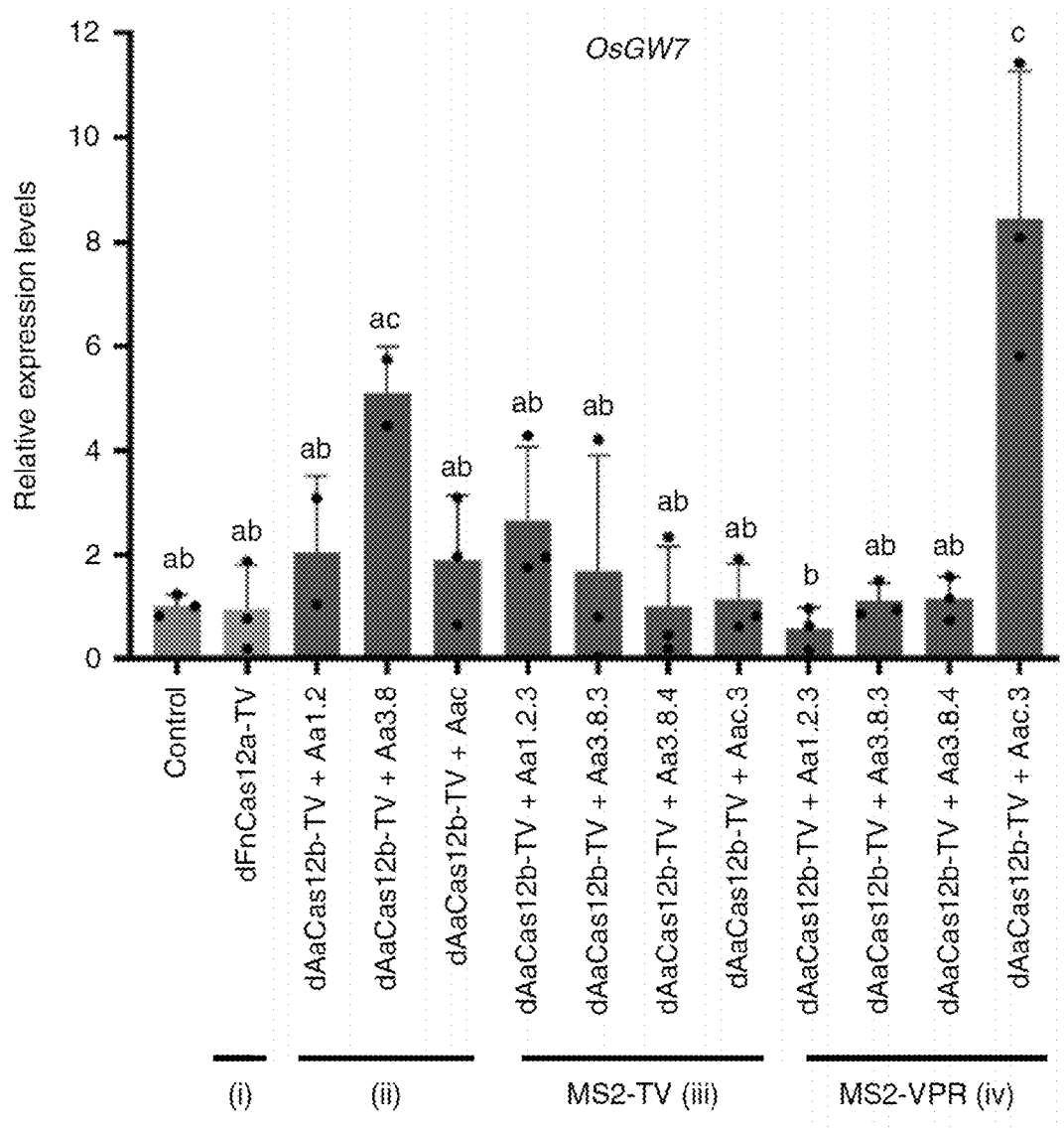

Until now, there has been no successful report of Cas12a transcriptional activation systems in plants. We previously reported an improved Cas9 based transcriptional activation system that uses engineered sgRNA2.0 scaffold with MS2 aptamers for recruiting transcriptional activators. Such guide RNA engineering could be applied to Cas12b, but not Cas12a, because Cas12a uses very short crRNAs which are incompatible with MS2 aptamer insertions. To establish efficient Cas12b based transcriptional activation systems, we first sought to engineer the sgRNA scaffold to improve the overall editing efficiency. We tested AaCas12b genome editing with the artsgRNA13 scaffold and three engineered artsgRNA13 scaffolds with 1-2 MS2 insertions. No editing activity was detected with these new scaffolds in rice protoplasts. However, AaCas12b, when coupled with the scaffolds Aa1.2 and Aa3.8, showed comparable editing efficiencies with the Aac scaffold at four independent target sites (FIG. 18). Recently, an engineered Cas12b from *Bacillus hisashii* (Bh), BhCas12b-v4, was reported for genome editing in human cells. We compared a rice codon-optimized BhCas12b-v4 with our AaCas12b systems and found AaCas12b showed equivalent or even better editing efficiency than BhCas12b-v4 (FIG. 18). We continued our focus on AaCas12b and sought to use engineered sgRNAs to recruit more activators for developing Cas12b based transcriptional activation systems. Four sgRNA scaffolds (Aac.3, Aa1.2.3, Aa3.8.3 and Aa3.8.4) that contained one MS2 aptamer near the 3' end were first tested for genome editing. While all four modified sgRNA scaffolds led to detectable editing activities at two target sites in rice protoplasts, Aa3.8.4 had the highest editing efficiency at ATTG-02 site (FIG. 19). Next, we sought to develop Cas12b transcriptional activation systems based on these MS2-containing scaffolds. A potent transcriptional activator, TV, was fused to the C-terminus of dAaCas12b. A dFnCas12a-TV fusion was also generated for comparison between Cas12a and Cas12b. Two potent activators, TV and VPR, were tested for MS2 based recruitment respectively. A total of 12 transcriptional activation configurations based on four general systems were tested (FIG. 20). Two genes, OsER1 and OsGW7, were separately targeted for transcriptional activation and in each case only one sgRNA was used. Two activation systems resulted in significant transcriptional activation, while the other 10 systems including dFnCas12a-TV failed to achieve so (FIGS. 21A and 21B). The dAaCas12b-TV, when coupled with Aa3.8 sgRNA scaffold, resulted in 3 to 5-fold activation of both target genes. Stronger transcriptional activation (5 to 8-fold) was achieved with the transcriptional system that is based on dAaCas12b-TV and Aac.3 sgRNA scaffold-mediated recruitment of MS2-VPR. Hence, we demonstrated a potent AaCas12b transcriptional activation system with simultaneous recruitment of TV and VPR by the dAaCas12b protein and engineered Aac.3 sgRNA, respectively.

Example 5: Vector Sequences

| Cas12b vectors | |
|---|---|
| pYPQ290 (AacCas12b) | SEQ ID NO: 27 |
| pYPQ291 (BthCas12b) | SEQ ID NO: 28 |
| pYPQ292 (AaCas12b) | SEQ ID NO: 29 |
| pYPQ293 (BhCas12b_v4) | SEQ ID NO: 30 |
| Catalytically dead Cas12b vectors | |
| pYPQ290-D570A | SEQ ID NO: 31 |
| pYPQ290-D977A | SEQ ID NO: 32 |
| pYPQ290-E848A | SEQ ID NO: 33 |
| pYPQ291-D573A | SEQ ID NO: 34 |
| pYPQ291-D951A | SEQ ID NO: 35 |
| pYPQ291-E827A | SEQ ID NO: 36 |
| pYPQ292-D570A | SEQ ID NO: 37 |
| pYPQ292-D977A | SEQ ID NO: 38 |
| pYPQ292-E848A | SEQ ID NO: 39 |
| Catalytically dead Cas12b fused with transcriptional repressor | |
| pYPQ290-D570A-SRDX | SEQ ID NO: 40 |
| pYPQ291-D573A-SRDX | SEQ ID NO: 41 |
| pYPQ292-D570A-SRDX | SEQ ID NO: 42 |
| Catalytically dead Cas12b fused with transcriptional activator | |
| pYPQ239A (dFnCas12a)-TV | SEQ ID NO: 43 |
| pYPQ292 (AaCas12b)-D570A-TV | SEQ ID NO: 44 |
| pYPQ292 (AaCas12b)-D570A-TV-MS2-TV | SEQ ID NO: 45 |
| pYPQ292 (AaCas12b)-D570A-TV-MS2-VPR | SEQ ID NO: 46 |
| sgRNA expression vectors | |
| pYPQ141-ZmUbi-RZ-Aac | SEQ ID NO: 47 |
| pYPQ141-ZmUbi-RZ-Bth | SEQ ID NO: 48 |
| pYPQ141-ZmUbi-RZ-Bh | SEQ ID NO: 49 |
| pYPQ141-ZmUbi-RZ-Aac.3 | SEQ ID NO: 50 |
| pYPQ141-ZmUbi-RZ-Aa1.2 | SEQ ID NO: 51 |
| pYPQ141-ZmUbi-RZ-Aa1.2.3 | SEQ ID NO: 52 |
| pYPQ141-ZmUbi-RZ-Aa3.8 | SEQ ID NO: 53 |
| pYPQ141-ZmUbi-RZ-Aa3.8.3 | SEQ ID NO: 54 |
| pYPQ141-ZmUbi-RZ-Aa3.8.4 | SEQ ID NO: 55 |

What is claimed is:

1. A method of modifying a nucleotide sequence at a target site in the genome of a plant cell, the method comprising:
   introducing into one or more plant cells
   (i) a DNA-targeting RNA, or a DNA polynucleotide encoding a DNA-targeting RNA; and
   (ii) a polynucleotide encoding a Cas12b polypeptide, wherein the polynucleotide encoding the Cas12b polypeptide is codon-optimized for expression in the plant cell and comprises a nucleotide sequence having at least 90% sequence identity to SEQ ID NO: 3, and
   culturing the plant cell under conditions in which the Cas12b polypeptide is expressed and cleaves the nucleotide sequence at the target site to produce a modified nucleotide sequence with an editing efficiency from 50% to 60%, wherein the editing efficiency is the number of plant cells having a modified nucleotide sequence relative to the total number of plant cells, wherein the target site is located immediately 3' of a PAM site in the genome of the plant cell, wherein the PAM site is ATTA, ATTC, or GTTG, wherein the plant cell is a rice plant cell, and wherein the target site is in *Oryza sativa* Epidermal Patterning Factor-Like protein 9 (OsEPFL9) or *Oryza sativa* Grain Size 3 (OsGS3).

2. The method of claim 1, further comprising:
   regenerating a plant comprising said modified nucleotide sequence from the plant cell.

3. The method of claim 1, wherein the cleaving of the nucleotide sequence at the target site comprises a staggered double strand break.

4. The method of claim 1, wherein said modified nucleotide sequence comprises insertion of heterologous DNA into the genome of the plant cell, deletion of a nucleotide sequence from the genome of the plant cell, or mutation of at least one nucleotide in the genome of the plant cell.

5. The method of claim 1, wherein the polynucleotide encoding the Cas12b polypeptide is the nucleotide sequence of SEQ ID NO: 3.

6. The method of claim 1, wherein the Cas12b polypeptide is from *Alicyclobacillus acidiphilus*.

7. The method of claim 1, wherein the expression of the Cas12b polypeptide is under the control of an inducible promoter, a constitutive promoter, a cell type-specific promoter, or a developmentally-preferred promoter.

8. The method of claim 1, wherein polynucleotide encoding the Cas12b polypeptide is present in a vector, and wherein the vector is the nucleotide sequence of SEQ ID NO: 29.

9. The method of claim 1, wherein the Cas12b polypeptide is fused to a deaminase domain or a reverse transcriptase.

* * * * *

SEQUENCE LISTING

<160> NUMBER OF SEQ ID NOS: 92

<210> SEQ ID NO 1
<211> LENGTH: 3387
<212> TYPE: DNA
<213> ORGANISM: Artificial Sequence
<220> FEATURE:

<223> OTHER INFORMATION: Codon optimized AacCas12b nucleic acid

<400> SEQUENCE: 1

```
atggcggtga agtcaataaa agttaaactc cgcctggacg atatgccaga aattcgggct      60
ggcctctgga agcttcacaa agaggttaac gctggcgtca gatattacac ggaatggttg     120
tcgctgctcc ggcaagaaaa tctctacaga aggtcgccca atggtgatgg ggaacaagag     180
tgcgacaaaa cggcggagga atgcaaagcg gaactccttg aaagacttcg cgcgagacaa     240
gtcgaaaacg gccatagagg cccggccggt tccgatgatg aattgcttca gcttgcgcgg     300
cagctttacg aattgctcgt gccgcaagcc ataggtgcaa aaggagacgc acaacaaatt     360
gcaagaaagt tcctctcccc gctcgcagac aaggatgccg tgggaggtct tggaatcgct     420
aaagcaggga taagccaag  atgggtgcga atgcggaag  caggtgagcc aggctgggaa     480
gaggagaagg agaaagccga acgaggaaa  tcagcggatc gcactgcaga cgtgttgaga     540
gccctcgcag actttggact taagccactg atgcgggttt acacggattc agagatgtcc     600
tcggtggaat ggaagccgct cagaaagggt caagccgtga acgtgggac  cgcgacatg     660
ttccagcagg caattgagcg gatgatgtcc tgggagtctt ggaaccaaag ggtcgggcaa     720
gaatatgcga actggtgga  gcaaaaaaat aggtttgaac aaaaaaattt cgttggtcaa     780
gagcatctgg ttcatttggt taatcaactt caacaagata tgaaagaagc atcacctggc     840
ttggaatcta agaacaaac  agcacactac gttacgggta gggcgttgag gggatcggat     900
aaagttttcg agaagtgggg taagttggcc ccgacgccc  ctttcgatct gtatgacgcc     960
gagataaaga cgttcagcg  gaggaacact cgccgctttg gttcgcacga tctgtttgca    1020
aaactggccg agcctgagta ccaggccctt ggcgggagg  atgcgtcgtt ccttacacgc    1080
tacgcggttt ataattcaat tctcagaaag ctcaatcacg cgaagatgtt tgcgactttc    1140
actcttccag atgcgacggc acaccctata tggactagat ttgataagtt ggggggcaac    1200
ttgcaccagt atacatttct gttcaacgaa ttcggcgaac gcaggcatgc aatcaggttc    1260
cataaacttt tgaaagtcga gatggtgtt  gccagggagg ttgacgatgt cacagtgcct    1320
atctcgatgt ccgaacaatt ggataacttg ctgcccagag atccgaacga accgattgca    1380
ctttatttca gggattatgg tgccgaacaa cactttacgg gtgagttcgg aggggccaag    1440
attcagtgca gacgggacca gcttgctcac atgcaccgca ggagaggggc tagggatgtg    1500
tatttgaacg tttcagttcg cgtgcagtcc caatccgagg cgcggggga  gcgcagacca    1560
ccatacgcgg ctgtcttccg gctggttggc gataaccata agcgttcgt  gcatttcgat    1620
aagctgagcg attacctcgc cgaacatcct gatgacggaa agttggggtc agagggcctt    1680
ctgtcgggcc tgagggtgat gtccgtggac ctgggattgc gcaccagtgc ctcgatcagc    1740
gttttaggg  tggccaggaa agatgagttg aaacccaact cgaaggggag ggttccgttc    1800
ttttcccta  taagggcaa cgataacttg gtcgcagtgc atgaaaggag ccaactgctc    1860
aaacttcccg gggagacaga gtccaaagat cttcgcgcta agggaaga  gagacaaaga    1920
actctccggc agctgcgcac gcagctcgca tacctgcggt tgcttgtccg ctgcggaagt    1980
gaagacgttg gcaggcgcga gaggtcatgg gccaaattga ttgagcagcc ggtcgacgcc    2040
gcaaatcaca tgactccgga ttggagggag gctttcgaga cgaactgca  gaagttgaag    2100
agtctgcatg gcatatgctc tgacaaagag tggatggacg cggtttacga gtccgtccgc    2160
cgggtctggc ggcacatggg gaaacaagtt cgcgattgga gaaggatgt  tagatccggg    2220
gaaaggccga gataagagg  ttatgccaaa gacgtggttg gtggaaattc tatcgaacag    2280
```

```
atcgaatatc ttgagaggca gtacaagttc ctcaagagtt ggtctttctt cggtaaagtc    2340
tctggacaag ttataagagc agaaaagggg agccggttcg ctatcacctt gcggaacac    2400 atagaccacg caaaagaaga cagactgaag aagctggcgg acagaattat catgaagcg    2460 ctggggtacg tttacgcgct ggacgaaagg gggaaaggta atgggtggc caaatacccg    2520 ccatgccagt tgatattgct ggaagaattg tccgaatatc aatttaataa cgatagaccg    2580
ccatccgaga caaccaact tatgcaatgg tctcaccggg agttttcca ggagttgatc    2640 aaccaagctc aagtgcacga tctgcttgtt ggtacaatgt acgcagcgtt ttcctcacgc    2700
ttcgacgcta gaacaggagc gccgggaatt cggtgccgga gggtgcctgc gaggtgtact    2760
caggagcaca acccggagcc atttccctgg tggttgaata aattcgttgt ggaacatacg    2820
ttggatgctt gcccgcttcg ggcggacgac ctcattccga cgggtgaggg cgagattttc    2880
gtgtcgccat tctcggctga ggaagggac ttccatcaaa tccatgctga cctcaatgcg    2940
gcgcaaaatc tgcagcagag attgtggagt gattttgaca tctctcagat caggcttcgg    3000
tgcgattggg gagaagtcga tggtgaactc gttctcattc cgagactcac cggtaaaagg    3060
actgctgatt catattcgaa caaagttttt tacactaaca caggggtcac ttattatgaa    3120
agagaacgcg gtaagaagcg ccgcaaggtg ttcgcgcaag agaaactttc cgaggaagag    3180
gccgagttgc tcgttgaagc tgacgaagct cgcgagaagt ccgtcgttct gatgcgggat    3240
ccttctggca ataaacag ggggaattgg acacggcaga aggaattttg gtccatggtg    3300
aatcagcgca tagaaggtta tctggtcaaa cagatcagaa gcagggttcc cctccaggat    3360
tcagcgtgcg agaacacggg cgatatt                                       3387
```

<210> SEQ ID NO 2
<211> LENGTH: 3324
<212> TYPE: DNA
<213> ORGANISM: Artificial Sequence
<220> FEATURE:
<223> OTHER INFORMATION: Codon optimized BthCas12b nucleic acid

<400> SEQUENCE: 2

```
atggccacaa ggtctttcat acttaagata gagccaaacg aagaggtcaa aaagggattg      60
tggaaaaccc atgaagtcct gaaccatggc attgcctact acatgaacat cctgaaactt     120
atacggcagg aggctattta tgagcaccac gagcaggatc aaaaaaccc caaaaaggtt     180 tcgaaggctg aaatccaggc cgaactgtgg gacttcgttc tcaaaatgca gaaatgtaat     240
tcgttcactc atgaagttga caagacgtc gtgtttaaca ttttgaggga gctttacgag     300
gagttggttc cgagctccgt cgaaaagaag ggtgaagcaa atcagctgtc gaataagttc     360
ttgtaccctt tggtggaccc gaacagccaa tctggaaaag ggacagcatc atcagggcgg     420
aagcctcggt ggtataactt gaagattgct ggagacccct cgtgggaaga ggaaaagaaa     480
aagtgggagg aagataagaa gaaggaccca cttgccaaaa ttctcggcaa acttgccgaa     540
tatggattga taccgctgtt catccccttt acggattcta acgaacccat cgttaaagaa     600
atcaagtgga tggaaaaatc tcgcaatcag tccgtccgga ggctggacaa agatatgttt     660
atacaagctt tggaacgctt tctctcgtgg gagtcgtgga atcttaaggt caaagaagag     720
tatgaaaagg tcgagaagga acacaagaca ctggaggaga ggattaagga agacattcaa     780
gcattcaagt cactggagca atacgaaaag gaacggcagg agcaattgct tcgcgacacg     840
ctcaatacca atgaatatag gctttccaag aggggcctga ggaggatggcg ggaaataatc     900
```

```
cagaaatggc tcaagatgga cgagaatgaa ccttcagaaa atatctcga ggtttttaaa    960 gattaccaaa ggaaacatcc acgcgaggca ggggattaca gcgtgtacga gtttctctcc   1020
aagaaggaaa accattttat ctggcgcaat catcccgaat acccgtacct ctatgcgacg   1080
ttctgcgaaa tagacaaaaa gaaaaaagat gctaagcaac aagcgacttt cacacttgca   1140
gatcccataa atcacccatt gtgggtgcgg tttgaagaaa ggtcgggctc taacctcaat   1200
aagtacagaa ttttgacgga gcagttgcac acagaaaagc tgaagaagaa gttgacggtt   1260
cagctggatc gccttatcta cccaaccgag tctggtggct gggaagagaa ggggaaagtc   1320
gacatagtgt tgctgccatc taggcagttc tataaccaga ttttctcga tatagaagaa   1380 aagggtaaac atgcatttac gtataaagac gagtccataa agtttccact gaaaggaaca   1440
cttggcggcg caagggtgca gtttgatcgg gaccaccttc gcaggtaccc ccacaaggtt   1500
gaaagtggaa acgttggacg gatctatttt aatatgaccg tcaacataga acccacagaa   1560
tcccctgttt ccaaatccct gaaaatacac cgggacgatt ttcctaaatt tgtgaacttt   1620
aaaccgaagg agttgaccga gtggataaag gacagtaaag ggaaaaagct gaagtccggt   1680
atcgaaagcc tggagattgg gctcagagtt atgtcgatag atctgggtca aaggcaggca   1740
gcagccgcct ctatatttga ggtcgtggac cagaagcccg acattgaagg taaactgttc   1800
tttccgatta aggggacgga actctacgca gtccatcgcg cctccttcaa tataaagctg   1860
ccgggcgaaa cactggttaa atcacgcgag gttttgcgca aagcgcggga agacaacctg   1920
aaactcatga atcaaaagct caatttcctg cgcaatgtgt tgcacttcca gcagtttgag   1980
gatattaccg aaagagagaa aagggttaca aaatggatat cccggcaaga aaactctgat   2040
gttccgctgg tttaccagga tgagcttata cagattaggg aacttatgta taaaccttac   2100
aaagattggg ttgcattcct caagcagctg cataagagac ttgaagtcga gatcggcaaa   2160
gaagtcaaac actggcgcaa gagcctgagc gatggtcgga aagggttgta cggaatcagt   2220
ttgaaaaata tcgacgaaat agatagaacc aggaaatttt tgttgcgctg gtcactgaga   2280
ccaacggaac cgggagaagt cagaaggttg gagccaggcc agagatttgc aattgaccag   2340
ctgaaccatc tgaatgcact gaaagaggac agattgaaga gatggcgaa tacgattatt   2400 atgcatgctt tgggttattg ttacgacgtt aggaagaaga aatggcaggc caagaacct   2460 gcgtgccaaa tcatcctgtt cgaagatctg agtaactaca atccgtatga agaaaggagt   2520
cgcttcgaga acagtaaact gatgaaatgg tcccggcgcg ataccacg ccaagttgcg   2580 cttcaagggg aaatatacgg gcttcaagtt ggggaagttg gagcgcagtt ttctagccgg   2640
ttccacgcca agacagggtc cccgggtata aggtgcagtg tggtgacgaa agaaaagttg   2700
caggataata gattctttaa aaatcttcaa cgggaagggc gcctgacgct tgacaagatt   2760
gcagtgttga agaggggga tttgtacccc gataaaggcg gggagaagtt catttctttg   2820
tcgaaggacc gcaagttggt tacgacgcat gcagacatta acgcagcaca aaatctgcaa   2880
aaaagattct ggactcggac gcatggtttt tacaaggttt actgtaaagc atatcaagtc   2940
gatggtcaga cggtttacat tcccgaatct aaagatcaga acagaaaat cattgaggag   3000 ttcggtgaag gttactttat actcaaggac ggtgtttacg aatggggtaa tgctggtaaa   3060
ctgaaaatta agaagggtc ctccaagcaa tcatcttctg agctcgtcga cagcgacatc   3120
cttaaggata gcttcgatct tgcctctgag ctcaagggag aaaagttgat gctgtatcgc   3180
gatcctagtg gaaatgtctt tccctcagat aaatggatgg cagcaggtgt gttcttcggg   3240
aaattggaac gcatactgat atcaaaactg accaatcaat actctatatc tactattgaa   3300
```

```
gacgattcaa gtaagcaatc gatg                                            3324
```

<210> SEQ ID NO 3
<211> LENGTH: 3387
<212> TYPE: DNA
<213> ORGANISM: Artificial Sequence
<220> FEATURE:
<223> OTHER INFORMATION: Codon optimized AaCas12b nucleic acid

<400> SEQUENCE: 3

```
atggccgtca agtccatgaa ggtcaagttg cgcctggata catgccaga gatcagagcc      60
ggactttgga aacttcacac cgaggttaat gcgggtgtgc ggtactatac ggaatggctt    120
agccttttga ggcaagaaaa tctttatcgg aggagtccca atggcgatgg agaacaagaa    180
tgctataaaa ctgctgagga atgcaaggct gaactccttg agagactcag agcccgccaa    240
gttgagaatg ggcactgcgg ccctgctggg agtgatgacg aactgctgca attggcacgg    300
caactttatg aacttctggt cccacaagca atcggggcta aggtgatgc gcagcaaatc     360
gcaaggaagt ttcttagtcc ccttgccgac aaggatgccg tgggtggttt gggaatagca    420
aaagcaggaa ataagcctag gtgggttcgg atgagggagg ctggagagcc aggttgggaa    480
gaggaaaagg ctaaagccga ggcgagaaag agtacggata aaccgccga tgttcttcgc     540
gctcttgcag acttcggtct taaacctctt atgagagtct acacagactc agacatgtcc    600
agcgtgcagt ggaaaccact tcgcaaagga caagcggtca gaacctggga tagagacatg    660
ttccaacaag cgatcgaaag aatgatgagt tgggaatcgt ggaatcagcg cgttggagaa    720
gcgtacgcaa agctcgtgga caaaagtcg aggtttgaac agaaaaattt tgtgggacaa     780
gaacatcttg tccaacttgt caatcaactt caacaagaca tgaaggaagc atcacacggc    840
ctggagtcga agaacaaac tgcgcattac ttgactggga gagcgctgag agggagcgac     900
aaagttttg agaagtggga aaaactcgat cctgatgccc catttgacct ctatgatacc    960
gaaatcaaga atgttcaacg gaggaatact cgcaggttcg gatctcatga tctgtttgcg   1020
aagctcgcgg aacctaaata tcaggcgctc tggagagagg acgcttcttt cctcacgagg    1080
tatgcggttt acaatagcat tgtcagaaaa ctgaatcacg ctaaaatgtt tgcgactttt   1140
actcttccgg atgctaccgc ccacccgatc tggacgcggt ttgacaaaact cggcggcaac   1200
ctgcaccagt acactttctt gtttaacgaa tttggcgagg caggcacgc cattcggttt    1260
cagaagctgt tgacggttga ggatggcgtt gctaaagagg tcgacgacgt cacggttccg   1320
atttctatgt ccgcgcagct ggatgacctc ttgcctcggg acccacacga gctcgttgca   1380
ctctacttcc aggactacgg tgcagaacaa catctggctg agagtttgg cggcgcgaaa    1440
attcaatacc gccgcgatca attgaaccac ctgcacgcca agagaggcgc cagagatgtc   1500
taccttaatc tgagcgtccg cgttcagtca caatccgaag ccaggggaga aggcgccct    1560
ccgtatgcag cggtcttcag gcttgttggc gataaccacc gcgcgtttgt tcactttgat   1620
aaattgtcag attacctcgc agaacaccca gacgatggta agctggggtc ggaaggtttg   1680
ctctctgggc tcagagtcat gtcagttgac ttgggtctta ggacttccgc gagcatatct    1740
gtcttccgcg tcgcaagaaa ggacgaattg aagccgaaca gtgaaggccg gtcccttttt   1800
tgcttcccga tcgaagggaa cgaaaacctc gttgctgtcc acgagcggag ccaactgttg   1860
aagcttcccg tgaaacgga atcgaaagat ctgagagcga tcagagaaga gcgccaaagg   1920
acgcttagac agctccggac gcaacttgca tacttgcgcc ttctggttcg ctgcggtagt   1980
```

```
gaagacgttg gaagaagaga gaggtcatgg gctaaactca tagagcaacc tatggatgct    2040
aatcaaatga cgcctgattg gagagaagca ttcgaagacg aacttcagaa actgaaatcc    2100
ctttacggga tatgcggcga tcgcgagtgg acagaagcag tgtatgagtc tgtgaggcgc    2160
gtgtggcggc atatgggtaa acaggtgcgc gattggagaa aagacgttag gagcggggaa    2220
agacctaaga tacggggata tcagaaagac gttgtcgggg gaaatagcat tgaacagatt    2280
gaatatttgg agcgccaata taagttcctc aaatcctggt cttttcttcgg caaagtgtca    2340 ggccaggtga tacgcgcgga aaagggatcg cgctttgcaa taactctgag agaacatatt    2400
gatcatgcca agaagatcg gttgaagaaa ctcgccgata gaatcatcat ggaggcgctt    2460
ggttatgtct acgccttgga cgatgaacgg ggaaagggaa agtgggtcgc caagtatcca    2520
ccttgccaac tcattctcct cgaagaactt ccgaatacc agtttaacaa cgatcggccg    2580
ccatcagaga ataatcaact gatgcagtgg tcccatcgcg gtgtgtttca agagttgctc    2640
aatcaggccc aagtccatga tctgcttgtt ggcacaatgt atgcagcctt ttcctcccgg    2700
tttgatgcaa gaacaggggc tcctggcata cgctgtagac gggtcccggc gaggtgcgcc    2760
cgcgaacaaa accctgaacc gttccctgg tggttgaaca agttcgttgc ggagcacaag    2820
ctggacgggt gtcctctgcg ggccgacgat cttattccca ccgggaagg ggaattcttt    2880 gtgagcctt tctcggcgga ggaaggggat tttcaccaaa tacatgcaga tcttaatgcc    2940
gcacaaaatt tgcagaggag actgtggtca gactttgata ttagtcagat acgcctccgc    3000
tgtgactggg gagaggtcga tggcgagcct gtgttgatac caagaacgac cggaaagagg    3060
acagccgatt cgtatggaaa caaggttttt tacacgaaga cgggcgttac ttactacgaa    3120
agagaaagag ggaagaagag aaggaaagtc tttgcccaag aagaattgag cgaggaagaa    3180
gccgagctct tggtcgaagc ggacgaggca cgggaaaagt ctgtcgtcct catgagggac    3240
ccttccggaa ttattaaccg gggagattgg acgcggcaga aagagttttg gtccatggtt    3300
aatcaacgca tagaaggcta ccttgtcaag caaataagaa gtcgcgtgag attgcaggag    3360
agtgcatgtg agaacactgg ggacata                                        3387
```

<210> SEQ ID NO 4
<211> LENGTH: 3324
<212> TYPE: DNA
<213> ORGANISM: Artificial Sequence
<220> FEATURE:
<223> OTHER INFORMATION: Codon optimized BhCas12b nucleic acid

<400> SEQUENCE: 4

```
atggccacca gatcgttcat cttgaaaatc gaacccaatg aagaggttaa aaagggcctg      60
tggaaaaccc acgaggtgtt gaatcatggt atcgcgtact atatgaatat acttaagctc     120
ataagacagg aagccattta tgagcatcat gaacaggatc ctaagaaccc caaaaaagtc     180
tctaaggcag aaatacaggc tgagctttgg gactttgtgc tcaagatgca aaagtgcaat     240
tcatttaccc acgaggttga taagacgaa gtcttcaata ttcttcggga attgtatgaa     300
gaactggtcc catcatcggt ggaaaagaaa ggtgaagcta accaacttag caataagttt     360
ctgtatccgc tcgttgaccc gaattctcaa tcgggaaaag ggactgcctc ctcgggacgg     420
aaaccacggt ggtataacct gaaaatagca ggggacccaa gttgggagga ggagaagaaa     480
aaatgggagg aggacaagaa gaaggacccc cttgctaaga tactcggcaa gcttgctgaa     540
tatgggttga ttcctctttt cattcccctat acgatagca atgaaccaat tgtcaaggag     600
atcaagtgga tggagaaatc gcggaatcag agtgttagaa ggttggacaa agacatgttt     660
```

```
atacaggcgc tggagagatt cctgtcgtgg aatcgtgga  acttgaaggt taaggaggaa    720
tatgaaaaag tcgaaaagga atataagacg cttgaagaac ggattaaaga agatattcag    780
gctcttaaag cccttgagca gtatgaaaag gaacggcaag agcaactcct tcgggatacc    840
ttgaacacaa acgagtatcg cctctcgaag cggggtctgc gcggctggag agaaatcata    900
caaaagtggc ttaagatgga tgagaatgag ccgagcgaga agtacctgga ggttttaaa     960 gattatcaaa ggaaacatcc gagagaggcg ggggattatt cggtgtatga gtttctctcc   1020
aaaaaagaga atcacttcat ttggagaaat caccggaat accctacct ttatgctaca    1080 ttttgcgaga ttgataagaa aaaaaggat gccaaacaac aagccacctt taccctggcg    1140
gaccccatca accacccatt gtgggttcgc tttgaggaga gaagcggatc taatcttaat    1200
aaatatagaa tccttacgga acagttgcat acggagaaac tgaaaaaaaa gctcaccgtc    1260
caactcgatc gcttgatcta tcctacagaa tcgggaggat gggaagagaa gggtaaagtt    1320
gatattgtcc tccttccatc tagacaattc tataaccaaa tcttcttgga catagaggag    1380
aagggtaaac acgcctttac ttacaaagac gaatccatta agtttcccct gaaagggaca    1440
ttgggaggag cccgcgtcca atttgatcgg gaccaccttc gccggtatcc ccacaaagtc    1500
gaaagcggca atgtcgggcg gatctacttc aacatgacag ttaatattga gcctacagaa    1560
tccccagtct ccaagtcgct gaagatacat cgcgacgatt ttcctaaagt tgtgaatttt    1620
aaacctaagg aactgacgga atggattaag gattctaaag gcaaaaagtt gaaatctgga    1680
atcgagtctc tcgaaatagg acttagggtg atgagtatag atcttgggca aagacaagcg    1740
gccgctgcat caatctttga agtcgtggac caaaaacccg atattgaagg caagcttttc    1800
ttccccatta agggaacgga gctctacgcc gtccatcgcg cctcatttaa cataaaactg    1860
ccaggcgaga ccctggttaa gagtcgcgag gtcttgcgca aggcgcgcga agataatctt    1920
aagcttatga accaaaaact taatttcctc aggaacgtgc tgcattttca acaatttgaa    1980
gatattactg agagagaaaa acgggtcaca aaatggatct ctcgccaaga aaacagcgat    2040
gtcccacttg tgtatcagga tgaacttatt caaattagag agttgatgta taaaccgtac    2100
aaggattggg tggcgttttt gaaacagctc cacaagcgcc tggaggtgga aatagggaaa    2160
gaagttaagc actggcgcaa atccctgagc gacggcagga aggggcttta cgggattagc    2220
ctgaagaaca ttgacgaaat cgaccggact agaaaattcc ttctcaggtg gagtctgagg    2280
cctactgagc cgggtgaagt tcgccgcttg gaaccaggcc agcgctttgc gattgatcag    2340
ttgaatcacc ttaacgccct taagaggat cggcttaaga agatggcgaa taccattatt    2400
atgcacgcgt tgggctattg ttacgacgtg agaaagaaga agtggcaggc taaaaatccc    2460
gcgtgccaga tcatcctctt cgaagatctt tccaactaca acccatatgg cgagaggtca    2520
aggttcgaga atagtcggct gatgaaatgg agtcgcaggg aaatcccacg ccaggttgcc    2580
ctgcaaggag aaatctatgg ccttcaagtt ggtgaggtcg gggcgcaatt cagcagccgg    2640
tttcacgcga aaactggtag tccggggata cgctgccggg tggtcacaaa agagaaactc    2700
caggataacc ggttttttaa aaatctgcag agggaaggtc gcctgactct tgataaaatc    2760
gcagtgctga aagagggtga cctctatccc gacaaaggtg cgagaaatt cataagcctc    2820 tccaaggatc gcaaatgtgt cacgactcac gcagacatta acgcggcgca aaacctccaa    2880
aagcggtttt ggaccagaac ccacggtttc tataaagtct attgcaaagc ctaccaggtt    2940
gacggtcaga cggtgtatat cccagaatcc aaggatcaaa agcaaaagat cattgaagaa    3000
```

-continued

```
tttggtgaag gatattttat tcttaaggac ggcgtctacg agtgggtcaa tgcggggaag    3060
cttaaaatta aaaagggctc ttccaagcaa tcgtcgagcg agctcgtcga ctcagacatc    3120
ctgaaagact catttgatct ggccagtgag ttgaaaggcg aaaagctcat gttgtacagg    3180
gatccttctg gaaatgtgtt cccctctgat aagtggatgg ccgcaggcgt cttctttggc    3240
aaactggaga gaatactcat atcaaagttg acaaaccagt attcaataag cacaatagaa    3300
gatgactcaa gcaagcaaag catg                                           3324

<210> SEQ ID NO 5
<211> LENGTH: 1129
<212> TYPE: PRT
<213> ORGANISM: Alicyclobacillus acidoterrestris

<400> SEQUENCE: 5

Met Ala Val Lys Ser Ile Lys Val Lys Leu Arg Leu Asp Asp Met Pro
1               5                   10                  15

Glu Ile Arg Ala Gly Leu Trp Lys Leu His Lys Glu Val Asn Ala Gly
            20                  25                  30

Val Arg Tyr Tyr Thr Glu Trp Leu Ser Leu Leu Arg Gln Glu Asn Leu
        35                  40                  45

Tyr Arg Arg Ser Pro Asn Gly Asp Gly Glu Gln Glu Cys Asp Lys Thr
    50                  55                  60

Ala Glu Glu Cys Lys Ala Glu Leu Leu Glu Arg Leu Arg Ala Arg Gln
65                  70                  75                  80

Val Glu Asn Gly His Arg Gly Pro Ala Gly Ser Asp Asp Glu Leu Leu
                85                  90                  95

Gln Leu Ala Arg Gln Leu Tyr Glu Leu Leu Val Pro Gln Ala Ile Gly
            100                 105                 110

Ala Lys Gly Asp Ala Gln Gln Ile Ala Arg Lys Phe Leu Ser Pro Leu
        115                 120                 125

Ala Asp Lys Asp Ala Val Gly Gly Leu Gly Ile Ala Lys Ala Gly Asn
    130                 135                 140

Lys Pro Arg Trp Val Arg Met Arg Glu Ala Gly Glu Pro Gly Trp Glu
145                 150                 155                 160

Glu Glu Lys Glu Lys Ala Glu Thr Arg Lys Ser Ala Asp Arg Thr Ala
                165                 170                 175

Asp Val Leu Arg Ala Leu Ala Asp Phe Gly Leu Lys Pro Leu Met Arg
            180                 185                 190

Val Tyr Thr Asp Ser Glu Met Ser Ser Val Glu Trp Lys Pro Leu Arg
        195                 200                 205

Lys Gly Gln Ala Val Arg Thr Trp Asp Arg Asp Met Phe Gln Gln Ala
    210                 215                 220

Ile Glu Arg Met Met Ser Trp Glu Ser Trp Asn Gln Arg Val Gly Gln
225                 230                 235                 240

Glu Tyr Ala Lys Leu Val Glu Gln Lys Asn Arg Phe Glu Gln Lys Asn
                245                 250                 255

Phe Val Gly Gln Glu His Leu Val His Leu Val Asn Gln Leu Gln Gln
            260                 265                 270

Asp Met Lys Glu Ala Ser Pro Gly Leu Glu Ser Lys Glu Gln Thr Ala
        275                 280                 285

His Tyr Val Thr Gly Arg Ala Leu Arg Gly Ser Asp Lys Val Phe Glu
    290                 295                 300

Lys Trp Gly Lys Leu Ala Pro Asp Ala Pro Phe Asp Leu Tyr Asp Ala
305                 310                 315                 320
```

```
Glu Ile Lys Asn Val Gln Arg Asn Thr Arg Arg Phe Gly Ser His
                325                 330                 335

Asp Leu Phe Ala Lys Leu Ala Glu Pro Glu Tyr Gln Ala Leu Trp Arg
                340                 345                 350

Glu Asp Ala Ser Phe Leu Thr Arg Tyr Ala Val Tyr Asn Ser Ile Leu
                355                 360                 365

Arg Lys Leu Asn His Ala Lys Met Phe Ala Thr Phe Thr Leu Pro Asp
                370                 375                 380

Ala Thr Ala His Pro Ile Trp Thr Arg Phe Asp Lys Leu Gly Gly Asn
385                 390                 395                 400

Leu His Gln Tyr Thr Phe Leu Phe Asn Glu Phe Gly Glu Arg Arg His
                405                 410                 415

Ala Ile Arg Phe His Lys Leu Leu Lys Val Glu Asn Gly Val Ala Arg
                420                 425                 430

Glu Val Asp Asp Val Thr Val Pro Ile Ser Met Ser Glu Gln Leu Asp
                435                 440                 445

Asn Leu Leu Pro Arg Asp Pro Asn Glu Pro Ile Ala Leu Tyr Phe Arg
                450                 455                 460

Asp Tyr Gly Ala Glu Gln His Phe Thr Gly Glu Phe Gly Gly Ala Lys
465                 470                 475                 480

Ile Gln Cys Arg Arg Asp Gln Leu Ala His Met His Arg Arg Arg Gly
                485                 490                 495

Ala Arg Asp Val Tyr Leu Asn Val Ser Val Arg Val Gln Ser Gln Ser
                500                 505                 510

Glu Ala Arg Gly Glu Arg Pro Pro Tyr Ala Ala Val Phe Arg Leu
                515                 520                 525

Val Gly Asp Asn His Arg Ala Phe Val His Phe Asp Lys Leu Ser Asp
                530                 535                 540

Tyr Leu Ala Glu His Pro Asp Asp Gly Lys Leu Gly Ser Glu Gly Leu
545                 550                 555                 560

Leu Ser Gly Leu Arg Val Met Ser Val Asp Leu Gly Leu Arg Thr Ser
                565                 570                 575

Ala Ser Ile Ser Val Phe Arg Val Ala Arg Lys Asp Glu Leu Lys Pro
                580                 585                 590

Asn Ser Lys Gly Arg Val Pro Phe Phe Phe Pro Ile Lys Gly Asn Asp
                595                 600                 605

Asn Leu Val Ala Val His Glu Arg Ser Gln Leu Leu Lys Leu Pro Gly
                610                 615                 620

Glu Thr Glu Ser Lys Asp Leu Arg Ala Ile Arg Glu Glu Arg Gln Arg
625                 630                 635                 640

Thr Leu Arg Gln Leu Arg Thr Gln Leu Ala Tyr Leu Arg Leu Leu Val
                645                 650                 655

Arg Cys Gly Ser Glu Asp Val Gly Arg Arg Glu Arg Ser Trp Ala Lys
                660                 665                 670

Leu Ile Glu Gln Pro Val Asp Ala Ala Asn His Met Thr Pro Asp Trp
                675                 680                 685

Arg Glu Ala Phe Glu Asn Glu Leu Gln Lys Leu Lys Ser Leu His Gly
                690                 695                 700

Ile Cys Ser Asp Lys Glu Trp Met Asp Ala Val Tyr Glu Ser Val Arg
705                 710                 715                 720

Arg Val Trp Arg His Met Gly Lys Gln Val Arg Asp Trp Arg Lys Asp
                725                 730                 735
```

-continued

Val Arg Ser Gly Glu Arg Pro Lys Ile Arg Gly Tyr Ala Lys Asp Val
            740                 745                 750

Val Gly Gly Asn Ser Ile Glu Gln Ile Glu Tyr Leu Glu Arg Gln Tyr
        755                 760                 765

Lys Phe Leu Lys Ser Trp Ser Phe Phe Gly Lys Val Ser Gly Gln Val
    770                 775                 780

Ile Arg Ala Glu Lys Gly Ser Arg Phe Ala Ile Thr Leu Arg Glu His
785                 790                 795                 800

Ile Asp His Ala Lys Glu Asp Arg Leu Lys Lys Leu Ala Asp Arg Ile
                805                 810                 815

Ile Met Glu Ala Leu Gly Tyr Val Tyr Ala Leu Asp Glu Arg Gly Lys
            820                 825                 830

Gly Lys Trp Val Ala Lys Tyr Pro Pro Cys Gln Leu Ile Leu Leu Glu
        835                 840                 845

Glu Leu Ser Glu Tyr Gln Phe Asn Asn Asp Arg Pro Pro Ser Glu Asn
    850                 855                 860

Asn Gln Leu Met Gln Trp Ser His Arg Gly Val Phe Gln Glu Leu Ile
865                 870                 875                 880

Asn Gln Ala Gln Val His Asp Leu Leu Val Gly Thr Met Tyr Ala Ala
                885                 890                 895

Phe Ser Ser Arg Phe Asp Ala Arg Thr Gly Ala Pro Gly Ile Arg Cys
            900                 905                 910

Arg Arg Val Pro Ala Arg Cys Thr Gln Glu His Asn Pro Glu Pro Phe
        915                 920                 925

Pro Trp Trp Leu Asn Lys Phe Val Val Glu His Thr Leu Asp Ala Cys
    930                 935                 940

Pro Leu Arg Ala Asp Asp Leu Ile Pro Thr Gly Glu Gly Glu Ile Phe
945                 950                 955                 960

Val Ser Pro Phe Ser Ala Glu Glu Gly Asp Phe His Gln Ile His Ala
                965                 970                 975

Asp Leu Asn Ala Ala Gln Asn Leu Gln Gln Arg Leu Trp Ser Asp Phe
            980                 985                 990

Asp Ile Ser Gln Ile Arg Leu Arg Cys Asp Trp Gly Glu Val Asp Gly
        995                 1000                1005

Glu Leu Val Leu Ile Pro Arg Leu Thr Gly Lys Arg Thr Ala Asp
    1010                1015                1020

Ser Tyr Ser Asn Lys Val Phe Tyr Thr Asn Thr Gly Val Thr Tyr
    1025                1030                1035

Tyr Glu Arg Glu Arg Gly Lys Lys Arg Arg Lys Val Phe Ala Gln
    1040                1045                1050

Glu Lys Leu Ser Glu Glu Ala Glu Leu Leu Val Glu Ala Asp
    1055                1060                1065

Glu Ala Arg Glu Lys Ser Val Val Leu Met Arg Asp Pro Ser Gly
    1070                1075                1080

Ile Ile Asn Arg Gly Asn Trp Thr Arg Gln Lys Glu Phe Trp Ser
    1085                1090                1095

Met Val Asn Gln Arg Ile Glu Gly Tyr Leu Val Lys Gln Ile Arg
    1100                1105                1110

Ser Arg Val Pro Leu Gln Asp Ser Ala Cys Glu Asn Thr Gly Asp
    1115                1120                1125

Ile

<210> SEQ ID NO 6

```
<211> LENGTH: 1108
<212> TYPE: PRT
<213> ORGANISM: Bacillus thermoamylovorans

<400> SEQUENCE: 6

Met Ala Thr Arg Ser Phe Ile Leu Lys Ile Glu Pro Asn Glu Val
1               5                   10                  15

Lys Lys Gly Leu Trp Lys Thr His Glu Val Leu Asn His Gly Ile Ala
            20                  25                  30

Tyr Tyr Met Asn Ile Leu Lys Leu Ile Arg Gln Glu Ala Ile Tyr Glu
            35                  40                  45

His His Glu Gln Asp Pro Lys Asn Pro Lys Lys Val Ser Lys Ala Glu
50                  55                  60

Ile Gln Ala Glu Leu Trp Asp Phe Val Leu Lys Met Gln Lys Cys Asn
65                  70                  75                  80

Ser Phe Thr His Glu Val Asp Lys Asp Val Phe Asn Ile Leu Arg
                85                  90                  95

Glu Leu Tyr Glu Glu Leu Val Pro Ser Ser Val Glu Lys Lys Gly Glu
            100                 105                 110

Ala Asn Gln Leu Ser Asn Lys Phe Leu Tyr Pro Leu Val Asp Pro Asn
            115                 120                 125

Ser Gln Ser Gly Lys Gly Thr Ala Ser Ser Gly Arg Lys Pro Arg Trp
130                 135                 140

Tyr Asn Leu Lys Ile Ala Gly Asp Pro Ser Glu Glu Glu Lys Lys
145                 150                 155                 160

Lys Trp Glu Glu Asp Lys Lys Lys Asp Pro Leu Ala Lys Ile Leu Gly
                165                 170                 175

Lys Leu Ala Glu Tyr Gly Leu Ile Pro Leu Phe Ile Pro Phe Thr Asp
            180                 185                 190

Ser Asn Glu Pro Ile Val Lys Glu Ile Lys Trp Met Glu Lys Ser Arg
            195                 200                 205

Asn Gln Ser Val Arg Arg Leu Asp Lys Asp Met Phe Ile Gln Ala Leu
    210                 215                 220

Glu Arg Phe Leu Ser Trp Glu Ser Trp Asn Leu Lys Val Lys Glu Glu
225                 230                 235                 240

Tyr Glu Lys Val Glu Lys Glu His Lys Thr Leu Glu Glu Arg Ile Lys
                245                 250                 255

Glu Asp Ile Gln Ala Phe Lys Ser Leu Glu Gln Tyr Glu Lys Glu Arg
            260                 265                 270

Gln Glu Gln Leu Leu Arg Asp Thr Leu Asn Thr Asn Glu Tyr Arg Leu
        275                 280                 285

Ser Lys Arg Gly Leu Arg Gly Trp Arg Glu Ile Ile Gln Lys Trp Leu
    290                 295                 300

Lys Met Asp Glu Asn Glu Pro Ser Glu Lys Tyr Leu Glu Val Phe Lys
305                 310                 315                 320

Asp Tyr Gln Arg Lys His Pro Arg Glu Ala Gly Asp Tyr Ser Val Tyr
                325                 330                 335

Glu Phe Leu Ser Lys Lys Glu Asn His Phe Ile Trp Arg Asn His Pro
            340                 345                 350

Glu Tyr Pro Tyr Leu Tyr Ala Thr Phe Cys Glu Ile Asp Lys Lys Lys
        355                 360                 365

Lys Asp Ala Lys Gln Gln Ala Thr Phe Thr Leu Ala Asp Pro Ile Asn
    370                 375                 380

His Pro Leu Trp Val Arg Phe Glu Glu Arg Ser Gly Ser Asn Leu Asn
```

-continued

```
            385                 390                 395                 400

Lys Tyr Arg Ile Leu Thr Glu Gln Leu His Thr Glu Lys Leu Lys Lys
                    405                 410                 415

Lys Leu Thr Val Gln Leu Asp Arg Leu Ile Tyr Pro Thr Glu Ser Gly
                420                 425                 430

Gly Trp Glu Glu Lys Gly Lys Val Asp Ile Val Leu Leu Pro Ser Arg
            435                 440                 445

Gln Phe Tyr Asn Gln Ile Phe Leu Asp Ile Glu Glu Lys Gly Lys His
        450                 455                 460

Ala Phe Thr Tyr Lys Asp Glu Ser Ile Lys Phe Pro Leu Lys Gly Thr
465                 470                 475                 480

Leu Gly Gly Ala Arg Val Gln Phe Asp Arg Asp His Leu Arg Arg Tyr
                485                 490                 495

Pro His Lys Val Glu Ser Gly Asn Val Gly Arg Ile Tyr Phe Asn Met
                500                 505                 510

Thr Val Asn Ile Glu Pro Thr Glu Ser Pro Val Ser Lys Ser Leu Lys
                515                 520                 525

Ile His Arg Asp Asp Phe Pro Lys Phe Val Asn Phe Lys Pro Lys Glu
            530                 535                 540

Leu Thr Glu Trp Ile Lys Asp Ser Lys Gly Lys Lys Leu Lys Ser Gly
545                 550                 555                 560

Ile Glu Ser Leu Glu Ile Gly Leu Arg Val Met Ser Ile Asp Leu Gly
                565                 570                 575

Gln Arg Gln Ala Ala Ala Ser Ile Phe Glu Val Val Asp Gln Lys
            580                 585                 590

Pro Asp Ile Glu Gly Lys Leu Phe Phe Pro Ile Lys Gly Thr Glu Leu
            595                 600                 605

Tyr Ala Val His Arg Ala Ser Phe Asn Ile Lys Leu Pro Gly Glu Thr
        610                 615                 620

Leu Val Lys Ser Arg Glu Val Leu Arg Lys Ala Arg Glu Asp Asn Leu
625                 630                 635                 640

Lys Leu Met Asn Gln Lys Leu Asn Phe Leu Arg Asn Val Leu His Phe
                645                 650                 655

Gln Gln Phe Glu Asp Ile Thr Glu Arg Glu Lys Arg Val Thr Lys Trp
            660                 665                 670

Ile Ser Arg Gln Glu Asn Ser Asp Val Pro Leu Val Tyr Gln Asp Glu
        675                 680                 685

Leu Ile Gln Ile Arg Glu Leu Met Tyr Lys Pro Tyr Lys Asp Trp Val
        690                 695                 700

Ala Phe Leu Lys Gln Leu His Lys Arg Leu Glu Val Glu Ile Gly Lys
705                 710                 715                 720

Glu Val Lys His Trp Arg Lys Ser Leu Ser Asp Gly Arg Lys Gly Leu
                725                 730                 735

Tyr Gly Ile Ser Leu Lys Asn Ile Asp Glu Ile Asp Arg Thr Arg Lys
                740                 745                 750

Phe Leu Leu Arg Trp Ser Leu Arg Pro Thr Glu Pro Gly Glu Val Arg
            755                 760                 765

Arg Leu Glu Pro Gly Gln Arg Phe Ala Ile Asp Gln Leu Asn His Leu
        770                 775                 780

Asn Ala Leu Lys Glu Asp Arg Leu Lys Lys Met Ala Asn Thr Ile Ile
785                 790                 795                 800

Met His Ala Leu Gly Tyr Cys Tyr Asp Val Arg Lys Lys Lys Trp Gln
                805                 810                 815
```

Ala Lys Asn Pro Ala Cys Gln Ile Ile Leu Phe Glu Asp Leu Ser Asn
            820                 825                 830

Tyr Asn Pro Tyr Glu Glu Arg Ser Arg Phe Glu Asn Ser Lys Leu Met
            835                 840                 845

Lys Trp Ser Arg Arg Glu Ile Pro Arg Gln Val Ala Leu Gln Gly Glu
        850                 855                 860

Ile Tyr Gly Leu Gln Val Gly Glu Val Gly Ala Gln Phe Ser Arg
865                 870                 875                 880

Phe His Ala Lys Thr Gly Ser Pro Gly Ile Arg Cys Ser Val Val Thr
                885                 890                 895

Lys Glu Lys Leu Gln Asp Asn Arg Phe Phe Lys Asn Leu Gln Arg Glu
            900                 905                 910

Gly Arg Leu Thr Leu Asp Lys Ile Ala Val Leu Lys Glu Gly Asp Leu
        915                 920                 925

Tyr Pro Asp Lys Gly Gly Glu Lys Phe Ile Ser Leu Ser Lys Asp Arg
930                 935                 940

Lys Leu Val Thr Thr His Ala Asp Ile Asn Ala Ala Gln Asn Leu Gln
945                 950                 955                 960

Lys Arg Phe Trp Thr Arg Thr His Gly Phe Tyr Lys Val Tyr Cys Lys
                965                 970                 975

Ala Tyr Gln Val Asp Gly Gln Thr Val Tyr Ile Pro Glu Ser Lys Asp
            980                 985                 990

Gln Lys Gln Lys Ile Ile Glu Glu Phe Gly Glu Gly Tyr Phe Ile Leu
        995                 1000                1005

Lys Asp Gly Val Tyr Glu Trp Gly Asn Ala Gly Lys Leu Lys Ile
    1010                1015                1020

Lys Lys Gly Ser Ser Lys Gln Ser Ser Ser Glu Leu Val Asp Ser
    1025                1030                1035

Asp Ile Leu Lys Asp Ser Phe Asp Leu Ala Ser Glu Leu Lys Gly
    1040                1045                1050

Glu Lys Leu Met Leu Tyr Arg Asp Pro Ser Gly Asn Val Phe Pro
    1055                1060                1065

Ser Asp Lys Trp Met Ala Ala Gly Val Phe Phe Gly Lys Leu Glu
    1070                1075                1080

Arg Ile Leu Ile Ser Lys Leu Thr Asn Gln Tyr Ser Ile Ser Thr
    1085                1090                1095

Ile Glu Asp Asp Ser Ser Lys Gln Ser Met
    1100                1105

<210> SEQ ID NO 7
<211> LENGTH: 1129
<212> TYPE: PRT
<213> ORGANISM: Alicyclobacillus acidiphilus

<400> SEQUENCE: 7

Met Ala Val Lys Ser Met Lys Val Lys Leu Arg Leu Asp Asn Met Pro
1               5                   10                  15

Glu Ile Arg Ala Gly Leu Trp Lys Leu His Thr Glu Val Asn Ala Gly
            20                  25                  30

Val Arg Tyr Tyr Thr Glu Trp Leu Ser Leu Leu Arg Gln Glu Asn Leu
        35                  40                  45

Tyr Arg Arg Ser Pro Asn Gly Asp Gly Glu Gln Glu Cys Tyr Lys Thr
    50                  55                  60

Ala Glu Glu Cys Lys Ala Glu Leu Leu Glu Arg Leu Arg Ala Arg Gln

```
                65                  70                  75                  80
Val Glu Asn Gly His Cys Gly Pro Ala Gly Ser Asp Asp Glu Leu Leu
                        85                  90                  95
Gln Leu Ala Arg Gln Leu Tyr Glu Leu Leu Val Pro Gln Ala Ile Gly
                    100                 105                 110
Ala Lys Gly Asp Ala Gln Ile Ala Arg Lys Phe Leu Ser Pro Leu
                115                 120                 125
Ala Asp Lys Asp Ala Val Gly Gly Leu Gly Ile Ala Lys Ala Gly Asn
            130                 135                 140
Lys Pro Arg Trp Val Arg Met Arg Glu Ala Gly Pro Gly Trp Glu
145                 150                 155                 160
Glu Glu Lys Ala Lys Ala Glu Ala Arg Lys Ser Thr Asp Arg Thr Ala
                    165                 170                 175
Asp Val Leu Arg Ala Leu Ala Asp Phe Gly Leu Lys Pro Leu Met Arg
                180                 185                 190
Val Tyr Thr Asp Ser Asp Met Ser Ser Val Gln Trp Lys Pro Leu Arg
            195                 200                 205
Lys Gly Gln Ala Val Arg Thr Trp Asp Arg Asp Met Phe Gln Gln Ala
210                 215                 220
Ile Glu Arg Met Met Ser Trp Glu Ser Trp Asn Gln Arg Val Gly Glu
225                 230                 235                 240
Ala Tyr Ala Lys Leu Val Glu Gln Lys Ser Arg Phe Glu Gln Lys Asn
                245                 250                 255
Phe Val Gly Gln Glu His Leu Val Gln Leu Val Asn Gln Leu Gln Gln
                260                 265                 270
Asp Met Lys Glu Ala Ser His Gly Leu Glu Ser Lys Glu Gln Thr Ala
            275                 280                 285
His Tyr Leu Thr Gly Arg Ala Leu Arg Gly Ser Asp Lys Val Phe Glu
            290                 295                 300
Lys Trp Glu Lys Leu Asp Pro Asp Ala Pro Phe Asp Leu Tyr Asp Thr
305                 310                 315                 320
Glu Ile Lys Asn Val Gln Arg Arg Asn Thr Arg Arg Phe Gly Ser His
                325                 330                 335
Asp Leu Phe Ala Lys Leu Ala Glu Pro Lys Tyr Gln Ala Leu Trp Arg
            340                 345                 350
Glu Asp Ala Ser Phe Leu Thr Arg Tyr Ala Val Tyr Asn Ser Ile Val
            355                 360                 365
Arg Lys Leu Asn His Ala Lys Met Phe Ala Thr Phe Thr Leu Pro Asp
        370                 375                 380
Ala Thr Ala His Pro Ile Trp Thr Arg Phe Asp Lys Leu Gly Gly Asn
385                 390                 395                 400
Leu His Gln Tyr Thr Phe Leu Phe Asn Glu Phe Gly Glu Gly Arg His
                    405                 410                 415
Ala Ile Arg Phe Gln Lys Leu Leu Thr Val Glu Asp Gly Val Ala Lys
                420                 425                 430
Glu Val Asp Asp Val Thr Val Pro Ile Ser Met Ser Ala Gln Leu Asp
            435                 440                 445
Asp Leu Leu Pro Arg Asp Pro His Glu Leu Val Ala Leu Tyr Phe Gln
        450                 455                 460
Asp Tyr Gly Ala Glu Gln His Leu Ala Gly Glu Phe Gly Gly Ala Lys
465                 470                 475                 480
Ile Gln Tyr Arg Arg Asp Gln Leu Asn His Leu His Ala Arg Arg Gly
                485                 490                 495
```

```
Ala Arg Asp Val Tyr Leu Asn Leu Ser Val Arg Val Gln Ser Gln Ser
            500                 505                 510

Glu Ala Arg Gly Glu Arg Arg Pro Pro Tyr Ala Ala Val Phe Arg Leu
            515                 520                 525

Val Gly Asp Asn His Arg Ala Phe Val His Phe Asp Lys Leu Ser Asp
            530                 535                 540

Tyr Leu Ala Glu His Pro Asp Asp Gly Lys Leu Gly Ser Glu Gly Leu
545                 550                 555                 560

Leu Ser Gly Leu Arg Val Met Ser Val Asp Leu Gly Leu Arg Thr Ser
                565                 570                 575

Ala Ser Ile Ser Val Phe Arg Val Ala Arg Lys Asp Glu Leu Lys Pro
                580                 585                 590

Asn Ser Glu Gly Arg Val Pro Phe Cys Phe Pro Ile Glu Gly Asn Glu
                595                 600                 605

Asn Leu Val Ala Val His Glu Arg Ser Gln Leu Leu Lys Leu Pro Gly
            610                 615                 620

Glu Thr Glu Ser Lys Asp Leu Arg Ala Ile Arg Glu Arg Gln Arg
625                 630                 635                 640

Thr Leu Arg Gln Leu Arg Thr Gln Leu Ala Tyr Leu Arg Leu Leu Val
                645                 650                 655

Arg Cys Gly Ser Glu Asp Val Gly Arg Arg Glu Arg Ser Trp Ala Lys
                660                 665                 670

Leu Ile Glu Gln Pro Met Asp Ala Asn Gln Met Thr Pro Asp Trp Arg
                675                 680                 685

Glu Ala Phe Glu Asp Glu Leu Gln Lys Leu Lys Ser Leu Tyr Gly Ile
            690                 695                 700

Cys Gly Asp Arg Glu Trp Thr Glu Ala Val Tyr Glu Ser Val Arg Arg
705                 710                 715                 720

Val Trp Arg His Met Gly Lys Gln Val Arg Asp Trp Arg Lys Asp Val
                725                 730                 735

Arg Ser Gly Glu Arg Pro Lys Ile Arg Gly Tyr Gln Lys Asp Val Val
                740                 745                 750

Gly Gly Asn Ser Ile Glu Gln Ile Glu Tyr Leu Glu Arg Gln Tyr Lys
            755                 760                 765

Phe Leu Lys Ser Trp Ser Phe Phe Gly Lys Val Ser Gly Gln Val Ile
            770                 775                 780

Arg Ala Glu Lys Gly Ser Arg Phe Ala Ile Thr Leu Arg Glu His Ile
785                 790                 795                 800

Asp His Ala Lys Glu Asp Arg Leu Lys Lys Leu Ala Asp Arg Ile Ile
                805                 810                 815

Met Glu Ala Leu Gly Tyr Val Tyr Ala Leu Asp Asp Glu Arg Gly Lys
            820                 825                 830

Gly Lys Trp Val Ala Lys Tyr Pro Pro Cys Gln Leu Ile Leu Leu Glu
            835                 840                 845

Glu Leu Ser Glu Tyr Gln Phe Asn Asn Asp Arg Pro Pro Ser Glu Asn
            850                 855                 860

Asn Gln Leu Met Gln Trp Ser His Arg Gly Val Phe Gln Glu Leu Leu
865                 870                 875                 880

Asn Gln Ala Gln Val His Asp Leu Leu Val Gly Thr Met Tyr Ala Ala
                885                 890                 895

Phe Ser Ser Arg Phe Asp Ala Arg Thr Gly Ala Pro Gly Ile Arg Cys
            900                 905                 910
```

```
Arg Arg Val Pro Ala Arg Cys Ala Arg Glu Gln Asn Pro Glu Pro Phe
            915                 920                 925

Pro Trp Trp Leu Asn Lys Phe Val Ala Glu His Lys Leu Asp Gly Cys
    930                 935                 940

Pro Leu Arg Ala Asp Asp Leu Ile Pro Thr Gly Glu Gly Phe Phe
945                 950                 955                 960

Val Ser Pro Phe Ser Ala Glu Glu Gly Asp Phe His Gln Ile His Ala
            965                 970                 975

Asp Leu Asn Ala Ala Gln Asn Leu Gln Arg Arg Leu Trp Ser Asp Phe
            980                 985                 990

Asp Ile Ser Gln Ile Arg Leu Arg Cys Asp Trp Gly Glu Val Asp Gly
            995                 1000                1005

Glu Pro Val Leu Ile Pro Arg Thr Thr Gly Lys Arg Thr Ala Asp
    1010                1015                1020

Ser Tyr Gly Asn Lys Val Phe Tyr Thr Lys Thr Gly Val Thr Tyr
    1025                1030                1035

Tyr Glu Arg Glu Arg Gly Lys Lys Arg Ala Lys Val Phe Ala Gln
    1040                1045                1050

Glu Glu Leu Ser Glu Glu Ala Glu Leu Leu Val Glu Ala Asp
    1055                1060                1065

Glu Ala Arg Glu Lys Ser Val Val Leu Met Arg Asp Pro Ser Gly
    1070                1075                1080

Ile Ile Asn Arg Gly Asp Trp Thr Arg Gln Lys Glu Phe Trp Ser
    1085                1090                1095

Met Val Asn Gln Arg Ile Glu Gly Tyr Leu Val Lys Gln Ile Arg
    1100                1105                1110

Ser Arg Val Arg Leu Gln Glu Ser Ala Cys Glu Asn Thr Gly Asp
    1115                1120                1125

Ile

<210> SEQ ID NO 8
<211> LENGTH: 1108
<212> TYPE: PRT
<213> ORGANISM: Bacillus hisashii

<400> SEQUENCE: 8

Met Ala Thr Arg Ser Phe Ile Leu Lys Ile Glu Pro Asn Glu Val
1               5                   10                  15

Lys Lys Gly Leu Trp Lys Thr His Glu Val Leu Asn His Gly Ile Ala
            20                  25                  30

Tyr Tyr Met Asn Ile Leu Lys Leu Ile Arg Gln Glu Ala Ile Tyr Glu
            35                  40                  45

His His Glu Gln Asp Pro Lys Asn Pro Lys Val Ser Lys Ala Glu
    50                  55                  60

Ile Gln Ala Glu Leu Trp Asp Phe Val Leu Lys Met Gln Lys Cys Asn
65                  70                  75                  80

Ser Phe Thr His Glu Val Asp Lys Asp Glu Val Phe Asn Ile Leu Arg
            85                  90                  95

Glu Leu Tyr Glu Glu Leu Val Pro Ser Ser Val Glu Lys Lys Gly Glu
            100                 105                 110

Ala Asn Gln Leu Ser Asn Lys Phe Leu Tyr Pro Leu Val Asp Pro Asn
            115                 120                 125

Ser Gln Ser Gly Lys Gly Thr Ala Ser Ser Gly Arg Lys Pro Arg Trp
            130                 135                 140
```

```
Tyr Asn Leu Lys Ile Ala Gly Asp Pro Ser Trp Glu Glu Lys Lys
145                 150                 155                 160

Lys Trp Glu Glu Asp Lys Lys Asp Pro Leu Ala Lys Ile Leu Gly
        165                 170                 175

Lys Leu Ala Glu Tyr Gly Leu Ile Pro Leu Phe Ile Pro Tyr Thr Asp
            180                 185                 190

Ser Asn Glu Pro Ile Val Lys Glu Ile Lys Trp Met Glu Lys Ser Arg
        195                 200                 205

Asn Gln Ser Val Arg Arg Leu Asp Lys Asp Met Phe Ile Gln Ala Leu
    210                 215                 220

Glu Arg Phe Leu Ser Trp Glu Ser Trp Asn Leu Lys Val Lys Glu Glu
225                 230                 235                 240

Tyr Glu Lys Val Glu Lys Glu Tyr Lys Thr Leu Glu Glu Arg Ile Lys
            245                 250                 255

Glu Asp Ile Gln Ala Leu Lys Ala Leu Glu Gln Tyr Glu Lys Glu Arg
            260                 265                 270

Gln Glu Gln Leu Leu Arg Asp Thr Leu Asn Thr Asn Glu Tyr Arg Leu
        275                 280                 285

Ser Lys Arg Gly Leu Arg Gly Trp Arg Glu Ile Ile Gln Lys Trp Leu
        290                 295                 300

Lys Met Asp Glu Asn Glu Pro Ser Glu Lys Tyr Leu Glu Val Phe Lys
305                 310                 315                 320

Asp Tyr Gln Arg Lys His Pro Arg Glu Ala Gly Asp Tyr Ser Val Tyr
            325                 330                 335

Glu Phe Leu Ser Lys Lys Glu Asn His Phe Ile Trp Arg Asn His Pro
        340                 345                 350

Glu Tyr Pro Tyr Leu Tyr Ala Thr Phe Cys Glu Ile Asp Lys Lys Lys
        355                 360                 365

Lys Asp Ala Lys Gln Ala Thr Phe Thr Leu Ala Asp Pro Ile Asn
    370                 375                 380

His Pro Leu Trp Val Arg Phe Glu Glu Arg Ser Gly Ser Asn Leu Asn
385                 390                 395                 400

Lys Tyr Arg Ile Leu Thr Glu Gln Leu His Thr Glu Lys Leu Lys Lys
            405                 410                 415

Lys Leu Thr Val Gln Leu Asp Arg Leu Ile Tyr Pro Thr Glu Ser Gly
        420                 425                 430

Gly Trp Glu Glu Lys Gly Lys Val Asp Ile Val Leu Leu Pro Ser Arg
        435                 440                 445

Gln Phe Tyr Asn Gln Ile Phe Leu Asp Ile Glu Glu Lys Gly Lys His
    450                 455                 460

Ala Phe Thr Tyr Lys Asp Glu Ser Ile Lys Phe Pro Leu Lys Gly Thr
465                 470                 475                 480

Leu Gly Gly Ala Arg Val Gln Phe Asp Arg Asp His Leu Arg Arg Tyr
            485                 490                 495

Pro His Lys Val Glu Ser Gly Asn Val Gly Arg Ile Tyr Phe Asn Met
        500                 505                 510

Thr Val Asn Ile Glu Pro Thr Glu Ser Pro Val Ser Lys Ser Leu Lys
        515                 520                 525

Ile His Arg Asp Asp Phe Pro Lys Val Val Asn Phe Lys Pro Lys Glu
    530                 535                 540

Leu Thr Glu Trp Ile Lys Asp Ser Lys Gly Lys Lys Leu Lys Ser Gly
545                 550                 555                 560

Ile Glu Ser Leu Glu Ile Gly Leu Arg Val Met Ser Ile Asp Leu Gly
```

```
                565                 570                 575
Gln Arg Gln Ala Ala Ala Ser Ile Phe Glu Val Val Asp Gln Lys
            580                 585                 590

Pro Asp Ile Glu Gly Lys Leu Phe Phe Pro Ile Lys Gly Thr Glu Leu
            595                 600                 605

Tyr Ala Val His Arg Ala Ser Phe Asn Ile Lys Leu Pro Gly Glu Thr
            610                 615                 620

Leu Val Lys Ser Arg Glu Val Leu Arg Lys Ala Arg Glu Asp Asn Leu
625                 630                 635                 640

Lys Leu Met Asn Gln Lys Leu Asn Phe Leu Arg Asn Val Leu His Phe
            645                 650                 655

Gln Gln Phe Glu Asp Ile Thr Glu Arg Glu Lys Arg Val Thr Lys Trp
            660                 665                 670

Ile Ser Arg Gln Glu Asn Ser Asp Val Pro Leu Val Tyr Gln Asp Glu
            675                 680                 685

Leu Ile Gln Ile Arg Glu Leu Met Tyr Lys Pro Tyr Lys Asp Trp Val
            690                 695                 700

Ala Phe Leu Lys Gln Leu His Lys Arg Leu Glu Val Glu Ile Gly Lys
705                 710                 715                 720

Glu Val Lys His Trp Arg Lys Ser Leu Ser Asp Gly Arg Lys Gly Leu
                725                 730                 735

Tyr Gly Ile Ser Leu Lys Asn Ile Asp Glu Ile Asp Arg Thr Arg Lys
            740                 745                 750

Phe Leu Leu Arg Trp Ser Leu Arg Pro Thr Glu Pro Gly Glu Val Arg
            755                 760                 765

Arg Leu Glu Pro Gly Gln Arg Phe Ala Ile Asp Gln Leu Asn His Leu
            770                 775                 780

Asn Ala Leu Lys Glu Asp Arg Leu Lys Lys Met Ala Asn Thr Ile Ile
785                 790                 795                 800

Met His Ala Leu Gly Tyr Cys Tyr Asp Val Arg Lys Lys Lys Trp Gln
                805                 810                 815

Ala Lys Asn Pro Ala Cys Gln Ile Ile Leu Phe Glu Asp Leu Ser Asn
            820                 825                 830

Tyr Asn Pro Tyr Gly Glu Arg Ser Arg Phe Glu Asn Ser Arg Leu Met
            835                 840                 845

Lys Trp Ser Arg Arg Glu Ile Pro Arg Gln Val Ala Leu Gln Gly Glu
            850                 855                 860

Ile Tyr Gly Leu Gln Val Gly Glu Val Gly Ala Gln Phe Ser Ser Arg
865                 870                 875                 880

Phe His Ala Lys Thr Gly Ser Pro Gly Ile Arg Cys Arg Val Val Thr
                885                 890                 895

Lys Glu Lys Leu Gln Asp Asn Arg Phe Phe Lys Asn Leu Gln Arg Glu
            900                 905                 910

Gly Arg Leu Thr Leu Asp Lys Ile Ala Val Leu Lys Glu Gly Asp Leu
            915                 920                 925

Tyr Pro Asp Lys Gly Gly Glu Lys Phe Ile Ser Leu Ser Lys Asp Arg
            930                 935                 940

Lys Cys Val Thr Thr His Ala Asp Ile Asn Ala Ala Gln Asn Leu Gln
945                 950                 955                 960

Lys Arg Phe Trp Thr Arg Thr His Gly Phe Tyr Lys Val Tyr Cys Lys
                965                 970                 975

Ala Tyr Gln Val Asp Gly Gln Thr Val Tyr Ile Pro Glu Ser Lys Asp
            980                 985                 990
```

```
Gln Lys Gln Lys Ile Ile Glu Glu  Phe Gly Glu Gly Tyr  Phe Ile Leu
        995                 1000                 1005

Lys Asp  Gly Val Tyr Glu Trp  Val Asn Ala Gly Lys  Leu Lys Ile
    1010                 1015                 1020

Lys Lys  Gly Ser Ser Lys Gln  Ser Ser Ser Glu Leu  Val Asp Ser
    1025                 1030                 1035

Asp Ile  Leu Lys Asp Ser Phe  Asp Leu Ala Ser Glu  Leu Lys Gly
    1040                 1045                 1050

Glu Lys  Leu Met Leu Tyr Arg  Asp Pro Ser Gly Asn  Val Phe Pro
    1055                 1060                 1065

Ser Asp  Lys Trp Met Ala Ala  Gly Val Phe Phe Gly  Lys Leu Glu
    1070                 1075                 1080

Arg Ile  Leu Ile Ser Lys Leu  Thr Asn Gln Tyr Ser  Ile Ser Thr
    1085                 1090                 1095

Ile Glu  Asp Asp Ser Ser Lys  Gln Ser Met
    1100                 1105

<210> SEQ ID NO 9
<211> LENGTH: 3387
<212> TYPE: DNA
<213> ORGANISM: Artificial Sequence
<220> FEATURE:
<223> OTHER INFORMATION: AacCas12b-D570A nucleic acid

<400> SEQUENCE: 9
atggcggtga agtcaataaa agttaaactc cgcctggacg atatgccaga aattcgggct      60
ggcctctgga agcttcacaa agaggttaac gctggcgtca gatattacac ggaatggttg     120
tcgctgctcc ggcaagaaaa tctctacaga aggtcgccca atggtgatgg ggaacaagag     180
tgcgacaaaa cggcggagga atgcaaagcg gaactccttg aaagacttcg cgcgagacaa     240
gtcgaaaacg gccatagagg cccggccggt tccgatgatg aattgcttca gcttgcgcgg     300
cagctttacg aattgctcgt gccgcaagcc ataggtgcaa aaggagatgc acaacaaatt     360
gcaagaaagt tcctctcccc gctcgcagac aaggatgccg tgggaggtct tggaatcgct     420 aaaagcaggga ataagccaag atgggtgcgg atgcgggaag caggtgagcc aggctgggaa     480
gaggagaagg agaaagccga acgaggaaaa tcagcggatc gcactgcaga cgtgttgaga     540
gccctcgcag actttggact taagccactg atgcgggttt acacggattc agagatgtcc     600
tcggtggaat ggaagccgct cagaaagggt caagccgtga aacgtgggac cgcgacatg      660 ttccagcagg caattgagcg gatgatgtcc tgggagtctt ggaaccaaag ggtcgggcaa     720
gaatatgcga aactggtgga gcaaaaaaat aggtttgaac aaaaaaattt cgttggtcaa     780
gagcatctgt tcatttggt taatcaactt caacaagata tgaaagaagc atcacctggc     840
ttggaatcta agaacaaac agcacactac gttacgggta gggcgttgag gggatcggat     900
aaagttttcg agaagtgggg taagttggcc cccgacgccc ctttcgatct gtatgacgcc     960
gagataaaga cgttcagcg aggaacact cgccgctttg gttcgcacga tctgtttgca    1020
aaactggccg agcctgagta ccaggcccct tggcggagg atgcgtcgtt ccttacacgc    1080
tacgcggttt ataattcaat tctcagaaag ctcaatcacg cgaagatgtt tgcgactttc    1140
actcttccag atgcgacggc acaccctata tggactagat tgataagtt gggggcaac    1200 ttgcaccagt atacatttct gttcaacgaa ttcggcgaac gcaggcatgc aatcaggttc    1260
cataaacttt tgaaagtcga gaatggtgtt gccagggagg ttgacgatgt cacagtgcct    1320
```

| | |
|---|---|
| atctcgatgt ccgaacaatt ggataacttg ctgcccagag atccgaacga accgattgca | 1380 |
| ctttatttca gggattatgg tgccgaacaa cactttacgg gtgagttcgg aggggccaag | 1440 |
| attcagtgca gacgggacca gcttgctcac atgcaccgca ggagaggggc tagggatgtg | 1500 |
| tatttgaacg tttcagttcg cgtgcagtcc aatccgagg cgcgggggga gcgcagacca | 1560 |
| ccatacgcgg ctgtcttccg gctggttggc gataaccata gagcgttcgt gcatttcgat | 1620 |
| aagctgagcg attacctcgc cgaacatcct gatgacggaa agttggggtc agagggctt | 1680 |
| ctgtcgggcc tgagggtgat gtccgtggcc ctgggattgc gcaccagtgc ctcgatcagc | 1740 |
| gttttttaggg tggccaggaa agatgagttg aaacccaact cgaaggggag ggttccgttc | 1800 |
| tttttcccta taagggcaa cgataacttg gtcgcagtgc atgaaaggag ccaactgctc | 1860 |
| aaacttcccg gggagacaga gtccaaagat cttcgcgcta aagggaaga gagacaaaga | 1920 |
| actctccggc agctgcgcac gcagctcgca tacctgcggt tgcttgtccg ctgcggaagt | 1980 |
| gaagacgttg gcaggcgcga gaggtcatgg gccaaattga ttgagcagcc ggtcgacgcc | 2040 |
| gcaaatcaca tgactccgga ttggaggag gctttcgaga cgaactgca gaagttgaag | 2100 |
| agtctgcatg gcatatgctc tgacaaagag tggatggacg cggtttacga gtccgtccgc | 2160 |
| cgggtctggc ggcacatggg gaaacaagtt cgcgattgga gaaggatgt tagatccggg | 2220 |
| gaaaggccga agataagagg ttatgccaaa gacgtggttg gtggaaattc tatcgaacag | 2280 |
| atcgaatatc ttgagaggca gtacaagttc ctcaagagtt ggtctttctt cggtaaagtc | 2340 |
| tctggacaag ttataagagc agaaaagggg agccggttcg ctatcacctt gcgggaacac | 2400 |
| atagaccacg caaagaaga cagactgaag aagctggcgg acagaattat catggaagcg | 2460 |
| ctggggtacg tttacgcgct ggacgaaagg gggaaggta atgggtggc caaatacccg | 2520 |
| ccatgccagt tgatattgct ggaagaattg tccgaatatc aatttaataa cgatagaccg | 2580 |
| ccatccgaga caaccaact tatgcaatgg tctcaccggg gagttttcca ggagttgatc | 2640 |
| aaccaagctc aagtgcacga tctgcttgtt ggtacaatgt acgcagcgtt tcctcacgc | 2700 |
| ttcgacgcta aacaggagc gccgggaatt cggtgccgga gggtgcctgc gaggtgtact | 2760 |
| caggagcaca cccggagcc atttccctgg tggttaata aattcgttgt ggaacatacg | 2820 |
| ttggatgctt gcccgcttcg ggcggacgac ctcattccga cgggtgaggg cgagattttc | 2880 |
| gtgtcgccat tctcggctga ggaagggac ttccatcaaa tccatgctga cctcaatgcg | 2940 |
| gcgcaaaatc tgcagcagag attgtggagt gattttgaca tctctcagat caggcttcgg | 3000 |
| tgcgattggg gagaagtcga tggtgaactc gttctcattc cgagactcac cggtaaaagg | 3060 |
| actgctgatt catattcgaa caaagttttt tacactaaca caggggtcac ttattatgaa | 3120 |
| agagaacgcg gtaagaagcg ccgcaaggtg ttcgcgcaag agaaactttc cgaggaagag | 3180 |
| gccgagttgc tcgttgaagc tgacgaagct cgcgagaagt ccgtcgttct gatgcgggat | 3240 |
| ccttctggca taataaacag ggggaattgg acacggcaga aggaatttg gtccatggtg | 3300 |
| aatcagcgca tagaaggtta tctggtcaaa cagatcagaa gcagggttcc cctccaggat | 3360 |
| tcagcgtgcg agaacacggg cgatatt | 3387 |

<210> SEQ ID NO 10
<211> LENGTH: 3387
<212> TYPE: DNA
<213> ORGANISM: Artificial Sequence
<220> FEATURE:
<223> OTHER INFORMATION: AacCas12b-D977A nucleic acid

<400> SEQUENCE: 10

```
atggcggtga agtcaataaa agttaaactc cgcctggacg atatgccaga aattcgggct      60
ggcctctgga agcttcacaa agaggttaac gctggcgtca gatattacac ggaatggttg     120
tcgctgctcc ggcaagaaaa tctctacaga aggtcgccca atggtgatgg ggaacaagag     180
tgcgacaaaa cggcggagga atgcaaagcg aactccttg aaagacttcg cgcgagacaa      240
gtcgaaaacg gccatagagg cccggccggt tccgatgatg aattgcttca gcttgcgcgg     300
cagctttacg aattgctcgt gccgcaagcc ataggtgcaa aaggagatgc acaacaaatt     360
gcaagaaagt tcctctcccc gctcgcagac aaggatgccg tgggaggtct tggaatcgct     420
aaagcaggga taagccaag atgggtgcgg atgcgggaag caggtgagcc aggctgggaa      480
gaggagaagg agaaagccga acgaggaaa tcagcggatc gcactgcaga cgtgttgaga      540
gccctcgcag actttggact taagccactg atgcgggttt acacggattc agagatgtcc     600
tcggtggaat ggaagccgct cagaaagggt caagccgtga acgtgggaa ccgcgacatg      660
ttccagcagg caattgagcg gatgatgtcc tgggagtctt ggaaccaaag gtcgggcaa      720
gaatatgcga aactggtgga gcaaaaaaat aggtttgaac aaaaaaattt cgttggtcaa     780
gagcatctgg ttcatttggt taatcaactt caacaagata tgaaagaagc atcacctggc     840
ttggaatcta agaacaaac agcacactac gttacgggta gggcgttgag gggatcggat      900
aaagttttcg agaagtgggg taagttggcc cccgacgccc ctttcgatct gtatgacgcc     960
gagataaaga acgttcagcg gaggaacact cgccgctttg gttcgcacga tctgtttgca    1020
aaactggccg agcctgagta ccaggcccttt ggcgggagg atgcgtcgtt ccttacacgc    1080
tacgcggttt ataattcaat tctcagaaag ctcaatcacg cgaagatgtt tgcgactttc    1140
actcttccag atgcgacggc acaccctata tggactagat ttgataagtt gggggcaac    1200
ttgcaccagt atacatttct gttcaacgaa ttcggcgaac gcaggcatgc aatcaggttc    1260
cataaacttt tgaaagtcga gaatggtgtt gccaggagg ttgacgatgt cacagtgcct    1320
atctcgatgt ccgaacaatt ggataacttg ctgcccagag atccgaacga accgattgca    1380
ctttatttca gggattatgg tgccgaacaa cactttacgg gtgagttcgg aggggccaag    1440
attcagtgca gacgggacca gcttgctcac atgcaccgca ggagagggc tagggatgtg    1500
tatttgaacg tttcagttcg cgtgcagtcc caatccgagg cgcgggggga gcgcagacca    1560
ccatacgcgg ctgtcttccg gctggttggc gataaccata gagcgttcgt gcatttcgat    1620
aagctgagcg attacctcgc cgaacatcct gatgacggaa agttgggggtc agaggggctt    1680
ctgtcgggcc tgagggtgat gtccgtgac ctggggattgc gcaccagtgc ctcgatcagc    1740
gttttttagg tggccaggaa agatgagttg aaacccaact cgaaggggag ggttccgttc    1800
ttttccccta taagggcaa cgataacttg gtcgcagtgc atgaaaggag ccaactgctc    1860
aaacttcccg gggagacaga gtccaaagat cttcgcgcta agggaagaga gacaaaga    1920
actctccggc agctgcgcac gcagctcgca tacctgcggt tgcttgtccg ctgcggaagt    1980
gaagacgttg gcaggcgcga gaggtcatgg gccaaattga ttgagcagcc ggtcgacgcc    2040
gcaaatcaca tgactccgga ttggagggag gctttcgaga acgaactgca gaagttgaag    2100
agtctgcatg gcatatgctc tgacaaagag tggatggacg cggtttacga gtccgtccgc    2160
cgggtctggc ggcacatggg gaaacaagtt cgcgattgga gaaggatgt tagatccggg    2220
gaaaggccga agataagagg ttatgccaaa gacgtggttg gtggaaattc tatcgaacag    2280
atcgaatatc ttgagaggca gtacaagttc ctcaagagtt ggtctttctt cggtaaagtc    2340
```

| | |
|---|---|
| tctggacaag ttataagagc agaaaagggg agccggttcg ctatcacctt gcgggaacac | 2400 |
| atagaccacg caaaagaaga cagactgaag aagctggcgg acagaattat catggaagcg | 2460 |
| ctggggtacg tttacgcgct ggacgaaagg gggaaaggta atgggtggc caaatacccg | 2520 |
| ccatgccagt tgatattgct ggaagaattg tccgaatatc aatttaataa cgatagaccg | 2580 |
| ccatccgaga caaccaact tatgcaatgg tctcaccggg gagttttcca ggagttgatc | 2640 |
| aaccaagctc aagtgcacga tctgcttgtt ggtacaatgt acgcagcgtt ttcctcacgc | 2700 |
| ttcgacgcta aacaggagc gccgggaatt cggtgccgga gggtgcctgc gaggtgtact | 2760 |
| caggagcaca acccggagcc atttccctgg tggttgaata aattcgttgt ggaacatacg | 2820 |
| ttggatgctt gcccgcttcg ggcggacgac ctcattccga cgggtgaggg cgagattttc | 2880 |
| gtgtcgccat tctcggctga ggaagggac ttccatcaaa tccatgctgc cctcaatgcg | 2940 |
| gcgcaaaatc tgcagcagag attgtggagt gattttgaca tctctcagat caggcttcgg | 3000 |
| tgcgattggg gagaagtcga tggtgaactc gttctcattc cgagactcac cggtaaaagg | 3060 |
| actgctgatt catattcgaa caaagttttt tacactaaca caggggtcac ttattatgaa | 3120 |
| agagaacgcg gtaagaagcg ccgcaaggtg ttcgcgcaag agaaactttc cgaggaagag | 3180 |
| gccgagttgc tcgttgaagc tgacgaagct cgcgagaagt ccgtcgttct gatgcgggat | 3240 |
| ccttctggca taataaacag ggggaattgg acacggcaga aggaattttg gtccatggtg | 3300 |
| aatcagcgca tagaaggtta tctggtcaaa cagatcagaa gcagggttcc cctccaggat | 3360 |
| tcagcgtgcg agaacacggg cgatatt | 3387 |

<210> SEQ ID NO 11
<211> LENGTH: 3387
<212> TYPE: DNA
<213> ORGANISM: Artificial Sequence
<220> FEATURE:
<223> OTHER INFORMATION: AacCas12b-E848A nucleic acid

<400> SEQUENCE: 11

| | |
|---|---|
| atggcggtga agtcaataaa agttaaactc cgcctggacg atatgccaga aattcgggct | 60 |
| ggcctctgga agcttcacaa agaggttaac gctggcgtca gatattacac ggaatggttg | 120 |
| tcgctgctcc ggcaagaaaa tctctacaga aggtcgccca atggtgatgg ggaacaagag | 180 |
| tgcgacaaaa cggcggagga atgcaaagcg gaactccttg aaagacttcg cgcgagacaa | 240 |
| gtcgaaaacg gccatagagg ccccggccggt tccgatgatg aattgcttca gcttgcgcgg | 300 |
| cagctttacg aattgctcgt gccgcaagcc ataggtgcaa aaggagatgc acaacaaatt | 360 |
| gcaagaaagt tcctctcccc gctcgcagac aaggatgccg tgggaggtct tggaatcgct | 420 |
| aaagcaggga taagccaag atgggtgcgg atgcgggaag caggtgagcc aggctgggaa | 480 |
| gaggagaagg agaaagccga aacgaggaaa tcagcggatc gcactgcaga cgtgttgaga | 540 |
| gccctcgcag actttggact taagccactg atgcgggttt acacggattc agagatgtcc | 600 |
| tcggtggaat ggaagccgct cagaaagggt caagccgtga aacgtgggga ccgcgacatg | 660 |
| ttccagcagg caattgagcg gatgatgtcc tgggagtctt ggaaccaaag ggtcgggcaa | 720 |
| gaatatgcga aactggtgga gcaaaaaaat aggtttgaac aaaaaaattt cgttggtcaa | 780 |
| gagcatctgg ttcatttggt taatcaactt caacaagata tgaaagaagc atcacctggc | 840 |
| ttggaatcta agaacaaac agcacactac gttacgggta gggcgttgag gggatcggat | 900 |
| aaagttttcg agaagtgggg taagttggcc cccgacgccc ctttcgatct gtatgacgcc | 960 |
| gagataaaga acgttcagcg gaggaacact cgccgctttg gttcgcacga tctgtttgca | 1020 |

```
aaactggccg agcctgagta ccaggcccct tggcgggagg atgcgtcgtt ccttacacgc    1080
tacgcggttt ataattcaat tctcagaaag ctcaatcacg cgaagatgtt tgcgactttc    1140
actcttccag atgcgacggc acaccctata tggactagat ttgataagtt gggggggcaac   1200 ttgcaccagt atacatttct gttcaacgaa ttcggcgaac gcaggcatgc aatcaggttc    1260
cataaacttt tgaaagtcga aatggtgtt gccagggagg ttgacgatgt cacagtgcct     1320
atctcgatgt ccgaacaatt ggataacttg ctgcccagag atccgaacga accgattgca    1380
ctttatttca gggattatgg tgccgaacaa cactttacgg gtgagttcgg aggggccaag    1440
attcagtgca gacgggacca gcttgctcac atgcaccgca ggagaggggc tagggatgtg    1500
tatttgaacg tttcagttcg cgtgcagtcc caatccgagg cgcgggggga gcgcagacca    1560
ccatacgcgc tgtcttccg gctggttggc gataaccata gagcgttcgt gcatttcgat      1620
aagctgagcg attacctcgc cgaacatcct gatgacggaa agttgggggtc agagggggctt   1680 ctgtcgggcc tgagggtgat gtccgtggac ctgggattgc gcaccagtgc ctcgatcagc    1740
gtttttaggg tggccaggaa agatgagttg aaacccaact cgaaggggag ggttccgttc    1800
tttttcccta taagggcaa cgataacttg gtcgcagtgc atgaaaggag ccaactgctc     1860
aaacttcccg gggagacaga gtccaaagat cttcgcgcta aagggaaga gagacaaaga    1920 actctccggc agctgcgcac gcagctcgca tacctgcggt tgcttgtccg ctgcggaagt    1980
gaagacgttg gcaggcgcga gaggtcatgg gccaaattga ttgagcagcc ggtcgacgcc    2040
gcaaatcaca tgactccgga ttggaggggag gcttttcgaga acgaactgca gaagttgaag  2100
agtctgcatg gcatatgctc tgacaaagag tggatggacg cggtttacga gtccgtccgc    2160
cgggtctggc ggcacatggg gaaacaagtt cgcgattgga gaaaggatgt tagatccggg    2220
gaaaggccga agataagagg ttatgccaaa gacgtggttg gtggaaattc tatcgaacag    2280
atcgaatatc ttgagaggca gtacaagttc ctcaagagtt ggtctttctt cggtaaagtc    2340
tctggacaag ttataagagc agaaaagggg agccggttcg ctatcacctt gcgggaacac   2400
atagaccacg caaaagaaga cagactgaag aagctggcgg acagaattat catgaaagcg    2460
ctggggtacg tttacgcgct ggacgaaagg gggaaaggta aatgggtggc caaatacccg    2520
ccatgccagt tgatattgct ggccgaattg tccgaatatc aatttaataa cgatagaccg    2580
ccatccgaga caaccaact tatgcaatgg tctcaccggg gagttttcca ggagttgatc     2640
aaccaagctc aagtgcacga tctgcttgtt ggtacaatgt acgcagcgtt ttcctcacgc    2700
ttcgacgcta aacaggagc gccgggaatt cggtgccgga gggtgcctgc gaggtgtact    2760
caggagcaca acccggagcc atttccctgg tggttgaata aattcgttgt ggaacatacg    2820
ttggatgctt gcccgcttcg ggcggacgac ctcattccga cgggtgaggg cgagattttc    2880
gtgtcgccat tctcggctga ggaagggac ttccatcaaa tccatgctga cctcaatgcg     2940
gcgcaaaatc tgcagcagag attgtggagt gattttgaca tctctcagat caggcttcgg   3000
tgcgattggg gagaagtcga tggtgaactc gttctcattc cgagactcac cggtaaaagg    3060
actgctgatt catattcgaa caaagttttt tacactaaca caggggtcac ttattatgaa   3120
agagaacgcg gtaagaagcg ccgcaaggtg ttcgcgcaag agaaactttc cgaggaagag   3180
gccgagttgc tcgttgaagc tgacgaagct cgcgagaagt ccgtcgttct gatgcgggat   3240
ccttctggca taaaacag ggggaattgg acacggcaga aggaatttg gtccatggtg      3300 aatcagcgca tagaaggtta tctggtcaaa cagatcagaa gcagggttcc cctccaggat   3360
```

```
tcagcgtgcg agaacacggg cgatatt                                3387
```

<210> SEQ ID NO 12
<211> LENGTH: 3324
<212> TYPE: DNA
<213> ORGANISM: Artificial Sequence
<220> FEATURE:
<223> OTHER INFORMATION: BthCas12b-D573A nucleic acid

<400> SEQUENCE: 12

```
atggccacaa ggtctttcat acttaagata gagccaaacg aagaggtcaa aagggattg     60
tggaaaaccc atgaagtcct gaaccatggc attgcctact acatgaacat cctgaaactt    120
atacggcagg aggctattta tgagcaccac gagcaggatc caaaaaaccc caaaaaggtt    180
tcgaaggctg aaatccaggc cgaactgtgg gacttcgttc tcaaaatgca gaaatgtaat    240
tcgttcactc atgaagttga caaagacgtc gtgtttaaca ttttgaggga gctttacgag    300
gagttggttc cgagctccgt cgaaaagaag ggtgaagcaa atcagctgtc gaataagttc    360
ttgtacccct tggtggaccc gaacagccaa tctggaaaag ggacagcatc atcagggcgg    420
aagcctcggt ggtataactt gaagattgct ggagaccctt cgtgggaaga ggaaaagaaa    480
aagtgggagg aagataagaa gaaggaccca cttgccaaaa ttctcggcaa acttgccgaa    540
tatggattga taccgctgtt catcccctt acggattcta acgaaccat cgttaaagaa     600
atcaagtgga tggaaaaatc tcgcaatcag tccgtccgga ggctgacaa agatatgttt    660
atacaagctt tggaacgctt tctctcgtgg gagtcgtgga atcttaaggt caagaagag    720
tatgaaaagg tcgagaagga acacaagaca ctggaggaga ggattaagga agacattcaa    780
gcattcaagt cactggagca atacgaaaag gaacggcagg agcaattgct tcgcgacacg    840
ctcaatacca tgaatatag ctttccaag aggggcctga ggatggcg ggaaataatc       900
cagaaatggc tcaagatgga cgagaatgaa ccttcagaaa atatctcga ggttttaaa    960
gattaccaaa ggaaacatcc acgcgaggca ggggattaca cgtgtacga gttttctctcc   1020
aagaaggaaa accattttat ctggcgcaat catcccgaat acccgtacct ctatgcgacg   1080
ttctgcgaaa tagacaaaaa gaaaaaagat gctaagcaac aagcgacttt cacacttgca   1140
gatcccataa atcacccatt gtgggtgcgg tttgaagaaa ggtcgggctc taacctcaat   1200
aagtacagaa ttttgacgga gcagttgcac acagaaaagc tgaagaagaa gttgacggtt   1260
cagctggatc gccttatcta cccaaccgag tctggtggct gggaagagaa ggggaaagtc   1320
gacatagtgt tgctgccatc taggcagttc tataaccaga ttttttctcga tatagaagaa   1380
aagggtaaac atgcatttac gtataaagac gagtccataa agtttccact gaaaggaaca   1440
cttggcggcg caagggtgca gtttgatcgg gaccaccttc gcaggtaccc ccacaaggtt   1500
gaaagtggaa acgttggacg gatctatttt aatatgaccg tcaacataga acccacagaa   1560
tcccctgttt ccaaatccct gaaaatacac cgggacgatt ttcctaaatt tgtgaacttt   1620
aaaccgaagg agttgaccga gtggataaag gacagtaaag ggaaaaagct gaagtccggt   1680
atcgaaagcc tggagattgg gctcagagtt atgtcgatag cgctgggtca aaggcaggca   1740
gcagccgcct ctatatttga ggtcgtggac cagaagcccg acattgaagg taaactgttc   1800
tttccgatta aggggacgga actctacgca gtccatcgcg cctccttcaa tataaagctg   1860
ccgggcgaaa cactggttaa atcacgcgag gttttgcgca agcgcgggga agacaacctg   1920
aaactcatga atcaaaagct caatttcctg cgcaatgtgt tgcacttcca gcagtttgag   1980
gatattaccg aaagagagaa aagggttaca aatggatat cccggcaaga aaactctgat   2040
```

```
gttccgctgg tttaccagga tgagcttata cagattaggg aacttatgta taaaccttac   2100
aaagattggg ttgcattcct caagcagctg cataagagac ttgaagtcga gatcggcaaa   2160
gaagtcaaac actggcgcaa gagcctgagc gatggtcgga aagggttgta cggaatcagt   2220
ttgaaaaata tcgacgaaat agatagaacc aggaaatttt tgttgcgctg gtcactgaga   2280
ccaacggaac cgggagaagt cagaaggttg gagccaggcc agagatttgc aattgaccag   2340
ctgaaccatc tgaatgcact gaaagaggac agattgaaga gatggcgaa tacgattatt    2400 atgcatgctt tgggttattg ttacgacgtt aggaagaaga atggcaggc caagaaccct    2460 gcgtgccaaa tcatcctgtt cgaagatctg agtaactaca atccgtatga gaaaggagt    2520 cgcttcgaga acagtaaact gatgaaatgg tcccggcgcg agataccacg ccaagttgcg   2580
cttcaagggg aaatatacgg gcttcaagtt ggggaagttg gagcgcagtt ttctagccgg   2640
ttccacgcca agacagggtc cccgggtata aggtgcagtg tggtgacgaa agaaaagttg   2700
caggataata gattctttaa aaatcttcaa cgggaagggc gcctgacgct tgacaagatt   2760
gcagtgttga agagggggga tttgtacccc gataaaggcg gggagaagtt catttctttg   2820
tcgaaggacc gcaagttggt tacgacgcat gcagacatta acgcagcaca aaatctgcaa   2880
aaaagattct ggactcggac gcatggtttt tacaaggttt actgtaaagc atatcaagtc   2940
gatggtcaga cggtttacat tcccgaatct aaagatcaga acagaaaat cattgaggag    3000 ttcggtgaag gttactttat actcaaggac ggtgtttacg aatgggtaa tgctggtaaa    3060 ctgaaaatta agaaggggtc ctccaagcaa tcatcttctg agctcgtcga cagcgacatc   3120
cttaaggata gcttcgatct tgcctctgag ctcaagggag aaaagttgat gctgtatcgc   3180
gatcctagtg gaaatgtctt tccctcagat aaatggatgg cagcaggtgt gttcttcggg   3240
aaattggaac gcatactgat atcaaaactg accaatcaat actctatatc tactattgaa   3300
gacgattcaa gtaagcaatc gatg                                          3324
```

<210> SEQ ID NO 13
<211> LENGTH: 3324
<212> TYPE: DNA
<213> ORGANISM: Artificial Sequence
<220> FEATURE:
<223> OTHER INFORMATION: BthCas12b-D951A nucleic acid

<400> SEQUENCE: 13

```
atggccacaa ggtctttcat acttaagata gagccaaacg aagaggtcaa aagggattg     60 tggaaaaccc atgaagtcct gaaccatggc attgcctact acatgaacat cctgaaactt    120
atacggcagg aggctattta tgagcaccac gagcaggatc caaaaaaccc caaaaaggtt    180
tcgaaggctg aaatccaggc cgaactgtgg gacttcgttc tcaaaatgca gaaatgtaat    240
tcgttcactc atgaagttga caaagacgtc gtgtttaaca ttttgaggga gctttacgag    300
gagttggttc cgagctccgt cgaaaagaag ggtgaagcaa atcagctgtc gaataagttc    360
ttgtaccctt tggtggaccc gaacagccaa tctggaaaag ggacagcatc atcagggcgg    420
aagcctcggt ggtataactt gaagattgct ggagacccct cgtgggaaga ggaaaagaaa    480
aagtgggagg aagataagaa gaaggaccca cttgccaaaa ttctcggcaa acttgccgaa    540
tatggattga taccgctgtt catcccctt acggattcta acgaaccat cgttaaagaa      600 atcaagtgga tggaaaaatc tcgcaatcag tccgtccga ggctgacaa agatatgttt      660 atacaagctt tggaacgctt tctctcgtgg gagtcgtgga atcttaaggt caaagaagag   720
```

```
tatgaaaagg tcgagaagga acacaagaca ctggaggaga ggattaagga agacattcaa    780
gcattcaagt cactggagca atacgaaaag gaacggcagg agcaattgct tcgcgacacg    840
ctcaatacca atgaatatag gctttccaag aggggcctga gaggatggcg ggaaataatc    900
cagaaatggc tcaagatgga cgagaatgaa ccttcagaaa aatatctcga ggtttttaaa    960
gattaccaaa ggaaacatcc acgcgaggca ggggattaca gcgtgtacga gtttctctcc   1020
aagaaggaaa accattttat ctggcgcaat catcccgaat acccgtacct ctatgcgacg   1080
ttctgcgaaa tagacaaaaa gaaaaaagat gctaagcaac aagcgacttt cacacttgca   1140
gatcccataa atcacccatt gtgggtgcgg tttgaagaaa ggtcgggctc taacctcaat   1200
aagtacagaa ttttgacgga gcagttgcac acagaaaagc tgaagaagaa gttgacggtt   1260
cagctggatc gccttatcta cccaaccgag tctggtggct gggaagagaa ggggaaagtc   1320
gacatagtgt tgctgccatc taggcagttc tataaccaga ttttctcga tatagaagaa    1380
aagggtaaac atgcatttac gtataaagac gagtccataa agtttccact gaaaggaaca   1440
cttggcggcg caagggtgca gtttgatcgg gaccaccttc gcaggtaccc ccacaaggtt   1500
gaaagtggaa acgttggacg gatctatttt aatatgaccg tcaacataga acccacagaa   1560
tccccctgttt ccaaatccct gaaaatacac cgggacgatt ttcctaaatt tgtgaacttt   1620
aaaccgaagg agttgaccga gtggataaag gacagtaaag ggaaaaagct gaagtccggt   1680
atcgaaagcc tggagattgg gctcagagtt atgtcgatag atctgggtca aaggcaggca   1740
gcagccgcct ctatatttga ggtcgtggac cagaagcccg acattgaagg taaactgttc   1800
tttccgatta aggggacgga actctacgca gtccatcgcg cctccttcaa tataaagctg   1860
ccgggcgaaa cactggttaa atcacgcgag gttttgcgca agcgcggga agacaacctg   1920
aaactcatga atcaaaagct caatttcctg cgcaatgtgt tgcacttcca gcagtttgag   1980
gatattaccg aaagagagaa aagggttaca aaatggatat cccggcaaga aaactctgat   2040
gttccgctgg tttaccagga tgagcttata cagattaggg aacttatgta taaaccttac   2100
aaagattggg ttgcattcct caagcagctg cataagagac ttgaagtcga gatcggcaaa   2160
gaagtcaaac actggcgcaa gagcctgagc gatggtcgga aagggttgta cggaatcagt   2220
ttgaaaaata tcgacgaaat agatagaacc aggaaatttt tgttgcgctg gtcactgaga   2280
ccaacggaac cggagaagt cagaaggttg gagccaggcc agagatttgc aattgaccag   2340
ctgaaccatc tgaatgcact gaaagaggac agattgaaga agatggcgaa tacgattatt   2400
atgcatgctt tgggttattg ttacgacgtt aggaagaaga aatggcaggc caagaaccct   2460
gcgtgccaaa tcatcctgtt cgaagatctg agtaactaca atccgtatga agaaaggagt   2520
cgcttcgaga acagtaaact gatgaaatgg tcccggcgcg agataccacg ccaagttgcg   2580
cttcaagggg aaatatacgg gcttcaagtt ggggaagttg gagcgcagtt ttctagccgg   2640
ttccacgcca agacagggtc cccgggtata aggtgcagtg tggtgacgaa agaaaagttg   2700
caggataata gattctttaa aaatcttcaa cgggaagggc gcctgacgct tgacaagatt   2760
gcagtgttga agaggggga tttgtacccc gataaaggcg gggagaagtt catttctttg   2820
tcgaaggacc gcaagttggt tacgacgcat gcagccatta acgcagcaca aaatctgcaa   2880
aaaagattct ggactcggac gcatggtttt tacaaggttt actgtaaagc atatcaagtc   2940
gatggtcaga cggtttacat tcccgaatct aaagatcaga aacagaaaat cattgaggag   3000
ttcggtgaag gttactttat actcaaggac ggtgtttacg aatggggtaa tgctggtaaa   3060
ctgaaaatta agaagggggtc ctccaagcaa tcatcttctg agctcgtcga cagcgacatc   3120
```

```
cttaaggata gcttcgatct tgcctctgag ctcaagggag aaaagttgat gctgtatcgc      3180
gatcctagtg gaaatgtctt tccctcagat aaatggatgg cagcaggtgt gttcttcggg      3240
aaattggaac gcatactgat atcaaaactg accaatcaat actctatatc tactattgaa      3300
gacgattcaa gtaagcaatc gatg                                             3324

<210> SEQ ID NO 14
<211> LENGTH: 3324
<212> TYPE: DNA
<213> ORGANISM: Artificial Sequence
<220> FEATURE:
<223> OTHER INFORMATION: BthCas12b-D951A nucleic acid

<400> SEQUENCE: 14
atggccacaa ggtctttcat acttaagata gagccaaacg aagaggtcaa aaagggattg        60
tggaaaaccc atgaagtcct gaaccatggc attgcctact acatgaacat cctgaaactt       120
atacggcagg aggctatttt atgagcaccac gagcaggatc caaaaaaccc caaaaaggtt      180
tcgaaggctg aaatccaggc cgaactgtgg gacttcgttc tcaaaatgca gaaatgtaat       240
tcgttcactc atgaagttga caaagacgtc gtgtttaaca ttttgaggga gctttacgag       300
gagttggttc cgagctccgt cgaaaagaag ggtgaagcaa atcagctgtc gaataagttc       360
ttgtacccct tggtggaccc gaacagccaa tctggaaaag ggacagcatc atcagggcgg       420
aagcctcggt ggtataactt gaagattgct ggagacccct cgtgggaaga ggaaaagaaa       480
aagtgggagg aagataagaa gaaggaccca cttgccaaaa ttctcggcaa acttgccgaa       540
tatggattga taccgctgtt catccccttt acggattcta acgaacccat cgttaaagaa       600
atcaagtgga tggaaaaatc tcgcaatcag tccgtccgga ggctggacaa agatatgttt       660
atacaagctt tggaacgctt tctctcgtgg gagtcgtgga atcttaaggt caaagaagag       720
tatgaaaagg tcgagaagga acacaagaca ctggaggaga ggattaagga agacattcaa       780
gcattcaagt cactggagca atacgaaaag gaacggcagg agcaattgct tcgcgacacg       840
ctcaatacca tgaatatag ctttccaag aggggcctga gaggatggcg ggaaataatc        900
cagaaatggc tcaagatgga cgagaatgaa ccttcagaaa aatatctcga ggttttttaaa     960 gattaccaaa ggaaacatcc acgcgaggca ggggattaca gcgtgtacga gtttctctcc      1020
aagaaggaaa accattttat ctggcgcaat catcccgaat acccgtacct ctatgcgacg       1080
ttctgcgaaa tagacaaaaa gaaaaaagat gctaagcaac aagcgacttt cacacttgca      1140
gatcccataa atcacccatt gtgggtgcgg tttgaagaaa ggtcgggctc taaccctcaat    1200 aagtacagaa ttttgacgga gcagttgcac acagaaaagc tgaagaagaa gttgacggtt      1260
cagctggatc gccttatcta cccaaccgag tctggtggct gggaagagaa ggggaaagtc      1320
gacatagtgt tgctgccatc taggcagttc tataaccaga ttttttctcga tatagaagaa    1380 aagggtaaac atgcatttac gtataaagac gagtccataa agtttccact gaaaggaaca      1440
cttggcggcg caagggtgca gtttgatcgg gaccaccttc gcaggtaccc ccacaaggtt      1500
gaaagtggaa acgttggacg gatctatttt aatatgaccg tcaacataga acccacagaa      1560
tcccctgttt ccaaatccct gaaaatacac cgggacgatt ttcctaaatt tgtgaacttt      1620
aaaccgaagg agttgaccga gtggataaag gacagtaaag ggaaaaagct gaagtccggt      1680
atcgaaagcc tggagattgg gctcagagtt atgtcgatag atctgggtca aaggcaggca      1740
gcagccgcct ctatatttga ggtcgtggac cagaagcccg acattgaagg taaactgttc      1800
```

| | |
|---|---|
| tttccgatta agggacgga actctacgca gtccatcgcg cctccttcaa tataaagctg | 1860 |
| ccgggcgaaa cactggttaa atcacgcgag gttttgcgca aagcgcggga agacaacctg | 1920 |
| aaactcatga atcaaaagct caatttcctg cgcaatgtgt tgcacttcca gcagtttgag | 1980 |
| gatattaccg aaagagagaa aagggttaca aaatggatat cccggcaaga aaactctgat | 2040 |
| gttccgctgg tttaccagga tgagcttata cagattaggg aacttatgta taaaccttac | 2100 |
| aaagattggg ttgcattcct caagcagctg cataagagac ttgaagtcga gatcggcaaa | 2160 |
| gaagtcaaac actggcgcaa gagcctgagc gatggtcgga aagggttgta cggaatcagt | 2220 |
| ttgaaaaata tcgacgaaat agatagaacc aggaaatttt tgttgcgctg gtcactgaga | 2280 |
| ccaacggaac cgggagaagt cagaaggttg gagccaggcc agagatttgc aattgaccag | 2340 |
| ctgaaccatc tgaatgcact gaaagaggac agattgaaga gatggcgaa tacgattatt | 2400 |
| atgcatgctt tgggttattg ttacgacgtt aggaagaaga aatggcaggc caagaacct | 2460 |
| gcgtgccaaa tcatcctgtt cgccgatctg agtaactaca atccgtatga agaaaggagt | 2520 |
| cgcttcgaga acagtaaact gatgaaatgg tcccggcgcg agataccacg ccaagttgcg | 2580 |
| cttcaagggg aaatatacgg gcttcaagtt ggggaagttg gagcgcagtt ttctagccgg | 2640 |
| ttccacgcca agacagggtc cccgggtata aggtgcagtg tggtgacgaa agaaaagttg | 2700 |
| caggataata gattctttaa aaatcttcaa cgggaagggc gcctgacgct tgacaagatt | 2760 |
| gcagtgttga agaggggga tttgtacccc gataaaggcg gggagaagtt catttctttg | 2820 |
| tcgaaggacc gcaagttggt tacgacgcat gcagacatta acgcagcaca aaatctgcaa | 2880 |
| aaaagattct ggactcggac gcatggtttt tacaaggttt actgtaaagc atatcaagtc | 2940 |
| gatggtcaga cggtttacat tcccgaatct aaagatcaga acagaaaat cattgaggag | 3000 |
| ttcggtgaag gttactttat actcaaggac ggtgtttacg aatgggtaa tgctggtaaa | 3060 |
| ctgaaaatta gaaggggtc ctccaagcaa tcatcttctg agctcgtcga cagcgacatc | 3120 |
| cttaaggata gcttcgatct tgcctctgag ctcaagggag aaaagttgat gctgtatcgc | 3180 |
| gatcctagtg gaaatgtctt tccctcagat aaatggatgg cagcaggtgt gttcttcggg | 3240 |
| aaattggaac gcatactgat atcaaaactg accaatcaat actctatatc tactattgaa | 3300 |
| gacgattcaa gtaagcaatc gatg | 3324 |

<210> SEQ ID NO 15  
<211> LENGTH: 3387  
<212> TYPE: DNA  
<213> ORGANISM: Artificial Sequence  
<220> FEATURE:  
<223> OTHER INFORMATION: AaCas12b-D570A nucleic acid

<400> SEQUENCE: 15

| | |
|---|---|
| atggccgtca gtccatgaa ggtcaagttg cgcctggata acatgccaga gatcagagcc | 60 |
| ggactttgga aacttcacac cgaggttaat gcgggtgtgc ggtactatac ggaatggctt | 120 |
| agccttttga ggcaagaaaa tctttatcgg aggagtccca atggcgatgg agaacaagaa | 180 |
| tgctataaaa ctgctgagga atgcaaggct gaactccttg agagactcag agcccgccaa | 240 |
| gttgagaatg ggcactgcgg ccctgctggg agtgatgacg aactgctgca attggcacgg | 300 |
| caactttatg aacttctggt cccacaagca atcggggcta aggtgatgc gcagcaaatc | 360 |
| gcaaggaagt tcttagtcc ccttgccgac aaggatgccg tgggtggttt gggaatagca | 420 |
| aaagcaggaa ataagcctag gtgggttcgg atgagggagg ctgagagcc aggttgggaa | 480 |
| gaggaaaagg ctaaagccga ggcgagaaag agtacggata gaaccgccga tgttcttcgc | 540 |

```
gctcttgcag acttcggtct taaacctctt atgagagtct acacagactc agacatgtcc      600
agcgtgcagt ggaaaccact tcgcaaagga caagcggtca gaacctggga tagagacatg      660
ttccaacaag cgatcgaaag aatgatgagt tgggaatcgt ggaatcagcg cgttggagaa      720
gcgtacgcaa agctcgtgga acaaaagtcg aggtttgaac agaaaaattt tgtgggacaa      780
gaacatcttg tccaacttgt caatcaactt caacaagaca tgaaggaagc atcacacggc      840
ctggagtcga agaacaaac tgcgcattac ttgactggga gagcgctgag agggagcgac      900
aaagtttttg agaagtggga aaaactcgat cctgatgccc catttgacct ctatgatacc      960
gaaatcaaga atgttcaacg gaggaatact cgcaggttcg gatctcatga tctgtttgcg      1020
aagctcgcgg aacctaaata tcaggcgctc tggagagagg acgcttcttt cctcacgagg      1080
tatgcggttt acaatagcat tgtcagaaaa ctgaatcacg ctaaaatgtt tgcgactttt      1140
actcttccgg atgctaccgc ccacccgatc tggacgcggt ttgacaaact cggcggcaac      1200
ctgcaccagt acactttctt gtttaacgaa tttggcgagg gcaggcacgc cattcggttt      1260
cagaagctgt tgacggttga ggatggcgtt gctaaagagg tcgacgacgt cacggttccg      1320
atttctatgt ccgcgcagct ggatgacctc ttgcctcggg acccacacga gctcgttgca      1380
ctctacttcc aggactacgg tgcagaacaa catctggctg gagagtttgg cggcgcgaaa      1440
attcaatacc gccgcgatca attgaaccac ctgcacgcca agaggcgc cagagatgtc       1500 taccttaatc tgagcgtccg cgttcagtca caatccgaag ccaggggaga aaggcgccct      1560
ccgtatgcag cggtcttcag gcttgttggc gataaccacc gcgcgtttgt tcactttgat      1620
aaattgtcag attcctcgc agaacaccca gacgatggta agctggggtc ggaaggtttg       1680
ctctctgggc tcagagtcat gtcagttgcc ttgggtctta ggacttccgc gagcatatct      1740
gtcttccgcg tcgcaagaaa ggacgaattg aagccgaaca gtgaaggccg ggtccctttt      1800
tgcttcccga tcgaagggaa cgaaaacctc gttgctgtcc acgagcggag ccaactgttg      1860
aagcttcccg gtgaaacgga atcgaaagat ctgagagcga tcagagaaga gcgccaaagg      1920
acgcttagac agctccggac gcaacttgca tacttgcgcc ttctggttcg ctgcggtagt      1980
gaagacgttg gaagaagaga gaggtcatgg gctaaactca tagagcaacc tatggatgct      2040
aatcaaatga cgcctgattg gagagaagca ttcgaagacg aacttcagaa actgaaatcc      2100
ctttacggga tatgcggcga tcgcgagtgg acagaagcag tgtatgagtc tgtgaggcgc      2160
gtgtggcggc atatgggtaa acaggtgcgc gattggagaa aagacgttag gagcggggaa      2220
agacctaaga tacggggata tcagaaagac gttgtcgggg gaaatagcat tgaacagatt      2280
gaatatttgg agcgccaata taagttcctc aaatcctggt ctttcttcgg caaagtgtca      2340
ggccaggtga tacgcgcgga aaagggatcg cgctttgcaa taactctgag agaacatatt      2400
gatcatgcca agaagatcg gttgaagaaa ctcgccgata gaatcatcat ggaggcgctt       2460
ggttatgtct acgccttgga cgatgaacgg ggaaagggaa agtgggtcgc caagtatcca      2520
ccttgccaac tcattctcct cgaagaactt tccgaatacc agtttaacaa cgatcggccg      2580
ccatcagaga ataatcaact gatgcagtgg tcccatcgcg gtgtgttca agagttgctc        2640 aatcaggccc aagtccatga tctgcttgtt ggcacaatgt atgcagcctt ttcctcccgg      2700
tttgatgcaa gaacaggggc tcctggcata cgctgtagac gggtcccggc gaggtgcgcc      2760
cgcgaacaaa accctgaacc gttccctgg tggttgaaca agttcgttgc ggagcacaag       2820
ctggacgggt gtcctctgcg ggccgacgat cttattccca ccggggaagg ggaattcttt      2880
```

```
gtgagcccttt tctcggcgga ggaaggggat tttcaccaaa tacatgcaga tcttaatgcc   2940
gcacaaaatt tgcagaggag actgtggtca gactttgata ttagtcagat acgcctccgc   3000
tgtgactggg gagaggtcga tggcgagcct gtgttgatac caagaacgac cggaaagagg   3060
acagccgatt cgtatggaaa caaggttttt tacacgaaga cgggcgttac ttactacgaa   3120
agagaaagag ggaagaagag aaggaaagtc tttgcccaag aagaattgag cgaggaagaa   3180
gccgagctct tggtcgaagc ggacgaggca cgggaaaagt ctgtcgtcct catgagggac   3240
ccttccggaa ttattaaccg gggagattgg acgcggcaga aagagttttg gtccatggtt   3300
aatcaacgca tagaaggcta ccttgtcaag caaataagaa gtcgcgtgag attgcaggag   3360
agtgcatgtg agaacactgg ggacata                                      3387

<210> SEQ ID NO 16
<211> LENGTH: 3387
<212> TYPE: DNA
<213> ORGANISM: Artificial Sequence
<220> FEATURE:
<223> OTHER INFORMATION: AaCas12b-D977A nucleic acid

<400> SEQUENCE: 16
atggccgtca agtccatgaa ggtcaagttg cgcctggata catgccaga gatcagagcc     60 ggactttgga aacttcacac cgaggttaat gcgggtgtgc ggtactatac ggaatggctt    120
agccttttga ggcaagaaaa tctttatcgg aggagtccca atggcgatgg agaacaagaa    180
tgctataaaa ctgctgagga atgcaaggct gaactccttg agagactcag agcccgccaa    240
gttgagaatg ggcactgcgg ccctgctggg agtgatgacg aactgctgca attggcacgg    300
caactttatg aacttctggt cccacaagca atcggggcta aggtgatgc gcagcaaatc     360 gcaaggaagt ttcttagtcc ccttgccgac aaggatgccg tggtggttt gggaatagca    420 aaagcaggaa ataagcctag gtgggttcgg atgagggagg ctggagagcc aggttgggaa    480
gaggaaaagg ctaaagccga ggcgagaaag agtacggata gaaccgccga tgttcttcgc    540
gctcttgcag acttcggtct taaacctctt atgagagtct acacagactc agacatgtcc    600
agcgtgcagt ggaaaccact tcgcaaagga caagcggtca gaacctggga tagagacatg    660
ttccaacaag cgatcgaaag aatgatgagt tgggaatcgt ggaatcagcg cgttggagaa    720
gcgtacgcaa agctcgtgga acaaaaagtcg aggtttgaac agaaaaattt tgtgggacaa    780
gaacatcttg tccaacttgt caatcaactt caacaagaca tgaaggaagc atcacacggc    840
ctggagtcga agaacaaac tgcgcattac ttgactggga gagcgctgag agggagcgac    900 aaagttttg agaagtggga aaaactcgat cctgatgccc catttgacct ctatgatacc    960
gaaatcaaga tgttcaacg gaggaatact cgcaggttcg gatctcatga tctgtttgcg   1020
aagctcgcgg aaccctaaata tcaggcgctc tggagagagg acgcttcttt cctcacgagg   1080
tatgcggttt acaatagcat tgtcagaaaa ctgaatcacg ctaaaatgtt tgcgactttt   1140
actcttccgg atgctaccgc ccacccgatc tggacgcggt tgacaaaact cggcggcaac   1200
ctgcaccagt acactttctt gtttaacgaa tttggcgagg gcaggcacgc cattcggttt   1260
cagaagctgt tgacggttga ggatggcgtt gctaaagagg tcgacgacgt cacggttccg   1320
atttctatgt ccgcgcagct ggatgacctc ttgcctcggg acccacacga gctcgttgca   1380
ctctacttcc aggactacgg tgcagaacaa catctggctg agagtttgg cggcgcgaaa   1440 attcaatacc gccgcgatca attgaaccac ctgcacgcca aagaggcgc cagagatgtc   1500 taccttaatc tgagcgtccg cgttcagtca caatccgaag ccaggggaga aaggcgccct   1560
```

-continued

```
ccgtatgcag cggtcttcag gcttgttggc gataaccacc gcgcgtttgt tcactttgat    1620
aaattgtcag attacctcgc agaacaccca gacgatggta agctgggtc ggaaggtttg    1680 ctctctgggc tcagagtcat gtcagttgac ttgggtctta ggacttccgc gagcatatct   1740
gtcttccgcg tcgcaagaaa ggacgaattg aagccgaaca gtgaaggccg gtcccctttt   1800
tgcttcccga tcgaagggaa cgaaaacctc gttgctgtcc acgagcggag ccaactgttg   1860
aagcttcccg gtgaaacgga atcgaaagat ctgagagcga tcagagaaga gcgccaaagg   1920
acgcttagac agctccggac gcaacttgca tacttgcgcc ttctggttcg ctgcggtagt   1980
gaagacgttg gaagaagaga gaggtcatgg gctaaactca tagagcaacc tatggatgct   2040
aatcaaatga cgcctgattg gagagaagca ttcgaagacg aacttcagaa actgaaatcc   2100
ctttacggga tatgcggcga tcgcgagtgg acagaagcag tgtatgagtc tgtgaggcgc   2160
gtgtggcggc atatgggtaa acaggtgcgc gattggagaa aagacgttag gagcggggaa   2220
agacctaaga tacggggata tcagaaagac gttgtcgggg gaaatagcat tgaacagatt   2280
gaatatttgg agcgccaata taagttcctc aaatcctggt ctttcttcgg caaagtgtca   2340
ggccaggtga tacgcgcgga aaagggatcg cgctttgcaa taactctgag agaacatatt   2400
gatcatgcca agaagatcg gttgaagaaa ctcgccgata gaatcatcat ggaggcgctt    2460
ggttatgtct acgccttgga cgatgaacgg ggaaagggaa gtgggtcgc caagtatcca    2520 ccttgccaac tcattctcct cgaagaactt tccgaatacc agtttaacaa cgatcggccg   2580
ccatcagaga ataatcaact gatgcagtgg tcccatcgcg gtgtgtttca agagttgctc   2640
aatcaggccc aagtccatga tctgcttgtt ggcacaatgt atgcagcctt ttcctcccgg   2700
tttgatgcaa gaacaggggc tcctggcata cgctgtagac gggtcccggc gaggtgcgcc   2760
cgcgaacaaa accctgaacc gttcccctgg tggttgaaca agttcgttgc ggagcacaag   2820
ctggacgggt gtcctctgcg ggccgacgat cttattccca ccggggaagg ggaattcttt   2880 gtgagcccctt tctcggcgga ggaaggggat tttcaccaaa tacatgcagc gcttaatgcc   2940
gcacaaaatt tgcagaggag actgtggtca gactttgata ttagtcagat acgcctccgc   3000
tgtgactggg gagaggtcga tggcgagcct gtgttgatac aagaacgac cggaaagagg    3060 acagccgatt cgtatggaaa caaggttttt tacacgaaga cgggcgttac ttactacgaa   3120
agagaaagag ggaagaagag aaggaaagtc tttgcccaag aagaattgag cgaggaagaa    3180
gccgagctct tggtcgaagc ggacgaggca cgggaaaagt ctgtcgtcct catgagggac   3240
ccttccggaa ttattaaccg gggagattgg acgcggcaga aagagttttg gtccatggtt   3300
aatcaacgca tagaaggcta ccttgtcaag caaataagaa gtcgcgtgag attgcaggag   3360
agtgcatgtg agaacactgg ggacata                                       3387
```

<210> SEQ ID NO 17
<211> LENGTH: 3387
<212> TYPE: DNA
<213> ORGANISM: Artificial Sequence
<220> FEATURE:
<223> OTHER INFORMATION: AaCas12b-E848A nucleic acid

<400> SEQUENCE: 17

```
atggccgtca agtccatgaa ggtcaagttg cgcctggata acatgccaga gatcagagcc     60
ggactttgga aacttcacac cgaggttaat gcgggtgtgc ggtactatac ggaatggctt    120
agccttttga ggcaagaaaa tctttatcgg aggagtccca atggcgatgg agaacaagaa    180
```

-continued

```
tgctataaaa ctgctgagga atgcaaggct gaactccttg agagactcag agcccgccaa        240
gttgagaatg ggcactgcgg ccctgctggg agtgatgacg aactgctgca attggcacgg        300
caactttatg aacttctggt cccacaagca atcggggcta aggtgatgc gcagcaaatc        360 gcaaggaagt ttcttagtcc ccttgccgac aaggatgccg tgggtggttt gggaatagca        420
aaagcaggaa ataagcctag gtgggttcgg atgagggagg ctggagagcc aggttgggaa        480
gaggaaaagg ctaaagccga ggcgagaaag agtacggata gaaccgccga tgttcttcgc        540
gctcttgcag acttcggtct aaacctctt atgagagtct acacagactc agacatgtcc         600
agcgtgcagt ggaaaccact tcgcaaagga caagcggtca gaacctggga tagagacatg        660
ttccaacaag cgatcgaaag aatgatgagt tgggaatcgt ggaatcagcg cgttggagaa        720
gcgtacgcaa agctcgtgga acaaaagtcg aggtttgaac agaaaaattt tgtgggacaa        780
gaacatcttg tccaacttgt caatcaactt caacaagaca tgaaggaagc atcacacggc        840
ctggagtcga agaacaaac tgcgcattac ttgactggga gagcgctgag agggagcgac         900 aaagttttg agaagtggga aaaactcgat cctgatgccc catttgacct ctatgatacc         960
gaaatcaaga atgttcaacg gaggaatact cgcaggttcg gatctcatga tctgtttgcg       1020
aagctcgcgg aacctaaata tcaggcgctc tggagagagg acgcttcttt cctcacgagg       1080
tatgcggttt acaatagcat tgtcagaaaa ctgaatcacg ctaaatgtt tgcgactttt        1140 actcttccgg atgctaccgc ccacccgatc tggacgcgt ttgacaaact cggcggcaac        1200
ctgcaccagt acactttctt gtttaacgaa tttggcgagg gcaggcacgc cattcggttt       1260
cagaagctgt tgacggttga ggatggcgtt gctaaagagg tcgacgacgt cacggttccg       1320
atttctatgt ccgcgcagct ggatgacctc ttgcctcggg acccacacga gctcgttgca       1380
ctctacttcc aggactacgg tgcagaacaa catctggctg gagagtttgg cggcgcgaaa       1440
attcaatacc gccgcgatca attgaaccac ctgcacgcca aagaggcgc cagagatgtc       1500 taccttaatc tgagcgtccg cgttcagtca caatccgaag ccaggggaga aaggcgccct       1560
ccgtatgcag cggtcttcag gcttgttggc gataaccacc gcgcgtttgt tcactttgat       1620
aaattgtcag attacctcgc agaacaccca gacgatggta agctgggtc ggaaggtttg        1680 ctctctgggc tcagagtcat gtcagttgac ttgggtctta ggacttccgc gagcatatct       1740
gtcttccgcg tcgcaagaaa ggacgaattg aagccgaaca gtgaaggccg ggtcccttt        1800 tgcttcccga tcgaagggaa cgaaaacctc gttgctgtcc acgagcggag ccaactgttg       1860
aagcttcccg gtgaaacgga atcgaaagat ctgagagcga tcagagaaga gcgccaaagg       1920
acgcttagac agctccggac gcaacttgca tacttgcgcc ttctggttcg ctgcggtagt       1980
gaagacgttg gaagaagaga gaggtcatgg gctaaactca tagagcaacc tatggatgct      2040
aatcaaatga cgcctgattg gagagaagca ttcgaagacg aacttcagaa actgaaatcc      2100
ctttacggga tatgcggcga tcgcgagtgg acagaagcag tgtatgagtc tgtgaggcgc      2160
gtgtggcggc atatgggtaa acaggtgcgc gattggagaa aagacgttag gagcggggaa      2220
agacctaaga tacggggata tcagaaagac gttgtcgggg gaaatagcat tgaacagatt     2280
gaatatttgg agcgccaata taagttcctc aaatcctggt ctttcttcgg caaagtgtca      2340
ggccaggtga tacgcgcgga aaagggatcg cgcttttgcaa taactctgag agaacatatt     2400
gatcatgcca aagaagatcg gttgaagaaa ctcgccgata gaatcatcat ggaggcgctt      2460
ggttatgtct acgccttgga cgatgaacgg ggaaagggaa agtgggtcgc caagtatcca      2520
ccttgccaac tcattctcct cgccgaactt tccgaatacc agtttaacaa cgatcggccg      2580
```

```
ccatcagaga ataatcaact gatgcagtgg tcccatcgcg gtgtgtttca agagttgctc    2640
aatcaggccc aagtccatga tctgcttgtt ggcacaatgt atgcagcctt ttcctcccgg    2700
tttgatgcaa gaacaggggc tcctggcata cgctgtagac gggtcccggc gaggtgcgcc    2760
cgcgaacaaa accctgaacc gttccccctg tggttgaaca agttcgttgc ggagcacaag    2820
ctggacgggt gtcctctgcg ggccgacgat cttattccca ccggggaagg ggaattcttt    2880
gtgagccctt tctcggcgga ggaagggggat tttcaccaaa tacatgcaga tcttaatgcc    2940
gcacaaaatt tgcagaggag actgtggtca gactttgata ttagtcagat acgcctccgc    3000
tgtgactggg gagaggtcga tggcgagcct gtgttgatac caagaacgac cggaaagagg    3060
acagccgatt cgtatggaaa caaggttttt tacacgaaga cgggcgttac ttactacgaa    3120
agagaaagag ggaagaagag aaggaaagtc tttgcccaag aagaattgag cgaggaagaa    3180
gccgagctct tggtcgaagc ggacgaggca cgggaaaagt ctgtcgtcct catgagggac    3240
ccttccggaa ttattaaccg gggagattgg acgcggcaga aagagttttg gtccatggtt    3300
aatcaacgca tagaaggcta ccttgtcaag caaataagaa gtcgcgtgag attgcaggag    3360
agtgcatgtg agaacactgg ggacata                                        3387
```

<210> SEQ ID NO 18
<211> LENGTH: 1129
<212> TYPE: PRT
<213> ORGANISM: Artificial Sequence
<220> FEATURE:
<223> OTHER INFORMATION: AacCas12b-D570A protein

<400> SEQUENCE: 18

```
Met Ala Val Lys Ser Ile Lys Val Lys Leu Arg Leu Asp Asp Met Pro
 1               5                  10                  15

Glu Ile Arg Ala Gly Leu Trp Lys Leu His Lys Glu Val Asn Ala Gly
             20                  25                  30

Val Arg Tyr Tyr Thr Glu Trp Leu Ser Leu Leu Arg Gln Glu Asn Leu
         35                  40                  45

Tyr Arg Arg Ser Pro Asn Gly Asp Gly Glu Gln Glu Cys Asp Lys Thr
     50                  55                  60

Ala Glu Glu Cys Lys Ala Glu Leu Leu Glu Arg Leu Arg Ala Arg Gln
 65                  70                  75                  80

Val Glu Asn Gly His Arg Gly Pro Ala Gly Ser Asp Asp Glu Leu Leu
                 85                  90                  95

Gln Leu Ala Arg Gln Leu Tyr Glu Leu Leu Val Pro Gln Ala Ile Gly
            100                 105                 110

Ala Lys Gly Asp Ala Gln Gln Ile Ala Arg Lys Phe Leu Ser Pro Leu
        115                 120                 125

Ala Asp Lys Asp Ala Val Gly Gly Leu Gly Ile Ala Lys Ala Gly Asn
    130                 135                 140

Lys Pro Arg Trp Val Arg Met Arg Glu Ala Gly Glu Pro Gly Trp Glu
145                 150                 155                 160

Glu Glu Lys Glu Lys Ala Glu Thr Arg Lys Ser Ala Asp Arg Thr Ala
                165                 170                 175

Asp Val Leu Arg Ala Leu Ala Asp Phe Gly Leu Lys Pro Leu Met Arg
            180                 185                 190

Val Tyr Thr Asp Ser Glu Met Ser Ser Val Glu Trp Lys Pro Leu Arg
        195                 200                 205

Lys Gly Gln Ala Val Arg Thr Trp Asp Arg Asp Met Phe Gln Gln Ala
```

```
             210                 215                 220
Ile Glu Arg Met Met Ser Trp Glu Ser Trp Asn Gln Arg Val Gly Gln
225                 230                 235                 240

Glu Tyr Ala Lys Leu Val Glu Gln Lys Asn Arg Phe Glu Gln Lys Asn
                245                 250                 255

Phe Val Gly Gln Glu His Leu Val His Leu Val Asn Gln Leu Gln Gln
                    260                 265                 270

Asp Met Lys Glu Ala Ser Pro Gly Leu Glu Ser Lys Glu Gln Thr Ala
            275                 280                 285

His Tyr Val Thr Gly Arg Ala Leu Arg Gly Ser Asp Lys Val Phe Glu
        290                 295                 300

Lys Trp Gly Lys Leu Ala Pro Asp Ala Pro Phe Asp Leu Tyr Asp Ala
305                 310                 315                 320

Glu Ile Lys Asn Val Gln Arg Arg Asn Thr Arg Arg Phe Gly Ser His
                325                 330                 335

Asp Leu Phe Ala Lys Leu Ala Glu Pro Glu Tyr Gln Ala Leu Trp Arg
                340                 345                 350

Glu Asp Ala Ser Phe Leu Thr Arg Tyr Ala Val Tyr Asn Ser Ile Leu
            355                 360                 365

Arg Lys Leu Asn His Ala Lys Met Phe Ala Thr Phe Thr Leu Pro Asp
        370                 375                 380

Ala Thr Ala His Pro Ile Trp Thr Arg Phe Asp Lys Leu Gly Gly Asn
385                 390                 395                 400

Leu His Gln Tyr Thr Phe Leu Phe Asn Glu Phe Gly Glu Arg His
                405                 410                 415

Ala Ile Arg Phe His Lys Leu Leu Lys Val Glu Asn Gly Val Ala Arg
                420                 425                 430

Glu Val Asp Asp Val Thr Val Pro Ile Ser Met Ser Glu Gln Leu Asp
            435                 440                 445

Asn Leu Leu Pro Arg Asp Pro Asn Glu Pro Ile Ala Leu Tyr Phe Arg
        450                 455                 460

Asp Tyr Gly Ala Glu Gln His Phe Thr Gly Glu Phe Gly Gly Ala Lys
465                 470                 475                 480

Ile Gln Cys Arg Arg Asp Gln Leu Ala His Met His Arg Arg Gly
                485                 490                 495

Ala Arg Asp Val Tyr Leu Asn Val Ser Val Arg Val Gln Ser Gln Ser
            500                 505                 510

Glu Ala Arg Gly Glu Arg Arg Pro Pro Tyr Ala Ala Val Phe Arg Leu
        515                 520                 525

Val Gly Asp Asn His Arg Ala Phe Val His Phe Asp Lys Leu Ser Asp
    530                 535                 540

Tyr Leu Ala Glu His Pro Asp Asp Gly Lys Leu Gly Ser Glu Gly Leu
545                 550                 555                 560

Leu Ser Gly Leu Arg Val Met Ser Val Ala Leu Gly Leu Arg Thr Ser
                565                 570                 575

Ala Ser Ile Ser Val Phe Arg Val Ala Arg Lys Asp Glu Leu Lys Pro
            580                 585                 590

Asn Ser Lys Gly Arg Val Pro Phe Phe Pro Ile Lys Gly Asn Asp
        595                 600                 605

Asn Leu Val Ala Val His Glu Arg Ser Gln Leu Leu Lys Leu Pro Gly
    610                 615                 620

Glu Thr Glu Ser Lys Asp Leu Arg Ala Ile Arg Glu Glu Arg Gln Arg
625                 630                 635                 640
```

```
Thr Leu Arg Gln Leu Arg Thr Gln Leu Ala Tyr Leu Arg Leu Leu Val
                645                 650                 655

Arg Cys Gly Ser Glu Asp Val Gly Arg Arg Glu Arg Ser Trp Ala Lys
            660                 665                 670

Leu Ile Glu Gln Pro Val Asp Ala Ala Asn His Met Thr Pro Asp Trp
        675                 680                 685

Arg Glu Ala Phe Glu Asn Glu Leu Gln Lys Leu Lys Ser Leu His Gly
    690                 695                 700

Ile Cys Ser Asp Lys Glu Trp Met Asp Ala Val Tyr Glu Ser Val Arg
705                 710                 715                 720

Arg Val Trp Arg His Met Gly Lys Gln Val Arg Asp Trp Arg Lys Asp
                725                 730                 735

Val Arg Ser Gly Glu Arg Pro Lys Ile Arg Gly Tyr Ala Lys Asp Val
            740                 745                 750

Val Gly Gly Asn Ser Ile Glu Gln Ile Glu Tyr Leu Glu Arg Gln Tyr
        755                 760                 765

Lys Phe Leu Lys Ser Trp Ser Phe Phe Gly Lys Val Ser Gly Gln Val
    770                 775                 780

Ile Arg Ala Glu Lys Gly Ser Arg Phe Ala Ile Thr Leu Arg Glu His
785                 790                 795                 800

Ile Asp His Ala Lys Glu Asp Arg Leu Lys Lys Leu Ala Asp Arg Ile
                805                 810                 815

Ile Met Glu Ala Leu Gly Tyr Val Tyr Ala Leu Asp Glu Arg Gly Lys
            820                 825                 830

Gly Lys Trp Val Ala Lys Tyr Pro Pro Cys Gln Leu Ile Leu Leu Glu
        835                 840                 845

Glu Leu Ser Glu Tyr Gln Phe Asn Asn Asp Arg Pro Pro Ser Glu Asn
    850                 855                 860

Asn Gln Leu Met Gln Trp Ser His Arg Gly Val Phe Gln Glu Leu Ile
865                 870                 875                 880

Asn Gln Ala Gln Val His Asp Leu Leu Val Gly Thr Met Tyr Ala Ala
                885                 890                 895

Phe Ser Ser Arg Phe Asp Ala Arg Thr Gly Ala Pro Gly Ile Arg Cys
            900                 905                 910

Arg Arg Val Pro Ala Arg Cys Thr Gln Glu His Asn Pro Glu Pro Phe
        915                 920                 925

Pro Trp Trp Leu Asn Lys Phe Val Val Glu His Thr Leu Asp Ala Cys
    930                 935                 940

Pro Leu Arg Ala Asp Asp Leu Ile Pro Thr Gly Glu Gly Glu Ile Phe
945                 950                 955                 960

Val Ser Pro Phe Ser Ala Glu Glu Gly Asp Phe His Gln Ile His Ala
                965                 970                 975

Asp Leu Asn Ala Ala Gln Asn Leu Gln Gln Arg Leu Trp Ser Asp Phe
            980                 985                 990

Asp Ile Ser Gln Ile Arg Leu Arg Cys Asp Trp Gly Glu Val Asp Gly
        995                 1000                1005

Glu Leu Val Leu Ile Pro Arg Leu Thr Gly Lys Arg Thr Ala Asp
    1010                1015                1020

Ser Tyr Ser Asn Lys Val Phe Tyr Thr Asn Thr Gly Val Thr Tyr
    1025                1030                1035

Tyr Glu Arg Glu Arg Gly Lys Lys Arg Arg Lys Val Phe Ala Gln
    1040                1045                1050
```

```
Glu Lys Leu Ser Glu Glu Ala Glu Leu Leu Val Glu Ala Asp
    1055            1060                1065

Glu Ala Arg Glu Lys Ser Val Val Leu Met Arg Asp Pro Ser Gly
    1070            1075                1080

Ile Ile Asn Arg Gly Asn Trp Thr Arg Gln Lys Glu Phe Trp Ser
    1085            1090                1095

Met Val Asn Gln Arg Ile Glu Gly Tyr Leu Val Lys Gln Ile Arg
    1100            1105                1110

Ser Arg Val Pro Leu Gln Asp Ser Ala Cys Glu Asn Thr Gly Asp
    1115            1120                1125

Ile
```

<210> SEQ ID NO 19
<211> LENGTH: 1129
<212> TYPE: PRT
<213> ORGANISM: Artificial Sequence
<220> FEATURE:
<223> OTHER INFORMATION: AacCas12b-D977A protein

<400> SEQUENCE: 19

```
Met Ala Val Lys Ser Ile Lys Val Lys Leu Arg Leu Asp Asp Met Pro
1               5                   10                  15

Glu Ile Arg Ala Gly Leu Trp Lys Leu His Lys Glu Val Asn Ala Gly
                20                  25                  30

Val Arg Tyr Tyr Thr Glu Trp Leu Ser Leu Leu Arg Gln Glu Asn Leu
            35                  40                  45

Tyr Arg Arg Ser Pro Asn Gly Asp Gly Glu Gln Glu Cys Asp Lys Thr
    50                  55                  60

Ala Glu Glu Cys Lys Ala Glu Leu Leu Glu Arg Leu Arg Ala Arg Gln
65                  70                  75                  80

Val Glu Asn Gly His Arg Gly Pro Ala Gly Ser Asp Asp Glu Leu Leu
                85                  90                  95

Gln Leu Ala Arg Gln Leu Tyr Glu Leu Leu Val Pro Gln Ala Ile Gly
                100                 105                 110

Ala Lys Gly Asp Ala Gln Gln Ile Ala Arg Lys Phe Leu Ser Pro Leu
            115                 120                 125

Ala Asp Lys Asp Ala Val Gly Gly Leu Gly Ile Ala Lys Ala Gly Asn
    130                 135                 140

Lys Pro Arg Trp Val Arg Met Arg Glu Ala Gly Glu Pro Gly Trp Glu
145                 150                 155                 160

Glu Glu Lys Glu Lys Ala Glu Thr Arg Lys Ser Ala Asp Arg Thr Ala
                165                 170                 175

Asp Val Leu Arg Ala Leu Ala Asp Phe Gly Leu Lys Pro Leu Met Arg
            180                 185                 190

Val Tyr Thr Asp Ser Glu Met Ser Ser Val Glu Trp Lys Pro Leu Arg
    195                 200                 205

Lys Gly Gln Ala Val Arg Thr Trp Asp Arg Asp Met Phe Gln Gln Ala
210                 215                 220

Ile Glu Arg Met Met Ser Trp Glu Ser Trp Asn Gln Arg Val Gly Gln
225                 230                 235                 240

Glu Tyr Ala Lys Leu Val Glu Gln Lys Asn Arg Phe Glu Gln Lys Asn
                245                 250                 255

Phe Val Gly Gln Glu His Leu Val His Leu Val Asn Gln Leu Gln Gln
                260                 265                 270

Asp Met Lys Glu Ala Ser Pro Gly Leu Glu Ser Lys Glu Gln Thr Ala
```

```
            275                 280                 285
His Tyr Val Thr Gly Arg Ala Leu Arg Gly Ser Asp Lys Val Phe Glu
290                 295                 300

Lys Trp Gly Lys Leu Ala Pro Asp Ala Pro Phe Asp Leu Tyr Asp Ala
305                 310                 315                 320

Glu Ile Lys Asn Val Gln Arg Arg Asn Thr Arg Arg Phe Gly Ser His
                325                 330                 335

Asp Leu Phe Ala Lys Leu Ala Glu Pro Glu Tyr Gln Ala Leu Trp Arg
                340                 345                 350

Glu Asp Ala Ser Phe Leu Thr Arg Tyr Ala Val Tyr Asn Ser Ile Leu
                355                 360                 365

Arg Lys Leu Asn His Ala Lys Met Phe Ala Thr Phe Thr Leu Pro Asp
370                 375                 380

Ala Thr Ala His Pro Ile Trp Thr Arg Phe Asp Lys Leu Gly Gly Asn
385                 390                 395                 400

Leu His Gln Tyr Thr Phe Leu Phe Asn Glu Phe Gly Glu Arg Arg His
                405                 410                 415

Ala Ile Arg Phe His Lys Leu Leu Lys Val Glu Asn Gly Val Ala Arg
                420                 425                 430

Glu Val Asp Asp Val Thr Val Pro Ile Ser Met Ser Glu Gln Leu Asp
                435                 440                 445

Asn Leu Leu Pro Arg Asp Pro Asn Glu Pro Ile Ala Leu Tyr Phe Arg
450                 455                 460

Asp Tyr Gly Ala Glu Gln His Phe Thr Gly Glu Phe Gly Gly Ala Lys
465                 470                 475                 480

Ile Gln Cys Arg Arg Asp Gln Leu Ala His Met His Arg Arg Arg Gly
                485                 490                 495

Ala Arg Asp Val Tyr Leu Asn Val Ser Val Arg Val Gln Ser Gln Ser
                500                 505                 510

Glu Ala Arg Gly Glu Arg Arg Pro Pro Tyr Ala Ala Val Phe Arg Leu
                515                 520                 525

Val Gly Asp Asn His Arg Ala Phe Val His Phe Asp Lys Leu Ser Asp
                530                 535                 540

Tyr Leu Ala Glu His Pro Asp Asp Gly Lys Leu Gly Ser Glu Gly Leu
545                 550                 555                 560

Leu Ser Gly Leu Arg Val Met Ser Val Ala Leu Gly Leu Arg Thr Ser
                565                 570                 575

Ala Ser Ile Ser Val Phe Arg Val Ala Arg Lys Asp Glu Leu Lys Pro
                580                 585                 590

Asn Ser Lys Gly Arg Val Pro Phe Phe Pro Ile Lys Gly Asn Asp
                595                 600                 605

Asn Leu Val Ala Val His Glu Arg Ser Gln Leu Leu Lys Leu Pro Gly
                610                 615                 620

Glu Thr Glu Ser Lys Asp Leu Arg Ala Ile Arg Glu Glu Arg Gln Arg
625                 630                 635                 640

Thr Leu Arg Gln Leu Arg Thr Gln Leu Ala Tyr Leu Arg Leu Leu Val
                645                 650                 655

Arg Cys Gly Ser Glu Asp Val Gly Arg Arg Glu Arg Ser Trp Ala Lys
                660                 665                 670

Leu Ile Glu Gln Pro Val Asp Ala Ala Asn His Met Thr Pro Asp Trp
                675                 680                 685

Arg Glu Ala Phe Glu Asn Glu Leu Gln Lys Leu Lys Ser Leu His Gly
690                 695                 700
```

```
Ile Cys Ser Asp Lys Glu Trp Met Asp Ala Val Tyr Glu Ser Val Arg
705                 710                 715                 720

Arg Val Trp Arg His Met Gly Lys Gln Val Arg Asp Trp Arg Lys Asp
                725                 730                 735

Val Arg Ser Gly Glu Arg Pro Lys Ile Arg Gly Tyr Ala Lys Asp Val
            740                 745                 750

Val Gly Gly Asn Ser Ile Glu Gln Ile Glu Tyr Leu Glu Arg Gln Tyr
        755                 760                 765

Lys Phe Leu Lys Ser Trp Ser Phe Phe Gly Lys Val Ser Gly Gln Val
    770                 775                 780

Ile Arg Ala Glu Lys Gly Ser Arg Phe Ala Ile Thr Leu Arg Glu His
785                 790                 795                 800

Ile Asp His Ala Lys Glu Asp Arg Leu Lys Lys Leu Ala Asp Arg Ile
                805                 810                 815

Ile Met Glu Ala Leu Gly Tyr Val Tyr Ala Leu Asp Glu Arg Gly Lys
            820                 825                 830

Gly Lys Trp Val Ala Lys Tyr Pro Pro Cys Gln Leu Ile Leu Leu Glu
        835                 840                 845

Glu Leu Ser Glu Tyr Gln Phe Asn Asn Asp Arg Pro Pro Ser Glu Asn
    850                 855                 860

Asn Gln Leu Met Gln Trp Ser His Arg Gly Val Phe Gln Glu Leu Ile
865                 870                 875                 880

Asn Gln Ala Gln Val His Asp Leu Leu Val Gly Thr Met Tyr Ala Ala
                885                 890                 895

Phe Ser Ser Arg Phe Asp Ala Arg Thr Gly Ala Pro Gly Ile Arg Cys
            900                 905                 910

Arg Arg Val Pro Ala Arg Cys Thr Gln Glu His Asn Pro Glu Pro Phe
        915                 920                 925

Pro Trp Trp Leu Asn Lys Phe Val Val Glu His Thr Leu Asp Ala Cys
    930                 935                 940

Pro Leu Arg Ala Asp Asp Leu Ile Pro Thr Gly Glu Gly Glu Ile Phe
945                 950                 955                 960

Val Ser Pro Phe Ser Ala Glu Glu Gly Asp Phe His Gln Ile His Ala
                965                 970                 975

Asp Leu Asn Ala Ala Gln Asn Leu Gln Gln Arg Leu Trp Ser Asp Phe
            980                 985                 990

Asp Ile Ser Gln Ile Arg Leu Arg Cys Asp Trp Gly Glu Val Asp Gly
        995                 1000                1005

Glu Leu Val Leu Ile Pro Arg Leu Thr Gly Lys Arg Thr Ala Asp
    1010                1015                1020

Ser Tyr Ser Asn Lys Val Phe Tyr Thr Asn Thr Gly Val Thr Tyr
    1025                1030                1035

Tyr Glu Arg Glu Arg Gly Lys Lys Arg Arg Lys Val Phe Ala Gln
    1040                1045                1050

Glu Lys Leu Ser Glu Glu Glu Ala Glu Leu Leu Val Glu Ala Asp
    1055                1060                1065

Glu Ala Arg Glu Lys Ser Val Val Leu Met Arg Asp Pro Ser Gly
    1070                1075                1080

Ile Ile Asn Arg Gly Asn Trp Thr Arg Gln Lys Glu Phe Trp Ser
    1085                1090                1095

Met Val Asn Gln Arg Ile Glu Gly Tyr Leu Val Lys Gln Ile Arg
    1100                1105                1110
```

-continued

Ser Arg Val Pro Leu Gln Asp Ser Ala Cys Glu Asn Thr Gly Asp
    1115                1120                1125

Ile

<210> SEQ ID NO 20
<211> LENGTH: 1129
<212> TYPE: PRT
<213> ORGANISM: Artificial Sequence
<220> FEATURE:
<223> OTHER INFORMATION: AacCas12b-E848A protein

<400> SEQUENCE: 20

Met Ala Val Lys Ser Ile Lys Val Lys Leu Arg Leu Asp Asp Met Pro
1               5                   10                  15

Glu Ile Arg Ala Gly Leu Trp Lys Leu His Lys Glu Val Asn Ala Gly
            20                  25                  30

Val Arg Tyr Tyr Thr Glu Trp Leu Ser Leu Leu Arg Gln Glu Asn Leu
        35                  40                  45

Tyr Arg Arg Ser Pro Asn Gly Asp Gly Glu Gln Glu Cys Asp Lys Thr
    50                  55                  60

Ala Glu Glu Cys Lys Ala Glu Leu Leu Glu Arg Leu Arg Ala Arg Gln
65                  70                  75                  80

Val Glu Asn Gly His Arg Gly Pro Ala Gly Ser Asp Asp Glu Leu Leu
                85                  90                  95

Gln Leu Ala Arg Gln Leu Tyr Glu Leu Leu Val Pro Gln Ala Ile Gly
            100                 105                 110

Ala Lys Gly Asp Ala Gln Gln Ile Ala Arg Lys Phe Leu Ser Pro Leu
        115                 120                 125

Ala Asp Lys Asp Ala Val Gly Gly Leu Gly Ile Ala Lys Ala Gly Asn
    130                 135                 140

Lys Pro Arg Trp Val Arg Met Arg Glu Ala Gly Glu Pro Gly Trp Glu
145                 150                 155                 160

Glu Glu Lys Glu Lys Ala Glu Thr Arg Lys Ser Ala Asp Arg Thr Ala
                165                 170                 175

Asp Val Leu Arg Ala Leu Ala Asp Phe Gly Leu Lys Pro Leu Met Arg
            180                 185                 190

Val Tyr Thr Asp Ser Glu Met Ser Ser Val Glu Trp Lys Pro Leu Arg
        195                 200                 205

Lys Gly Gln Ala Val Arg Thr Trp Asp Arg Asp Met Phe Gln Gln Ala
    210                 215                 220

Ile Glu Arg Met Met Ser Trp Glu Ser Trp Asn Gln Arg Val Gly Gln
225                 230                 235                 240

Glu Tyr Ala Lys Leu Val Glu Gln Lys Asn Arg Phe Glu Gln Lys Asn
                245                 250                 255

Phe Val Gly Gln Glu His Leu Val His Leu Val Asn Gln Leu Gln Gln
            260                 265                 270

Asp Met Lys Glu Ala Ser Pro Gly Leu Glu Ser Lys Glu Gln Thr Ala
        275                 280                 285

His Tyr Val Thr Gly Arg Ala Leu Arg Gly Ser Asp Lys Val Phe Glu
    290                 295                 300

Lys Trp Gly Lys Leu Ala Pro Asp Ala Pro Phe Asp Leu Tyr Asp Ala
305                 310                 315                 320

Glu Ile Lys Asn Val Gln Arg Arg Asn Thr Arg Arg Phe Gly Ser His
                325                 330                 335

Asp Leu Phe Ala Lys Leu Ala Glu Pro Glu Tyr Gln Ala Leu Trp Arg

```
                340             345             350
Glu Asp Ala Ser Phe Leu Thr Arg Tyr Ala Val Tyr Asn Ser Ile Leu
            355                 360                 365

Arg Lys Leu Asn His Ala Lys Met Phe Ala Thr Phe Thr Leu Pro Asp
    370                 375                 380

Ala Thr Ala His Pro Ile Trp Thr Arg Phe Asp Lys Leu Gly Gly Asn
385                 390                 395                 400

Leu His Gln Tyr Thr Phe Leu Phe Asn Glu Phe Gly Glu Arg Arg His
                405                 410                 415

Ala Ile Arg Phe His Lys Leu Leu Lys Val Glu Asn Gly Val Ala Arg
            420                 425                 430

Glu Val Asp Asp Val Thr Val Pro Ile Ser Met Ser Glu Gln Leu Asp
        435                 440                 445

Asn Leu Leu Pro Arg Asp Pro Asn Glu Pro Ile Ala Leu Tyr Phe Arg
    450                 455                 460

Asp Tyr Gly Ala Glu Gln His Phe Thr Gly Glu Phe Gly Gly Ala Lys
465                 470                 475                 480

Ile Gln Cys Arg Arg Asp Gln Leu Ala His Met His Arg Arg Gly
                485                 490                 495

Ala Arg Asp Val Tyr Leu Asn Val Ser Val Arg Val Gln Ser Gln Ser
            500                 505                 510

Glu Ala Arg Gly Glu Arg Arg Pro Pro Tyr Ala Ala Val Phe Arg Leu
        515                 520                 525

Val Gly Asp Asn His Arg Ala Phe Val His Phe Asp Lys Leu Ser Asp
    530                 535                 540

Tyr Leu Ala Glu His Pro Asp Asp Gly Lys Leu Gly Ser Glu Gly Leu
545                 550                 555                 560

Leu Ser Gly Leu Arg Val Met Ser Val Asp Leu Gly Leu Arg Thr Ser
                565                 570                 575

Ala Ser Ile Ser Val Phe Arg Val Ala Arg Lys Asp Glu Leu Lys Pro
            580                 585                 590

Asn Ser Lys Gly Arg Val Pro Phe Phe Phe Pro Ile Lys Gly Asn Asp
        595                 600                 605

Asn Leu Val Ala Val His Glu Arg Ser Gln Leu Leu Lys Leu Pro Gly
    610                 615                 620

Glu Thr Glu Ser Lys Asp Leu Arg Ala Ile Arg Glu Glu Arg Gln Arg
625                 630                 635                 640

Thr Leu Arg Gln Leu Arg Thr Gln Leu Ala Tyr Leu Arg Leu Leu Val
                645                 650                 655

Arg Cys Gly Ser Glu Asp Val Gly Arg Arg Glu Arg Ser Trp Ala Lys
            660                 665                 670

Leu Ile Glu Gln Pro Val Asp Ala Ala Asn His Met Thr Pro Asp Trp
        675                 680                 685

Arg Glu Ala Phe Glu Asn Glu Leu Gln Lys Leu Lys Ser Leu His Gly
    690                 695                 700

Ile Cys Ser Asp Lys Glu Trp Met Asp Ala Val Tyr Glu Ser Val Arg
705                 710                 715                 720

Arg Val Trp Arg His Met Gly Lys Gln Val Arg Asp Trp Arg Lys Asp
                725                 730                 735

Val Arg Ser Gly Glu Arg Pro Lys Ile Arg Gly Tyr Ala Lys Asp Val
            740                 745                 750

Val Gly Gly Asn Ser Ile Glu Gln Ile Glu Tyr Leu Glu Arg Gln Tyr
        755                 760                 765
```

Lys Phe Leu Lys Ser Trp Ser Phe Gly Lys Val Ser Gly Gln Val
770                 775                 780

Ile Arg Ala Glu Lys Gly Ser Arg Phe Ala Ile Thr Leu Arg Glu His
785                 790                 795                 800

Ile Asp His Ala Lys Glu Asp Arg Leu Lys Lys Leu Ala Asp Arg Ile
            805                 810                 815

Ile Met Glu Ala Leu Gly Tyr Val Tyr Ala Leu Asp Glu Arg Gly Lys
            820                 825                 830

Gly Lys Trp Val Ala Lys Tyr Pro Pro Cys Gln Leu Ile Leu Leu Ala
            835                 840                 845

Glu Leu Ser Glu Tyr Gln Phe Asn Asn Asp Arg Pro Pro Ser Glu Asn
850                 855                 860

Asn Gln Leu Met Gln Trp Ser His Arg Gly Val Phe Gln Glu Leu Ile
865                 870                 875                 880

Asn Gln Ala Gln Val His Asp Leu Leu Val Gly Thr Met Tyr Ala Ala
            885                 890                 895

Phe Ser Ser Arg Phe Asp Ala Arg Thr Gly Ala Pro Gly Ile Arg Cys
            900                 905                 910

Arg Arg Val Pro Ala Arg Cys Thr Gln Glu His Asn Pro Glu Pro Phe
            915                 920                 925

Pro Trp Trp Leu Asn Lys Phe Val Val Glu His Thr Leu Asp Ala Cys
930                 935                 940

Pro Leu Arg Ala Asp Asp Leu Ile Pro Thr Gly Glu Gly Glu Ile Phe
945                 950                 955                 960

Val Ser Pro Phe Ser Ala Glu Gly Asp Phe His Gln Ile His Ala
            965                 970                 975

Asp Leu Asn Ala Ala Gln Asn Leu Gln Gln Arg Leu Trp Ser Asp Phe
            980                 985                 990

Asp Ile Ser Gln Ile Arg Leu Arg Cys Asp Trp Gly Glu Val Asp Gly
            995                 1000                1005

Glu Leu Val Leu Ile Pro Arg Leu Thr Gly Lys Arg Thr Ala Asp
1010                1015                1020

Ser Tyr Ser Asn Lys Val Phe Tyr Thr Asn Thr Gly Val Thr Tyr
1025                1030                1035

Tyr Glu Arg Glu Arg Gly Lys Lys Arg Arg Lys Val Phe Ala Gln
1040                1045                1050

Glu Lys Leu Ser Glu Glu Ala Glu Leu Leu Val Glu Ala Asp
1055                1060                1065

Glu Ala Arg Glu Lys Ser Val Val Leu Met Arg Asp Pro Ser Gly
1070                1075                1080

Ile Ile Asn Arg Gly Asn Trp Thr Arg Gln Lys Glu Phe Trp Ser
1085                1090                1095

Met Val Asn Gln Arg Ile Glu Gly Tyr Leu Val Lys Gln Ile Arg
1100                1105                1110

Ser Arg Val Pro Leu Gln Asp Ser Ala Cys Glu Asn Thr Gly Asp
1115                1120                1125

Ile

<210> SEQ ID NO 21
<211> LENGTH: 1108
<212> TYPE: PRT
<213> ORGANISM: Artificial Sequence
<220> FEATURE:
<223> OTHER INFORMATION: BthCas12b-D573A protein

<400> SEQUENCE: 21

```
Met Ala Thr Arg Ser Phe Ile Leu Lys Ile Glu Pro Asn Glu Val
1               5                   10                  15

Lys Lys Gly Leu Trp Lys Thr His Glu Val Leu Asn His Gly Ile Ala
            20                  25                  30

Tyr Tyr Met Asn Ile Leu Lys Leu Ile Arg Gln Glu Ala Ile Tyr Glu
            35                  40                  45

His His Glu Gln Asp Pro Lys Asn Pro Lys Lys Val Ser Lys Ala Glu
        50                  55                  60

Ile Gln Ala Glu Leu Trp Asp Phe Val Leu Lys Met Gln Lys Cys Asn
65                  70                  75                  80

Ser Phe Thr His Glu Val Asp Lys Asp Val Val Phe Asn Ile Leu Arg
                85                  90                  95

Glu Leu Tyr Glu Glu Leu Val Pro Ser Ser Val Glu Lys Lys Gly Glu
            100                 105                 110

Ala Asn Gln Leu Ser Asn Lys Phe Leu Tyr Pro Leu Val Asp Pro Asn
            115                 120                 125

Ser Gln Ser Gly Lys Gly Thr Ala Ser Ser Gly Arg Lys Pro Arg Trp
        130                 135                 140

Tyr Asn Leu Lys Ile Ala Gly Asp Pro Ser Trp Glu Glu Lys Lys
145                 150                 155                 160

Lys Trp Glu Glu Asp Lys Lys Lys Asp Pro Leu Ala Lys Ile Leu Gly
                165                 170                 175

Lys Leu Ala Glu Tyr Gly Leu Ile Pro Leu Phe Ile Pro Phe Thr Asp
            180                 185                 190

Ser Asn Glu Pro Ile Val Lys Glu Ile Lys Trp Met Glu Lys Ser Arg
            195                 200                 205

Asn Gln Ser Val Arg Arg Leu Asp Lys Asp Met Phe Ile Gln Ala Leu
        210                 215                 220

Glu Arg Phe Leu Ser Trp Glu Ser Trp Asn Leu Lys Val Lys Glu Glu
225                 230                 235                 240

Tyr Glu Lys Val Glu Lys Glu His Lys Thr Leu Glu Glu Arg Ile Lys
                245                 250                 255

Glu Asp Ile Gln Ala Phe Lys Ser Leu Glu Gln Tyr Glu Lys Glu Arg
            260                 265                 270

Gln Glu Gln Leu Leu Arg Asp Thr Leu Asn Thr Asn Glu Tyr Arg Leu
        275                 280                 285

Ser Lys Arg Gly Leu Arg Gly Trp Arg Glu Ile Ile Gln Lys Trp Leu
        290                 295                 300

Lys Met Asp Glu Asn Glu Pro Ser Glu Lys Tyr Leu Glu Val Phe Lys
305                 310                 315                 320

Asp Tyr Gln Arg Lys His Pro Arg Glu Ala Gly Asp Tyr Ser Val Tyr
                325                 330                 335

Glu Phe Leu Ser Lys Lys Glu Asn His Phe Ile Trp Arg Asn His Pro
            340                 345                 350

Glu Tyr Pro Tyr Leu Tyr Ala Thr Phe Cys Glu Ile Asp Lys Lys Lys
        355                 360                 365

Lys Asp Ala Lys Gln Gln Ala Thr Phe Thr Leu Ala Asp Pro Ile Asn
        370                 375                 380

His Pro Leu Trp Val Arg Phe Glu Glu Arg Ser Gly Ser Asn Leu Asn
385                 390                 395                 400

Lys Tyr Arg Ile Leu Thr Glu Gln Leu His Thr Glu Lys Leu Lys Lys
```

```
                405                 410                 415
Lys Leu Thr Val Gln Leu Asp Arg Leu Ile Tyr Pro Thr Glu Ser Gly
            420                 425                 430

Gly Trp Glu Glu Lys Gly Lys Val Asp Ile Val Leu Leu Pro Ser Arg
            435                 440                 445

Gln Phe Tyr Asn Gln Ile Phe Leu Asp Ile Glu Glu Lys Gly Lys His
            450                 455                 460

Ala Phe Thr Tyr Lys Asp Glu Ser Ile Lys Phe Pro Leu Lys Gly Thr
465                 470                 475                 480

Leu Gly Gly Ala Arg Val Gln Phe Asp Arg Asp His Leu Arg Arg Tyr
                485                 490                 495

Pro His Lys Val Glu Ser Gly Asn Val Gly Arg Ile Tyr Phe Asn Met
            500                 505                 510

Thr Val Asn Ile Glu Pro Thr Glu Ser Pro Val Ser Lys Ser Leu Lys
            515                 520                 525

Ile His Arg Asp Asp Phe Pro Lys Phe Val Asn Phe Lys Pro Lys Glu
            530                 535                 540

Leu Thr Glu Trp Ile Lys Asp Ser Lys Gly Lys Lys Leu Lys Ser Gly
545                 550                 555                 560

Ile Glu Ser Leu Glu Ile Gly Leu Arg Val Met Ser Ile Ala Leu Gly
                565                 570                 575

Gln Arg Gln Ala Ala Ala Ser Ile Phe Glu Val Val Asp Gln Lys
            580                 585                 590

Pro Asp Ile Glu Gly Lys Leu Phe Phe Pro Ile Lys Gly Thr Glu Leu
            595                 600                 605

Tyr Ala Val His Arg Ala Ser Phe Asn Ile Lys Leu Pro Gly Glu Thr
            610                 615                 620

Leu Val Lys Ser Arg Glu Val Leu Arg Lys Ala Arg Glu Asp Asn Leu
625                 630                 635                 640

Lys Leu Met Asn Gln Lys Leu Asn Phe Leu Arg Asn Val Leu His Phe
                645                 650                 655

Gln Gln Phe Glu Asp Ile Thr Glu Arg Glu Lys Arg Val Thr Lys Trp
            660                 665                 670

Ile Ser Arg Gln Glu Asn Ser Asp Val Pro Leu Val Tyr Gln Asp Glu
            675                 680                 685

Leu Ile Gln Ile Arg Glu Leu Met Tyr Lys Pro Tyr Lys Asp Trp Val
            690                 695                 700

Ala Phe Leu Lys Gln Leu His Lys Arg Leu Glu Val Glu Ile Gly Lys
705                 710                 715                 720

Glu Val Lys His Trp Arg Lys Ser Leu Ser Asp Gly Arg Lys Gly Leu
                725                 730                 735

Tyr Gly Ile Ser Leu Lys Asn Ile Asp Glu Ile Asp Arg Thr Arg Lys
            740                 745                 750

Phe Leu Leu Arg Trp Ser Leu Arg Pro Thr Glu Pro Gly Glu Val Arg
            755                 760                 765

Arg Leu Glu Pro Gly Gln Arg Phe Ala Ile Asp Gln Leu Asn His Leu
            770                 775                 780

Asn Ala Leu Lys Glu Asp Arg Leu Lys Lys Met Ala Asn Thr Ile Ile
785                 790                 795                 800

Met His Ala Leu Gly Tyr Cys Tyr Asp Val Arg Lys Lys Lys Trp Gln
                805                 810                 815

Ala Lys Asn Pro Ala Cys Gln Ile Ile Leu Phe Glu Asp Leu Ser Asn
            820                 825                 830
```

Tyr Asn Pro Tyr Glu Glu Arg Ser Arg Phe Glu Asn Ser Lys Leu Met
            835                 840                 845

Lys Trp Ser Arg Arg Glu Ile Pro Arg Gln Val Ala Leu Gln Gly Glu
    850                 855                 860

Ile Tyr Gly Leu Gln Val Gly Glu Val Gly Ala Gln Phe Ser Ser Arg
865                 870                 875                 880

Phe His Ala Lys Thr Gly Ser Pro Gly Ile Arg Cys Ser Val Val Thr
                885                 890                 895

Lys Glu Lys Leu Gln Asp Asn Arg Phe Phe Lys Asn Leu Gln Arg Glu
            900                 905                 910

Gly Arg Leu Thr Leu Asp Lys Ile Ala Val Leu Lys Glu Gly Asp Leu
            915                 920                 925

Tyr Pro Asp Lys Gly Glu Lys Phe Ile Ser Leu Ser Lys Asp Arg
            930                 935                 940

Lys Leu Val Thr Thr His Ala Asp Ile Asn Ala Ala Gln Asn Leu Gln
945                 950                 955                 960

Lys Arg Phe Trp Thr Arg Thr His Gly Phe Tyr Lys Val Tyr Cys Lys
                965                 970                 975

Ala Tyr Gln Val Asp Gly Gln Thr Val Tyr Ile Pro Gly Ser Lys Asp
            980                 985                 990

Gln Lys Gln Lys Ile Ile Glu Glu Phe Gly Glu Gly Tyr Phe Ile Leu
            995                 1000                1005

Lys Asp Gly Val Tyr Glu Trp Gly Asn Ala Gly Lys Leu Lys Ile
    1010                1015                1020

Lys Lys Gly Ser Ser Lys Gln Ser Ser Glu Leu Val Asp Ser
    1025                1030                1035

Asp Ile Leu Lys Asp Ser Phe Asp Leu Ala Ser Glu Leu Lys Gly
    1040                1045                1050

Glu Lys Leu Met Leu Tyr Arg Asp Pro Ser Gly Asn Val Phe Pro
    1055                1060                1065

Ser Asp Lys Trp Met Ala Ala Gly Val Phe Phe Gly Lys Leu Glu
    1070                1075                1080

Arg Ile Leu Ile Ser Lys Leu Thr Asn Gln Tyr Ser Ile Ser Thr
    1085                1090                1095

Ile Glu Asp Asp Ser Ser Lys Gln Ser Met
    1100                1105

<210> SEQ ID NO 22
<211> LENGTH: 1108
<212> TYPE: PRT
<213> ORGANISM: Artificial Sequence
<220> FEATURE:
<223> OTHER INFORMATION: BthCas12b-D951A protein

<400> SEQUENCE: 22

Met Ala Thr Arg Ser Phe Ile Leu Lys Ile Glu Pro Asn Glu Glu Val
1               5                   10                  15

Lys Lys Gly Leu Trp Lys Thr His Glu Val Leu Asn His Gly Ile Ala
            20                  25                  30

Tyr Tyr Met Asn Ile Leu Lys Leu Ile Arg Gln Glu Ala Ile Tyr Glu
        35                  40                  45

His His Glu Gln Asp Pro Lys Asn Pro Lys Lys Val Ser Lys Ala Glu
    50                  55                  60

Ile Gln Ala Glu Leu Trp Asp Phe Val Leu Lys Met Gln Lys Cys Asn
65                  70                  75                  80

```
Ser Phe Thr His Glu Val Asp Lys Asp Val Val Phe Asn Ile Leu Arg
                85                  90                  95
Glu Leu Tyr Glu Glu Leu Val Pro Ser Ser Val Glu Lys Lys Gly Glu
            100                 105                 110
Ala Asn Gln Leu Ser Asn Lys Phe Leu Tyr Pro Leu Val Asp Pro Asn
        115                 120                 125
Ser Gln Ser Gly Lys Gly Thr Ala Ser Gly Arg Lys Pro Arg Trp
    130                 135                 140
Tyr Asn Leu Lys Ile Ala Gly Asp Pro Ser Trp Glu Glu Lys Lys
145                 150                 155                 160
Lys Trp Glu Glu Asp Lys Lys Lys Asp Pro Leu Ala Lys Ile Leu Gly
                165                 170                 175
Lys Leu Ala Glu Tyr Gly Leu Ile Pro Leu Phe Ile Pro Phe Thr Asp
            180                 185                 190
Ser Asn Glu Pro Ile Val Lys Glu Ile Lys Trp Met Glu Lys Ser Arg
        195                 200                 205
Asn Gln Ser Val Arg Arg Leu Asp Lys Asp Met Phe Ile Gln Ala Leu
    210                 215                 220
Glu Arg Phe Leu Ser Trp Glu Ser Trp Asn Leu Lys Val Lys Glu Glu
225                 230                 235                 240
Tyr Glu Lys Val Glu Lys Glu His Lys Thr Leu Glu Glu Arg Ile Lys
                245                 250                 255
Glu Asp Ile Gln Ala Phe Lys Ser Leu Glu Gln Tyr Glu Lys Glu Arg
            260                 265                 270
Gln Glu Gln Leu Leu Arg Asp Thr Leu Asn Thr Asn Glu Tyr Arg Leu
        275                 280                 285
Ser Lys Arg Gly Leu Arg Gly Trp Arg Glu Ile Ile Gln Lys Trp Leu
    290                 295                 300
Lys Met Asp Glu Asn Glu Pro Ser Glu Lys Tyr Leu Glu Val Phe Lys
305                 310                 315                 320
Asp Tyr Gln Arg Lys His Pro Arg Glu Ala Gly Asp Tyr Ser Val Tyr
                325                 330                 335
Glu Phe Leu Ser Lys Lys Glu Asn His Phe Ile Trp Arg Asn His Pro
            340                 345                 350
Glu Tyr Pro Tyr Leu Tyr Ala Thr Phe Cys Glu Ile Asp Lys Lys Lys
        355                 360                 365
Lys Asp Ala Lys Gln Gln Ala Thr Phe Thr Leu Ala Asp Pro Ile Asn
    370                 375                 380
His Pro Leu Trp Val Arg Phe Glu Glu Arg Ser Gly Ser Asn Leu Asn
385                 390                 395                 400
Lys Tyr Arg Ile Leu Thr Glu Gln Leu His Thr Glu Lys Leu Lys Lys
                405                 410                 415
Lys Leu Thr Val Gln Leu Asp Arg Leu Ile Tyr Pro Thr Glu Ser Gly
            420                 425                 430
Gly Trp Glu Glu Lys Gly Lys Val Asp Ile Val Leu Leu Pro Ser Arg
        435                 440                 445
Gln Phe Tyr Asn Gln Ile Phe Leu Asp Ile Glu Glu Lys Gly Lys His
    450                 455                 460
Ala Phe Thr Tyr Lys Asp Glu Ser Ile Lys Phe Pro Leu Lys Gly Thr
465                 470                 475                 480
Leu Gly Gly Ala Arg Val Gln Phe Asp Arg Asp His Leu Arg Arg Tyr
                485                 490                 495
```

```
Pro His Lys Val Glu Ser Gly Asn Val Gly Arg Ile Tyr Phe Asn Met
            500                 505                 510

Thr Val Asn Ile Glu Pro Thr Glu Ser Pro Val Ser Lys Ser Leu Lys
            515                 520                 525

Ile His Arg Asp Asp Phe Pro Lys Phe Val Asn Phe Lys Pro Lys Glu
            530                 535                 540

Leu Thr Glu Trp Ile Lys Asp Ser Lys Gly Lys Lys Leu Lys Ser Gly
545                 550                 555                 560

Ile Glu Ser Leu Glu Ile Gly Leu Arg Val Met Ser Ile Asp Leu Gly
            565                 570                 575

Gln Arg Gln Ala Ala Ala Ser Ile Phe Glu Val Val Asp Gln Lys
            580                 585                 590

Pro Asp Ile Glu Gly Lys Leu Phe Phe Pro Ile Lys Gly Thr Glu Leu
            595                 600                 605

Tyr Ala Val His Arg Ala Ser Phe Asn Ile Lys Leu Pro Gly Glu Thr
            610                 615                 620

Leu Val Lys Ser Arg Glu Val Leu Arg Lys Ala Arg Glu Asp Asn Leu
625                 630                 635                 640

Lys Leu Met Asn Gln Lys Leu Asn Phe Leu Arg Asn Val Leu His Phe
            645                 650                 655

Gln Gln Phe Glu Asp Ile Thr Glu Arg Glu Lys Arg Val Thr Lys Trp
            660                 665                 670

Ile Ser Arg Gln Glu Asn Ser Asp Val Pro Leu Val Tyr Gln Asp Glu
            675                 680                 685

Leu Ile Gln Ile Arg Glu Leu Met Tyr Lys Pro Tyr Lys Asp Trp Val
            690                 695                 700

Ala Phe Leu Lys Gln Leu His Lys Arg Leu Glu Val Glu Ile Gly Lys
705                 710                 715                 720

Glu Val Lys His Trp Arg Lys Ser Leu Ser Asp Gly Arg Lys Gly Leu
            725                 730                 735

Tyr Gly Ile Ser Leu Lys Asn Ile Asp Glu Ile Asp Arg Thr Arg Lys
            740                 745                 750

Phe Leu Leu Arg Trp Ser Leu Arg Pro Thr Glu Pro Gly Glu Val Arg
            755                 760                 765

Arg Leu Glu Pro Gly Gln Arg Phe Ala Ile Asp Gln Leu Asn His Leu
770                 775                 780

Asn Ala Leu Lys Glu Asp Arg Leu Lys Lys Met Ala Asn Thr Ile Ile
785                 790                 795                 800

Met His Ala Leu Gly Tyr Cys Tyr Asp Val Arg Lys Lys Lys Trp Gln
            805                 810                 815

Ala Lys Asn Pro Ala Cys Gln Ile Ile Leu Phe Glu Asp Leu Ser Asn
            820                 825                 830

Tyr Asn Pro Tyr Glu Glu Arg Ser Arg Phe Glu Asn Ser Lys Leu Met
            835                 840                 845

Lys Trp Ser Arg Arg Glu Ile Pro Arg Gln Val Ala Leu Gln Gly Glu
            850                 855                 860

Ile Tyr Gly Leu Gln Val Gly Glu Val Gly Ala Gln Phe Ser Ser Arg
865                 870                 875                 880

Phe His Ala Lys Thr Gly Ser Pro Gly Ile Arg Cys Ser Val Val Thr
            885                 890                 895

Lys Glu Lys Leu Gln Asp Asn Arg Phe Phe Lys Asn Leu Gln Arg Glu
            900                 905                 910

Gly Arg Leu Thr Leu Asp Lys Ile Ala Val Leu Lys Glu Gly Asp Leu
```

```
            915                 920                 925
Tyr Pro Asp Lys Gly Gly Glu Lys Phe Ile Ser Leu Ser Lys Asp Arg
    930                 935                 940

Lys Leu Val Thr Thr His Ala Ala Ile Asn Ala Ala Gln Asn Leu Gln
945                 950                 955                 960

Lys Arg Phe Trp Thr Arg Thr His Gly Phe Tyr Lys Val Tyr Cys Lys
                965                 970                 975

Ala Tyr Gln Val Asp Gly Gln Thr Val Tyr Ile Pro Glu Ser Lys Asp
                980                 985                 990

Gln Lys Gln Lys Ile Ile Glu Glu Phe Gly Glu Gly Tyr Phe Ile Leu
                995                 1000                1005

Lys Asp Gly Val Tyr Glu Trp Gly Asn Ala Gly Lys Leu Lys Ile
    1010                1015                1020

Lys Lys Gly Ser Ser Lys Gln Ser Ser Ser Glu Leu Val Asp Ser
    1025                1030                1035

Asp Ile Leu Lys Asp Ser Phe Asp Leu Ala Ser Glu Leu Lys Gly
    1040                1045                1050

Glu Lys Leu Met Leu Tyr Arg Asp Pro Ser Gly Asn Val Phe Pro
    1055                1060                1065

Ser Asp Lys Trp Met Ala Ala Gly Val Phe Phe Gly Lys Leu Glu
    1070                1075                1080

Arg Ile Leu Ile Ser Lys Leu Thr Asn Gln Tyr Ser Ile Ser Thr
    1085                1090                1095

Ile Glu Asp Asp Ser Ser Lys Gln Ser Met
    1100                1105

<210> SEQ ID NO 23
<211> LENGTH: 1108
<212> TYPE: PRT
<213> ORGANISM: Artificial Sequence
<220> FEATURE:
<223> OTHER INFORMATION: BthCas12b-E827A protein

<400> SEQUENCE: 23

Met Ala Thr Arg Ser Phe Ile Leu Lys Ile Glu Pro Asn Glu Val
1               5                   10                  15

Lys Lys Gly Leu Trp Lys Thr His Glu Val Leu Asn His Gly Ile Ala
                20                  25                  30

Tyr Tyr Met Asn Ile Leu Lys Leu Ile Arg Gln Glu Ala Ile Tyr Glu
                35                  40                  45

His His Glu Gln Asp Pro Lys Asn Pro Lys Val Ser Lys Ala Glu
    50                  55                  60

Ile Gln Ala Glu Leu Trp Asp Phe Val Leu Lys Met Gln Lys Cys Asn
65                  70                  75                  80

Ser Phe Thr His Glu Val Asp Lys Asp Val Val Phe Asn Ile Leu Arg
                85                  90                  95

Glu Leu Tyr Glu Glu Leu Val Pro Ser Ser Val Glu Lys Lys Gly Glu
                100                 105                 110

Ala Asn Gln Leu Ser Asn Lys Phe Leu Tyr Pro Leu Val Asp Pro Asn
            115                 120                 125

Ser Gln Ser Gly Lys Gly Thr Ala Ser Ser Gly Arg Lys Pro Arg Trp
    130                 135                 140

Tyr Asn Leu Lys Ile Ala Gly Asp Pro Ser Trp Glu Glu Lys Lys
145                 150                 155                 160

Lys Trp Glu Glu Asp Lys Lys Lys Asp Pro Leu Ala Lys Ile Leu Gly
```

```
                    165                 170                 175
Lys Leu Ala Glu Tyr Gly Leu Ile Pro Leu Phe Ile Pro Phe Thr Asp
                180                 185                 190

Ser Asn Glu Pro Ile Val Lys Glu Ile Lys Trp Met Glu Lys Ser Arg
            195                 200                 205

Asn Gln Ser Val Arg Arg Leu Asp Lys Asp Met Phe Ile Gln Ala Leu
        210                 215                 220

Glu Arg Phe Leu Ser Trp Glu Ser Trp Asn Leu Lys Val Lys Glu Glu
225                 230                 235                 240

Tyr Glu Lys Val Glu Lys Glu His Lys Thr Leu Glu Glu Arg Ile Lys
                245                 250                 255

Glu Asp Ile Gln Ala Phe Lys Ser Leu Glu Gln Tyr Glu Lys Glu Arg
            260                 265                 270

Gln Glu Gln Leu Leu Arg Asp Thr Leu Asn Thr Asn Glu Tyr Arg Leu
        275                 280                 285

Ser Lys Arg Gly Leu Arg Gly Trp Arg Glu Ile Ile Gln Lys Trp Leu
290                 295                 300

Lys Met Asp Glu Asn Glu Pro Ser Glu Lys Tyr Leu Glu Val Phe Lys
305                 310                 315                 320

Asp Tyr Gln Arg Lys His Pro Arg Glu Ala Gly Asp Tyr Ser Val Tyr
                325                 330                 335

Glu Phe Leu Ser Lys Lys Glu Asn His Phe Ile Trp Arg Asn His Pro
            340                 345                 350

Glu Tyr Pro Tyr Leu Tyr Ala Thr Phe Cys Glu Ile Asp Lys Lys Lys
        355                 360                 365

Lys Asp Ala Lys Gln Gln Ala Thr Phe Thr Leu Ala Asp Pro Ile Asn
370                 375                 380

His Pro Leu Trp Val Arg Phe Glu Glu Arg Ser Gly Ser Asn Leu Asn
385                 390                 395                 400

Lys Tyr Arg Ile Leu Thr Glu Gln Leu His Thr Glu Lys Leu Lys Lys
                405                 410                 415

Lys Leu Thr Val Gln Leu Asp Arg Leu Ile Tyr Pro Thr Glu Ser Gly
            420                 425                 430

Gly Trp Glu Glu Lys Gly Lys Val Asp Ile Val Leu Leu Pro Ser Arg
        435                 440                 445

Gln Phe Tyr Asn Gln Ile Phe Leu Asp Ile Glu Glu Lys Gly Lys His
450                 455                 460

Ala Phe Thr Tyr Lys Asp Glu Ser Ile Lys Phe Pro Leu Lys Gly Thr
465                 470                 475                 480

Leu Gly Gly Ala Arg Val Gln Phe Asp Arg Asp His Leu Arg Arg Tyr
                485                 490                 495

Pro His Lys Val Glu Ser Gly Asn Val Gly Arg Ile Tyr Phe Asn Met
            500                 505                 510

Thr Val Asn Ile Glu Pro Thr Glu Ser Pro Val Ser Lys Ser Leu Lys
        515                 520                 525

Ile His Arg Asp Asp Phe Pro Lys Phe Val Asn Phe Lys Pro Lys Glu
530                 535                 540

Leu Thr Glu Trp Ile Lys Asp Ser Lys Gly Lys Lys Leu Lys Ser Gly
545                 550                 555                 560

Ile Glu Ser Leu Glu Ile Gly Leu Arg Val Met Ser Ile Asp Leu Gly
                565                 570                 575

Gln Arg Gln Ala Ala Ala Ala Ser Ile Phe Glu Val Val Asp Gln Lys
            580                 585                 590
```

```
Pro Asp Ile Glu Gly Lys Leu Phe Phe Pro Ile Lys Gly Thr Glu Leu
    595                 600                 605
Tyr Ala Val His Arg Ala Ser Phe Asn Ile Lys Leu Pro Gly Glu Thr
    610                 615                 620
Leu Val Lys Ser Arg Glu Val Leu Arg Lys Ala Arg Glu Asp Asn Leu
625                 630                 635                 640
Lys Leu Met Asn Gln Lys Leu Asn Phe Leu Arg Asn Val Leu His Phe
                645                 650                 655
Gln Gln Phe Glu Asp Ile Thr Glu Arg Glu Lys Arg Val Thr Lys Trp
            660                 665                 670
Ile Ser Arg Gln Glu Asn Ser Asp Val Pro Leu Val Tyr Gln Asp Glu
        675                 680                 685
Leu Ile Gln Ile Arg Glu Leu Met Tyr Lys Pro Tyr Lys Asp Trp Val
    690                 695                 700
Ala Phe Leu Lys Gln Leu His Lys Arg Leu Glu Val Glu Ile Gly Lys
705                 710                 715                 720
Glu Val Lys His Trp Arg Lys Ser Leu Ser Asp Gly Arg Lys Gly Leu
                725                 730                 735
Tyr Gly Ile Ser Leu Lys Asn Ile Asp Glu Ile Asp Arg Thr Arg Lys
            740                 745                 750
Phe Leu Leu Arg Trp Ser Leu Arg Pro Thr Glu Pro Gly Glu Val Arg
        755                 760                 765
Arg Leu Glu Pro Gly Gln Arg Phe Ala Ile Asp Gln Leu Asn His Leu
    770                 775                 780
Asn Ala Leu Lys Glu Asp Arg Leu Lys Lys Met Ala Asn Thr Ile Ile
785                 790                 795                 800
Met His Ala Leu Gly Tyr Cys Tyr Asp Val Arg Lys Lys Lys Trp Gln
                805                 810                 815
Ala Lys Asn Pro Ala Cys Gln Ile Ile Leu Phe Ala Asp Leu Ser Asn
            820                 825                 830
Tyr Asn Pro Tyr Glu Glu Arg Ser Arg Phe Glu Asn Ser Lys Leu Met
        835                 840                 845
Lys Trp Ser Arg Arg Glu Ile Pro Arg Gln Val Ala Leu Gln Gly Glu
    850                 855                 860
Ile Tyr Gly Leu Gln Val Gly Glu Val Gly Ala Gln Phe Ser Ser Arg
865                 870                 875                 880
Phe His Ala Lys Thr Gly Ser Pro Gly Ile Arg Cys Ser Val Val Thr
                885                 890                 895
Lys Glu Lys Leu Gln Asp Asn Arg Phe Lys Asn Leu Gln Arg Glu
            900                 905                 910
Gly Arg Leu Thr Leu Asp Lys Ile Ala Val Leu Lys Glu Gly Asp Leu
        915                 920                 925
Tyr Pro Asp Lys Gly Gly Glu Lys Phe Ile Ser Leu Ser Lys Asp Arg
    930                 935                 940
Lys Leu Val Thr Thr His Ala Asp Ile Asn Ala Ala Gln Asn Leu Gln
945                 950                 955                 960
Lys Arg Phe Trp Thr Arg Thr His Gly Phe Tyr Lys Val Tyr Cys Lys
                965                 970                 975
Ala Tyr Gln Val Asp Gly Gln Thr Val Tyr Ile Pro Glu Ser Lys Asp
            980                 985                 990
Gln Lys Gln Lys Ile Ile Glu Glu Phe Gly Glu Gly Tyr Phe Ile Leu
        995                 1000                1005
```

```
Lys Asp Gly Val Tyr Glu Trp Gly Asn Ala Gly Lys Leu Lys Ile
    1010                1015                1020

Lys Lys Gly Ser Ser Lys Gln Ser Ser Glu Leu Val Asp Ser
1025                1030                1035

Asp Ile Leu Lys Asp Ser Phe Asp Leu Ala Ser Glu Leu Lys Gly
    1040                1045                1050

Glu Lys Leu Met Leu Tyr Arg Asp Pro Ser Gly Asn Val Phe Pro
    1055                1060                1065

Ser Asp Lys Trp Met Ala Ala Gly Val Phe Phe Gly Lys Leu Glu
    1070                1075                1080

Arg Ile Leu Ile Ser Lys Leu Thr Asn Gln Tyr Ser Ile Ser Thr
    1085                1090                1095

Ile Glu Asp Asp Ser Ser Lys Gln Ser Met
    1100                1105
```

<210> SEQ ID NO 24
<211> LENGTH: 1129
<212> TYPE: PRT
<213> ORGANISM: Artificial Sequence
<220> FEATURE:
<223> OTHER INFORMATION: AaCas12b-D570A protein

<400> SEQUENCE: 24

```
Met Ala Val Lys Ser Met Lys Val Lys Leu Arg Leu Asp Asn Met Pro
1               5                   10                  15

Glu Ile Arg Ala Gly Leu Trp Lys Leu His Thr Glu Val Asn Ala Gly
                20                  25                  30

Val Arg Tyr Tyr Thr Glu Trp Leu Ser Leu Leu Arg Gln Glu Asn Leu
            35                  40                  45

Tyr Arg Arg Ser Pro Asn Gly Asp Gly Glu Gln Glu Cys Tyr Lys Thr
        50                  55                  60

Ala Glu Glu Cys Lys Ala Glu Leu Leu Glu Arg Leu Arg Ala Arg Gln
65                  70                  75                  80

Val Glu Asn Gly His Cys Gly Pro Ala Gly Ser Asp Asp Glu Leu Leu
                85                  90                  95

Gln Leu Ala Arg Gln Leu Tyr Glu Leu Leu Val Pro Gln Ala Ile Gly
            100                 105                 110

Ala Lys Gly Asp Ala Gln Gln Ile Ala Arg Lys Phe Leu Ser Pro Leu
        115                 120                 125

Ala Asp Lys Asp Ala Val Gly Gly Leu Gly Ile Ala Lys Ala Gly Asn
130                 135                 140

Lys Pro Arg Trp Val Arg Met Arg Glu Ala Gly Glu Pro Gly Trp Glu
145                 150                 155                 160

Glu Glu Lys Ala Lys Ala Glu Arg Lys Ser Thr Asp Arg Thr Ala
                165                 170                 175

Asp Val Leu Arg Ala Leu Ala Asp Phe Gly Leu Lys Pro Leu Met Arg
            180                 185                 190

Val Tyr Thr Asp Ser Asp Met Ser Ser Val Gln Trp Lys Pro Leu Arg
        195                 200                 205

Lys Gly Gln Ala Val Arg Thr Trp Asp Arg Asp Met Phe Gln Gln Ala
    210                 215                 220

Ile Glu Arg Met Met Ser Trp Glu Ser Trp Asn Gln Arg Val Gly Glu
225                 230                 235                 240

Ala Tyr Ala Lys Leu Val Glu Gln Lys Ser Arg Phe Glu Gln Lys Asn
                245                 250                 255
```

```
Phe Val Gly Gln Glu His Leu Val Gln Leu Val Asn Gln Leu Gln Gln
                260                 265                 270

Asp Met Lys Glu Ala Ser His Gly Leu Glu Ser Lys Glu Gln Thr Ala
            275                 280                 285

His Tyr Leu Thr Gly Arg Ala Leu Arg Gly Ser Asp Lys Val Phe Glu
        290                 295                 300

Lys Trp Glu Lys Leu Asp Pro Asp Ala Pro Phe Asp Leu Tyr Asp Thr
305                 310                 315                 320

Glu Ile Lys Asn Val Gln Arg Arg Asn Thr Arg Arg Phe Gly Ser His
                325                 330                 335

Asp Leu Phe Ala Lys Leu Ala Glu Pro Lys Tyr Gln Ala Leu Trp Arg
            340                 345                 350

Glu Asp Ala Ser Phe Leu Thr Arg Tyr Ala Val Tyr Asn Ser Ile Val
        355                 360                 365

Arg Lys Leu Asn His Ala Lys Met Phe Ala Thr Phe Thr Leu Pro Asp
    370                 375                 380

Ala Thr Ala His Pro Ile Trp Thr Arg Phe Asp Lys Leu Gly Gly Asn
385                 390                 395                 400

Leu His Gln Tyr Thr Phe Leu Phe Asn Glu Phe Gly Glu Gly Arg His
                405                 410                 415

Ala Ile Arg Phe Gln Lys Leu Leu Thr Val Glu Asp Gly Val Ala Lys
            420                 425                 430

Glu Val Asp Asp Val Thr Val Pro Ile Ser Met Ser Ala Gln Leu Asp
        435                 440                 445

Asp Leu Leu Pro Arg Asp Pro His Glu Leu Val Ala Leu Tyr Phe Gln
    450                 455                 460

Asp Tyr Gly Ala Glu Gln His Leu Ala Gly Glu Phe Gly Gly Ala Lys
465                 470                 475                 480

Ile Gln Tyr Arg Arg Asp Gln Leu Asn His Leu His Ala Arg Arg Gly
                485                 490                 495

Ala Arg Asp Val Tyr Leu Asn Leu Ser Val Arg Val Gln Ser Gln Ser
            500                 505                 510

Glu Ala Arg Gly Glu Arg Arg Pro Tyr Ala Ala Val Phe Arg Leu
        515                 520                 525

Val Gly Asp Asn His Arg Ala Phe Val His Phe Asp Lys Leu Ser Asp
    530                 535                 540

Tyr Leu Ala Glu His Pro Asp Asp Gly Lys Leu Gly Ser Glu Gly Leu
545                 550                 555                 560

Leu Ser Gly Leu Arg Val Met Ser Val Ala Leu Gly Leu Arg Thr Ser
                565                 570                 575

Ala Ser Ile Ser Val Phe Arg Val Ala Arg Lys Asp Glu Leu Lys Pro
            580                 585                 590

Asn Ser Glu Gly Arg Val Pro Phe Cys Phe Pro Ile Glu Gly Asn Glu
        595                 600                 605

Asn Leu Val Ala Val His Glu Arg Ser Gln Leu Leu Lys Leu Pro Gly
    610                 615                 620

Glu Thr Glu Ser Lys Asp Leu Arg Ala Ile Arg Glu Arg Gln Arg
625                 630                 635                 640

Thr Leu Arg Gln Leu Arg Thr Gln Leu Ala Tyr Leu Arg Leu Leu Val
                645                 650                 655

Arg Cys Gly Ser Glu Asp Val Gly Arg Arg Glu Arg Ser Trp Ala Lys
            660                 665                 670

Leu Ile Glu Gln Pro Met Asp Ala Asn Gln Met Thr Pro Asp Trp Arg
```

```
            675                 680                 685
Glu Ala Phe Glu Asp Glu Leu Gln Lys Leu Lys Ser Leu Tyr Gly Ile
        690                 695                 700
Cys Gly Asp Arg Glu Trp Thr Glu Ala Val Tyr Glu Ser Val Arg Arg
705                 710                 715                 720
Val Trp Arg His Met Gly Lys Gln Val Arg Asp Trp Arg Lys Asp Val
                725                 730                 735
Arg Ser Gly Glu Arg Pro Lys Ile Arg Gly Tyr Gln Lys Asp Val Val
            740                 745                 750
Gly Gly Asn Ser Ile Glu Gln Ile Glu Tyr Leu Glu Arg Gln Tyr Lys
            755                 760                 765
Phe Leu Lys Ser Trp Ser Phe Phe Gly Lys Val Ser Gly Gln Val Ile
        770                 775                 780
Arg Ala Glu Lys Gly Ser Arg Phe Ala Ile Thr Leu Arg Glu His Ile
785                 790                 795                 800
Asp His Ala Lys Glu Asp Arg Leu Lys Lys Leu Ala Asp Arg Ile Ile
                805                 810                 815
Met Glu Ala Leu Gly Tyr Val Tyr Ala Leu Asp Asp Glu Arg Gly Lys
            820                 825                 830
Gly Lys Trp Val Ala Lys Tyr Pro Pro Cys Gln Leu Ile Leu Leu Glu
        835                 840                 845
Glu Leu Ser Glu Tyr Gln Phe Asn Asn Asp Arg Pro Pro Ser Glu Asn
850                 855                 860
Asn Gln Leu Met Gln Trp Ser His Arg Gly Val Phe Gln Glu Leu Leu
865                 870                 875                 880
Asn Gln Ala Gln Val His Asp Leu Leu Val Gly Thr Met Tyr Ala Ala
                885                 890                 895
Phe Ser Ser Arg Phe Asp Ala Arg Thr Gly Ala Pro Gly Ile Arg Cys
            900                 905                 910
Arg Arg Val Pro Ala Arg Cys Ala Arg Glu Gln Asn Pro Glu Pro Phe
        915                 920                 925
Pro Trp Trp Leu Asn Lys Phe Val Ala Glu His Lys Leu Asp Gly Cys
    930                 935                 940
Pro Leu Arg Ala Asp Asp Leu Ile Pro Thr Gly Glu Gly Glu Phe Phe
945                 950                 955                 960
Val Ser Pro Phe Ser Ala Glu Glu Gly Asp Phe His Gln Ile His Ala
                965                 970                 975
Asp Leu Asn Ala Ala Gln Asn Leu Gln Arg Arg Leu Trp Ser Asp Phe
            980                 985                 990
Asp Ile Ser Gln Ile Arg Leu Arg Cys Asp Trp Gly Glu Val Asp Gly
        995                 1000                1005
Glu Pro Val Leu Ile Pro Arg Thr Thr Gly Lys Arg Thr Ala Asp
    1010                1015                1020
Ser Tyr Gly Asn Lys Val Phe Tyr Thr Lys Thr Gly Val Thr Tyr
    1025                1030                1035
Tyr Glu Arg Glu Arg Gly Lys Lys Arg Arg Lys Val Phe Ala Gln
    1040                1045                1050
Glu Glu Leu Ser Glu Glu Ala Glu Leu Leu Val Glu Ala Asp
    1055                1060                1065
Glu Ala Arg Glu Lys Ser Val Val Leu Met Arg Asp Pro Ser Gly
    1070                1075                1080
Ile Ile Asn Arg Gly Asp Trp Thr Arg Gln Lys Glu Phe Trp Ser
    1085                1090                1095
```

-continued

```
Met Val Asn Gln Arg Ile Glu Gly Tyr Leu Val Lys Gln Ile Arg
    1100                1105                1110
Ser Arg Val Arg Leu Gln Glu Ser Ala Cys Glu Asn Thr Gly Asp
    1115                1120                1125
Ile

<210> SEQ ID NO 25
<211> LENGTH: 1129
<212> TYPE: PRT
<213> ORGANISM: Artificial Sequence
<220> FEATURE:
<223> OTHER INFORMATION: AaCas12b-D977A protein

<400> SEQUENCE: 25

Met Ala Val Lys Ser Met Lys Val Lys Leu Arg Leu Asp Asn Met Pro
1               5                   10                  15
Glu Ile Arg Ala Gly Leu Trp Lys Leu His Thr Glu Val Asn Ala Gly
                20                  25                  30
Val Arg Tyr Tyr Thr Glu Trp Leu Ser Leu Leu Arg Gln Glu Asn Leu
            35                  40                  45
Tyr Arg Arg Ser Pro Asn Gly Asp Gly Glu Gln Glu Cys Tyr Lys Thr
    50                  55                  60
Ala Glu Glu Cys Lys Ala Glu Leu Leu Glu Arg Leu Arg Ala Arg Gln
65                  70                  75                  80
Val Glu Asn Gly His Cys Gly Pro Ala Gly Ser Asp Asp Glu Leu Leu
                85                  90                  95
Gln Leu Ala Arg Gln Leu Tyr Glu Leu Leu Val Pro Gln Ala Ile Gly
            100                 105                 110
Ala Lys Gly Asp Ala Gln Gln Ile Ala Arg Lys Phe Leu Ser Pro Leu
    115                 120                 125
Ala Asp Lys Asp Ala Val Gly Gly Leu Gly Ile Ala Lys Ala Gly Asn
130                 135                 140
Lys Pro Arg Trp Val Arg Met Arg Glu Ala Gly Glu Pro Gly Trp Glu
145                 150                 155                 160
Glu Glu Lys Ala Lys Ala Glu Ala Arg Lys Ser Thr Asp Arg Thr Ala
                165                 170                 175
Asp Val Leu Arg Ala Leu Ala Asp Phe Gly Leu Lys Pro Leu Met Arg
            180                 185                 190
Val Tyr Thr Asp Ser Asp Met Ser Ser Val Gln Trp Lys Pro Leu Arg
    195                 200                 205
Lys Gly Gln Ala Val Arg Thr Trp Asp Arg Asp Met Phe Gln Gln Ala
    210                 215                 220
Ile Glu Arg Met Met Ser Trp Glu Ser Trp Asn Gln Arg Val Gly Glu
225                 230                 235                 240
Ala Tyr Ala Lys Leu Val Glu Gln Lys Ser Arg Phe Glu Gln Lys Asn
                245                 250                 255
Phe Val Gly Gln Glu His Leu Val Gln Leu Val Asn Gln Leu Gln Gln
            260                 265                 270
Asp Met Lys Glu Ala Ser His Gly Leu Glu Ser Lys Glu Gln Thr Ala
    275                 280                 285
His Tyr Leu Thr Gly Arg Ala Leu Arg Gly Ser Asp Lys Val Phe Glu
    290                 295                 300
Lys Trp Glu Lys Leu Asp Pro Asp Ala Pro Phe Asp Leu Tyr Asp Thr
305                 310                 315                 320
```

-continued

Glu Ile Lys Asn Val Gln Arg Arg Asn Thr Arg Arg Phe Gly Ser His
            325                 330                 335

Asp Leu Phe Ala Lys Leu Ala Glu Pro Lys Tyr Gln Ala Leu Trp Arg
            340                 345                 350

Glu Asp Ala Ser Phe Leu Thr Arg Tyr Ala Val Tyr Asn Ser Ile Val
            355                 360                 365

Arg Lys Leu Asn His Ala Lys Met Phe Ala Thr Phe Thr Leu Pro Asp
370                 375                 380

Ala Thr Ala His Pro Ile Trp Thr Arg Phe Asp Lys Leu Gly Gly Asn
385                 390                 395                 400

Leu His Gln Tyr Thr Phe Leu Phe Asn Glu Phe Gly Glu Gly Arg His
            405                 410                 415

Ala Ile Arg Phe Gln Lys Leu Leu Thr Val Glu Asp Gly Val Ala Lys
            420                 425                 430

Glu Val Asp Asp Val Thr Val Pro Ile Ser Met Ser Ala Gln Leu Asp
            435                 440                 445

Asp Leu Leu Pro Arg Asp Pro His Glu Leu Val Ala Leu Tyr Phe Gln
            450                 455                 460

Asp Tyr Gly Ala Glu Gln His Leu Ala Gly Glu Phe Gly Gly Ala Lys
465                 470                 475                 480

Ile Gln Tyr Arg Arg Asp Gln Leu Asn His Leu His Ala Arg Arg Gly
            485                 490                 495

Ala Arg Asp Val Tyr Leu Asn Leu Ser Val Arg Val Gln Ser Gln Ser
            500                 505                 510

Glu Ala Arg Gly Glu Arg Arg Pro Pro Tyr Ala Ala Val Phe Arg Leu
            515                 520                 525

Val Gly Asp Asn His Arg Ala Phe Val His Phe Asp Lys Leu Ser Asp
            530                 535                 540

Tyr Leu Ala Glu His Pro Asp Asp Gly Lys Leu Gly Ser Glu Gly Leu
545                 550                 555                 560

Leu Ser Gly Leu Arg Val Met Ser Val Asp Leu Gly Leu Arg Thr Ser
            565                 570                 575

Ala Ser Ile Ser Val Phe Arg Val Ala Arg Lys Asp Glu Leu Lys Pro
            580                 585                 590

Asn Ser Glu Gly Arg Val Pro Phe Cys Phe Pro Ile Glu Gly Asn Glu
            595                 600                 605

Asn Leu Val Ala Val His Glu Arg Ser Gln Leu Leu Lys Leu Pro Gly
            610                 615                 620

Glu Thr Glu Ser Lys Asp Leu Arg Ala Ile Arg Glu Glu Arg Gln Arg
625                 630                 635                 640

Thr Leu Arg Gln Leu Arg Thr Gln Leu Ala Tyr Leu Arg Leu Leu Val
            645                 650                 655

Arg Cys Gly Ser Glu Asp Val Gly Arg Arg Glu Arg Ser Trp Ala Lys
            660                 665                 670

Leu Ile Glu Gln Pro Met Asp Ala Asn Gln Met Thr Pro Asp Trp Arg
            675                 680                 685

Glu Ala Phe Glu Asp Glu Leu Gln Lys Leu Lys Ser Leu Tyr Gly Ile
            690                 695                 700

Cys Gly Asp Arg Glu Trp Thr Glu Ala Val Tyr Glu Ser Val Arg Arg
705                 710                 715                 720

Val Trp Arg His Met Gly Lys Gln Val Arg Asp Trp Arg Lys Asp Val
            725                 730                 735

Arg Ser Gly Glu Arg Pro Lys Ile Arg Gly Tyr Gln Lys Asp Val Val

```
                    740                 745                 750
Gly Gly Asn Ser Ile Glu Gln Ile Glu Tyr Leu Glu Arg Gln Tyr Lys
            755                 760                 765
Phe Leu Lys Ser Trp Ser Phe Phe Gly Lys Val Ser Gly Gln Val Ile
            770                 775                 780
Arg Ala Glu Lys Gly Ser Arg Phe Ala Ile Thr Leu Arg Glu His Ile
785                 790                 795                 800
Asp His Ala Lys Glu Asp Arg Leu Lys Lys Leu Ala Asp Arg Ile Ile
                    805                 810                 815
Met Glu Ala Leu Gly Tyr Val Tyr Ala Leu Asp Asp Glu Arg Gly Lys
                    820                 825                 830
Gly Lys Trp Val Ala Lys Tyr Pro Pro Cys Gln Leu Ile Leu Leu Glu
            835                 840                 845
Glu Leu Ser Glu Tyr Gln Phe Asn Asn Asp Arg Pro Pro Ser Glu Asn
            850                 855                 860
Asn Gln Leu Met Gln Trp Ser His Arg Gly Val Phe Gln Glu Leu Leu
865                 870                 875                 880
Asn Gln Ala Gln Val His Asp Leu Leu Val Gly Thr Met Tyr Ala Ala
                    885                 890                 895
Phe Ser Ser Arg Phe Asp Ala Arg Thr Gly Ala Pro Gly Ile Arg Cys
                    900                 905                 910
Arg Arg Val Pro Ala Arg Cys Ala Arg Glu Gln Asn Pro Glu Pro Phe
            915                 920                 925
Pro Trp Trp Leu Asn Lys Phe Val Ala Glu His Lys Leu Asp Gly Cys
            930                 935                 940
Pro Leu Arg Ala Asp Asp Leu Ile Pro Thr Gly Glu Gly Glu Phe Phe
945                 950                 955                 960
Val Ser Pro Phe Ser Ala Glu Glu Gly Asp Phe His Gln Ile His Ala
                    965                 970                 975
Ala Leu Asn Ala Ala Gln Asn Leu Gln Arg Arg Leu Trp Ser Asp Phe
                    980                 985                 990
Asp Ile Ser Gln Ile Arg Leu Arg Cys Asp Trp Gly Glu Val Asp Gly
            995                 1000                1005
Glu Pro Val Leu Ile Pro Arg Thr Thr Gly Lys Arg Thr Ala Asp
            1010                1015                1020
Ser Tyr Gly Asn Lys Val Phe Tyr Thr Lys Thr Gly Val Thr Tyr
            1025                1030                1035
Tyr Glu Arg Glu Arg Gly Lys Lys Arg Arg Lys Val Phe Ala Gln
            1040                1045                1050
Glu Glu Leu Ser Glu Glu Glu Ala Glu Leu Leu Val Glu Ala Asp
            1055                1060                1065
Glu Ala Arg Glu Lys Ser Val Val Leu Met Arg Asp Pro Ser Gly
            1070                1075                1080
Ile Ile Asn Arg Gly Asp Trp Thr Arg Gln Lys Glu Phe Trp Ser
            1085                1090                1095
Met Val Asn Gln Arg Ile Glu Gly Tyr Leu Val Lys Gln Ile Arg
            1100                1105                1110
Ser Arg Val Arg Leu Gln Glu Ser Ala Cys Glu Asn Thr Gly Asp
            1115                1120                1125
Ile

<210> SEQ ID NO 26
<211> LENGTH: 1129
```

```
<212> TYPE: PRT
<213> ORGANISM: Artificial Sequence
<220> FEATURE:
<223> OTHER INFORMATION: AaCas12b-E848A protein

<400> SEQUENCE: 26

Met Ala Val Lys Ser Met Lys Val Lys Leu Arg Leu Asp Asn Met Pro
1               5                   10                  15

Glu Ile Arg Ala Gly Leu Trp Lys Leu His Thr Glu Val Asn Ala Gly
            20                  25                  30

Val Arg Tyr Tyr Thr Glu Trp Leu Ser Leu Leu Arg Gln Glu Asn Leu
        35                  40                  45

Tyr Arg Arg Ser Pro Asn Gly Asp Gly Glu Gln Glu Cys Tyr Lys Thr
50                  55                  60

Ala Glu Glu Cys Lys Ala Glu Leu Leu Glu Arg Leu Arg Ala Arg Gln
65                  70                  75                  80

Val Glu Asn Gly His Cys Gly Pro Ala Gly Ser Asp Asp Glu Leu Leu
                85                  90                  95

Gln Leu Ala Arg Gln Leu Tyr Glu Leu Leu Val Pro Gln Ala Ile Gly
            100                 105                 110

Ala Lys Gly Asp Ala Gln Gln Ile Ala Arg Lys Phe Leu Ser Pro Leu
        115                 120                 125

Ala Asp Lys Asp Ala Val Gly Gly Leu Gly Ile Ala Lys Ala Gly Asn
130                 135                 140

Lys Pro Arg Trp Val Arg Met Arg Glu Ala Gly Glu Pro Gly Trp Glu
145                 150                 155                 160

Glu Glu Lys Ala Lys Ala Glu Ala Arg Lys Ser Thr Asp Arg Thr Ala
                165                 170                 175

Asp Val Leu Arg Ala Leu Ala Asp Phe Gly Leu Lys Pro Leu Met Arg
            180                 185                 190

Val Tyr Thr Asp Ser Asp Met Ser Ser Val Gln Trp Lys Pro Leu Arg
        195                 200                 205

Lys Gly Gln Ala Val Arg Thr Trp Asp Arg Asp Met Phe Gln Gln Ala
210                 215                 220

Ile Glu Arg Met Met Ser Trp Glu Ser Trp Asn Gln Arg Val Gly Glu
225                 230                 235                 240

Ala Tyr Ala Lys Leu Val Glu Gln Lys Ser Arg Phe Glu Gln Lys Asn
                245                 250                 255

Phe Val Gly Gln Glu His Leu Val Gln Leu Val Asn Gln Leu Gln Gln
            260                 265                 270

Asp Met Lys Glu Ala Ser His Gly Leu Glu Ser Lys Glu Gln Thr Ala
        275                 280                 285

His Tyr Leu Thr Gly Arg Ala Leu Arg Gly Ser Asp Lys Val Phe Glu
        290                 295                 300

Lys Trp Glu Lys Leu Asp Pro Asp Ala Pro Phe Asp Leu Tyr Asp Thr
305                 310                 315                 320

Glu Ile Lys Asn Val Gln Arg Arg Asn Thr Arg Arg Phe Gly Ser His
                325                 330                 335

Asp Leu Phe Ala Lys Leu Ala Glu Pro Lys Tyr Gln Ala Leu Trp Arg
            340                 345                 350

Glu Asp Ala Ser Phe Leu Thr Arg Tyr Ala Val Tyr Asn Ser Ile Val
        355                 360                 365

Arg Lys Leu Asn His Ala Lys Met Phe Ala Thr Phe Thr Leu Pro Asp
        370                 375                 380
```

```
Ala Thr Ala His Pro Ile Trp Thr Arg Phe Asp Lys Leu Gly Gly Asn
385                 390                 395                 400

Leu His Gln Tyr Thr Phe Leu Phe Asn Glu Phe Gly Glu Gly Arg His
            405                 410                 415

Ala Ile Arg Phe Gln Lys Leu Leu Thr Val Glu Asp Gly Val Ala Lys
                420                 425                 430

Glu Val Asp Asp Val Thr Val Pro Ile Ser Met Ser Ala Gln Leu Asp
            435                 440                 445

Asp Leu Leu Pro Arg Asp Pro His Glu Leu Val Ala Leu Tyr Phe Gln
    450                 455                 460

Asp Tyr Gly Ala Glu Gln His Leu Ala Gly Glu Phe Gly Gly Ala Lys
465                 470                 475                 480

Ile Gln Tyr Arg Arg Asp Gln Leu Asn His Leu His Ala Arg Arg Gly
                485                 490                 495

Ala Arg Asp Val Tyr Leu Asn Leu Ser Val Arg Val Gln Ser Gln Ser
            500                 505                 510

Glu Ala Arg Gly Glu Arg Arg Pro Pro Tyr Ala Ala Val Phe Arg Leu
            515                 520                 525

Val Gly Asp Asn His Arg Ala Phe Val His Phe Asp Lys Leu Ser Asp
530                 535                 540

Tyr Leu Ala Glu His Pro Asp Asp Gly Lys Leu Gly Ser Glu Gly Leu
545                 550                 555                 560

Leu Ser Gly Leu Arg Val Met Ser Val Asp Leu Gly Leu Arg Thr Ser
                565                 570                 575

Ala Ser Ile Ser Val Phe Arg Val Ala Arg Lys Asp Glu Leu Lys Pro
                580                 585                 590

Asn Ser Glu Gly Arg Val Pro Phe Cys Phe Pro Ile Glu Gly Asn Glu
            595                 600                 605

Asn Leu Val Ala Val His Glu Arg Ser Gln Leu Leu Lys Leu Pro Gly
    610                 615                 620

Glu Thr Glu Ser Lys Asp Leu Arg Ala Ile Arg Glu Glu Arg Gln Arg
625                 630                 635                 640

Thr Leu Arg Gln Leu Arg Thr Gln Leu Ala Tyr Leu Arg Leu Leu Val
                645                 650                 655

Arg Cys Gly Ser Glu Asp Val Gly Arg Arg Glu Arg Ser Trp Ala Lys
            660                 665                 670

Leu Ile Glu Gln Pro Met Asp Ala Asn Gln Met Thr Pro Asp Trp Arg
            675                 680                 685

Glu Ala Phe Glu Asp Glu Leu Gln Lys Leu Lys Ser Leu Tyr Gly Ile
    690                 695                 700

Cys Gly Asp Arg Glu Trp Thr Glu Ala Val Tyr Glu Ser Val Arg Arg
705                 710                 715                 720

Val Trp Arg His Met Gly Lys Gln Val Arg Asp Trp Arg Lys Asp Val
                725                 730                 735

Arg Ser Gly Glu Arg Pro Lys Ile Arg Gly Tyr Gln Lys Asp Val Val
            740                 745                 750

Gly Gly Asn Ser Ile Glu Gln Ile Glu Tyr Leu Glu Arg Gln Tyr Lys
            755                 760                 765

Phe Leu Lys Ser Trp Ser Phe Phe Gly Lys Val Ser Gly Gln Val Ile
    770                 775                 780

Arg Ala Glu Lys Gly Ser Arg Phe Ala Ile Thr Leu Arg Glu His Ile
785                 790                 795                 800

Asp His Ala Lys Glu Asp Arg Leu Lys Lys Leu Ala Asp Arg Ile Ile
```

```
                805                 810                 815
Met Glu Ala Leu Gly Tyr Val Tyr Ala Leu Asp Asp Glu Arg Gly Lys
            820                 825                 830

Gly Lys Trp Val Ala Lys Tyr Pro Pro Cys Gln Leu Ile Leu Leu Ala
        835                 840                 845

Glu Leu Ser Glu Tyr Gln Phe Asn Asn Asp Arg Pro Pro Ser Glu Asn
    850                 855                 860

Asn Gln Leu Met Gln Trp Ser His Arg Gly Val Phe Gln Glu Leu Leu
865                 870                 875                 880

Asn Gln Ala Gln Val His Asp Leu Leu Val Gly Thr Met Tyr Ala Ala
                885                 890                 895

Phe Ser Ser Arg Phe Asp Ala Arg Thr Gly Ala Pro Gly Ile Arg Cys
            900                 905                 910

Arg Arg Val Pro Ala Arg Cys Ala Arg Glu Gln Asn Pro Glu Pro Phe
        915                 920                 925

Pro Trp Trp Leu Asn Lys Phe Val Ala Glu His Lys Leu Asp Gly Cys
    930                 935                 940

Pro Leu Arg Ala Asp Asp Leu Ile Pro Thr Gly Glu Gly Glu Phe Phe
945                 950                 955                 960

Val Ser Pro Phe Ser Ala Glu Glu Gly Asp Phe His Gln Ile His Ala
                965                 970                 975

Asp Leu Asn Ala Ala Gln Asn Leu Gln Arg Arg Leu Trp Ser Asp Phe
            980                 985                 990

Asp Ile Ser Gln Ile Arg Leu Arg Cys Asp Trp Gly Glu Val Asp Gly
        995                 1000                1005

Glu Pro Val Leu Ile Pro Arg Thr Thr Gly Lys Arg Thr Ala Asp
    1010                1015                1020

Ser Tyr Gly Asn Lys Val Phe Tyr Thr Lys Thr Gly Val Thr Tyr
    1025                1030                1035

Tyr Glu Arg Glu Arg Gly Lys Lys Arg Arg Lys Val Phe Ala Gln
    1040                1045                1050

Glu Glu Leu Ser Glu Glu Ala Glu Leu Leu Val Glu Ala Asp
    1055                1060                1065

Glu Ala Arg Glu Lys Ser Val Val Leu Met Arg Asp Pro Ser Gly
    1070                1075                1080

Ile Ile Asn Arg Gly Asp Trp Thr Arg Gln Lys Glu Phe Trp Ser
    1085                1090                1095

Met Val Asn Gln Arg Ile Glu Gly Tyr Leu Val Lys Gln Ile Arg
    1100                1105                1110

Ser Arg Val Arg Leu Gln Glu Ser Ala Cys Glu Asn Thr Gly Asp
    1115                1120                1125

Ile
```

<210> SEQ ID NO 27
<211> LENGTH: 6642
<212> TYPE: DNA
<213> ORGANISM: Artificial Sequence
<220> FEATURE:
<223> OTHER INFORMATION: Vector

<400> SEQUENCE: 27
tggaccagcc aggacagaaa tgcctcgact tcgctgctac ccaaggttgc cgggtgacgc    60
acaccgtgga aacggatgaa ggcacgaacc cagtggacat aagcctgttc ggttcgtaag   120
ctgtaatgca agtagcgtat gcgctcacgc aactggtcca gaaccttgac cgaacgcagc   180

```
ggtggtaacg gcgcagtggc ggttttcatg gcttgttatg actgtttttt tggggtacag      240
tctatgcctc gggcatccaa gcagcaagcg cgttacgccg tgggtcgatg tttgatgtta      300
tggagcagca acgatgttac gcagcagggc agtcgcccta aaacaaagtt aaacatcatg      360
agggaagcgg tgatcgccga agtatcgact caactatcag aggtagttgg cgtcatcgag      420
cgccatctcg aaccgacgtt gctggccgta catttgtacg gctccgcagt ggatggcggc      480
ctgaagccac acagtgatat tgatttgctg gttacggtga ccgtaaggct tgatgaaaca      540
acgcggcgag ctttgatcaa cgaccttttg gaaacttcgg cttcccctgg agagagcgag      600
attctccgcg ctgtagaagt caccattgtt gtgcacgacg acatcattcc gtggcgttat      660
ccagctaagc gcgaactgca atttggagaa tggcagcgca atgacattct gcaggtatc       720 ttcgagccag ccacgatcga cattgatctg gctatcttgc tgacaaaagc aagagaacat      780
agcgttgcct tggtaggtcc agcggcggag gaactctttg atccggttcc tgaacaggat      840
ctatttgagg cgctaaatga aaccttaacg ctatggaact cgccgcccga ctgggctggc      900
gatgagcgaa atgtagtgct tacgttgtcc cgcatttggt acagcgcagt aaccggcaaa      960
atcgcgccga aggatgtcgc tgccgactgg gcaatggagc gcctgccggc ccagtatcag     1020
cccgtcatac ttgaagctag acaggcttat cttggacaag aagaagatcg cttggcctcg     1080
cgcgcagatc agttggaaga atttgtccac tacgtgaaag gcgagatcac caaggtagtc     1140
ggcaaataac cctcgagcca cccatgacca aaatcccta acgtgagtta cgcgtcgttc     1200
cactgagcgt cagaccccgt agaaaagatc aaaggatctt cttgagatcc ttttttctg      1260 cgcgtaatct gctgcttgca acaaaaaaa ccaccgctac cagcggtggt ttgtttgccg      1320
gatcaagagc taccaactct ttttccgaag gtaactggct tcagcagagc gcagatacca     1380
aatactgtcc ttctagtgta gccgtagtta ggccaccact tcaagaactc tgtagcaccg     1440
cctacatacc tcgctctgct aatcctgtta ccagtggctg ctgccagtgg cgataagtcg     1500
tgtcttaccg ggttggactc aagacgatag ttaccggata aggcgcagcg gtcgggctga     1560
acggggggtt cgtgcacaca gcccagcttg gagcgaacga cctacaccga actgagatac     1620
ctacagcgtg agctatgaga aagcgccacg cttcccgaag ggagaaaggc ggacaggtat     1680
ccggtaagcg gcagggtcgg aacaggagag cgcacgaggg agcttccagg gggaaacgcc     1740
tggtatcttt atagtcctgt cgggtttcgc cacctctgac ttgagcgtcg attttttgtga    1800 tgctcgtcag ggggggggag cctatggaaa aacgccagca acgcggcctt tttacggttc     1860
ctggcctttt gctggccttt tgctcacatg ttctttcctg cgttatcccc tgattctgtg     1920
gataaccgta ttaccgcctt tgagtgagct gataccgctc gccgcagccg aacgaccgag     1980
cgcagcgagt cagtgagcga ggaagcggaa gagcgcccaa tacgcaaacc gcctctcccc     2040
gcgcgttggc cgattcatta atgcagctgg cacgacaggt ttcccgactg gaaagcgggc     2100
agtgagcgca acgcaattaa tacgcgtacc gcgagccagg aagagtttgt agaaacgcaa     2160
aaaggccatc cgtcaggatg gccttctgct tagtttgatg cctggcagtt tatggcgggc     2220
gtcctgcccg ccaccctccg ggccgttgct tcacaacgtt caaatccgct cccggcggat     2280
ttgtcctact caggagagcg ttcaccgaca acaacagat aaaacgaaag gcccagtctt      2340
ccgactgagc ctttcgtttt atttgatgcc tggcagttcc ctactctcgc gttaacgctt     2400
gcatggatgt tttcccagtc acgacgttgt aaaacgacgg ccagtcttaa gctcgggccc     2460
caaataatga ttttattttg actgatagtg acctgttcgt tgcaacaaat tgatgagcaa     2520
```

```
tgctttttta taatgccaac tttgtacaaa aaagcaggct ccgaattcgc ccttcaccat   2580
ggctcctaag aagaagcgga aggttggtat tcacggggtg cctgcggctg cggtgaagtc   2640
aataaaagtt aaactccgcc tggacgatat gccagaaatt cgggctggcc tctggaagct   2700
tcacaaagag gttaacgctg gcgtcagata ttacacggaa tggttgtcgc tgctccggca   2760
agaaaatctc tacagaaggt cgcccaatgg tgatggggaa caagagtgcg acaaaacggc   2820
ggaggaatgc aaagcggaac tccttgaaag acttcgcgcg agacaagtcg aaaacggcca   2880
tagaggcccg gccggttccg atgatgaatt gcttcagctt gcgcggcagc tttacgaatt   2940
gctcgtgccg caagccatag gtgcaaaagg agacgcacaa caaattgcaa gaaagttcct   3000
ctccccgctc gcagacaagg atgccgtggg aggtcttgga atcgctaaag cagggaataa   3060
gccaagatgg gtgcggatgc gggaagcagg tgagccaggc tgggaagagg agaaggagaa   3120
agccgaaacg aggaaatcag cggatcgcac tgcagacgtg ttgagagccc tcgcagactt   3180
tggacttaag ccactgatgc gggtttacac ggattcagag atgtcctcgg tggaatggaa   3240
gccgctcaga aagggtcaag ccgtgagaac gtgggaccgc gacatgttcc agcaggcaat   3300
tgagcggatg atgtcctggg agtcttggaa ccaagggtc gggcaagaat atgcgaaact   3360
ggtggagcaa aaaaataggt ttgaacaaaa aaatttcgtt ggtcaagagc atctggttca   3420
tttggttaat caacttcaac aagatatgaa agaagcatca cctggcttgg aatctaaaga   3480
acaaacagca cactacgtta cgggtagggc gttgagggga tcggataaag ttttcgagaa   3540
gtggggtaag ttggcccccg acgccccttt cgatctgtat gacgccgaga taagaacgt    3600 tcagcggagg aacactcgcc gctttggttc gcacgatctg tttgcaaaac tggccgagcc   3660
tgagtaccag gcccctttggc gggaggatgc gtcgttcctt acacgctacg cggtttataa   3720
ttcaattctc agaaagctca atcacgcgaa gatgtttgcg actttcactc ttccagatgc   3780
gacggcacac cctatatgga ctagatttga taagttgggg ggcaacttgc accagtatac   3840
atttctgttc aacgaattcg gcgaacgcag gcatgcaatc aggttccata aacttttgaa   3900
agtcgagaat ggtgttgcca gggaggttga cgatgtcaca gtgcctatct cgatgtccga   3960
acaattggat aacttgctgc ccagagatcc gaacgaaccg attgcacttt atttcaggga   4020
ttatggtgcc gaacaacact ttacgggtga gttcggaggg gccaagattc agtgcagacg   4080
ggaccagctt gctcacatgc accgcaggag agggctagg gatgtgtatt tgaacgtttc   4140
agttcgcgtg cagtcccaat ccgaggcgcg ggggagcgc agaccaccat acgcggctgt   4200
cttccggctg gttggcgata accatagagc gttcgtgcat ttcgataagc tgagcgatta   4260
cctcgccgaa catcctgatg acggaaagtt ggggtcagag gggcttctgt cgggcctgag   4320
ggtgatgtcc gtggacctgg gattgcgcac cagtgcctcg atcagcgttt ttaggggtggc   4380 caggaaagat gagttgaaac ccaactcgaa ggggagggtt ccgttctttt tccctataaa   4440
gggcaacgat aacttggtcg cagtgcatga aggagccaa ctgctcaaac ttcccgggga   4500
gacagagtcc aaagatcttc gcgctataag ggaagagaga caaagaactc tccggcagct   4560
gcgcacgcag ctcgcatacc tgcggttgct tgtccgctgc ggaagtgaag acgttggcag   4620
gcgcgagagg tcatgggcca aattgattga gcagccggtc gacgccgcaa tcacatgac   4680 tccggattgg agggaggctt tcgagaacga actgcagaag ttgaagagtc tgcatggcat   4740
atgctctgac aaaagtgga tggacgcggt ttacgagtcc gtccgccggg tctggcggca   4800
catggggaaa caagttcgcg attggagaaa ggatgttaga tccgggggaaa ggccgaagat   4860 aagaggttat gccaaagacg tggttggtgg aaattctatc gaacagatcg aatatcttga   4920
```

```
gaggcagtac aagttcctca agagttggtc tttcttcggt aaagtctctg gacaagttat    4980
aagagcagaa aaggggagcc ggttcgctat caccttgcgg gaacacatag accacgcaaa    5040
agaagacaga ctgaagaagc tggcggacag aattatcatg gaagcgctgg ggtacgttta    5100
cgcgctggac gaaaggggga aaggtaaatg ggtggccaaa tacccgccat gccagttgat    5160
attgctggaa gaattgtccg aatatcaatt taataacgat agaccgccat ccgagaacaa    5220
ccaacttatg caatggtctc accggggagt tttccaggag ttgatcaacc aagctcaagt    5280
gcacgatctg cttgttggta caatgtacgc agcgttttcc tcacgcttcg acgctagaac    5340
aggagcgccg ggaattcggt gccggagggt gcctgcgagg tgtactcagg agcacaaccc    5400
ggagccattt ccctggtggt tgaataaatt cgttgtggaa catacgttgg atgcttgccc    5460
gcttcgggcg gacgacctca ttccgacggg tgagggcgag attttcgtgt cgccattctc    5520
ggctgaggaa ggggacttcc atcaaatcca tgctgacctc aatgcggcgc aaaatctgca    5580
gcagagattg tggagtgatt ttgacatctc tcagatcagg cttcggtgcg attggggaga    5640
agtcgatggt gaactcgttc tcattccgag actcaccggt aaaaggactg ctgattcata    5700
ttcgaacaaa gttttttaca ctaacacagg ggtcacttat tatgaaagag aacgcggtaa    5760
gaagcgccgc aaggtgttcg cgcaagagaa actttccgag gaagaggccg agttgctcgt    5820
tgaagctgac gaagctcgcg agaagtccgt cgttctgatg cgggatcctt ctggcataat    5880
aaacaggggg aattggacac ggcagaagga attttggtcc atggtgaatc agcgcataga    5940
aggttatctg gtcaaacaga tcagaagcag ggttcccctc caggattcag cgtgcgagaa    6000
cacgggcgat attaagcgtc ctgctgccac caaaaaggcc ggacaggcta agaaaaagaa    6060
gtgagacgac tagtggcggc cgccgacgtc cgatcgttca acatttggc aataaagttt    6120 cttaagattg aatcctgttg ccggtcttgc gatgattatc atataatttc tgttgaatta    6180
cgttaagcat gtaataatta acatgtaatg catgacgtta tttatgagat gggtttttat    6240
gattagagtc ccgcaattat acatttaata cgcgatagaa acaaaatat agcgcgcaaa    6300 ctaggataaa ttatcgcgcg cggtgtcatc tatgttacta gatcgggaat tgatcccccc    6360
tcgacagctt ccggaaaggg cgaattcgca actttgtata caaagttga acgagaaacg    6420 taaaatgata taaatatcaa tatattaaat tagattttgc ataaaaaaca gactacataa    6480
tactgtaaaa cacaacatat ccagtcacta tgccatccag ctgatatccc ctatagtgag    6540
tcgtattaca tggtcatagc tgtttcctgg cagctctggc ccgtgtctca aaatctctga    6600
tgttacattg cacaagataa aaatatatca tcatgcctcc tc                      6642
```

<210> SEQ ID NO 28
<211> LENGTH: 6579
<212> TYPE: DNA
<213> ORGANISM: Artificial Sequence
<220> FEATURE:
<223> OTHER INFORMATION: Vector

<400> SEQUENCE: 28

```
tgttatgact gttttttttgg ggtacagtct atgcctcggg catccaagca gcaagcgcgt      60
tacgccgtgg gtcgatgttt gatgttatgg agcagcaacg atgttacgca gcagggcagt    120
cgccctaaaa caaagttaaa cattatgagg gaagcggtga tcgccgaagt atcgactcaa    180
ctatcagagg tagttggcgt catcgagcgc catctcgaac cgacgttgct ggccgtacat    240
ttgtacggct ccgcagtgga tggcggcctg aagccacaca gtgatattga tttgctggtt    300
```

```
acggtgaccg taaggcttga tgaaacaacg cggcgagctt tgatcaacga ccttttggaa    360
acttcggctt cccctggaga gagcgagatt ctccgcgctg tagaagtcac cattgttgtg    420
cacgacgaca tcattccgtg gcgttatcca gctaagcgcg aactgcaatt tggagaatgg    480
cagcgcaatg acattcttgc aggtatcttc gagccagcca cgatcgacat tgatctggct    540
atcttgctga caaaagcaag agaacatagc gttgccttgg taggtccagc ggcggaggaa    600
ctctttgatc cggttcctga acaggatcta tttgaggcgc taaatgaaac cttaacgcta    660
tggaactcgc cgcccgactg ggctggcgat gagcgaaatg tagtgcttac gttgtcccgc    720
atttggtaca gcgcagtaac cggcaaaatc gcgccgaagg atgtcgctgc cgactgggca    780
atggagcgcc tgccggccca gtatcagccc gtcatacttg aagctagaca ggcttatctt    840
ggacaagaag aagatcgctt ggcctcgcgc gcagatcagt tggaagaatt tgtccactac    900
gtgaaaggcg agatcaccaa ggtagtcggc aaataaccct cgagccaccc atgaccaaaa    960
tcccttaacg tgagttacgc gtcgttccac tgagcgtcag accccgtaga aaagatcaaa    1020
ggatcttctt gagatccttt ttttctgcgc gtaatctgct gcttgcaaac aaaaaaacca    1080
ccgctaccag cggtggtttg tttgccggat caagagctac caactctttt tccgaaggta    1140
actggcttca gcagagcgca gataccaaat actgttcttc tagtgtagcc gtagttaggc    1200
caccacttca agaactctgt agcaccgcct acatacctcg ctctgctaat cctgttacca    1260
gtggctgctg ccagtggcga taagtcgtgt cttaccgggt tggactcaag acgatagtta    1320
ccggataagg cgcagcggtc gggctgaacg gggggttcgt gcacacagcc cagcttggag    1380
cgaacgacct acaccgaact gagatacc  ta cagcgtgagc tatgagaaag cgccacgctt    1440
cccgaaggga gaaaggcgga caggtatccg gtaagcggca gggtcggaac aggagagcgc    1500
acgagggagc ttccagggggg aaacgcctgg tatctttata gtcctgtcgg gtttcgccac    1560
ctctgacttg agcgtcgatt tttgtgatgc tcgtcagggg ggcggagcct atggaaaaac    1620
gccagcaacg cggcctttt t  acggttcctg gccttttgct ggccttttgc tcacatgttc    1680
tttcctgcgt tatcccctga ttctgtggat aaccgtatta ccgcctttga gtgagctgat    1740
accgctcgcc gcagccgaac gaccgagcgc agcgagtcag tgagcgagga agcggaagag    1800
cgcccaatac gcaaaccgcc tctccccgcg cgttggccga ttcattaatg cagctggcac    1860
gacaggtttc ccgactggaa agcgggcagt gagcgcaacg caattaatac gcgtaccgcg    1920
agccaggaag agtttgtaga acgcaaaaa g  ggccatccgt caggatggcc ttctgcttag    1980
tttgatgcct ggcagtttat ggcgggcgtc ctgcccgcca cctccgggcc gttgcttca     2040 caacgttcaa atccgctccc ggcggatttg tcctactcag gagagcgttc accgacaaac    2100
aacagataaa acgaaaggcc cagtcttccg actgagcctt tcgttttatt tgatgcctgg    2160
cagttcccta ctctcgcgtt aacgcttgca tggatgtttt cccagtcacg acgttgtaaa    2220
acgacggcca gtcttaagct cgggcccaa a ataatgattt tattttgact gatagtgacc    2280
tgttcgttgc aacaaattga tgagcaatgc ttttttataa tgccaacttt gtacaaaaaa    2340
gcaggctccg aattcgccct tcaccatggc tcctaagaag aagcggaagg ttggtattca    2400 cgggg tgcct gcggctgcca caaggtcttt catacttaag atagagccaa acgaagaggt    2460
caaaaaggga ttgtggaaaa cccatgaagt cctgaaccat ggcattgcct actacatgaa    2520
catcctgaaa cttatacggc aggaggctat ttatgagcac cacgagcagg atccaaaaaa    2580
ccccaaaaag gtttcgaagg ctgaaatcca ggccgaactg tgggacttcg ttctcaaaat    2640
gcagaaatgt aattcgttca ctcatgaagt tgacaaagac gtcgtgttta acattttgag    2700
```

```
ggagctttac gaggagttgg ttccgagctc cgtcgaaaag aagggtgaag caaatcagct   2760
gtcgaataag ttcttgtacc ctttggtgga cccgaacagc caatctggaa aagggacagc   2820
atcatcaggg cggaagcctc ggtggtataa cttgaagatt gctggagacc cttcgtggga   2880
agaggaaaag aaaaagtggg aggaagataa gaagaaggac ccacttgcca aaattctcgg   2940
caaacttgcc gaatatggat tgataccgct gttcatcccc tttacggatt ctaacgaacc   3000
catcgttaaa gaaatcaagt ggatggaaaa atctcgcaat cagtccgtcc ggaggctgga   3060
caaagatatg tttatacaag ctttggaacg cttttctctcg tgggagtcgt ggaatcttaa   3120
ggtcaaagaa gagtatgaaa aggtcgagaa ggaacacaag acactggagg agaggattaa   3180
ggaagacatt caagcattca agtcactgga gcaatacgaa aaggaacggc aggagcaatt   3240
gcttcgcgac acgctcaata ccaatgaata taggctttcc aagaggggcc tgagaggatg   3300
gcgggaaata atccagaaat ggctcaagat ggacgagaat gaaccttcag aaaaatatct   3360
cgaggttttt aaagattacc aaaggaaaca tccacgcgag gcaggggatt acagcgtgta   3420
cgagtttctc tccaagaagg aaaaccattt tatctggcgc aatcatcccg aatacccgta   3480
cctctatgcg acgttctgcg aaatagacaa aaagaaaaaa gatgctaagc aacaagcgac   3540
tttcacactt gcagatccca taaatcaccc attgtgggtg cggtttgaag aaaggtcggg   3600
ctctaacctc aataagtaca gaattttgac ggagcagttg cacacagaaa agctgaagaa   3660
gaagttgacg gttcagctgg atcgccttat ctacccaacc gagtctggtg gctgggaaga   3720
gaaggggaaa gtcgacatag tgttgctgcc atctaggcag ttctataacc agattttctct   3780 cgatatagaa gaaaagggta acatgcatt tacgtataaa gacgagtcca taagtttcc   3840 actgaaagga acacttggcg gcgcaagggt gcagtttgat cgggaccacc ttcgcaggta   3900
cccccacaag gttgaaagtg gaaacgttgg acggatctat tttaatatga ccgtcaacat   3960
agaacccaca gaatcccctg tttccaaatc cctgaaaata caccgggacg attttcctaa   4020
atttgtgaac tttaaaccga aggagttgac cgagtggata aaggacagta aagggaaaaa   4080
gctgaagtcc ggtatcgaaa gcctggagat tgggctcaga gttatgtcga tagatctggg   4140
tcaaaggcag gcagcagccg cctctatatt tgaggtcgtg gaccagaagc ccgacattga   4200
aggtaaactg ttcttttcga ttaagggac ggaactctac gcagtccatc gcgcctcctt   4260
caatataaag ctgccgggcg aaacactggt taaatcacgc gaggttttgc gcaaagcgcg   4320
ggaagacaac ctgaaactca tgaatcaaaa gctcaatttc ctgcgcaatg tgttgcactt   4380
ccagcagttt gaggatatta ccgaaagaga gaaagggtt acaaaatgga tatcccggca   4440
agaaaactct gatgttccgc tggtttacca ggatgagctt atacagatta gggaacttat   4500
gtataaacct tacaaagatt gggttgcatt cctcaagcag ctgcataaga gacttgaagt   4560
cgagatcggc aaagaagtca acactggcg caagagcctg agcgatggtc ggaaagggtt   4620
gtacggaatc agtttgaaaa atatcgacga aatagataga accaggaaat ttttgttgcg   4680
ctggtcactg agaccaacgg aaccgggaga agtcagaagg ttggagccag ccagagatt   4740 tgcaattgac cagctgaacc atctgaatgc actgaaagag gacagattga agaagatggc   4800
gaatacgatt attatgcatg ctttgggtta ttgttacgac gttaggaaga gaaatggca   4860 ggccaagaac cctgcgtgcc aaatcatcct gttcgaagat ctgagtaact acaatccgta   4920
tgaagaaagg agtcgcttcg agaacagtaa actgatgaaa tggtcccggc gcagatacc   4980 acgccaagtt gcgcttcaag gggaaatata cgggcttcaa gttggggaag ttggagcgca   5040
```

-continued

| | |
|---|---|
| gttttctagc cggttccacg ccaagacagg gtccccgggt ataaggtgca gtgtggtgac | 5100 |
| gaaagaaaag ttgcaggata atagattctt taaaaatctt caacgggaag ggcgcctgac | 5160 |
| gcttgacaag attgcagtgt tgaaagaggg ggatttgtac cccgataaag gcggggagaa | 5220 |
| gttcatttct ttgtcgaagg accgcaagtt ggttacgacg catgcagaca ttaacgcagc | 5280 |
| acaaaatctg caaaaaagat tctggactcg gacgcatggt ttttacaagg tttactgtaa | 5340 |
| agcatatcaa gtcgatggtc agacggttta cattcccgaa tctaaagatc agaaacagaa | 5400 |
| aatcattgag gagttcggtg aaggttactt tatactcaag gacggtgttt acgaatgggg | 5460 |
| taatgctggt aaactgaaaa ttaagaaggg gtcctccaag caatcatctt ctgagctcgt | 5520 |
| cgacagcgac atccttaagg atagcttcga tcttgcctct gagctcaagg gagaaaagtt | 5580 |
| gatgctgtat cgcgatccta gtggaaatgt cttttccctca gataaatgga tggcagcagg | 5640 |
| tgtgttcttc gggaaattgg aacgcatact gatatcaaaa ctgaccaatc aatactctat | 5700 |
| atctactatt gaagacgatt caagtaagca atcgatgaag cgtcctgctg ccaccaaaaa | 5760 |
| ggccggacag gctaagaaaa agaagtgaga cgactagtgg cggccgccga cgtccgatcg | 5820 |
| ttcaaacatt tggcaataaa gtttcttaag attgaatcct gttgccggtc ttgcgatgat | 5880 |
| tatcatataa tttctgttga attacgttaa gcatgtaata attaacatgt aatgcatgac | 5940 |
| gttatttatg agatgggttt ttatgattag agtcccgcaa ttatacattt aatacgcgat | 6000 |
| agaaaacaaa atatagcgcg caaactagga taaattatcg cgcgcggtgt catctatgtt | 6060 |
| actagatcgg gaattgatcc cccctcgaca gcttccggaa agggcgaatt cgcaactttg | 6120 |
| tatacaaaag ttgaacgaga acgtaaaat gatataaata tcaatatatt aaattagatt | 6180 |
| ttgcataaaa aacagactac ataatactgt aaaacacaac atatccagtc actatgccat | 6240 |
| ccagctgata tcccctatag tgagtcgtat tacatggtca tagctgtttc ctggcagctc | 6300 |
| tggcccgtgt ctcaaaatct ctgatgttac attgcacaag ataaaaatat atcatcatgc | 6360 |
| ctcctctgga ccagccagga cagaaatgcc tcgacttcgc tgctacccaa ggttgccggg | 6420 |
| tgacgcacac cgtggaaacg gatgaaggca cgaacccagt ggacataagc ctgttcggtt | 6480 |
| cgtaagctgt aatgcaagta gcgtatgcgc tcacgcaact ggtccagaac cttgaccgaa | 6540 |
| cgcagcggtg gtaacggcgc agtggcggtt ttcatggct | 6579 |

<210> SEQ ID NO 29
<211> LENGTH: 6642
<212> TYPE: DNA
<213> ORGANISM: Artificial Sequence
<220> FEATURE:
<223> OTHER INFORMATION: Vector

<400> SEQUENCE: 29

| | |
|---|---|
| tggaccagcc aggacagaaa tgcctcgact tcgctgctac ccaaggttgc cgggtgacgc | 60 |
| acaccgtgga aacggatgaa ggcacgaacc cagtggacat aagcctgttc ggttcgtaag | 120 |
| ctgtaatgca agtagcgtat gcgctcacgc aactggtcca gaaccttgac cgaacgcagc | 180 |
| ggtggtaacg gcgcagtggc ggttttcatg gcttgttatg actgtttttt tggggtacag | 240 |
| tctatgcctc gggcatccaa gcagcaagcg cgttacgccg tgggtcgatg tttgatgtta | 300 |
| tggagcagca acgatgttac gcagcagggc agtcgcccta aacaaagtt aaacatcatg | 360 |
| agggaagcgg tgatcgccga agtatcgact caactatcag aggtagttgg cgtcatcgag | 420 |
| cgccatctcg aaccgacgtt gctggccgta catttgtacg gctccgcagt ggatggcggc | 480 |
| ctgaagccac acagtgatat tgatttgctg gttacggtga ccgtaaggct tgatgaaaca | 540 |

```
acgcggcgag ctttgatcaa cgacctttg gaaacttcgg cttcccctgg agagagcgag    600
attctccgcg ctgtagaagt caccattgtt gtgcacgacg acatcattcc gtggcgttat    660
ccagctaagc gcgaactgca atttggagaa tggcagcgca atgacattct tgcaggtatc    720
ttcgagccag ccacgatcga cattgatctg gctatcttgc tgacaaaagc aagagaacat    780
agcgttgcct tggtaggtcc agcggcggag gaactctttg atccggttcc tgaacaggat    840
ctatttgagg cgctaaatga aaccttaacg ctatggaact cgccgcccga ctgggctggc    900
gatgagcgaa atgtagtgct tacgttgtcc cgcatttggt acagcgcagt aaccggcaaa    960
atcgcgccga aggatgtcgc tgccgactgg gcaatggagc gcctgccggc ccagtatcag   1020
cccgtcatac ttgaagctag acaggcttat cttggacaag aagaagatcg cttggcctcg   1080
cgcgcagatc agttggaaga atttgtccac tacgtgaaag cgagatcac caaggtagtc    1140 ggcaaataac cctcgagcca cccatgacca aaatcccta acgtgagtta cgcgtcgttc    1200
cactgagcgt cagacccgt agaaaagatc aaaggatctt cttgagatcc ttttttctg     1260 cgcgtaatct gctgcttgca acaaaaaaa ccaccgctac cagcggtggt ttgtttgccg    1320
gatcaagagc taccaactct ttttccgaag gtaactggct tcagcagagc gcagatacca   1380
aatactgtcc ttctagtgta gccgtagtta ggccaccact tcaagaactc tgtagcaccg   1440
cctacatacc tcgctctgct aatcctgtta ccagtggctg ctgccagtgg cgataagtcg   1500
tgtcttaccg ggttggactc aagacgatag ttaccggata aggcgcagcg gtcgggctga   1560
acggggggtt cgtgcacaca gcccagcttg gagcgaacga cctacaccga actgagatac   1620
ctacagcgtg agctatgaga aagcgccacg cttcccgaag ggagaaaggc ggacaggtat   1680
ccggtaagcg gcagggtcgg aacaggagag cgcacgaggg agcttccagg gggaaacgcc   1740
tggtatcttt atagtcctgt cgggtttcgc cacctctgac ttgagcgtcg atttttgtga   1800
tgctcgtcag gggggcggag cctatggaaa aacgccagca acgcggcctt tttacggttc   1860
ctggcctttt gctggccttt tgctcacatg ttctttcctg cgttatcccc tgattctgtg   1920
gataaccgta ttaccgcctt tgagtgagct gataccgctc gccgcagccg aacgaccgag   1980
cgcagcgagt cagtgagcga ggaagcggaa gagcgcccaa tacgcaaacc gcctctcccc   2040
gcgcgttggc cgattcatta atgcagctgg cacgacaggt ttcccgactg gaaagcgggc   2100
agtgagcgca acgcaattaa tacgcgtacc gcgagccagg aagagtttgt agaaacgcaa   2160
aaaggccatc cgtcaggatg gccttctgct tagtttgatg cctggcagtt tatggcgggc   2220
gtcctgcccg ccaccctccg ggccgttgct tcacaacgtt caaatccgct cccggcggat   2280
ttgtcctact caggagagcg ttcaccgaca acaacagat aaaacgaaag gcccagtctt    2340
ccgactgagc ctttcgtttt atttgatgcc tggcagttcc ctactctcgc gttaacgctt   2400
gcatggatgt tttcccagtc acgacgttgt aaaacgacgg ccagtcttaa gctcgggccc   2460
caaataatga ttttattttg actgatagtg acctgttcgt tgcaacaaat tgatgagcaa   2520 tgcttttta taatgccaac tttgtacaaa aaagcaggct ccgaattcgc ccttcaccat    2580
ggctcctaag aagaagcgga aggttggtat tcacggggtg cctgcggctg ccgtcaagtc   2640
catgaaggtc aagttgcgcc tggataacat gccagagatc agagcggac tttggaaact    2700 tcacaccgag gttaatgcgg gtgtgcggta ctatacgaa tggcttagcc ttttgaggca    2760
agaaaatctt tatcggagga gtcccaatgg cgatggagaa caagaatgct ataaaactgc   2820
tgaggaatgc aaggctgaac tccttgagag actcagagcc cgccaagttg agaatgggca   2880
```

```
ctgcggccct gctgggagtg atgacgaact gctgcaattg gcacggcaac tttatgaact    2940
tctggtccca caagcaatcg gggctaaagg tgatgcgcag caaatcgcaa ggaagtttct    3000
tagtcccctt gccgacaagg atgccgtggg tggtttggga atagcaaaag caggaaataa    3060
gcctaggtgg gttcggatga gggaggctgg agagccaggt tgggaagagg aaaaggctaa    3120
agccgaggcg agaaagagta cggatagaac cgccgatgtt cttcgcgctc ttgcagactt    3180
cggtcttaaa cctcttatga gagtctacac agactcagac atgtccagcg tgcagtggaa    3240
accacttcgc aaaggacaag cggtcagaac ctgggataga gacatgttcc aacaagcgat    3300
cgaaagaatg atgagttggg aatcgtggaa tcagcgcgtt ggagaagcgt acgcaaagct    3360
cgtggaacaa aagtcgaggt ttgaacagaa aaattttgtg ggacaagaac atcttgtcca    3420
acttgtcaat caacttcaac aagacatgaa ggaagcatca cacggcctgg agtcgaaaga    3480
acaaactgcg cattacttga ctgggagagc gctgagaggg agcgacaaag ttttgagaa    3540
gtgggaaaaa ctcgatcctg atgccccatt tgacctctat gataccgaaa tcaagaatgt    3600
tcaacggagg aatactcgca ggttcggatc tcatgatctg tttgcgaagc tcgcggaacc    3660
taaatatcag gcgctctgga gagaggacgc ttctttcctc acgaggtatg cggtttacaa    3720
tagcattgtc agaaaactga atcacgctaa aatgtttgcg acttttactc ttccggatgc    3780
taccgcccac ccgatctgga cgcggtttga caaactcggc ggcaacctgc accagtacac    3840
tttcttgttt aacgaatttg gcgagggcag gcacgccatt cggttcaga agctgttgac    3900
ggttgaggat ggcgttgcta agaggtcga cgacgtcacg gttccgattt ctatgtccgc    3960
gcagctggat gacctcttgc ctcgggaccc acacgagctc gttgcactct acttccagga    4020
ctacggtgca gaacaacatc tggctggaga gtttggcggc gcgaaaattc aataccgccg    4080
cgatcaattg aaccacctgc acgccagaag aggcgccaga gatgtctacc ttaatctgag    4140
cgtccgcgtt cagtcacaat ccgaagccag gggagaaagg cgccctccgt atgcagcggt    4200
cttcaggctt gttggcgata accaccgcgc gtttgttcac tttgataaat tgtcagatta    4260
cctcgcagaa cacccagacg atggtaagct ggggtcggaa ggtttgctct ctgggctcag    4320
agtcatgtca gttgacttgg gtcttaggac ttccgcgagc atatctgtct ccgcgtcgc    4380
aagaaaggac gaattgaagc cgaacagtga aggccgggtc ccttttttgct tcccgatcga    4440
agggaacgaa aacctcgttg ctgtccacga gcggagccaa ctgttgaagc ttcccggtga    4500
aacggaatcg aaagatctga gagcgatcag agaagagcgc caaaggacgc ttagacagct    4560
ccggacgcaa cttgcatact tgcgccttct ggttcgctgc ggtagtgaag acgttggaag    4620
aagagagagg tcatgggcta aactcataga gcaacctatg gatgctaatc aaatgacgcc    4680
tgattggaga gaagcattcg aagacgaact tcagaaactg aaatccctt acgggatatg    4740
cggcgatcgc gagtggacag aagcagtgta tgagtctgtg aggcgcgtgt ggcggcatat    4800
gggtaaacag gtgcgcgatt ggagaaaaga cgttaggagc ggggaaagac ctaagatacg    4860
gggatatcag aaagacgttg tcgggggaaa tagcattgaa cagattgaat atttggagcg    4920
ccaatataag ttcctcaaat cctggtcttt cttcggcaaa gtgtcaggcc aggtgatacg    4980
cgcggaaaag ggatcgcgct ttgcaataac tctgagagaa catattgatc atgccaaaga    5040
agatcggttg aagaaactcg ccgatagaat catcatggag gcgcttggtt atgtctacgc    5100
cttggacgat gaacgggaa agggaaagtg ggtcgccaag tatccacctt gccaactcat    5160
tctcctcgaa gaactttccg aataccagtt taacaacgat cggccgccat cagagaataa    5220
tcaactgatg cagtcggtccc atcgcggtgt gtttcaagag ttgctcaatc aggcccaagt    5280
```

```
ccatgatctg cttgttggca caatgtatgc agccttttcc tcccggtttg atgcaagaac    5340
aggggctcct ggcatacgct gtagacgggt cccggcgagg tgcgcccgcg aacaaaaccc    5400
tgaaccgttc ccctggtggt tgaacaagtt cgttgcggag cacaagctgg acgggtgtcc    5460
tctgcgggcc gacgatctta ttcccaccgg ggaaggggaa ttctttgtga gcccttctc     5520
ggcggaggaa ggggatttc accaaataca tgcagatctt aatgccgcac aaaatttgca     5580
gaggagactg tggtcagact ttgatattag tcagatacgc ctccgctgtg actggggaga    5640
ggtcgatggc gagcctgtgt tgataccaag aacgaccgga agaggacag ccgattcgta      5700
tggaaacaag ttttttaca cgaagacggg cgttacttac tacgaaagag aaagagggaa     5760
gaagagaagg aaagtctttg cccaagaaga attgagcgag gaagaagccg agctcttggt    5820
cgaagcggac gaggcacggg aaaagtctgt cgtcctcatg agggacccctt ccggaattat   5880
taaccgggga gattggacgc ggcagaaaga gttttggtcc atggttaatc aacgcataga    5940
aggctaccctt gtcaagcaaa taagaagtcg cgtgagattg caggagagtg catgtgagaa   6000
cactggggac ataaagcgtc ctgctgccac caaaaaggcc ggacaggcta agaaaaagaa    6060
gtgagacgca tagtggcggc cgccgacgtc cgatcgttca aacatttggc aataaagttt    6120
cttaagattg aatcctgttg ccggtcttgc gatgattatc atataatttc tgttgaatta    6180
cgttaagcat gtaataatta acatgtaatg catgacgtta tttatgagat gggtttttat    6240
gattagagtc ccgcaattat acatttaata cgcgatagaa acaaaatat agcgcgcaaa     6300
ctaggataaa ttatcgcgcg cggtgtcatc tatgttacta gatcgggaat tgatcccccc    6360
tcgacagctt ccggaaaggg cgaattcgca actttgtata caaaagttga acgagaaacg    6420
taaaatgata taaatatcaa tatattaaat tagattttgc ataaaaaaca gactacataa    6480
tactgtaaaa cacaacatat ccagtcacta tgccatccag ctgatatccc ctatagtgag   6540
tcgtattaca tggtcatagc tgtttcctgg cagctctggc ccgtgtctca aaatctctga    6600
tgttacattg cacaagataa aaatatatca tcatgcctcc tc                        6642
```

<210> SEQ ID NO 30
<211> LENGTH: 6579
<212> TYPE: DNA
<213> ORGANISM: Artificial Sequence
<220> FEATURE:
<223> OTHER INFORMATION: Vector

<400> SEQUENCE: 30

```
tggaccagcc aggacagaaa tgcctcgact tcgctgctac ccaaggttgc cgggtgacgc      60
acaccgtgga aacggatgaa ggcacgaacc cagtggacat aagcctgttc ggttcgtaag    120
ctgtaatgca agtagcgtat gcgctcacgc aactggtcca gaaccttgac cgaacgcagc    180
ggtggtaacg gcgcagtggc ggttttcatg gcttgttatg actgtttttt tggggtacag    240
tctatgcctc gggcatccaa gcagcaagcg cgttacgccg tgggtcgatg tttgatgtta    300
tggagcagca acgatgttac gcagcagggc agtcgcccta aacaaagtt aaacatcatg     360
agggaagcgg tgatcgccga agtatcgact caactatcag aggtagttgg cgtcatcgag    420
cgccatctcg aaccgacgtt gctggccgta catttgtacg gctccgcagt ggatggcggc    480
ctgaagccac acagtgatat tgatttgctg gttacggtga ccgtaaggct tgatgaaaca    540
acgcggcgag ctttgatcaa cgaccttttg gaaacttcgg cttcccctgg agagagcgag    600
attctccgcg ctgtagaagt caccattgtt gtgcacgacg acatcattcc gtggcgttat    660
```

```
ccagctaagc gcgaactgca atttggagaa tggcagcgca atgacattct tgcaggtatc    720
ttcgagccag ccacgatcga cattgatctg gctatcttgc tgacaaaagc aagagaacat    780
agcgttgcct tggtaggtcc agcggcggag gaactctttg atccggttcc tgaacaggat    840
ctatttgagg cgctaaatga aaccttaacg ctatggaact cgccgcccga ctgggctggc    900
gatgagcgaa atgtagtgct tacgttgtcc cgcatttggt acagcgcagt aaccggcaaa    960
atcgcgccga aggatgtcgc tgccgactgg gcaatggagc gcctgccggc ccagtatcag   1020
cccgtcatac ttgaagctag acaggcttat cttggacaag aagaagatcg cttggcctcg   1080
cgcgcagatc agttggaaga atttgtccac tacgtgaaag gcgagatcac caaggtagtc   1140
ggcaaataac cctcgagcca cccatgacca aaatccctta acgtgagtta cgcgtcgttc   1200
cactgagcgt cagacccccgt agaaaagatc aaaggatctt cttgagatcc ttttttttctg   1260
cgcgtaatct gctgcttgca acaaaaaaaa ccaccgctac cagcggtggt ttgtttgccg   1320
gatcaagagc taccaactct tttccgaag gtaactggct tcagcagagc gcagatacca   1380
aatactgtcc ttctagtgta gccgtagtta ggccaccact tcaagaactc tgtagcaccg   1440
cctacatacc tcgctctgct aatcctgtta ccagtggctg ctgccagtgg cgataagtcg   1500
tgtcttaccg ggttggactc aagacgatag ttaccggata aggcgcagcg gtcgggctga   1560
acggggggtt cgtgcacaca gcccagcttg gagcgaacga cctacaccga actgagatac   1620
ctacagcgtg agctatgaga aagcgccacg cttcccgaag ggagaaaggc ggacaggtat   1680
ccggtaagcg gcagggtcgg aacaggagag cgcacgaggg agcttccagg gggaaacgcc   1740
tggtatcttt atagtcctgt cgggtttcgc cacctctgac ttgagcgtcg attttttgtga   1800
tgctcgtcag ggggcggag cctatggaaa aacgccagca acgcggcctt tttacggttc   1860
ctggcctttt gctggccttt tgctcacatg ttctttcctg cgttatcccc tgattctgtg   1920
gataaccgta ttaccgcctt tgagtgagct gataccgctc gccgcagccg aacgaccgag   1980
cgcagcgagt cagtgagcga ggaagcggaa gagcgcccaa tacgcaaacc gcctctcccc   2040
gcgcgttggc cgattcatta atgcagctgg cacgacaggt ttcccgactg gaaagcgggc   2100
agtgagcgca acgcaattaa tacgcgtacc gcgagccagg aagagtttgt agaaacgcaa   2160
aaaggccatc cgtcaggatg gccttctgct tagtttgatg cctggcagtt tatggcgggc   2220
gtcctgcccg ccaccctccg ggcgttgct tcacaacgtt caaatccgct cccggcggat   2280
ttgtcctact caggagagcg ttcaccgaca acaacagat aaaacgaaag gcccagtctt   2340
ccgactgagc ctttcgtttt atttgatgcc tggcagttcc ctactctcgc gttaacgctt   2400
gcatggatgt tttcccagtc acgacgttgt aaaacgacgg ccagtcttaa gctcgggccc   2460
caaataatga ttttattttg actgatagtg acctgttcgt tgcaacaaat tgatgagcaa   2520
tgcttttta taatgccaac tttgtacaaa aaagcaggct ccgaattcgc ccttcaccat   2580
ggctcctaag aagaagcgga aggttggtat tcacggggtg cctgcgctg ccaccagatc   2640
gttcatcttg aaaatcgaac ccaatgaaga ggttaaaaag gcctgtgga aacccacga   2700
ggtgttgaat catggtatcg cgtactatat gaatatactt aagctcataa gacaggaagc   2760
catttatgag catcatgaac aggatcctaa gaaccccaaa aaagtctcta aggcagaaat   2820
acaggctgag ctttgggact tgtgctcaa gatgcaaaag tgcaattcat ttacccacga   2880
ggttgataaa gacgaagtct tcaatattct tcgggaattg tatgaagaac tggtcccatc   2940
atcggtggaa aagaaaggtg aagctaacca acttagcaat aagtttctgt atccgctcgt   3000
tgacccgaat tctcaatcgg gaaaagggac tgcctcctcg ggacggaaac cacggtggta   3060
```

```
taacctgaaa atagcagggg acccaagttg ggaggaggag aagaaaaaat gggaggagga      3120
caagaagaag gaccccttg ctaagatact cggcaagctt gctgaatatg ggttgattcc       3180
tcttttcatt ccctatacgg atagcaatga accaattgtc aaggagatca agtggatgga      3240
gaaatcgcgg aatcagagtg ttagaaggtt ggacaaagac atgtttatac aggcgctgga     3300
gagattcctg tcgtgggaat cgtggaactt gaaggttaag gaggaatatg aaaaagtcga     3360
aaaggaatat aagacgcttg aagaacggat taaagaagat attcaggctc ttaaagccct     3420
tgagcagtat gaaaaggaac ggcaagagca actccttcgg gataccttga acacaaacga     3480
gtatcgcctc tcgaagcggg gtctgcgcgg ctggagagaa atcatacaaa agtggcttaa     3540
gatggatgag aatgagccga gcgagaagta cctggaggtt tttaaagatt atcaaaggaa     3600
acatccgaga gaggcggggg attattcggt gtatgagttt ctctccaaaa aagagaatca     3660
cttcatttgg agaaatcacc cggaataccc ctacctttat gctacatttt gcgagattga     3720
taagaaaaaa aaggatgcca aacaacaagc caccttacc ctggcggacc ccatcaacca      3780
cccattgtgg gttcgctttg aggagagaag cggatctaat cttaataaat atagaatcct     3840
tacgaaacag ttgcatacgg agaaactgaa aaaaagctc accgtccaac tcgatcgctt      3900
gatctatcct acagaatcgg gaggatggga agagaagggt aaagttgata ttgtcctcct     3960
tccatctaga caattctata accaaatctt cttggacata gaggagaagg gtaaacacgc     4020
ctttacttac aaagacgaat ccattaagtt tcccctgaaa gggacattgg gaggagcccg     4080
cgtccaattt gatcgggacc accttcgccg gtatccccac aaagtcgaaa gcggcaatgt     4140
cgggcggatc tacttcaaca tgacagttaa tattgagcct acagaatccc cagtctccaa     4200
gtcgctgaag atacatcgcg acgatttttcc taaagttgtg aattttaaac ctaaggaact    4260
gacggaatgg attaaggatt ctaaaggcaa aaagttgaaa tctggaatcg agtctctcga     4320
aataggactt agggtgatga gtatagatct tgggcaaaga caagcggccg ctgcatcaat     4380
ctttgaagtc gtggaccaaa aacccgatat tgaaggcaag ctttcttcc ccattaaggg      4440 aacggagctc tacgccgtcc atcgcgcctc atttaacata aaactgccag gcgagaccct     4500
ggttaagagt cgcgaggtct tgcgcaaggc gcgcgaagat aatcttaagc ttatgaacca     4560
aaaacttaat ttcctcagga acgtgctgca ttttcaacaa tttgaagata ttactgagag     4620
agaaaaacgg gtcacaaaat ggatctctcg ccaagaaaac agcgatgtcc cacttgtgta    4680
tcaggatgaa cttattcaaa ttagagagtt gatgtataaa ccgtacaagg attgggtggc     4740
gtttttgaaa cagctccaca agcgcctgga ggtggaaata gggaagaag ttaagcactg      4800 gcgcaaatcc ctgagcgacg gcaggaaggg gctttacggg attagcctga agaacattga    4860
cgaaatcgac cggactagaa aattccttct caggtggagt ctgaggccta ctgagccggg    4920
tgaagttcgc cgcttggaac caggccagcg ctttgcgatt gatcagttga atcaccttaa    4980
cgcccttaaa gaggatcggc ttaagaagat ggcgaatacc attattatgc acgcgtttggg    5040 ctattgttac gacgtgagaa agaagaagtg gcaggctaaa aatcccgcgt gccagatcat     5100
cctcttcgaa gatctttcca actacaaccc atatggcgag aggtcaaggt tcgagaatag    5160
tcggctgatg aaatgagtc gcaggggaaat cccacgccag gttgccctgc aaggagaaat    5220
ctatggcctt caagttggtg aggtcggggc gcaattcagc agccggtttc acgcgaaaac     5280
tggtagtccg gggatacgct gccgggtggt cacaaaagag aaactccagg ataaccggtt    5340
ttttaaaaat ctgcagaggg aaggtcgcct gactcttgat aaaatcgcag tgctgaaaga    5400
```

```
gggtgacctc tatcccgaca aaggtggcga gaaattcata agcctctcca aggatcgcaa    5460
atgtgtcacg actcacgcag acattaacgc ggcgcaaaac ctccaaaagc ggttttggac    5520
cagaacccac ggtttctata agtctattg caaagcctac caggttgacg gtcagacggt     5580
gtatatccca gaatccaagg atcaaaagca aaagatcatt gaagaatttg gtgaaggata    5640
ttttattctt aaggacggcg tctacgagtg ggtcaatgcg gggaagctta aaattaaaaa    5700
gggctcttcc aagcaatcgt cgagcgagct cgtcgactca gacatcctga agactcatt     5760 tgatctggcc agtgagttga aaggcgaaaa gctcatgttg tacagggatc cttctggaaa    5820
tgtgttcccc tctgataagt ggatggccgc aggcgtcttc tttggcaaac tggagagaat    5880
actcatatca agttgacaa accagtattc aataagcaca atagaagatg actcaagcaa     5940
gcaaagcatg aagcgtcctg ctgccaccaa aaaggccgga caggctaaga aaaagaagtg    6000
agacgactag tggcggccgc cgacgtccga tcgttcaaac atttggcaat aaagtttctt    6060
aagattgaat cctgttgccg gtcttgcgat gattatcata taatttctgt tgaattacgt    6120
taagcatgta ataattaaca tgtaatgcat gacgttattt atgagatggg ttttatgat     6180 tagagtcccg caattataca tttaatacgc gatagaaaac aaaatatagc gcgcaaacta    6240
ggataaatta tcgcgcgcgg tgtcatctat gttactagat cggaattga tcccccctcg     6300 acagcttccg gaaagggcga attcgcaact tgtatacaa agttgaacg agaaacgtaa      6360 aatgatataa atatcaatat attaaattag attttgcata aaaaacagac tacataatac    6420
tgtaaaacac aacatatcca gtcactatgc catccagctg atatcccta tagtgagtcg      6480 tattacatgg tcatagctgt ttcctggcag ctctggcccg tgtctcaaaa tctctgatgt    6540
tacattgcac aagataaaaa tatatcatca tgcctcctc                            6579

<210> SEQ ID NO 31
<211> LENGTH: 6642
<212> TYPE: DNA
<213> ORGANISM: Artificial Sequence
<220> FEATURE:
<223> OTHER INFORMATION: Vector

<400> SEQUENCE: 31
tggaccagcc aggacagaaa tgcctcgact tcgctgctac ccaaggttgc cgggtgacgc      60
acaccgtgga aacggatgaa ggcacgaacc cagtggacat aagcctgttc ggttcgtaag    120
ctgtaatgca agtagcgtat gcgctcacgc aactggtcca gaaccttgac cgaacgcagc    180
ggtggtaacg gcgcagtggc ggttttcatg gcttgttatg actgtttttt tggggtacag    240
tctatgcctc gggcatccaa gcagcaagcg cgttacgccg tgggtcgatg tttgatgtta    300
tggagcagca acgatgttac gcagcagggc agtcgcccta aacaaagtt aaacatcatg     360 agggaagcgg tgatcgccga agtatcgact caactatcag aggtagttgg cgtcatcgag    420
cgccatctcg aaccgacgtt gctggccgta catttgtacg gctccgcagt ggatggcggc    480
ctgaagccac acagtgatat tgatttgctg gttacggtga ccgtaaggct tgatgaaaca    540
acgcggcgag ctttgatcaa cgaccttttg gaaacttcgg cttcccctgg agagagcgag    600
attctccgcg ctgtagaagt caccattgtt gtgcacgacg acatcattcc gtggcgttat    660
ccagctaagc gcgaactgca atttggagaa tggcagcgca atgacattct tgcaggtatc    720
ttcgagccag ccacgatcga cattgatctg ctatcttgc tgacaaaagc aagagaacat    780
agcgttgcct tggtaggtcc agcggcggag gaactctttg atccggttcc tgaacaggat    840
ctatttgagg cgctaaatga aaccttaacg ctatggaact cgccgcccga ctgggctggc    900
```

```
gatgagcgaa atgtagtgct tacgttgtcc cgcatttggt acagcgcagt aaccggcaaa    960
atcgcgccga aggatgtcgc tgccgactgg gcaatggagc gcctgccggc ccagtatcag   1020
cccgtcatac ttgaagctag acaggcttat cttggacaag aagaagatcg cttggcctcg   1080
cgcgcagatc agttggaaga atttgtccac tacgtgaaag gcgagatcac caaggtagtc   1140
ggcaaataac cctcgagcca cccatgacca aaatcccctta acgtgagtta cgcgtcgttc   1200
cactgagcgt cagaccccgt agaaaagatc aaaggatctt cttgagatcc ttttttttctg  1260
cgcgtaatct gctgcttgca aacaaaaaaa ccaccgctac cagcggtggt ttgtttgccg   1320
gatcaagagc taccaactct ttttccgaag gtaactggct tcagcagagc gcagatacca   1380
aatactgtcc ttctagtgta gccgtagtta ggccaccact tcaagaactc tgtagcaccg   1440
cctacatacc tcgctctgct aatcctgtta ccagtggctg ctgccagtgg cgataagtcg   1500
tgtcttaccg ggttggactc aagacgatag ttaccggata aggcgcagcg gtcgggctga   1560
acgggggggtt cgtgcacaca gcccagcttg gagcgaacga cctacaccga actgagatac   1620
ctacagcgtg agctatgaga aagcgccacg cttcccgaag ggagaaaggc ggacaggtat   1680
ccggtaagcg gcagggtcgg aacaggagag cgcacgaggg agcttccagg gggaaacgcc   1740
tggtatcttt atagtcctgt cgggtttcgc cacctctgac ttgagcgtcg attttttgtga  1800
tgctcgtcag gggggcggag cctatggaaa aacgccagca acgcggcctt tttacggttc   1860
ctggcctttt gctggccttt tgctcacatg ttctttcctg cgttatcccc tgattctgtg   1920
gataaccgta ttaccgcctt tgagtgagct gataccgctc gccgcagccg aacgaccgag   1980
cgcagcgagt cagtgagcga ggaagcggaa gagcgcccaa tacgcaaacc gcctctcccc   2040
gcgcgttggc cgattcatta atgcagctgg cacgacaggt ttcccgactg gaaagcgggc   2100
agtgagcgca acgcaattaa tacgcgtacc gcgagccagg aagagtttgt agaaacgcaa   2160
aaaggccatc cgtcaggatg gccttctgct tagtttgatg cctggcagtt tatggcgggc   2220
gtcctgcccg ccaccctccg gccgttgct tcacaacgtt caaatccgct cccggcggat    2280
ttgtcctact caggagagcg ttcaccgaca acaacagat aaaacgaaag gcccagtctt    2340
ccgactgagc ctttcgtttt atttgatgcc tggcagttcc ctactctcgc gttaacgctt   2400
gcatggatgt tttcccagtc acgacgttgt aaaacgacgg ccagtcttaa gctcgggccc   2460
caaataatga ttttatttg actgatagt acctgttcgt tgcaacaaat tgatgagcaa     2520
tgctttttta taatgccaac tttgtacaaa aaagcaggct ccgaattcgc ccttcaccat   2580
ggctcctaag aagaagcgga aggttggtat tcacggggtg cctgcggctg cggtgaagtc   2640
aataaaagtt aaactccgcc tggacgatat gccagaaatt cgggctggcc tctggaagct   2700
tcacaaagag gttaacgctg gcgtcagata ttacacggaa tggttgtcgc tgctccggca   2760
agaaaatctc tacagaaggt cgcccaatgg tgatggggaa caagagtgcg acaaaacggc   2820
ggaggaatgc aaagcggaac tccttgaaag acttcgcgcg agacaagtcg aaaacggcca   2880
tagaggcccg gccggttccg atgatgaatt gcttcagctt gcgcggcagc tttacgaatt   2940
gctcgtgccg caagccatag gtgcaaaagg agatgcacaa caaattgcaa gaaagttcct   3000
ctccccgctc gcagacaagg atgccgtggg aggtcttgga atcgctaaag cagggaataa   3060
gccaagatgg gtgcggatgc gggaagcagg tgagccaggc tgggaagagg agaaggagaa   3120
agccgaaacg aggaaatcag cggatcgcac tgcagacgtg ttgagagccc tcgcagactt   3180
tggacttaag ccactgatgc gggtttacac ggattcagag atgtcctcgg tggaatggaa   3240
```

```
gccgctcaga aagggtcaag ccgtgagaac gtgggaccgc gacatgttcc agcaggcaat     3300
tgagcggatg atgtcctggg agtcttggaa ccaaagggtc gggcaagaat atgcgaaact     3360
ggtggagcaa aaaataggt ttgaacaaaa aaatttcgtt ggtcaagagc atctggttca     3420
tttggttaat caacttcaac aagatatgaa agaagcatca cctggcttgg aatctaaaga     3480
acaaacagca cactacgtta cgggtagggc gttgagggga tcggataaag ttttcgagaa     3540
gtggggtaag ttggcccccg acgcccctt cgatctgtat gacgccgaga taaagaacgt     3600
tcagcggagg aacactcgcc gctttggttc gcacgatctg tttgcaaaac tggccgagcc     3660
tgagtaccag gccctttggc gggaggatgc gtcgttcctt acacgctacg cggtttataa     3720
ttcaattctc agaaagctca atcacgcgaa gatgtttgcg actttcactc ttccagatgc     3780
gacggcacac cctatatgga ctagatttga taagttgggg ggcaacttgc accagtatac     3840
atttctgttc aacgaattcg gcgaacgcag gcatgcaatc aggttccata aacttttgaa     3900
agtcgagaat ggtgttgcca gggaggttga cgatgtcaca gtgcctatct cgatgtccga     3960
acaattggat aacttgctgc ccagagatcc gaacgaaccg attgcacttt atttcaggga     4020
ttatggtgcc gaacaacact ttacgggtga gttcggaggg gccaagattc agtgcagacg     4080
ggaccagctt gctcacatgc accgcaggag aggggctagg gatgtgtatt tgaacgtttc     4140
agttcgcgtg cagtcccaat ccgaggcgcg ggggagcgc agaccaccat acgcggctgt     4200 cttccgctg gttggcgata ccatagagc gttcgtgcat ttcgataagc tgagcgatta     4260
cctcgccgaa catcctgatg acggaaagtt gggtcagag gggcttctgt cgggcctgag     4320
ggtgatgtcc gtgccctgg gattgcgcac cagtgcctcg atcagcgttt ttagggtggc     4380
caggaaagat gagttgaaac ccaactcgaa ggggagggtt ccgttctttt tccctataaa     4440
gggcaacgat aacttggtcg cagtgcatga aaggagccaa ctgctcaaac ttcccgggga     4500
gacagagtcc aaagatcttc gcgctataag ggaagagaga caaagaactc tccggcagct     4560
gcgcacgcag ctcgcatacc tgcggttgct tgtccgctgc ggaagtgaag acgttggcag     4620
gcgcgagagg tcatgggcca aattgattga gcagccggtc gacgccgcaa atcacatgac     4680
tccggattgg agggaggctt tcgagaacga actgcagaag ttgaagagtc tgcatggcat     4740
atgctctgac aaagagtgga tggacgcggt ttacgagtcc gtccgccggg tctggcggca     4800
catggggaaa caagttcgcg attggagaaa ggatgttaga tccggggaaa ggccgaagat     4860
aagaggttat gccaaagacg tggttggtgg aaattctatc gaacagatcg aatatcttga     4920
gaggcagtac aagttcctca agagttggtc tttcttcggt aaagtctctg gacaagttat     4980
aagagcagaa aaggggagcc ggttcgctat caccttgcgg gaacacatag accacgcaaa     5040
agaagacaga ctgaagaagc tggcggacag aattatcatg gaagcgctgg ggtacgttta     5100
cgcgctggac gaaaggggga aaggtaaatg ggtggccaaa tacccgccat gccagttgat     5160
attgctggaa gaattgtccg aatatcaatt taataacgat agaccgccat ccgagaacaa     5220
ccaacttatg caatggtctc accggggagt ttttccagga ttgatcaacc aagctcaagt     5280
gcacgatctg cttgttggta caatgtacgc agcgttttcc tcacgcttcg acgctagaac     5340
aggagcgccg ggaattcgt gccggagggt gcctgcgagg tgtactcagg agcacaaccc     5400
ggagccattt ccctggtggt tgaataaatt cgttgtggaa catacgttgg atgcttgccc     5460
gcttcgggcg gacgacctca ttccgacggg tgagggcgag attttcgtgt cgccattctc     5520
ggctgaggaa ggggacttcc atcaaatcca tgctgacctc aatgcggcgc aaaatctgca     5580
gcagagattg tggagtgatt ttgacatctc tcagatcagg cttcggtgcg attggggaga     5640
```

| | |
|---|---|
| agtcgatggt gaactcgttc tcattccgag actcaccggt aaaaggactg ctgattcata | 5700 |
| ttcgaacaaa gttttttaca ctaacacagg ggtcacttat tatgaaagag aacgcggtaa | 5760 |
| gaagcgccgc aaggtgttcg cgcaagagaa actttccgag gaagaggccg agttgctcgt | 5820 |
| tgaagctgac gaagctcgcg agaagtccgt cgttctgatg cgggatcctt ctggcataat | 5880 |
| aaacagggg aattggacac ggcagaagga attttggtcc atggtgaatc agcgcataga | 5940 |
| aggttatctg gtcaaacaga tcagaagcag ggttcccctc caggattcag cgtgcgagaa | 6000 |
| cacgggcgat attaagcgtc ctgctgccac caaaaaggcc ggacaggcta agaaaaagaa | 6060 |
| gtgagacgac tagtggcggc cgccgacgtc cgatcgttca acatttggc aataaagttt | 6120 |
| cttaagattg aatcctgttg ccggtcttgc gatgattatc ataatttc tgttgaatta | 6180 |
| cgttaagcat gtaataatta acatgtaatg catgacgtta tttatgagat gggttttat | 6240 |
| gattagagtc ccgcaattat acatttaata cgcgatagaa aacaaaatat agcgcgcaaa | 6300 |
| ctaggataaa ttatcgcgcg cggtgtcatc tatgttacta gatcgggaat tgatcccccc | 6360 |
| tcgacagctt ccggaaaggg cgaattcgca actttgtata caaaagttga acgagaaacg | 6420 |
| taaaatgata taaatatcaa tatattaaat tagattttgc ataaaaaaca gactacataa | 6480 |
| tactgtaaaa cacaacatat ccagtcacta tgccatccag ctgatatccc ctatagtgag | 6540 |
| tcgtattaca tggtcatagc tgtttcctgg cagctctggc ccgtgtctca aaatctctga | 6600 |
| tgttacattg cacaagataa aaatatatca tcatgcctcc tc | 6642 |

<210> SEQ ID NO 32
<211> LENGTH: 6642
<212> TYPE: DNA
<213> ORGANISM: Artificial Sequence
<220> FEATURE:
<223> OTHER INFORMATION: Vector

<400> SEQUENCE: 32

| | |
|---|---|
| tggaccagcc aggacagaaa tgcctcgact tcgctgctac ccaaggttgc cgggtgacgc | 60 |
| acaccgtgga aacggatgaa ggcacgaacc cagtggacat aagcctgttc ggttcgtaag | 120 |
| ctgtaatgca agtagcgtat gcgctcacgc aactggtcca gaaccttgac cgaacgcagc | 180 |
| ggtggtaacg gcgcagtggc ggttttcatg gcttgttatg actgtttttt tggggtacag | 240 |
| tctatgcctc gggcatccaa gcagcaagcg cgttacgccg tgggtcgatg tttgatgtta | 300 |
| tggagcagca acgatgttac gcagcagggc agtcgcccta aaacaaagtt aaacatcatg | 360 |
| agggaagcgg tgatcgccga agtatcgact caactatcag aggtagttgg cgtcatcgag | 420 |
| cgccatctcg aaccgacgtt gctggccgta catttgtacg gctccgcagt ggatggcggc | 480 |
| ctgaagccac acagtgatat tgatttgctg gttacggtga ccgtaaggct tgatgaaaca | 540 |
| acgcggcgag ctttgatcaa cgaccttttg gaaacttcgg cttcccctgg agagagcgag | 600 |
| attctccgcg ctgtagaagt caccattgtt gtgcacgacg acatcattcc gtggcgttat | 660 |
| ccagctaagc gcgaactgca atttggagaa tggcagcgca atgacattct tgcaggtatc | 720 |
| ttcgagccag ccacgatcga cattgatctg gctatcttgc tgacaaaagc aagagaacat | 780 |
| agcgttgcct tggtaggtcc agcggcggag gaactctttg atccggttcc tgaacaggat | 840 |
| ctatttgagg cgctaaatga aaccttaacg ctatggaact cgccgcccga ctgggctggc | 900 |
| gatgagcgaa atgtagtgct tacgttgtcc cgcatttggt acagcgcagt aaccggcaaa | 960 |
| atcgcgccga aggatgtcgc tgccgactgg gcaatggagc gcctgccggc ccagtatcag | 1020 |

```
cccgtcatac ttgaagctag acaggcttat cttggacaag aagaagatcg cttggcctcg    1080
cgcgcagatc agttggaaga atttgtccac tacgtgaaag gcgagatcac caaggtagtc    1140
ggcaaataac cctcgagcca cccatgacca aaatcccttc acgtgagtta cgcgtcgttc    1200
cactgagcgt cagaccccgt agaaaagatc aaaggatctt cttgagatcc ttttttttctg   1260
cgcgtaatct gctgcttgca aacaaaaaaa ccaccgctac cagcggtggt ttgtttgccg    1320
gatcaagagc taccaactct ttttccgaag gtaactggct tcagcagagc gcagatacca    1380
aatactgtcc ttctagtgta gccgtagtta ggccaccact tcaagaactc tgtagcaccg    1440
cctacatacc tcgctctgct aatcctgtta ccagtggctg ctgccagtgg cgataagtcg    1500
tgtcttaccg ggttggactc aagacgatag ttaccggata aggcgcagcg gtcgggctga    1560
acggggggtt cgtgcacaca gcccagcttg gagcgaacga cctacaccga actgagatac    1620
ctacagcgtg agctatgaga aagcgccacg cttcccgaag ggagaaaggc ggacaggtat    1680
ccggtaagcg gcagggtcgg aacaggagag cgcacgaggg agcttccagg gggaaacgcc    1740
tggtatcttt atagtcctgt cgggtttcgc cacctctgac ttgagcgtcg attttttgtga  1800
tgctcgtcag ggggcggag  cctatggaaa aacgccagca acgcggcctt tttacggttc    1860
ctggcctttt gctggccttt tgctcacatg ttctttcctg cgttatcccc tgattctgtg    1920
gataaccgta ttaccgcctt tgagtgagct gataccgctc gccgcagccg aacgaccgag    1980
cgcagcgagt cagtgagcga ggaagcggaa gagcgcccaa tacgcaaacc gcctctcccc    2040
gcgcgttggc cgattcatta atgcagctgg cacgacaggt ttcccgactg gaaagcgggc    2100
agtgagcgca acgcaattaa tacgcgtacc gcgagccagg aagagtttgt agaaacgcaa    2160
aaaggccatc cgtcaggatg gccttctgct tagtttgatg cctggcagtt tatggcgggc    2220
gtcctgcccg ccacccctcc ggccgttgct tcacaacgtt caaatccgct cccggcggat    2280
ttgtcctact caggagagcg ttcaccgaca acaacagat  aaaacgaaag gcccagtctt    2340
ccgactgagc ctttcgtttt atttgatgcc tggcagttcc ctactctcgc gttaacgctt    2400
gcatggatgt tttcccagtc acgacgttgt aaaacgacgg ccagtcttaa gctcgggccc    2460
caaataatga ttttattttg actgatagtg acctgttcgt tgcaacaaat tgatgagcaa    2520
tgcttttttta taatgccaac tttgtacaaa aaagcaggct ccgaattcgc ccttcaccat   2580
ggctcctaag aagaagcgga aggttggtat tcacggggtg cctgcggctg cggtgaagtc    2640
aataaaagtt aaactccgcc tggacgatat gccagaaatt cgggctggcc tctggaagct    2700
tcacaaagag gttaacgctg gcgtcagata ttacacggaa tggttgtcgc tgctccggca    2760
agaaaatctc tacagaaggt cgcccaatgg tgatggggaa caagagtgcg acaaaacggc    2820
ggaggaatgc aaagcggaac tccttgaaag acttcgcgcg agacaagtcg aaaacggcca    2880
tagaggcccg gccggttccg atgatgaatt gcttcagctt gcgcggcagc tttacgaatt    2940
gctcgtgccg caagccatag gtgcaaaagg agatgcacaa caaattgcaa gaaagttcct    3000
ctccccgctc gcagacaagg atgccgtggg aggtcttgga atcgctaaag cagggaataa    3060
gccaagatgg gtgcggatgc gggaagcagg tgagccaggc tgggaagagg agaaggagaa    3120
agccgaaacg aggaaatcag cggatcgcac tgcagacgtg ttgagagccc tcgcagactt    3180
tggacttaag ccactgatgc gggtttacac ggattcagag atgtcctcgg tggaatggaa    3240
gccgctcaga aagggtcaag ccgtgagaac gtgggaccgc gacatgttcc agcaggcaat    3300
tgagcggatg atgtcctggg agtcttggaa ccaaagggtc gggcaagaat atgcgaaact    3360
ggtggagcaa aaaaatagqt ttgaacaaaa aaatttcgtt ggtcaagagc atctggttca    3420
```

```
tttggttaat caacttcaac aagatatgaa agaagcatca cctggcttgg aatctaaaga    3480
acaaacagca cactacgtta cgggtagggc gttgagggga tcggataaag ttttcgagaa    3540
gtggggtaag ttggcccccg acgccccttt cgatctgtat gacgccgaga taaagaacgt    3600
tcagcggagg aacactcgcc gctttggttc gcacgatctg tttgcaaaac tggccgagcc    3660
tgagtaccag gcccttggc gggaggatgc gtcgttcctt acacgctacg cggtttataa    3720
ttcaattctc agaaagctca atcacgcgaa gatgtttgcg actttcactc ttccagatgc    3780
gacggcacac cctatatgga ctagatttga taagttgggg ggcaacttgc accagtatac    3840
atttctgttc aacgaattcg gcgaacgcag gcatgcaatc aggttccata aacttttgaa    3900
agtcgagaat ggtgttgcca gggaggttga cgatgtcaca gtgcctatct cgatgtccga    3960
acaattggat aacttgctgc ccagagatcc gaacgaaccg attgcacttt atttcaggga    4020
ttatggtgcc gaacaacact ttacgggtga gttcggaggg gccaagattc agtgcagacg    4080
ggaccagctt gctcacatgc accgcaggag aggggctagg gatgtgtatt tgaacgtttc    4140
agttcgcgtg cagtcccaat ccgaggcgcg ggggagcgc agaccaccat acgcggctgt    4200
cttccggctg gttggcgata accatagagc gttcgtgcat ttcgataagc tgagcgatta    4260
cctcgccgaa catcctgatg acggaaagtt ggggtcagag gggcttctgt cgggcctgag    4320
ggtgatgtcc gtggacctgg gattgcgcac cagtgcctcg atcagcgttt ttagggtggc    4380
caggaaagat gagttgaaac ccaactcgaa ggggagggtt ccgttctttt tccctataaa    4440
gggcaacgat aacttggtcg cagtgcatga aaggagccaa ctgctcaaac ttcccgggga    4500
gacagagtcc aaagatcttc gcgctataag ggaagagaga caaagaactc tccggcagct    4560
gcgcacgcag ctcgcatacc tgcggttgct tgtccgctgc ggaagtgaag acgttggcag    4620
gcgcgagagg tcatgggcca aattgattga gcagccggtc gacgccgcaa atcacatgac    4680
tccggattgg agggaggctt tcgagaacga actgcagaag ttgaagagtc tgcatggcat    4740
atgctctgac aaagagtgga tggacgcggt ttacgagtcc gtccgccggg tctggcggca    4800
catggggaaa caagttcgcg attggagaaa ggatgttaga tccggggaaa ggccgaagat    4860
aagaggttat gccaaagacg tggttggtgg aaattctatc gaacagatcg aatatcttga    4920
gaggcagtac aagttcctca agagttggtc tttcttcggt aaagtctctg acaagttat    4980 aagagcagaa aaggggagcc ggttcgctat caccttgcgg gaacacatag accacgcaaa    5040
agaagacaga ctgaagaagc tggcggacag aattatcatg gaagcgctgg ggtacgttta    5100
cgcgctggac gaaaggggga aaggtaaatg ggtggccaaa tacccgccat gccagttgat    5160
attgctggaa gaattgtccg aatatcaatt taataacgat agaccgccat ccgagaacaa    5220
ccaacttatg caatggtctc accggggagt tttccaggag ttgatcaacc aagctcaagt    5280
gcacgatctg cttgttggta caatgtacgc agcgttttcc tcacgcttcg acgctagaac    5340
aggagcgccg ggaattcggt gccggagggt gcctgcgagg tgtactcagg agcacaaccc    5400
ggagccattt ccctggtggt tgaataaatt cgttgtggaa catacgttgg atgcttgccc    5460
gcttcgggcg gacgacctca ttccgacggg tgagggcgag attttcgtgt cgccattctc    5520
ggctgaggaa ggggacttcc atcaaatcca tgctgccctc aatgcggcgc aaaatctgca    5580
gcagagattg tggagtgatt ttgacatctc tcagatcagg cttcggtgcg attggggaga    5640
agtcgatggt gaactcgttc tcattccgag actcaccggt aaaaggactg ctgattcata    5700
ttcgaacaaa gttttttaca ctaacacagg ggtcacttat tatgaaagag aacgcggtaa    5760
```

| | |
|---|---|
| gaagcgccgc aaggtgttcg cgcaagagaa actttccgag gaagaggccg agttgctcgt | 5820 |
| tgaagctgac gaagctcgcg agaagtccgt cgttctgatg cgggatcctt ctggcataat | 5880 |
| aaacaggggg aattggacac ggcagaagga attttggtcc atggtgaatc agcgcataga | 5940 |
| aggttatctg gtcaaacaga tcagaagcag ggttcccctc caggattcag cgtgcgagaa | 6000 |
| cacgggcgat attaagcgtc ctgctgccac caaaaaggcc ggacaggcta agaaaaagaa | 6060 |
| gtgagacgac tagtggcggc cgccgacgtc cgatcgttca acatttggc aataaagttt | 6120 |
| cttaagattg aatcctgttg ccggtcttgc gatgattatc atataatttc tgttgaatta | 6180 |
| cgttaagcat gtaataatta acatgtaatg catgacgtta tttatgagat gggtttttat | 6240 |
| gattagagtc ccgcaattat acatttaata cgcgatagaa acaaaatat agcgcgcaaa | 6300 |
| ctaggataaa ttatcgcgcg cggtgtcatc tatgttacta gatcgggaat tgatccccc | 6360 |
| tcgacagctt ccggaaaggg cgaattcgca actttgtata caaaagttga acgagaaacg | 6420 |
| taaaatgata taaatatcaa tatattaaat tagattttgc ataaaaaaca gactacataa | 6480 |
| tactgtaaaa cacaacatat ccagtcacta tgccatccag ctgatatccc ctatagtgag | 6540 |
| tcgtattaca tggtcatagc tgtttcctgg cagctctggc ccgtgtctca aaatctctga | 6600 |
| tgttacattg cacaagataa aaatatatca tcatgcctcc tc | 6642 |

<210> SEQ ID NO 33
<211> LENGTH: 6642
<212> TYPE: DNA
<213> ORGANISM: Artificial Sequence
<220> FEATURE:
<223> OTHER INFORMATION: Vector

<400> SEQUENCE: 33

| | |
|---|---|
| tggaccagcc aggacagaaa tgcctcgact tcgctgctac ccaaggttgc cgggtgacgc | 60 |
| acaccgtgga aacggatgaa ggcacgaacc cagtggacat aagcctgttc ggttcgtaag | 120 |
| ctgtaatgca agtagcgtat gcgctcacgc aactggtcca gaaccttgac cgaacgcagc | 180 |
| ggtggtaacg gcgcagtggc ggttttcatg gcttgttatg actgtttttt tggggtacag | 240 |
| tctatgcctc gggcatccaa gcagcaagcg cgttacgccg tgggtcgatg tttgatgtta | 300 |
| tggagcagca acgatgttac gcagcagggc agtcgcccta aaacaaagtt aaacatcatg | 360 |
| agggaagcgg tgatcgccga agtatcgact caactatcag aggtagttgg cgtcatcgag | 420 |
| cgccatctcg aaccgacgtt gctggccgta catttgtacg gctccgcagt ggatggcggc | 480 |
| ctgaagccac acagtgatat tgatttgctg gttacggtga ccgtaaggct tgatgaaaca | 540 |
| acgcggcgag ctttgatcaa cgaccttttg gaaacttcgg cttcccctgg agagagcgag | 600 |
| attctccgcg ctgtagaagt caccattgtt gtgcacgacg acatcattcc gtggcgttat | 660 |
| ccagctaagc gcgaactgca atttggagaa tggcagcgca atgacattct tgcaggtatc | 720 |
| ttcgagccag ccacgatcga cattgatctg gctatcttgc tgacaaaagc aagagaacat | 780 |
| agcgttgcct tggtaggtcc agcggcggag gaactctttg atccggttcc tgaacaggat | 840 |
| ctatttgagg cgctaaatga aaccttaacg ctatggaact cgccgcccga ctgggctggc | 900 |
| gatgagcgaa atgtagtgct tacgttgtcc cgcatttggt acagcgcagt aaccggcaaa | 960 |
| atcgcgccga aggatgtcgc tgccgactgg gcaatggagc gcctgccggc ccagtatcag | 1020 |
| cccgtcatac ttgaagctag acaggcttat cttggacaag aagaagatcg cttggcctcg | 1080 |
| cgcgcagatc agttggaaga atttgtccac tacgtgaaag gcgagatcac caaggtagtc | 1140 |
| ggcaaataac cctcgagcca cccatgacca aaatccctta acgtgagtta cgcgtcgttc | 1200 |

```
cactgagcgt cagaccccgt agaaaagatc aaaggatctt cttgagatcc ttttttcctg    1260
cgcgtaatct gctgcttgca aacaaaaaaa ccaccgctac cagcggtggt ttgtttgccg    1320
gatcaagagc taccaactct ttttccgaag gtaactggct tcagcagagc gcagatacca    1380
aatactgtcc ttctagtgta gccgtagtta ggccaccact tcaagaactc tgtagcaccg    1440
cctacatacc tcgctctgct aatcctgtta ccagtggctg ctgccagtgg cgataagtcg    1500
tgtcttaccg ggttggactc aagacgatag ttaccggata aggcgcagcg gtcgggctga    1560
acggggggtt cgtgcacaca gcccagcttg gagcgaacga cctacaccga actgagatac    1620
ctacagcgtg agctatgaga aagcgccacg cttcccgaag ggagaaaggc ggacaggtat    1680
ccggtaagcg gcagggtcgg aacaggagag cgcacgaggg agcttccagg gggaaacgcc    1740
tggtatcttt atagtcctgt cgggtttcgc cacctctgac ttgagcgtcg attttttgtga   1800
tgctcgtcag gggggcggag cctatggaaa aacgccagca acgcggcctt tttacggttc    1860
ctggcctttt gctggccttt tgctcacatg ttctttcctg cgttatcccc tgattctgtg    1920
gataaccgta ttaccgcctt tgagtgagct gataccgctc gccgcagccg aacgaccgag    1980
cgcagcgagt cagtgagcga ggaagcggaa gagcgcccaa tacgcaaacc gcctctcccc    2040
gcgcgttggc cgattcatta atgcagctgg cacgacaggt ttcccgactg gaaagcgggc    2100
agtgagcgca acgcaattaa tacgcgtacc gcgagccagg aagagtttgt agaaacgcaa    2160
aaaggccatc cgtcaggatg gccttctgct tagtttgatg cctggcagtt tatggcgggc    2220
gtcctgcccg ccacccctcc ggccgttgct tcacaacgtt caaatccgct cccggcggat    2280
ttgtcctact caggagagcg ttcaccgaca acaacagat aaaacgaaag gcccagtctt     2340
ccgactgagc ctttcgtttt atttgatgcc tggcagttcc ctactctcgc gttaacgctt    2400
gcatggatgt tttcccagtc acgacgttgt aaaacgacgg ccagtcttaa gctcgggccc    2460
caaataatga ttttattttg actgatagtg acctgttcgt tgcaacaaat tgatgagcaa    2520
tgcttttttta taatgccaac tttgtacaaa aaagcaggct ccgaattcgc ccttcaccat   2580
ggctcctaag aagaagcgga aggttggtat tcacggggtg cctgcggctg cggtgaagtc    2640
aataaaagtt aaactccgcc tggacgatat gccagaaatt cgggctggcc tctgaaagct   2700
tcacaaagag gttaacgctg gcgtcagata ttacacggaa tggttgtcgc tgctccggca    2760
agaaaatctc tacagaaggt cgcccaatgg tgatggggaa caagagtgcg acaaaacggc    2820
ggaggaatgc aaagcggaac tccttgaaag acttcgcgcg agacaagtcg aaaacggcca    2880
tagaggcccg gccggttccg atgatgaatt gcttcagctt gcgcggcagc tttacgaatt    2940
gctcgtgccg caagccatag gtgcaaaagg agatgcacaa caaattgcaa gaaagttcct    3000
ctccccgctc gcagacaagg atgccgtggg aggtcttgga atcgctaaag cagggaataa    3060
gccaagatgg gtgcggatgc gggaagcagg tgagccaggc tgggaagagg agaaggagaa    3120
agccgaaacg aggaaatcag cggatcgcac tgcagacgtg ttgagagccc tcgcagactt    3180
tggacttaag ccactgatgc gggtttacac ggattcagag atgtcctcgg tggaatggaa    3240
gccgctcaga aagggtcaag ccgtgagaac gtgggaccgc gacatgttcc agcaggcaat    3300
tgagcggatg atgtcctggg agtcttggaa ccaaagggtc gggcaagaat atgcgaaact    3360
ggtggagcaa aaaaatagtt ttgaacaaaa aaatttcgtt ggtcaagagc atctggttca    3420
tttggttaat caacttcaac aagatatgaa agaagcatca cctggcttgg aatctaaaga    3480
acaaacagca cactacgtta cgggtagggc gttgaggggga tcggataaag ttttcgagaa    3540
```

```
gtggggtaag ttggccccccg acgccccttt cgatctgtat gacgccgaga taaagaacgt    3600
tcagcggagg aacactcgcc gctttggttc gcacgatctg tttgcaaaac tggccgagcc    3660
tgagtaccag gcccttttggc gggaggatgc gtcgttcctt acacgctacg cggtttataa    3720
ttcaattctc agaaagctca atcacgcgaa gatgtttgcg acttttcactc ttccagatgc    3780 gacggcacac cctatatgga ctagatttga taagttgggg ggcaacttgc accagtatac    3840
atttctgttc aacgaattcg gcgaacgcag gcatgcaatc aggttccata aacttttgaa    3900
agtcgagaat ggtgttgcca gggaggttga cgatgtcaca gtgcctatct cgatgtccga    3960
acaattggat aacttgctgc ccagagatcc gaacgaaccg attgcactttt atttcaggga    4020 ttatggtgcc gaacaacact ttacgggtga gttcggaggg gccaagattc agtgcagacg    4080
ggaccagctt gctcacatgc accgcaggag aggggctagg gatgtgtatt tgaacgtttc    4140
agttcgcgtg cagtcccaat ccgaggcgcg gggggagcgc agaccaccat acgcggctgt    4200
cttccggctg gttggcgata accatagagc gttcgtgcat ttcgataagc tgagcgatta    4260
cctcgccgaa catcctgatg acggaaagtt gggggtcagag gggcttctgt cgggcctgag    4320
ggtgatgtcc gtggacctgg gattgcgcac cagtgcctcg atcagcgttt ttagggtggc    4380
caggaaagat gagttgaaac ccaactcgaa ggggagggtt ccgttctttt tccctataaa    4440
gggcaacgat aacttggtcg cagtgcatga aaggagccaa ctgctcaaac ttcccgggga    4500
gacagagtcc aaagatcttc gcgctataag ggaagagaga caaagaactc tccggcagct    4560
gcgcacgcag ctcgcatacc tgcggttgct tgtccgctgc ggaagtgaag acgttggcag    4620
gcgcgagagg tcatgggcca aattgattga gcagccggtc gacgccgcaa atcacatgac    4680
tccggattgg agggaggctt tcgagaacga actgcagaag ttgaagagtc tgcatggcat    4740
atgctctgac aaagagtgga tggacgcggt ttacgagtcc gtccgccggg tctggcggca    4800
catggggaaa caagttcgcg attggagaaa ggatgttaga tccggggaaa ggccgaagat    4860
aagaggttat gccaaagacg tggttggtgg aaattctatc gaacagatcg aatatcttga    4920
gaggcagtac aagttcctca agagttggtc tttcttcggt aaagtctctg gacaagttat    4980
aagagcagaa aaggggagcc ggttcgctat caccttgcgg gaacacatag accacgcaaa    5040
agaagacaga ctgaagaagc tggcggacag aattatcatg gaagcgctgg ggtacgttta    5100
cgcgctggac gaaagggggga aaggtaaatg ggtggccaaa tacccgccat gccagttgat    5160
attgctggcc gaattgtccg aatatcaatt taataacgat agaccgccat ccgagaacaa    5220
ccaacttatg caatggtctc accggggagt ttttccaggag ttgatcaacc aagctcaagt    5280
gcacgatctg cttgttggta caatgtacgc agcgttttcc tcacgcttcg acgctagaac    5340
aggagcgccg ggaattcggt gccggagggt gcctgcgagg tgtactcagg agcacaaccc    5400
ggagccattt ccctggtggt tgaataaatt cgttgtggaa catacgttgg atgcttgccc    5460
gcttcgggcg gacgacctca ttccgacggg tgagggcgag attttcgtgt cgccattctc    5520
ggctgaggaa ggggacttcc atcaaatcca tgctgacctc aatgcggcgc aaaatctgca    5580
gcagagattg tggagtgatt ttgacatctc tcagatcagg cttcggtgcg attggggaga    5640
agtcgatggt gaactcgttc tcattccgag actcaccggt aaaaggactg ctgattcata    5700
ttcgaacaaa gttttttaca ctaacacagg ggtcacttat tatgaaagag aacgcggtaa    5760
gaagcgccgc aaggtgttcg cgcaagagaa acttttccgag gaagaggccg agttgctcgt    5820
tgaagctgac gaagctcgcg agaagtccgt cgttctgatg cgggatcctt ctggcataat    5880
aaacaggggg aattggacac ggcagaagga atttttggtcc atggtgaatc agcgcataga    5940
```

-continued

```
aggttatctg gtcaaacaga tcagaagcag ggttcccctc caggattcag cgtgcgagaa      6000
cacgggcgat attaagcgtc ctgctgccac caaaaaggcc ggacaggcta agaaaaagaa      6060
gtgagacgac tagtggcggc cgccgacgtc cgatcgttca acatttggc aataaagttt       6120 cttaagattg aatcctgttg ccggtcttgc gatgattatc atataatttc tgttgaatta      6180
cgttaagcat gtaataatta acatgtaatg catgacgtta tttatgagat ggttttttat      6240
gattagagtc ccgcaattat acatttaata cgcgatagaa acaaaatat agcgcgcaaa       6300 ctaggataaa ttatcgcgcg cggtgtcatc tatgttacta gatcgggaat tgatcccccc      6360
tcgacagctt ccgaaaggg cgaattcgca actttgtata caaagttga acgagaaacg        6420 taaaatgata taaatatcaa tatattaaat tagattttgc ataaaaaaca gactacataa      6480
tactgtaaaa cacaacatat ccagtcacta tgccatccag ctgatatccc ctatagtgag      6540
tcgtattaca tggtcatagc tgtttcctgg cagctctggc ccgtgtctca aaatctctga     6600
tgttacattg cacaagataa aaatatatca tcatgcctcc tc                         6642
```

<210> SEQ ID NO 34
<211> LENGTH: 6579
<212> TYPE: DNA
<213> ORGANISM: Artificial Sequence
<220> FEATURE:
<223> OTHER INFORMATION: Vector

<400> SEQUENCE: 34

```
tggaccagcc aggacagaaa tgcctcgact tcgctgctac ccaaggttgc cgggtgacgc        60
acaccgtgga aacggatgaa ggcacgaacc cagtggacat aagcctgttc ggttcgtaag      120
ctgtaatgca agtagcgtat gcgctcacgc aactggtcca gaaccttgac cgaacgcagc      180
ggtggtaacg gcgcagtggc ggttttcatg gcttgttatg actgtttttt tggggtacag      240
tctatgcctc gggcatccaa gcagcaagcg cgttacgccg tgggtcgatg tttgatgtta      300
tggagcagca acgatgttac gcagcagggc agtcgcccta aaacaaagtt aaacatcatg      360
agggaagcgg tgatcgccga agtatcgact caactatcag aggtagttgg cgtcatcgag      420
cgccatctcg aaccgacgtt gctggccgta catttgtacg gctccgcagt ggatggcggc      480
ctgaagccac acagtgatat tgatttgctg gttacggtga ccgtaaggct tgatgaaaca      540
acgcggcgag ctttgatcaa cgaccttttg gaaacttcgg cttcccctgg agagagcgag     600
attctccgcg ctgtagaagt caccattgtt gtgcacgacg acatcattcc gtggcgttat      660
ccagctaagc gcgaactgca atttggagaa tggcagcgca atgacattct tgcaggtatc      720
ttcgagccag ccacgatcga cattgatctg ctatcttgc tgacaaaagc aagagaacat      780
agcgttgcct tggtaggtcc agcggcggag gaactctttg atccggttcc tgaacaggat      840
ctatttgagg cgctaaatga aaccttaacg ctatggaact cgccgcccga ctgggctggc      900
gatgagcgaa atgtagtgct tacgttgtcc cgcatttggt acagcgcagt aaccggcaaa     960
atcgcgccga aggatgtcgc tgccgactgg gcaatggagc gcctgccggc ccagtatcag     1020
cccgtcatac ttgaagctag acaggcttat cttggacaag aagaagatcg cttggcctcg     1080
cgcgcagatc agttggaaga atttgtccac tacgtgaaag gcgagatcac caaggtagtc     1140
ggcaaataac cctcgagcca cccatgacca aaatccctta acgtgagtta cgcgtcgttc     1200
cactgagcgt cagaccccgt agaaaagatc aaaggatctt cttgagatcc ttttttttctg    1260 cgcgtaatct gctgcttgca acaaaaaaa ccaccgctac cagcggtggt ttgtttgccg     1320
```

```
gatcaagagc taccaactct ttttccgaag gtaactggct tcagcagagc gcagatacca  1380
aatactgtcc ttctagtgta gccgtagtta ggccaccact tcaagaactc tgtagcaccg  1440
cctacatacc tcgctctgct aatcctgtta ccagtggctg ctgccagtgg cgataagtcg  1500
tgtcttaccg ggttggactc aagacgatag ttaccggata aggcgcagcg gtcgggctga  1560
acgggggggtt cgtgcacaca gcccagcttg gagcgaacga cctacaccga actgagatac  1620
ctacagcgtg agctatgaga aagcgccacg cttcccgaag ggagaaaggc ggacaggtat  1680
ccggtaagcg gcagggtcgg aacaggagag cgcacgaggg agcttccagg gggaaacgcc  1740
tggtatcttt atagtcctgt cgggtttcgc cacctctgac ttgagcgtcg atttttgtga  1800
tgctcgtcag gggggcggag cctatggaaa aacgccagca acgcggcctt tttacggttc  1860
ctggcctttt gctggccttt tgctcacatg ttctttcctg cgttatcccc tgattctgtg  1920
gataaccgta ttaccgcctt tgagtgagct gataccgctc gccgcagccg aacgaccgag  1980
cgcagcgagt cagtgagcga ggaagcggaa gagcgcccaa tacgcaaacc gcctctcccc  2040
gcgcgttggc cgattcatta atgcagctgg cacgacaggt ttcccgactg gaaagcgggc  2100
agtgagcgca acgcaattaa tacgcgtacc gcgagccagg aagagtttgt agaaacgcaa  2160
aaaggccatc cgtcaggatg gccttctgct tagtttgatg cctggcagtt tatggcgggc  2220
gtcctgcccg ccacccctccg ggccgttgct tcacaacgtt caaatccgct cccggcggat  2280
ttgtcctact caggagagcg ttcaccgaca acaacagat aaaacgaaag cccagtctt  2340
ccgactgagc ctttcgtttt atttgatgcc tggcagttcc ctactctcgc gttaacgctt  2400
gcatggatgt tttcccagtc acgacgttgt aaaacgacgg ccagtcttaa gctcgggccc  2460
caaataatga ttttattttg actgatagtg acctgttcgt tgcaacaaat tgatgagcaa  2520
tgctttttta taatgccaac tttgtacaaa aaagcaggct ccgaattcgc ccttcaccat  2580
ggctcctaag aagaagcgga aggttggtat tcacggggtg cctgcggctg ccacaaggtc  2640
tttcatactt aagatagagc caaacgaaga ggtcaaaaag ggattgtgga aaacccatga  2700
agtcctgaac catggcattg cctactacat gaacatcctg aaacttatac ggcaggaggc  2760
tatttatgag caccacgagc aggatccaaa aaaccccaaa aaggtttcga aggctgaaat  2820
ccaggccgaa ctgtgggact tcgttctcaa aatgcagaaa tgtaattcgt tcactcatga  2880
agttgacaaa gacgtcgtgt ttaacatttt gagggagctt tacgaggagt tggttccgag  2940
ctccgtcgaa aagaagggtg aagcaaatca gctgtcgaat aagttcttgt acccttttggt  3000
ggacccgaac agccaatctg gaaaagggac agcatcatca gggcggaagc ctcggtggta  3060
taacttgaag attgctggag acccttcgtg ggaagaggaa aagaaaaagt gggaggaaga  3120
taagaagaag gacccacttg ccaaaattct cggcaaactt gccgaatatg gattgatacc  3180
gctgttcatc ccctttacgg attctaacga acccatcgtt aaagaaatca gtggatgga  3240
aaaatctcgc aatcagtccg tccggaggct ggacaaagat atgtttatac aagctttgga  3300
acgctttctc tcgtgggagt cgtggaatct taaggtcaaa gaagagtatg aaaaggtcga  3360
gaaggaacac aagacactgg aggagaggat taaggaagac attcaagcat tcaagtcact  3420
ggagcaatac gaaaaggaac ggcaggagca attgcttcgc gacacgctca ataccaatga  3480
atataggctt tccaagaggg gcctgagagg atggcggaa ataatccaga aatggctcaa  3540
gatggacgag aatgaacctt cagaaaaata tctcgaggtt tttaaagatt accaaaggaa  3600
acatccacgc gaggcagggg attacagcgt gtacgagttt ctctccaaga aggaaaacca  3660
ttttatctgg cgcaatcatc ccgaataccc gtacctctat gcgacgttct gcgaaataga  3720
```

```
caaaaagaaa aaagatgcta agcaacaagc gactttcaca cttgcagatc ccataaatca   3780
cccattgtgg gtgcggtttg aagaaaggtc gggctctaac ctcaataagt acagaatttt   3840
gacggagcag ttgcacacag aaaagctgaa gaagaagttg acggttcagc tggatcgcct   3900
tatctaccca accgagtctg gtggctggga agagaagggg aaagtcgaca tagtgttgct   3960
gccatctagg cagttctata accagatttt tctcgatata aagaaaagg gtaaacatgc    4020
atttacgtat aaagacgagt ccataaagtt tccactgaaa ggaacacttg gcggcgcaag   4080
ggtgcagttt gatcgggacc accttcgcag gtaccccac aaggttgaaa gtggaaacgt    4140
tggacggatc tattttaata tgaccgtcaa catagaaccc acagaatccc ctgtttccaa   4200
atccctgaaa atacaccggg acgattttcc taaatttgtg aactttaaac cgaaggagtt   4260
gaccgagtgg ataaaggaca gtaagggaa aaagctgaag tccggtatcg aaagcctgga    4320
gattgggctc agagttatgt cgatagcgct gggtcaaagg caggcagcag ccgcctctat   4380
atttgaggtc gtggaccaga agcccgacat tgaaggtaaa ctgttctttc cgattaaggg   4440
gacggaactc tacgcagtcc atcgcgcctc cttcaatata aagctgccgg gcgaaacact   4500
ggttaaatca cgcgaggttt tgcgcaaagc gcgggaagac aacctgaaac tcatgaatca   4560
aaagctcaat ttcctgcgca atgtgttgca cttccagcag tttgaggata ttaccgaaag   4620
agagaaaagg gttacaaaat ggatatcccg gcaagaaaac tctgatgttc cgctggttta   4680
ccaggatgag cttatacaga ttagggaact tatgtataaa ccttacaaag attgggttgc   4740
attcctcaag cagctgcata agagacttga agtcgagatc ggcaaagaag tcaaacactg   4800
gcgcaagagc ctgagcgatg gtcggaaagg gttgtacgga atcagtttga aaaatatcga   4860
cgaaatagat agaaccagga aattttttgtt gcgctggtca ctgagaccaa cggaaccggg   4920
agaagtcaga aggttggagc caggccagag atttgcaatt gaccagctga accatctgaa   4980
tgcactgaaa gaggacagat tgaagaagat ggcgaatacg attattatgc atgctttggg   5040
ttattgttac gacgttagga agaagaaatg gcaggccaag aaccctgcgt gccaaatcat   5100
cctgttcgaa gatctgagta actacaatcc gtatgaagaa aggagtcgct tcgagaacag   5160
taaactgatg aaatggtccc ggcgcgagat accacgccaa gttgcgcttc aaggggaaat   5220
atacgggctt caagttgggg aagttggagc gcagttttct agccggttcc acgccaagac   5280
agggtccccg ggtataaggt gcagtgtggt gacgaaagaa aagttgcagg ataatagatt   5340
ctttaaaaat cttcaacggg aagggcgcct gacgcttgac aagattgcag tgttgaaaga   5400
gggggatttg taccccgata aaggcgggga gaagttcatt tctttgtcga aggaccgcaa   5460
gttggttacg acgcatgcag acattaacgc agcacaaaat ctgcaaaaaa gattctggac   5520
tcggacgcat ggtttttaca aggtttactg taaagcatat caagtcgatg gtcagacggt   5580
ttacattccc gaatctaaag atcagaaaca gaaaatcatt gaggagttcg gtgaaggtta   5640
ctttatactc aaggacggtg tttacgaatg gggtaatgct ggtaaactga aaattaagaa   5700
ggggtcctcc aagcaatcat cttctgagct cgtcgacagc gacatcctta aggatagctt   5760
cgatcttgcc tctgagctca gggagaaaa gttgatgctg tatcgcgatc ctagtggaaa   5820
tgtctttccc tcagataaat ggatggcagc aggtgtgttc ttcgggaaat tggaacgcat   5880
actgatatca aaactgacca atcaatactc tatatctact attgaagacg attcaagtaa   5940
gcaatcgatg aagcgtcctg ctgccaccaa aaaggccgga caggctaaga aaagaagtg    6000
agacgactag tggcggccgc cgacgtccga tcgttcaaac atttggcaat aaagtttctt   6060
```

| | | |
|---|---|---|
| aagattgaat cctgttgccg gtcttgcgat gattatcata taatttctgt tgaattacgt | 6120 | |
| taagcatgta ataattaaca tgtaatgcat gacgttattt atgagatggg tttttatgat | 6180 | |
| tagagtcccg caattataca tttaatacgc gatagaaaac aaaatatagc gcgcaaacta | 6240 | |
| ggataaatta tcgcgcgcgg tgtcatctat gttactagat cgggaattga tccccctcg | 6300 | |
| acagcttccg gaaagggcga attcgcaact ttgtatacaa aagttgaacg agaaacgtaa | 6360 | |
| aatgatataa atatcaatat attaaattag attttgcata aaaaacagac tacataatac | 6420 | |
| tgtaaaacac aacatatcca gtcactatgc catccagctg atatccccta tagtgagtcg | 6480 | |
| tattacatgg tcatagctgt ttcctggcag ctctggcccg tgtctcaaaa tctctgatgt | 6540 | |
| tacattgcac aagataaaaa tatatcatca tgcctcctc | 6579 | |

<210> SEQ ID NO 35
<211> LENGTH: 6579
<212> TYPE: DNA
<213> ORGANISM: Artificial Sequence
<220> FEATURE:
<223> OTHER INFORMATION: Vector

<400> SEQUENCE: 35

| | | |
|---|---|---|
| tggaccagcc aggacagaaa tgcctcgact tcgctgctac ccaaggttgc cgggtgacgc | 60 | |
| acaccgtgga aacggatgaa ggcacgaacc cagtggacat aagcctgttc ggttcgtaag | 120 | |
| ctgtaatgca agtagcgtat gcgctcacgc aactggtcca gaaccttgac cgaacgcagc | 180 | |
| ggtggtaacg gcgcagtggc ggttttcatg gcttgttatg actgtttttt tggggtacag | 240 | |
| tctatgcctc gggcatccaa gcagcaagcg cgttacgccg tgggtcgatg tttgatgtta | 300 | |
| tggagcagca acgatgttac gcagcagggc agtcgcccta aaacaaagtt aaacatcatg | 360 | |
| agggaagcgg tgatcgccga gtatcgact caactatcag aggtagttgg cgtcatcgag | 420 | |
| cgccatctcg aaccgacgtt gctggccgta catttgtacg gctccgcagt ggatggcggc | 480 | |
| ctgaagccac acagtgatat tgatttgctg gttacggtga ccgtaaggct tgatgaaaca | 540 | |
| acgcggcgag ctttgatcaa cgacctttg gaaacttcgg cttcccctgg agagagcgag | 600 | |
| attctccgcg ctgtagaagt caccattgtt gtgcacgacg acatcattcc gtggcgttat | 660 | |
| ccagctaagc gcgaactgca atttggagaa tggcagcgca atgacattct tgcaggtatc | 720 | |
| ttcgagccag ccacgatcga cattgatctg gctatcttgc tgacaaaagc aagagaacat | 780 | |
| agcgttgcct tggtaggtcc agcggcggag gaactctttg atccggttcc tgaacaggat | 840 | |
| ctatttgagg cgctaaatga aaccttaacg ctatggaact cgccgcccga ctgggctggc | 900 | |
| gatgagcgaa atgtagtgct tacgttgtcc cgcatttggt acagcgcagt aaccggcaaa | 960 | |
| atcgcgccga aggatgtcgc tgccgactgg gcaatggagc gcctgccggc ccagtatcag | 1020 | |
| cccgtcatac ttgaagctag acaggcttat cttggacaag aagaagatcg cttggcctcg | 1080 | |
| cgcgcagatc agttggaaga atttgtccac tacgtgaaag gcgagatcac caaggtagtc | 1140 | |
| ggcaaataac cctcgagcca cccatgacca aaatccctta acgtgagtta cgcgtcgttc | 1200 | |
| cactgagcgt cagacccgt agaaaagatc aaggatctt cttgagatcc ttttttttctg | 1260 | |
| cgcgtaatct gctgcttgca acaaaaaaa ccaccgctac cagcggtggt ttgtttgccg | 1320 | |
| gatcaagagc taccaactct ttttccgaag gtaactggct tcagcagagc gcagatacca | 1380 | |
| aatactgtcc ttctagtgta gccgtagtta ggccaccact tcaagaactc tgtagcaccg | 1440 | |
| cctacatacc tcgctctgct aatcctgtta ccagtggctg ctgccagtgg cgataagtcg | 1500 | |
| tgtcttaccg ggttggactc aagacgatag ttaccggata aggcgcagcg gtcgggctga | 1560 | |

```
acgggggtt cgtgcacaca gcccagcttg gagcgaacga cctacaccga actgagatac    1620
ctacagcgtg agctatgaga aagcgccacg cttcccgaag ggagaaaggc ggacaggtat    1680
ccggtaagcg gcagggtcgg aacaggagag cgcacgaggg agcttccagg gggaaacgcc    1740
tggtatcttt atagtcctgt cgggtttcgc cacctctgac ttgagcgtcg atttttgtga    1800
tgctcgtcag gggggcggag cctatggaaa aacgccagca acgcggcctt tttacggttc    1860
ctggcctttt gctggccttt tgctcacatg ttctttcctg cgttatcccc tgattctgtg    1920
gataaccgta ttaccgcctt tgagtgagct gataccgctc gccgcagccg aacgaccgag    1980
cgcagcgagt cagtgagcga ggaagcggaa gagcgcccaa tacgcaaacc gcctctcccc    2040
gcgcgttggc cgattcatta atgcagctgg cacgacaggt ttcccgactg gaaagcgggc    2100
agtgagcgca acgcaattaa tacgcgtacc gcgagccagg aagagtttgt agaaacgcaa    2160
aaaggccatc cgtcaggatg gccttctgct tagtttgatg cctggcagtt tatggcgggc    2220
gtcctgcccg ccaccctccg ggccgttgct tcacaacgtt caaatccgct cccggcggat    2280
ttgtcctact caggagagcg ttcaccgaca acaacagat aaaacgaaag gcccagtctt    2340
ccgactgagc ctttcgtttt atttgatgcc tggcagttcc ctactctcgc gttaacgctt    2400
gcatggatgt tttcccagtc acgacgttgt aaaacgacgg ccagtcttaa gctcgggccc    2460
caaataatga ttttattttg actgatagtg acctgttcgt tgcaacaaat tgatgagcaa    2520 tgcttttta taatgccaac tttgtacaaa aaagcaggct ccgaattcgc ccttcaccat    2580
ggctcctaag aagaagcgga aggttggtat tcacggggtg cctgcggctg ccacaaggtc    2640
tttcatactt aagatagagc caaacgaaga ggtcaaaaag ggattgtgga aaacccatga    2700
agtcctgaac catggcattg cctactacat gaacatcctg aaacttatac ggcaggaggc    2760
tatttatgag caccacgagc aggatccaaa aaaccccaaa aaggtttcga aggctgaaat    2820
ccaggccgaa ctgtgggact tcgttctcaa aatgcagaaa tgtaattcgt tcactcatga    2880
agttgacaaa gacgtcgtgt ttaacatttt gagggagctt tacgaggagt tggttccgag    2940
ctccgtcgaa aagaagggtg aagcaaatca gctgtcgaat aagttcttgt accctttggt    3000
ggacccgaac agccaatctg gaaaagggac agcatcatca gggcggaagc ctcggtggta    3060
taacttgaag attgctggag acccttcgtg ggaagaggaa aagaaaaagt gggaggaaga    3120
taagaagaag gacccacttg ccaaaattct cggcaaactt gccgaatatg gattgatacc    3180
gctgttcatc cccttacgg attctaacga acccatcgtt aaagaaatca gtggatgga    3240 aaaatctcgc aatcagtccg tccggaggct ggacaaagat atgtttatac aagctttgga    3300
acgctttctc tcgtgggagt cgtggaatct taaggtcaaa aagagtatg aaaaggtcga    3360 gaaggaacac aagacactgg aggagaggat taaggaagac attcaagcat tcaagtcact    3420
ggagcaatac gaaaaggaac ggcaggagca attgcttcgc gacacgctca ataccaatga    3480
atataggctt tccaagaggg gcctgagagg atggcgggaa taatccaga aatggctcaa    3540 gatggacgag aatgaacctt cagaaaata tctcgaggtt tttaaagatt accaaaggaa    3600
acatccacgc gaggcagggg attacagcgt gtacgagttt ctctccaaga aggaaaacca    3660
ttttatctgg cgcaatcatc ccgaatacc gtacctctat gcgacgttct gcgaaataga    3720 caaaagaaa aaagatgcta agcaacaagc gactttcaca cttgcagatc ccataaatca    3780
cccattgtgg gtgcggtttg aagaaggtc gggctctaac ctcaataagt acagaatttt    3840
gacggagcag ttgcacacag aaaagctgaa gaagaagttg acggttcagc tggatcgcct    3900
```

| | |
|---|---|
| tatctaccca accgagtctg gtggctggga agagaagggg aaagtcgaca tagtgttgct | 3960 |
| gccatctagg cagttctata accagatttt tctcgatata gaagaaaagg gtaaacatgc | 4020 |
| atttacgtat aaagacgagt ccataaagtt tccactgaaa ggaacacttg gcggcgcaag | 4080 |
| ggtgcagttt gatcgggacc accttcgcag gtaccccac aaggttgaaa gtggaaacgt | 4140 |
| tggacggatc tattttaata tgaccgtcaa catagaaccc acagaatccc ctgtttccaa | 4200 |
| atccctgaaa atacaccggg acgattttcc taaatttgtg aactttaaac cgaaggagtt | 4260 |
| gaccgagtgg ataaaggaca gtaaagggaa aaagctgaag tccggtatcg aaagcctgga | 4320 |
| gattgggctc agagttatgt cgatagatct gggtcaaagg caggcagcag ccgcctctat | 4380 |
| atttgaggtc gtggaccaga agcccgacat tgaaggtaaa ctgttctttc cgattaaggg | 4440 |
| gacggaactc tacgcagtcc atcgcgcctc cttcaatata aagctgccgg gcgaaacact | 4500 |
| ggttaaatca cgcgaggttt tgcgcaaagc gcgggaagac aacctgaaac tcatgaatca | 4560 |
| aaagctcaat ttcctgcgca atgtgttgca cttccagcag tttgaggata ttaccgaaag | 4620 |
| agagaaaagg gttacaaaat ggatatcccg gcaagaaaac tctgatgttc cgctggttta | 4680 |
| ccaggatgag cttatacaga ttagggaact tatgtataaa ccttacaaag attgggttgc | 4740 |
| attcctcaag cagctgcata agagacttga agtcgagatc ggcaaagaag tcaaacactg | 4800 |
| gcgcaagagc ctgagcgatg gtcggaaagg gttgtacgga atcagtttga aaaatatcga | 4860 |
| cgaaatagat agaaccagga aattttgtt gcgctggtca ctgagaccaa cggaaccggg | 4920 |
| agaagtcaga aggttggagc caggccagag atttgcaatt gaccagctga accatctgaa | 4980 |
| tgcactgaaa gaggacagat tgaagaagat ggcgaatacg attattatgc atgctttggg | 5040 |
| ttattgttac gacgttagga agaagaaatg gcaggccaag aaccctgcgt gccaaatcat | 5100 |
| cctgttcgaa gatctgagta actacaatcc gtatgaagaa aggagtcgct tcgagaacag | 5160 |
| taaactgatg aaatggtccc ggcgcgagat accacgccaa gttgcgcttc aaggggaaat | 5220 |
| atacgggctt caagttgggg aagttggagc gcagttttct agccggttcc acgccaagac | 5280 |
| agggtccccg ggtataaggt gcagtgtggt gacgaaagaa aagttgcagg ataatagatt | 5340 |
| cttaaaat cttcaacggg aagggcgcct gacgcttgac aagattgcag tgttgaaaga | 5400 |
| gggggatttg taccccgata aaggcgggga gaagttcatt tctttgtcga aggaccgcaa | 5460 |
| gttggttacg acgcatgcag ccattaacgc agcacaaaat ctgcaaaaaa gattctggac | 5520 |
| tcggacgcat ggttttttaca aggtttactg taaagcatat caagtcgatg gtcagacggt | 5580 |
| ttacattccc gaatctaaag atcagaaaca gaaaatcatt gaggagttcg gtgaaggtta | 5640 |
| ctttatactc aaggacggtg tttacgaatg gggtaatgct ggtaaactga aaattaagaa | 5700 |
| ggggtcctcc aagcaatcat cttctgagct cgtcgacagc gacatcctta aggatagctt | 5760 |
| cgatcttgcc tctgagctca agggagaaaa gttgatgctg tatcgcgatc ctagtggaaa | 5820 |
| tgtctttccc tcagataaat ggatggcagc aggtgtgttc ttcgggaaat tggaacgcat | 5880 |
| actgatatca aaactgacca atcaatactc tatatctact attgaagacg attcaagtaa | 5940 |
| gcaatcgatg aagcgtcctg ctgccaccaa aaaggccgga caggctaaga aaaagaagtg | 6000 |
| agacgactag tggcggccgc cgacgtccga tcgttcaaac atttggcaat aaagtttctt | 6060 |
| aagattgaat cctgttgccg gtcttgcgat gattatcata atttctgt tgaattacgt | 6120 |
| taagcatgta ataattaaca tgtaatgcat gacgttattt atgagatggg ttttatgat | 6180 |
| tagagtcccg caattataca tttaatacgc gatagaaaac aaaatatagc gcgcaaacta | 6240 |
| ggataaatta tcgcgcgcgg tgtcatctat gttactagat cgggaattga tcccccctcg | 6300 |

```
acagcttccg gaaagggcga attcgcaact ttgtatacaa aagttgaacg agaaacgtaa      6360
aatgatataa atatcaatat attaaattag attttgcata aaaaacagac tacataatac      6420
tgtaaaacac aacatatcca gtcactatgc catccagctg atatccccta tagtgagtcg      6480
tattacatgg tcatagctgt ttcctggcag ctctggcccg tgtctcaaaa tctctgatgt      6540
tacattgcac aagataaaaa tatatcatca tgcctcctc                             6579
```

<210> SEQ ID NO 36
<211> LENGTH: 6579
<212> TYPE: DNA
<213> ORGANISM: Artificial Sequence
<220> FEATURE:
<223> OTHER INFORMATION: Vector

<400> SEQUENCE: 36

```
tggaccagcc aggacagaaa tgcctcgact tcgctgctac ccaaggttgc cgggtgacgc        60
acaccgtgga acggatgaa ggcacgaacc cagtggacat aagcctgttc ggttcgtaag        120
ctgtaatgca agtagcgtat gcgctcacgc aactggtcca gaaccttgac cgaacgcagc       180
ggtggtaacg gcgcagtggc ggttttcatg gcttgttatg actgtttttt tggggtacag       240
tctatgcctc gggcatccaa gcagcaagcg cgttacgccg tgggtcgatg tttgatgtta       300
tggagcagca acgatgttac gcagcagggc agtcgcccta aacaaagtt aaacatcatg        360 agggaagcgg tgatcgccga agtatcgact caactatcag aggtagttgg cgtcatcgag       420
cgccatctcg aaccgacgtt gctggccgta catttgtacg gctccgcagt ggatggcggc       480
ctgaagccac acagtgatat tgatttgctg gttacggtga ccgtaaggct tgatgaaaca      540
acgcggcgag ctttgatcaa cgaccttttg gaaacttcgg cttcccctgg agagagcgag      600
attctccgcg ctgtagaagt caccattgtt gtgcacgacg acatcattcc gtggcgttat     660
ccagctaagc gcgaactgca atttggagaa tggcagcgca atgacattct tgcaggtatc     720
ttcgagccag ccacgatcga cattgatctg gctatcttgc tgacaaaagc aagagaacat     780
agcgttgcct tggtaggtcc agcggcggag gaactctttg atccggttcc tgaacaggat     840
ctatttgagg cgctaaatga aaccttaacg ctatggaact cgccgccgga ctgggctggc    900
gatgagcgaa atgtagtgct tacgttgtcc cgcatttggt acagcgcagt aaccggcaaa     960
atcgcgccga aggatgtcgc tgccgactgg gcaatggagc gcctgccggc ccagtatcag    1020
cccgtcatac ttgaagctag acaggcttat cttggacaag aagaagatcg cttggcctcg    1080
cgcgcagatc agttggaaga atttgtccac tacgtgaaag gcgagatcac caaggtagtc    1140
ggcaaataac cctcgagcca cccatgacca aaatcccctta acgtgagtta cgcgtcgttc   1200
cactgagcgt cagaccccgt agaaaagatc aaaggatctt cttgagatcc ttttttttctg   1260 cgcgtaatct gctgcttgca acaaaaaaa ccaccgctac cagcggtggt ttgtttgccg    1320
gatcaagagc taccaactct ttttccgaag gtaactggct tcagcagagc gcagatacca    1380
aatactgtcc ttctagtgta gccgtagtta ggccaccact tcaagaactc tgtagcaccg    1440
cctacatacc tcgctctgct aatcctgtta ccagtggctg ctgccagtgg cgataagtcg    1500
tgtcttaccg ggttggactc aagacgatag ttaccggata aggcgcagcg gtcgggctga    1560
acggggggtt cgtgcacaca gcccagcttg gagcgaacga cctacaccga actgagatac    1620
ctacagcgtg agctatgaga aagcgccacg cttcccgaag ggagaaaggc ggacaggtat    1680
ccggtaagcg gcagggtcgg aacaggagag cgcacgaggg agcttccagg gggaaacgcc    1740
```

-continued

```
tggtatcttt atagtcctgt cgggtttcgc cacctctgac ttgagcgtcg attttgtga        1800
tgctcgtcag gggggcggag cctatggaaa aacgccagca acgcggcctt tttacggttc        1860
ctggcctttt gctggccttt tgctcacatg ttctttcctg cgttatcccc tgattctgtg        1920
gataaccgta ttaccgcctt tgagtgagct gataccgctc gccgcagccg aacgaccgag        1980
cgcagcgagt cagtgagcga ggaagcggaa gagcgcccaa tacgcaaacc gcctctcccc        2040
gcgcgttggc cgattcatta atgcagctgg cacgacaggt ttcccgactg gaaagcgggc        2100
agtgagcgca acgcaattaa tacgcgtacc gcgagccagg aagagtttgt agaaacgcaa        2160
aaaggccatc cgtcaggatg ccttctgct tagtttgatg cctggcagtt tatggcgggc         2220
gtcctgcccg ccaccctccg ggccgttgct tcacaacgtt caaatccgct cccggcggat        2280
ttgtcctact caggagagcg ttcaccgaca acaacagat aaaacgaaag cccagtctt          2340
ccgactgagc ctttcgtttt atttgatgcc tggcagttcc ctactctcgc gttaacgctt        2400
gcatggatgt tttcccagtc acgacgttgt aaaacgacgg ccagtcttaa gctcgggccc        2460
caaataatga ttttattttg actgatagtg acctgttcgt tgcaacaaat tgatgagcaa        2520
tgcttttta taatgccaac tttgtacaaa aaagcaggct ccgaattcgc ccttcaccat        2580
ggctcctaag aagaagcgga aggttggtat tcacggggtg cctgcggctg ccacaaggtc        2640
tttcatactt aagatagagc caaacgaaga ggtcaaaaag ggattgtgga aaacccatga        2700
agtcctgaac catggcattg cctactacat gaacatcctg aaacttatac ggcaggaggc        2760
tattttatgag caccacgagc aggatccaaa aaaccccaaa aaggtttcga aggctgaaat        2820
ccaggccgaa ctgtgggact tcgttctcaa aatgcagaaa tgtaattcgt tcactcatga        2880
agttgacaaa gacgtcgtgt ttaacatttt gagggagctt tacgaggagt tggttccgag        2940
ctccgtcgaa aagaagggtg aagcaaatca gctgtcgaat aagttcttgt acctttggt         3000
ggacccgaac agccaatctg gaaaagggac agcatcatca gggcggaagc tcggtggta         3060
taacttgaag attgctggag acccttcgtg ggaagaggaa aagaaaaagt gggaggaaga        3120
taagaagaag gacccacttg ccaaaattct cggcaaactt gccgaatatg gattgatacc        3180
gctgttcatc cccttttacgg attctaacga acccatcgtt aaagaaatca gtggatgga       3240
aaaatctcgc aatcagtccg tccggaggct ggacaaagat atgtttatac aagctttgga        3300
acgctttctc tcgtgggagt cgtggaatct taaggtcaaa gaagagtatg aaaaggtcga        3360
gaaggaacac aagacactgg aggagaggat taaggaagac attcaagcat tcaagtcact        3420
ggagcaaatac gaaaaggaac ggcaggagca attgcttcgc gacacgctca ataccaatga        3480
atataggctt tccaagaggg gcctgagagg atggcgggaa ataatccaga aatggctcaa        3540
gatggacgag aatgaacctt cagaaaaata tctcgaggtt tttaaagatt accaaaggaa        3600
acatccacgc gaggcagggg attacagcgt gtacgagttt ctctccaaga aggaaaacca        3660
ttttatctgg cgcaatcatc ccgaataccc gtacctctat gcgacgttct gcgaaataga        3720
caaaaagaaa aaagatgcta agcaacaagc gactttcaca cttgcagatc ccataaatca        3780
cccattgtgg gtgcggtttg aagaaggtc gggctctaac ctcaataagt acagaatttt         3840
gacggagcag ttgcacacag aaaagctgaa gaagaagttg acggttcagc tggatcgcct        3900
tatctaccca accgagtctg gtggctggga agagaaggg aaagtcgaca tagtgttgct         3960
gccatctagg cagttctata accagatttt tctcgatata gaagaaaagg gtaaacatgc        4020
atttacgtat aaagacgagt ccataaagtt tccactgaaa ggaacacttg gcggcgcaag        4080
ggtgcagttt gatcgggacc accttcgcag gtaccccac aaggttgaaa gtggaaacgt          4140
```

-continued

```
tggacggatc tattttaata tgaccgtcaa catagaaccc acagaatccc ctgtttccaa    4200
atccctgaaa atacaccggg acgattttcc taaatttgtg aactttaaac cgaaggagtt    4260
gaccgagtgg ataaaggaca gtaaagggaa aaagctgaag tccggtatcg aaagcctgga    4320
gattgggctc agagttatgt cgatagatct gggtcaaagg caggcagcag ccgcctctat    4380
atttgaggtc gtggaccaga agcccgacat tgaaggtaaa ctgttctttc cgattaaggg    4440
gacggaactc tacgcagtcc atcgcgcctc cttcaatata aagctgccgg gcgaaacact    4500
ggttaaatca cgcgaggttt tgcgcaaagc gcgggaagac aacctgaaac tcatgaatca    4560
aaagctcaat ttcctgcgca atgtgttgca cttccagcag tttgaggata ttaccgaaag    4620
agagaaaagg gttacaaaat ggatatcccg gcaagaaaac tctgatgttc cgctggttta    4680
ccaggatgag cttatacaga ttagggaact tatgtataaa ccttacaaag attgggttgc    4740
attcctcaag cagctgcata agagacttga agtcgagatc ggcaaagaag tcaaacactg    4800
gcgcaagagc ctgagcgatg tcggaaaggg gttgtacgga atcagtttga aaatatcga    4860 cgaaatagat agaaccagga aattttgtt gcgctggtca ctgagaccaa cggaaccggg    4920
agaagtcaga aggttggagc caggccagag atttgcaatt gaccagctga accatctgaa    4980
tgcactgaaa gaggacagat tgaagaagat ggcgaatacg attattatgc atgctttggg    5040
ttattgttac gacgttagga agaagaaatg gcaggccaag aacccgcgt gccaaatcat    5100 cctgttcgcc gatctgagta actacaatcc gtatgaagaa aggagtcgct tcgagaacag    5160
taaactgatg aaatggtccc ggcgcgagat accacgccaa gttgcgcttc aaggggaaat    5220
atacgggctt caagttgggg aagttggagc gcagttttct agccggttcc acgccaagac    5280
agggtccccg ggtataaggt gcagtgtggt gacgaaagaa aagttgcagg ataatagatt    5340
ctttaaaaat cttcaacggg aagggcgcct gacgcttgac aagattgcag tgttgaaaga    5400
gggggatttg tacccccgata aaggcgggga gaagttcatt tctttgtcga aggaccgcaa    5460
gttggttacg acgcatgcag acattaacgc agcacaaaat ctgcaaaaaa gattctggac    5520
tcggacgcat ggttttttaca aggtttactg taaagcatat caagtcgatg gtcagacggt    5580
ttacattccc gaatctaaag atcagaaaca gaaaatcatt gaggagttcg gtgaaggtta    5640
ctttatactc aaggacggtg tttacgaatg gggtaatgct ggtaaactga aaattaagaa    5700
ggggtcctcc aagcaatcat cttctgagct cgtcgacagc gacatcctta aggatagctt    5760
cgatcttgcc tctgagctca agggagaaaa gttgatgctg tatcgcgatc ctagtggaaa    5820
tgtctttccc tcagataaat ggatggcagc aggtgtgttc ttcgggaaat tggaacgcat    5880
actgatatca aaactgacca atcaatactc tatatctact attgaagacg attcaagtaa    5940
gcaatcgatg aagcgtcctg ctgccaccaa aaaggccgga caggctaaga aaagaagtg    6000 agacgactag tggcggccgc cgacgtccga tcgttcaaac attttggcaat aaagtttctt    6060 aagattgaat cctgttgccg gtcttgcgat gattatcata taatttctgt tgaattacgt    6120
taagcatgta ataattaaca tgtaatgcat gacgttattt atgagatggg ttttatgat    6180 tagagtcccg caattataca tttaatacgc gatagaaaac aaaatatagc gcgcaaacta    6240
ggataaatta tcgcgcgcgg tgtcatctat gttactagat cgggaattga tccccctcg    6300 acagcttccg gaaagggcga attcgcaact ttgtatacaa agttgaacg agaaacgtaa    6360 aatgatataa atatcaatat attaaattag attttgcata aaaaacagac tacataatac    6420
tgtaaaacac aacatatcca gtcactatgc catccagctg atatccccta tagtgagtcg    6480
```

| | | | | |
|---|---|---|---|---|
| tattacatgg | tcatagctgt | ttcctggcag | ctctggcccg | tgtctcaaaa tctctgatgt | 6540 |
| tacattgcac | aagataaaaa | tatatcatca | tgcctcctc | | 6579 |

<210> SEQ ID NO 37
<211> LENGTH: 6642
<212> TYPE: DNA
<213> ORGANISM: Artificial Sequence
<220> FEATURE:
<223> OTHER INFORMATION: Vector

<400> SEQUENCE: 37

| | | | | |
|---|---|---|---|---|
| tggaccagcc | aggacagaaa | tgcctcgact | tcgctgctac | ccaaggttgc cgggtgacgc | 60 |
| acaccgtgga | aacggatgaa | ggcacgaacc | cagtggacat | aagcctgttc ggttcgtaag | 120 |
| ctgtaatgca | agtagcgtat | gcgctcacgc | aactggtcca | gaaccttgac cgaacgcagc | 180 |
| ggtggtaacg | gcgcagtggc | ggttttcatg | gcttgttatg | actgtttttt tggggtacag | 240 |
| tctatgcctc | gggcatccaa | gcagcaagcg | cgttacgccg | tgggtcgatg tttgatgtta | 300 |
| tggagcagca | acgatgttac | gcagcagggc | agtcgcccta | aaacaaagtt aaacatcatg | 360 |
| agggaagcgg | tgatcgccga | agtatcgact | caactatcag | aggtagttgg cgtcatcgag | 420 |
| cgccatctcg | aaccgacgtt | gctggccgta | catttgtacg | gctccgcagt ggatggcggc | 480 |
| ctgaagccac | acagtgatat | tgatttgctg | gttacggtga | ccgtaaggct tgatgaaaca | 540 |
| acgcggcgag | ctttgatcaa | cgaccttttg | gaaacttcgg | cttcccctgg agagagcgag | 600 |
| attctccgcg | ctgtagaagt | caccattgtt | gtgcacgacg | acatcattcc gtggcgttat | 660 |
| ccagctaagc | gcgaactgca | atttggagaa | tggcagcgca | atgacattct tgcaggtatc | 720 |
| ttcgagccag | ccacgatcga | cattgatctg | gctatcttgc | tgacaaaagc aagagaacat | 780 |
| agcgttgcct | tggtaggtcc | agcggcggag | gaactctttg | atccggttcc tgaacaggat | 840 |
| ctatttgagg | cgctaaatga | aaccttaacg | ctatggaact | cgccgcccga ctgggctggc | 900 |
| gatgagcgaa | atgtagtgct | tacgttgtcc | cgcatttggt | acagcgcagt aaccggcaaa | 960 |
| atcgcgccga | aggatgtcgc | tgccgactgg | gcaatggagc | gcctgccggc ccagtatcag | 1020 |
| cccgtcatac | ttgaagctag | acaggcttat | cttggacaag | aagaagatcg cttggcctcg | 1080 |
| cgcgcagatc | agttggaaga | atttgtccac | tacgtgaaag | gcgagatcac caaggtagtc | 1140 |
| ggcaaataac | cctcgagcca | cccatgacca | aaatcccttac | gtgagttac gcgtcgttc | 1200 |
| cactgagcgt | cagaccccgt | agaaaagatc | aaaggatctt | cttgagatcc ttttttttctg | 1260 |
| cgcgtaatct | gctgcttgca | acaaaaaaa | ccaccgctac | cagcggtggt ttgtttgccg | 1320 |
| gatcaagagc | taccaactct | ttttccgaag | gtaactggct | tcagcagagc gcagatacca | 1380 |
| aatactgtcc | ttctagtgta | gccgtagtta | ggccaccact | tcaagaactc tgtagcaccg | 1440 |
| cctacatacc | tcgctctgct | aatcctgtta | ccagtggctg | ctgccagtgg cgataagtcg | 1500 |
| tgtcttaccg | ggttggactc | aagacgatag | ttaccggata | aggcgcagcg gtcgggctga | 1560 |
| acggggggtt | cgtgcacaca | gcccagcttg | gagcgaacga | cctacaccga actgagatac | 1620 |
| ctacagcgtg | agctatgaga | aagcgccacg | cttcccgaag | ggagaaaggc ggacaggtat | 1680 |
| ccggtaagcg | gcagggtcgg | aacaggagag | cgcacgaggg | agcttccagg ggaaacgcc | 1740 |
| tggtatcttt | atagtcctgt | cgggtttcgc | cacctctgac | ttgagcgtcg attttttgtga | 1800 |
| tgctcgtcag | gggggcggag | cctatggaaa | aacgccagca | acgcggcctt tttacggttc | 1860 |
| ctggcctttt | gctggccttt | tgctcacatg | ttctttcctg | cgttatcccc tgattctgtg | 1920 |
| gataaccgta | ttaccgcctt | tgagtgagct | gataccgctc | gccgcagccg aacgaccgag | 1980 |

```
cgcagcgagt cagtgagcga ggaagcggaa gagcgcccaa tacgcaaacc gcctctcccc    2040
gcgcgttggc cgattcatta atgcagctgg cacgacaggt ttcccgactg gaaagcgggc    2100
agtgagcgca acgcaattaa tacgcgtacc gcgagccagg aagagtttgt agaaacgcaa    2160
aaaggccatc cgtcaggatg gccttctgct tagtttgatg cctggcagtt tatggcgggc    2220
gtcctgcccg ccaccctccg ggccgttgct tcacaacgtt caaatccgct cccggcggat    2280
ttgtcctact caggagagcg ttcaccgaca acaacagat aaaacgaaag cccagtctt     2340 ccgactgagc ctttcgtttt atttgatgcc tggcagttcc ctactctcgc gttaacgctt    2400
gcatggatgt tttcccagtc acgacgttgt aaaacgacgg ccagtcttaa gctcgggccc    2460
caaataatga ttttattttg actgatagtg acctgttcgt tgcaacaaat tgatgagcaa    2520 tgcttttta taatgccaac tttgtacaaa aaagcaggct ccgaattcgc ccttcaccat    2580
ggctcctaag aagaagcgga aggttggtat tcacggggtg cctgcggctg ccgtcaagtc    2640
catgaaggtc aagttgcgcc tggataacat gccagagatc agagccggac tttggaaact    2700
tcacaccgag gttaatgcgg gtgtgcggta ctatacggaa tggcttagcc ttttgaggca    2760
agaaaatctt tatcggagga gtcccaatgg cgatggagaa caagaatgct ataaaactgc    2820
tgaggaatgc aaggctgaac tccttgagag actcagagcc cgccaagttg agaatgggca    2880
ctgcggccct gctgggagtg atgacgaact gctgcaattg gcacggcaac tttatgaact    2940
tctggtccca caagcaatcg gggctaaagg tgatgcgcag caaatcgcaa ggaagtttct    3000
tagtcccctt gccgacaagg atgccgtggg tggtttggga atagcaaaag caggaaataa    3060
gcctaggtgg gttcggatga gggaggctgg agagccaggt tgggaagagg aaaaggctaa    3120
agccgaggcg agaaagagta cggatagaac cgccgatgtt cttcgcgctc ttgcagactt    3180
cggtcttaaa cctcttatga gagtctacac agactcagac atgtccagcg tgcagtggaa    3240
accacttcgc aaaggacaag cggtcagaac ctgggataga gacatgttcc aacaagcgat    3300
cgaaagaatg atgagttggg aatcgtggaa tcagcgcgtt ggagaagcgt acgcaaagct    3360
cgtggaacaa agtcgaggt ttgaacagaa aaattttgtg ggacaagaac atcttgtcca    3420
acttgtcaat caacttcaac aagacatgaa ggaagcatca cacggcctgg agtcgaaaga    3480
acaaactgcg cattacttga ctgggagagc gctgagaggg agcgacaaag ttttgagaa    3540 gtgggaaaaa ctcgatcctg atgccccatt tgacctctat gataccgaaa tcaagaatgt    3600 tcaacgagg aatactcgca ggttcggatc tcatgatctg tttgcgaagc tcgcggaacc    3660
taaatatcag gcgctctgga gagaggacgc ttctttcctc acgaggtatg cggtttacaa    3720
tagcattgtc agaaaactga atcacgctaa aatgtttgcg acttttactc ttccggatgc    3780
taccgcccac ccgatctgga cgcggtttga caaactcggc ggcaacctgc accagtacac    3840
tttcttgttt aacgaatttg gcgagggcag gcacgccatt cggtttcaga agctgttgac    3900
ggttgaggat ggcgttgcta agaggtcga cgacgtcacg gttccgattt ctatgtccgc    3960
gcagctggat gacctcttgc ctcgggaccc acacgagctc gttgcactct acttccagga    4020
ctacggtgca gaacaacatc tggctggaga gtttggcggc gcgaaaattc aataccgccg    4080
cgatcaattg aaccacctgc acgccagaag aggcgccaga gatgtctacc ttaatctgag    4140
cgtccgcgtt cagtcacaat ccgaagccag gggagaaagg cgccctccgt atgcagcggt    4200
cttcaggctt gttggcgata accaccgcgc gtttgttcac tttgataaat tgtcagatta    4260
cctcgcagaa cacccagacg atggtaagct ggggtcggaa ggtttgctct ctgggctcag    4320
```

```
agtcatgtca gttgccttgg gtcttaggac ttccgcgagc atatctgtct tccgcgtcgc   4380
aagaaaggac gaattgaagc cgaacagtga aggcccgggtc ccttttttgct tcccgatcga   4440
agggaacgaa aacctcgttg ctgtccacga gcggagccaa ctgttgaagc ttcccggtga   4500
aacgaatcg aaagatctga gagcgatcag agaagagcgc caaggacgc ttagacagct   4560
ccggacgcaa cttgcatact tgcgccttct ggttcgctgc ggtagtgaag acgttggaag   4620
aagagagagg tcatgggcta aactcataga gcaacctatg gatgctaatc aaatgacgcc   4680
tgattggaga gaagcattcg aagacgaact tcagaaactg aaatccctttt acgggatatg   4740
cggcgatcgc gagtggacag aagcagtgta tgagtctgtg aggcgcgtgt ggcggcatat   4800
gggtaaacag gtgcgcgatt ggagaaaaga cgttaggagc ggggaaagac ctaagatacg   4860
gggatatcag aaagacgttg tcgggggaaa tagcattgaa cagattgaat atttggagcg   4920
ccaatataag ttcctcaaat cctggtctttt cttcggcaaa gtgtcaggcc aggtgatacg   4980
cgcggaaaag ggatcgcgct ttgcaataac tctgagagaa catattgatc atgccaaaga   5040
agatcggttg aagaaactcg ccgatagaat catcatggag gcgcttggtt atgtctacgc   5100
cttggacgat gaacggggaa agggaaagtg ggtcgccaag tatccacctt gccaactcat   5160
tctcctcgaa gaactttccg aataccagtt taacaacgat cggccgccat cagagaataa   5220
tcaactgatg cagtggtccc atcgcggtgt gtttcaagag ttgctcaatc aggcccaagt   5280
ccatgatctg cttgttggca caatgtatgc agccttttcc tcccggtttg atgcaagaac   5340
agggggctcct ggcatacgct gtagacgggt cccggcgagg tgcgcccgcg aacaaaaccc   5400
tgaaccgttc ccctggtggt tgaacaagtt cgttgcggag cacaagctgg acgggtgtcc   5460
tctgcgggcc gacgatctta ttcccaccgg ggaaggggaa ttctttgtga gccctttctc   5520
ggcggaggaa ggggattttc accaaataca tgcagatctt aatgccgcac aaaatttgca   5580
gaggagactg tggtcagact ttgatattag tcagatacgc ctccgctgtg actggggaga   5640
ggtcgatggc gagcctgtgt tgataccaag aacgaccgga aagaggacag ccgattcgta   5700
tggaaacaag gttttttaca cgaagacggg cgttacttac tacgaaagag aaagagggaa   5760
gaagagaagg aaagtctttg cccaagaaga attgagcgag gaagaagccg agctcttggt   5820
cgaagcggac gaggcacggg aaaagtctgt cgtcctcatg agggaccctt ccggaattat   5880
taaccgggga gattggacgc ggcagaaaga gttttggtcc atggttaatc aacgcataga   5940
aggctacctt gtcaagcaaa taagaagtcg cgtgagattg caggagagtg catgtgagaa   6000
cactggggac ataaagcgtc ctgctgccac caaaaaggcc ggacaggcta agaaaaagaa   6060
gtgagacgac tagtggcggc cgccgacgtc cgatcgttca aacatttggc aataaagttt   6120
cttaagattg aatcctgttg ccggtcttgc gatgattatc atataatttc tgttgaatta   6180
cgttaagcat gtaataatta acatgtaatg catgacgtta tttatgagat gggtttttat   6240
gattagagtc ccgcaattat acatttaata gcgatagaa aacaaaatat agcgcgcaaa   6300
ctaggataaa ttatcgcgcg cggtgtcatc tatgttacta gatcgggaat tgatcccccc   6360
tcgacagctt ccggaaaggg cgaattcgca actttgtata caaaagttga acgagaaacg   6420
taaaatgata taaatatcaa tatattaaat tagattttgc ataaaaaaca gactacataa   6480
tactgtaaaa cacaacatat ccagtcacta tgccatccag ctgatatccc ctatagtgag   6540
tcgtattaca tggtcatagc tgtttcctgg cagctctggc ccgtgtctca aaatctctga   6600
tgttacattg cacaagataa aaatatatca tcatgcctcc tc                      6642
```

<210> SEQ ID NO 38
<211> LENGTH: 6642
<212> TYPE: DNA
<213> ORGANISM: Artificial Sequence
<220> FEATURE:
<223> OTHER INFORMATION: Vector

<400> SEQUENCE: 38

| | | | | | |
|---|---|---|---|---|---|
| tggaccagcc | aggacagaaa | tgcctcgact | tcgctgctac | ccaaggttgc | cgggtgacgc | 60 |
| acaccgtgga | aacggatgaa | ggcacgaacc | cagtggacat | aagcctgttc | ggttcgtaag | 120 |
| ctgtaatgca | agtagcgtat | gcgctcacgc | aactggtcca | gaaccttgac | cgaacgcagc | 180 |
| ggtggtaacg | gcgcagtggc | ggttttcatg | gcttgttatg | actgtttttt | tggggtacag | 240 |
| tctatgcctc | gggcatccaa | gcagcaagcg | cgttacgccg | tgggtcgatg | tttgatgtta | 300 |
| tggagcagca | acgatgttac | gcagcagggc | agtcgccta | aaacaaagtt | aaacatcatg | 360 |
| agggaagcgg | tgatcgccga | agtatcgact | caactatcag | aggtagttgg | cgtcatcgag | 420 |
| cgccatctcg | aaccgacgtt | gctggccgta | catttgtacg | gctccgcagt | ggatggcggc | 480 |
| ctgaagccac | acagtgatat | tgatttgctg | gttacggtga | ccgtaaggct | tgatgaaaca | 540 |
| acgcggcgag | cttTgatcaa | cgaccttttg | gaaacttcgg | cttcccctgg | agagagcgag | 600 |
| attctccgcg | ctgtagaagt | caccattgtt | gtgcacgacg | acatcattcc | gtggcgttat | 660 |
| ccagctaagc | gcgaactgca | atttggagaa | tggcagcgca | atgacattct | tgcaggtatc | 720 |
| ttcgagccag | ccacgatcga | cattgatctg | gctatcttgc | tgacaaaagc | aagagaacat | 780 |
| agcgttgcct | tggtaggtcc | agcggcgag | gaactctttg | atccggttcc | tgaacaggat | 840 |
| ctatttgagg | cgctaaatga | aaccttaacg | ctatggaact | cgccgcccga | ctgggctggc | 900 |
| gatgagcgaa | atgtagtgct | tacgttgtcc | cgcatttggt | acagcgcagt | aaccggcaaa | 960 |
| atcgcgccga | aggatgtcgc | tgccgactgg | gcaatggagc | gcctgccggc | ccagtatcag | 1020 |
| cccgtcatac | ttgaagctag | acaggcttat | cttggacaag | aagaagatcg | cttggcctcg | 1080 |
| cgcgcagatc | agttggaaga | atttgtccac | tacgtgaaag | gcgagatcac | caaggtagtc | 1140 |
| ggcaaataac | cctcgagcca | cccatgacca | aaatcccta | acgtgagtta | cgcgtcgttc | 1200 |
| cactgagcgt | cagaccccgt | agaaaagatc | aaaggatctt | cttgagatcc | ttttttctg | 1260 |
| cgcgtaatct | gctgcttgca | acaaaaaaa | ccaccgctac | cagcggtggt | ttgtttgccg | 1320 |
| gatcaagagc | taccaactct | ttttccgaag | gtaactggct | tcagcagagc | gcagatacca | 1380 |
| aatactgtcc | ttctagtgta | gccgtagtta | ggccaccact | tcaagaactc | tgtagcaccg | 1440 |
| cctacatacc | tcgctctgct | aatcctgtta | ccagtggctg | ctgccagtgg | cgataagtcg | 1500 |
| tgtcttaccg | ggttggactc | aagacgatag | ttaccggata | aggcgcagcg | gtcgggctga | 1560 |
| acggggggtt | cgtgcacaca | gcccagcttg | gagcgaacga | cctacaccga | actgagatac | 1620 |
| ctacagcgtg | agctatgaga | aagcgccacg | cttcccgaag | ggagaaaggc | ggacaggtat | 1680 |
| ccggtaagcg | gcagggtcgg | aacaggagag | cgcacgaggg | agcttccagg | gggaaacgcc | 1740 |
| tggtatcttt | atagtcctgt | cgggtttcgc | cacctctgac | ttgagcgtcg | attttttgtga | 1800 |
| tgctcgtcag | gggggcggag | cctatggaaa | aacgccagca | acgcggcctt | tttacggttc | 1860 |
| ctggccttt | gctggccttt | tgctcacatg | ttctttcctg | cgttatcccc | tgattctgtg | 1920 |
| gataaccgta | ttaccgcctt | tgagtgagct | gataccgctc | gccgcagccg | aacgaccgag | 1980 |
| cgcagcgagt | cagtgagcga | ggaagcggaa | gagcgcccaa | tacgcaaacc | gcctctcccc | 2040 |
| gcgcgttggc | cgattcatta | atgcagctgg | cacgacaggt | ttcccgactg | gaaagcgggc | 2100 |

-continued

```
agtgagcgca acgcaattaa tacgcgtacc gcgagccagg aagagtttgt agaaacgcaa    2160
aaaggccatc cgtcaggatg gccttctgct tagtttgatg cctggcagtt tatggcgggc    2220
gtcctgcccg ccaccctccg ggccgttgct tcacaacgtt caaatccgct cccggcggat    2280
ttgtcctact caggagagcg ttcaccgaca acaacagat aaaacgaaag cccagtctt     2340 ccgactgagc ctttcgtttt atttgatgcc tggcagttcc ctactctcgc gttaacgctt    2400
gcatggatgt tttcccagtc acgacgttgt aaaacgacgg ccagtcttaa gctcgggccc    2460
caaataatga ttttattttg actgatagtg acctgttcgt tgcaacaaat tgatgagcaa    2520
tgctttttta taatgccaac tttgtacaaa aaagcaggct ccgaattcgc ccttcaccat    2580
ggctcctaag aagaagcgga aggttggtat tcacggggtg cctgcggctg ccgtcaagtc    2640
catgaaggtc aagttgcgcc tggataacat gccagagatc agagccggac tttgaaact    2700 tcacaccgag gttaatgcgg gtgtgcggta ctatacggaa tggcttagcc ttttgaggca    2760
agaaaatctt tatcgagga gtcccaatgc cgatggagaa caagaatgct ataaaactgc    2820
tgaggaatgc aaggctgaac tccttgagag actcagagcc cgccaagttg agaatgggca    2880
ctgcggccct gctgggagtg atgacgaact gctgcaattg gcacggcaac tttatgaact    2940
tctggtccca caagcaatcg gggctaaagg tgatgcgcag caaatcgcaa ggaagtttct    3000 tagtccccctt gccgacaagg atgccgtggg tggtttggga atagcaaaag caggaaataa    3060
gcctaggtgg gttcggatga gggaggctgg agagccaggt tggaagagg aaaaggctaa    3120 agccgaggcg agaaagagta cggatagaac cgccgatgtt cttcgcgctc ttgcagactt    3180
cggtcttaaa cctcttatga gagtctacac agactcagac atgtccagcg tgcagtggaa    3240
accacttcgc aaaggacaag cggtcagaac ctgggataga gacatgttcc aacaagcgat    3300
cgaaagaatg atgagttggg aatcgtggaa tcagcgcgtt ggagaagcgt acgcaaagct    3360
cgtggaacaa aagtcgaggt ttgaacagaa aaattttgtg ggacaagaac atcttgtcca    3420
acttgtcaat caacttcaac aagacatgaa ggaagcatca cacggcctgg agtcgaaaga    3480
acaaactgcg cattacttga ctgggagagc gctgagaggg agcgacaaag ttttgagaa     3540 gtgggaaaaa ctcgatcctg atgccccatt tgacctctat gataccgaaa tcaagaatgt    3600
tcaacggagg aatactcgca ggttcggatc tcatgatctg tttgcgaagc tcgcggaacc    3660
taaatatcag gcgctctgga gagggacgc ttctttcctc acgaggtatg cggtttacaa     3720
tagcattgtc agaaaactga atcacgctaa aatgtttgcg acttttactc ttccggatgc    3780
taccgcccac ccgatctgga cgcggtttga caaactcggc ggcaacctgc accagtacac    3840
tttcttgttt aacgaatttg gcgagggcag gcacgccatt cggtttcaga agctgttgac    3900
ggttgaggat ggcgttgcta aagaggtcga cgacgtcacg gttccgattt ctatgtccgc    3960
gcagctggat gacctcttgc ctcgggaccc acacgagctc gttgcactct acttccagga    4020
ctacggtgca gaacaacatc tggctggaga gtttggcggc gcgaaaattc aataccgccg    4080
cgatcaattg aaccacctgc acgccagaag aggcgccaga gatgtctacc ttaatctgag    4140
cgtccgcgtt cagtcacaat ccgaagccag gggagaaagg cgccctccgt atgcagcggt    4200
cttcaggctt gttggcgata accaccgcgc gttttgttcac tttgataaat tgtcagatta    4260
cctcgcagaa cacccagacg atggtaagct ggggtcggaa ggtttgctct ctgggctcag    4320
agtcatgtca gttgacttgg gtcttaggac ttccgcgagc atatctgtct tccgcgtcgc    4380
aagaaaggac gaattgaagc cgaacagtga aggcccgggtc ccttttttgct tcccgatcga    4440 agggaacgaa aacctcgttg ctgtccacga gcggagccaa ctgttgaagc ttcccggtga    4500
```

```
aacggaatcg aaagatctga gagcgatcag agaagagcgc caaaggacgc ttagacagct    4560
ccggacgcaa cttgcatact tgcgccttct ggttcgctgc ggtagtgaag acgttggaag    4620
aagagagagg tcatgggcta aactcataga gcaacctatg gatgctaatc aaatgacgcc    4680
tgattggaga gaagcattcg aagacgaact tcagaaactg aaatccctt acgggatatg    4740 cggcgatcgc gagtggacag aagcagtgta tgagtctgtg aggcgcgtgt ggcggcatat    4800
gggtaaacag gtgcgcgatt ggagaaaaga cgttaggagc ggggaaagac ctaagatacg    4860
gggatatcag aaagacgttg tcgggggaaa tagcattgaa cagattgaat atttggagcg    4920
ccaatataag ttcctcaaat cctggtcttt cttcggcaaa gtgtcaggcc aggtgatacg    4980
cgcggaaaag ggatcgcgct ttgcaataac tctgagagaa catattgatc atgccaaaga    5040
agatcggttg aagaaactcg ccgatagaat catcatggag gcgcttggtt atgtctacgc    5100
cttggacgat gaacggggaa agggaaagtg ggtcgccaag tatccaccttt gccaactcat    5160 tctcctcgaa gaactttccg aataccagtt taacaacgat cggccgccat cagagaataa    5220
tcaactgatg cagtggtccc atcgcggtgt gtttcaagag ttgctcaatc aggcccaagt    5280
ccatgatctg cttgttggca caatgtatgc agccttttcc tcccggtttg atgcaagaac    5340
aggggctcct ggcatacgct gtagacgggt cccggcgagg tgcgcccgcg aacaaaaccc    5400
tgaaccgttc ccctggtggt tgaacaagtt cgttgcggag cacaagctgg acgggtgtcc    5460
tctgcgggcc gacgatctta ttcccaccgg ggaagggaa ttctttgtga gcccttctc    5520 ggcgaggaa ggggattttc accaaataca tgcagcgctt aatgccgcac aaaatttgca    5580
gaggagactg tggtcagact ttgatattag tcagatacgc ctccgctgtg actggggaga    5640
ggtcgatggc gagcctgtgt tgataccaag aacgaccgga aagaggacag ccgattcgta    5700
tggaaacaag gttttttaca cgaagacggg cgttacttac tacgaaagag aaagagggaa    5760
gaagagaagg aaagtctttg cccaagaaga attgagcgag gaagaagccg agctcttggt    5820
cgaagcggac gaggcacggg aaaagtctgt cgtcctcatg agggacccctt ccggaattat    5880 taaccgggga gattggacgc ggcagaaaga gttttggtcc atggttaatc aacgcataga    5940
aggctacctt gtcaagcaaa taagaagtcg cgtgagattg caggagagtg catgtgagaa    6000
cactggggac ataaagcgtc ctgctgccac caaaaaggcc ggacaggcta agaaaaagaa    6060
gtgagacgac tagtggcggc cgccgacgtc cgatcgttca aacatttggc aataaagttt    6120
cttaagattg aatcctgttg ccggtcttgc gatgattatc atataaatttc tgttgaatta    6180 cgttaagcat gtaataatta acatgtaatg catgacgtta tttatgagat gggttttat    6240 gattagagtc ccgcaattat acatttaata cgcgatagaa aacaaaatat agcgcgcaaa    6300
ctaggataaa ttatcgcgcg cggtgtcatc tatgttacta gatcgggaat tgatccccc    6360 tcgacagctt ccggaaaggg cgaattcgca actttgtata caaagttga acgagaaacg    6420 taaaatgata taaatatcaa tatattaaat tagattttgc ataaaaaaca gactacataa    6480
tactgtaaaa cacaacatat ccagtcacta tgccatccag ctgatatccc ctatagtgag    6540
tcgtattaca tggtcatagc tgtttcctgg cagctctggc ccgtgtctca aaatctctga    6600
tgttacattg cacaagataa aaatatatca tcatgcctcc tc                      6642
```

<210> SEQ ID NO 39
<211> LENGTH: 6642
<212> TYPE: DNA
<213> ORGANISM: Artificial Sequence
<220> FEATURE:

<223> OTHER INFORMATION: Vector

<400> SEQUENCE: 39

```
tggaccagcc aggacagaaa tgcctcgact tcgctgctac ccaaggttgc cgggtgacgc        60
acaccgtgga acggatgaa ggcacgaacc cagtggacat aagcctgttc ggttcgtaag       120
ctgtaatgca agtagcgtat gcgctcacgc aactggtcca gaaccttgac cgaacgcagc       180
ggtggtaacg gcgcagtggc ggttttcatg gcttgttatg actgttttt tggggtacag       240
tctatgcctc gggcatccaa gcagcaagcg cgttacgccg tgggtcgatg tttgatgtta       300
tggagcagca acgatgttac gcagcagggc agtcgcccta aaacaaagtt aaacatcatg       360
agggaagcgg tgatcgccga agtatcgact caactatcag aggtagttgg cgtcatcgag       420
cgccatctcg aaccgacgtt gctggccgta catttgtacg gctccgcagt ggatggcggc       480
ctgaagccac acagtgatat tgatttgctg gttacggtga ccgtaaggct tgatgaaaca       540
acgcggcgag ctttgatcaa cgaccttttg gaaacttcgg cttccctgg agagagcgag       600
attctccgcg ctgtagaagt caccattgtt gtgcacgacg acatcattcc gtggcgttat       660
ccagctaagc gcgaactgca atttggagaa tggcagcgca atgacattct gcaggtatc       720
ttcgagccca ccacgatcga cattgatctg gctatcttgc tgacaaaagc aagagaacat       780
agcgttgcct tggtaggtcc agcggcggag gaactctttg atccggttcc tgaacaggat       840
ctatttgagg cgctaaatga aaccttaacg ctatggaact cgccgcccga ctgggctggc       900
gatgagcgaa atgtagtgct tacgttgtcc cgcatttggt acagcgcagt aaccggcaaa       960
atcgcgccga aggatgtcgc tgccgactgg gcaatggagc gcctgccggc ccagtatcag      1020
cccgtcatac ttgaagctag acaggcttat cttggacaag aagaagatcg cttggcctcg      1080
cgcgcagatc agttggaaga atttgtccac tacgtgaaag gcgagatcac caaggtagtc      1140
ggcaaataac cctcgagcca cccatgacca aaatcccta acgtgagtta cgcgtcgttc      1200
cactgagcgt cagacccgt agaaaagatc aaaggatctt cttgagatcc ttttttctg      1260
cgcgtaatct gctgcttgca acaaaaaaa ccaccgctac cagcggtggt ttgtttgccg      1320
gatcaagagc taccaactct tttccgaag gtaactggct tcagcagagc gcagatacca      1380
aatactgtcc ttctagtgta gccgtagtta ggccaccact tcaagaactc tgtagcaccg      1440
cctacatacc tcgctctgct aatcctgtta ccagtggctg ctgccagtgg cgataagtcg      1500
tgtcttaccg ggttggactc aagacgatag ttaccggata aggcgcagcg gtcgggctga      1560
acgggggtt cgtgcacaca gcccagcttg gagcgaacga cctacaccga actgagatac      1620
ctacagcgtg agctatgaga aagcgccacg cttcccgaag ggagaaaggc ggacaggtat      1680
ccggtaagcg gcagggtcgg aacaggagag cgcacgaggg agcttccagg gggaaacgcc      1740
tggtatcttt atagtcctgt cgggtttcgc cacctctgac ttgagcgtcg attttttgtga      1800
tgctcgtcag gggggcggag cctatggaaa aacgccagca acgcggcctt tttacggttc      1860
ctggcctttt gctggccttt tgctcacatg ttctttcctg cgttatcccc tgattctgtg      1920
gataaccgta ttaccgcctt tgagtgagct gataccgctc gccgcagccg aacgaccgag      1980
cgcagcgagt cagtgagcga ggaagcggaa gagcgcccaa tacgcaaacc gcctctcccc      2040
gcgcgttggc cgattcatta atgcagctgg cacgacaggt ttcccgactg gaaagcgggc      2100
agtgagcgca acgcaattaa tacgcgtacc gcgagccagg aagagtttgt agaaacgcaa      2160
aaaggccatc cgtcaggatg gccttctgct tagtttgatg cctggcagtt tatgcgggc      2220
gtcctgcccg ccacccctccg ggccgttgct tcacaacgtt caaatccgct cccggcggat      2280
```

-continued

```
ttgtcctact caggagagcg ttcaccgaca acaacagat aaaacgaaag gcccagtctt    2340
ccgactgagc ctttcgtttt atttgatgcc tggcagttcc ctactctcgc gttaacgctt    2400
gcatggatgt tttcccagtc acgacgttgt aaaacgacgg ccagtcttaa gctcgggccc    2460
caaataatga ttttattttg actgatagtg acctgttcgt tgcaacaaat tgatgagcaa    2520
tgcttttta taatgccaac tttgtacaaa aaagcaggct ccgaattcgc ccttcaccat    2580
ggctcctaag aagaagcgga aggttggtat tcacggggtg cctgcggctg ccgtcaagtc    2640
catgaaggtc aagttgcgcc tggataacat gccagagatc agagccggac tttggaaact    2700
tcacaccgag gttaatgcgg gtgtgcggta ctatacggaa tggcttagcc ttttgaggca    2760
agaaaatctt tatcggagga gtcccaatgg cgatggagaa caagaatgct ataaaactgc    2820
tgaggaatgc aaggctgaac tccttgagag actcagagcc cgccaagttg agaatgggca    2880
ctgcggccct gctgggagtg atgacgaact gctgcaattg gcacggcaac tttatgaact    2940
tctggtccca caagcaatcg ggctaaaagg tgatgcgcag caaatcgcaa ggaagtttct    3000
tagtcccctt gccgacaagg atgccgtggg tggtttggga atagcaaaag caggaaataa    3060
gcctaggtgg gttcggatga gggaggctgg agagccaggt tgggaagagg aaaaggctaa    3120
agccgaggcg agaaagagta cggatagaac cgccgatgtt cttcgcgctc ttgcagactt    3180
cggtcttaaa cctcttatga gagtctacac agactcagac atgtccagcg tgcagtggaa    3240
accacttcgc aaaggacaag cggtcagaac ctgggataga gacatgttcc aacaagcgat    3300
cgaaagaatg atgagttggg aatcgtggaa tcagcgcgtt ggagaagcgt acgcaaagct    3360
cgtggaacaa aagtcgaggt ttgaacagaa aaattttgtg ggacaagaac atcttgtcca    3420
acttgtcaat caacttcaac aagacatgaa ggaagcatca cacggcctgg agtcgaaaga    3480
acaaactgcg cattacttga ctgggagagc gctgagaggg agcgacaaag ttttgagaa    3540
gtggaaaaa ctcgatcctg atgccccatt tgacctctat gataccgaaa tcaagaatgt    3600
tcaacggagg aatactcgca ggttcggatc tcatgatctg tttgcgaagc tcgcggaacc    3660
taaatatcag gcgctctgga gagggacgc ttctttcctc acgaggtatg cggtttacaa    3720
tagcattgtc agaaaactga atcacgctaa aatgtttgcg acttttactc ttccggatgc    3780
taccgcccac ccgatctgga cgcggtttga caaactcggc ggcaacctgc accagtacac    3840
tttcttgttt aacgaatttg gcgagggcag gcacgccatt cggttcaga agctgttgac    3900
ggttgaggat ggcgttgcta agaggtcga cgacgtcacg gttccgattt ctatgtccgc    3960
gcagctggat gacctcttgc ctcgggaccc acacgagctc gttgcactct acttccagga    4020
ctacggtgca gaacaacatc tggctggaga gtttggcggc gcgaaaattc aataccgccg    4080
cgatcaattg aaccacctgc acgccagaag aggcgccaga gatgtctacc ttaatctgag    4140
cgtccgcgtt cagtcacaat ccgaagccag gggagaaagg cgccctccgt atgcagcggt    4200
cttcaggctt gttggcgata accaccgcg gtttgttcac tttgataaat tgtcagatta    4260
cctcgcagaa cacccagacg atggtaagct ggggtcggaa ggtttgctct ctgggctcag    4320
agtcatgtca gttgacttgg gtcttaggac ttccgcgagc atatctgtct tccgcgtcgc    4380
aagaaaggac gaattgaagc cgaacagtga aggccgggtc ccttttttgct tcccgatcga    4440
agggaacgaa aacctcgttg ctgtccacga gcggagccaa ctgttgaagc ttcccggtga    4500
aacgaatcg aaagatctga gagcgatcag agaagagcgc caaaggacgc ttagacagct    4560
ccggacgcaa cttgcatact tgcgccttct ggttcgctgc ggtagtgaag acgttggaag    4620
```

```
aagagagagg tcatgggcta aactcataga gcaacctatg gatgctaatc aaatgacgcc    4680
tgattggaga gaagcattcg aagacgaact tcagaaactg aaatccctttt acgggatatg   4740 cggcgatcgc gagtggacag aagcagtgta tgagtctgtg aggcgcgtgt ggcggcatat   4800
gggtaaacag gtgcgcgatt ggagaaaaga cgttaggagc ggggaaagac ctaagatacg   4860
gggatatcag aaagacgttg tcgggggaaa tagcattgaa cagattgaat atttggagcg   4920
ccaatataag ttcctcaaat cctggtcttt cttcggcaaa gtgtcaggcc aggtgatacg   4980
cgcggaaaag ggatcgcgct ttgcaataac tctgagagaa catattgatc atgccaaaga   5040
agatcggttg aagaaactcg ccgatagaat catcatggag gcgcttggtt atgtctacgc   5100
cttggacgat gaacggggaa agggaaagtg ggtcgccaag tatccacctt gccaactcat   5160
tctcctcgcc gaactttccg aataccagtt taacaacgat cggccgccat cagagaataa   5220
tcaactgatg cagtggtccc atcgcggtgt gtttcaagag ttgctcaatc aggcccaagt   5280
ccatgatctg cttgttggca caatgtatgc agccttttcc tcccggtttg atgcaagaac   5340
aggggctcct ggcatacgct gtagacgggt cccggcgagg tgcgcccgcg aacaaaaccc   5400
tgaaccgttc ccctggtggt tgaacaagtt cgttgcggag cacaagctgg acgggtgtcc   5460
tctgcgggcc gacgatctta ttcccaccgg ggaaggggaa ttctttgtga gcccttctc    5520 ggcggaggaa ggggattttc accaaataca tgcagatctt aatgccgcac aaaatttgca   5580
gaggagactg tggtcagact ttgatattag tcagatacgc ctccgctgtg actggggaga   5640
ggtcgatggc gagcctgtgt tgataccaag aacgaccgga aagaggacag ccgattcgta   5700
tggaaacaag gttttttaca cgaagacggg cgttacttac tacgaaagag aaagagggaa   5760
gaagagaagg aaagtctttg cccaagaaga attgagcgag gaagaagccg agctcttggt   5820
cgaagcggac gaggcacggg aaaagtctgt cgtcctcatg agggaccctt ccggaattat   5880
taaccgggga gattggacgc ggcagaaaga gttttggtcc atggttaatc aacgcataga   5940
aggctacctt gtcaagcaaa taagaagtcg cgtgagattg caggagagtg catgtgagaa   6000
cactggggac ataaagcgtc ctgctgccac caaaaaggcc ggacaggcta agaaaaagaa   6060
gtgagacgac tagtggcggc cgccgacgtc cgatcgttca acatttggc aataaagttt   6120 cttaagattg aatcctgttg ccggtcttgc gatgattatc atataatttc tgttgaatta   6180
cgttaagcat gtaataatta acatgtaatg catgacgtta tttatgagat gggtttttat   6240
gattagagtc ccgcaattat acatttaata cgcgatagaa aacaaaatat agcgcgcaaa   6300
ctaggataaa ttatcgcgcg cggtgtcatc tatgttacta gatcgggaat tgatcccccc   6360
tcgacagctt ccggaaaggg cgaattcgca actttgtata caaaagttga acgagaaacg   6420
taaaatgata taaatatcaa tatattaaat tagattttgc ataaaaaaca gactacataa   6480
tactgtaaaa cacaacatat ccagtcacta tgccatccag ctgatatccc ctatagtgag   6540
tcgtattaca tggtcatagc tgtttcctgg cagctctggc ccgtgtctca aaatctctga   6600
tgttacattg cacaagataa aaatatatca tcatgcctcc tc                      6642
```

<210> SEQ ID NO 40
<211> LENGTH: 6788
<212> TYPE: DNA
<213> ORGANISM: Artificial Sequence
<220> FEATURE:
<223> OTHER INFORMATION: Vector

<400> SEQUENCE: 40

```
tggaccagcc aggacagaaa tgcctcgact tcgctgctac ccaaggttgc cgggtgacgc    60
```

-continued

```
acaccgtgga aacggatgaa ggcacgaacc cagtggacat aagcctgttc ggttcgtaag    120
ctgtaatgca agtagcgtat gcgctcacgc aactggtcca gaaccttgac cgaacgcagc    180
ggtggtaacg gcgcagtggc ggttttcatg gcttgttatg actgtttttt tggggtacag    240
tctatgcctc gggcatccaa gcagcaagcg cgttacgccg tgggtcgatg tttgatgtta    300
tggagcagca acgatgttac gcagcagggc agtcgcccta aaacaaagtt aaacatcatg    360
agggaagcgg tgatcgccga agtatcgact caactatcag aggtagttgg cgtcatcgag    420
cgccatctcg aaccgacgtt gctggccgta catttgtacg gctccgcagt ggatggcggc    480
ctgaagccac acagtgatat tgatttgctg gttacggtga ccgtaaggct tgatgaaaca    540
acgcggcgag ctttgatcaa cgaccttttg gaaacttcgg cttcccctgg agagagcgag    600
attctccgcg ctgtagaagt caccattgtt gtgcacgacg acatcattcc gtggcgttat    660
ccagctaagc gcgaactgca atttggagaa tggcagcgca atgacattct tgcaggtatc    720
ttcgagccag ccacgatcga cattgatctg gctatcttgc tgacaaaagc aagagaacat    780
agcgttgcct tggtaggtcc agcggcggag gaactctttg atccggttcc tgaacaggat    840
ctatttgagg cgctaaatga aaccttaacg ctatggaact cgccgcccga ctgggctggc    900
gatgagcgaa atgtagtgct tacgttgtcc cgcatttggt acagcgcagt aaccggcaaa    960
atcgcgccga aggatgtcgc tgccgactgg gcaatggagc gcctgccggc ccagtatcag   1020
cccgtcatac ttgaagctag acaggcttat cttggacaag aagaagatcg cttggcctcg   1080
cgcgcagatc agttggaaga atttgtccac tacgtgaaag gcgagatcac caaggtagtc   1140
ggcaaataac cctcgagcca cccatgacca aaatccctta acgtgagtta cgcgtcgttc   1200
cactgagcgt cagaccccgt agaaaagatc aaaggatctt cttgagatcc ttttttttсtg   1260 cgcgtaatct gctgcttgca acaaaaaaa ccaccgctac cagcggtggt ttgtttgccg   1320
gatcaagagc taccaactct ttttccgaag gtaactggct tcagcagagc gcagatacca   1380
aatactgtcc ttctagtgta gccgtagtta ggccaccact tcaagaactc tgtagcaccg   1440
cctacatacc tcgctctgct aatcctgtta ccagtggctg ctgccagtgg cgataagtcg   1500
tgtcttaccg ggttggactc aagacgatag ttaccggata aggcgcagcg gtcgggctga   1560
acggggggtt cgtgcacaca gcccagcttg gagcgaacga cctacaccga actgagatac   1620
ctacagcgtg agctatgaga aagcgccacg cttcccgaag ggagaaaggc ggacaggtat   1680
ccggtaagcg gcagggtcgg aacaggagag cgcacgaggg agcttccagg gggaaacgcc   1740
tggtatcttt atagtcctgt cgggtttcgc cacctctgac ttgagcgtcg attttttgtga   1800 tgctcgtcag ggggcggag cctatggaaa aacgccagca acgcggcctt tttacggttc   1860
ctggcctttt gctggccttt tgctcacatg ttctttcctg cgttatcccc tgattctgtg   1920 ataaccgta ttaccgcctt tgagtgagct gataccgctc gccgcagccg aacgaccgag   1980
cgcagcgagt cagtgagcga ggaagcggaa gagcgcccaa tacgcaaacc gcctctcccc   2040
gcgcgttggc cgattcatta atgcagctgg cacgacaggt ttcccgactg gaaagcgggc   2100
agtgagcgca acgcaattaa tacgcgtacc gcgagccagg aagagtttgt agaaacgcaa   2160
aaaggccatc cgtcaggatg gccttctgct tagtttgatg cctggcagtt tatggcgggc   2220
gtcctgcccg ccaccctccg ggccgttgct tcacaacgtt caaatccgct cccggcggat   2280
ttgtcctact caggagagcg ttcaccgaca acaacagat aaaacgaaag cccagtctt   2340 ccgactgagc ctttcgtttt atttgatgcc tggcagttcc ctactctcgc gttaacgctt   2400
```

```
gcatggatgt tttcccagtc acgacgttgt aaaacgacgg ccagtcttaa gctcgggccc    2460
caaataatga ttttattttg actgatagtg acctgttcgt tgcaacaaat tgatgagcaa    2520 tgcttttttta taatgccaac tttgtacaaa aaagcaggct ccgaattcgc ccttcaccat    2580
ggctcctaag aagaagcgga aggttggtat tcacggggtg cctgcggctg cggtgaagtc    2640
aataaaagtt aaactccgcc tggacgatat gccagaaatt cgggctggcc tctggaagct    2700
tcacaaagag gttaacgctg gcgtcagata ttacacggaa tggttgtcgc tgctccggca    2760
agaaaatctc tacagaaggt cgcccaatgg tgatggggaa caagagtgcg acaaaacggc    2820
ggaggaatgc aaagcggaac tccttgaaag acttcgcgcg agacaagtcg aaaacggcca    2880
tagaggcccg gccggttccg atgatgaatt gcttcagctt gcgcggcagc tttacgaatt    2940
gctcgtgccg caagccatag gtgcaaaagg agatgcacaa caaattgcaa gaaagttcct    3000
ctccccgctc gcagacaagg atgccgtggg aggtcttgga atcgctaaag cagggaataa    3060
gccaagatgg gtgcggatgc gggaagcagg tgagccaggc tgggaagagg agaaggagaa    3120
agccgaaacg aggaaatcag cggatcgcac tgcagacgtg ttgagagccc tcgcagactt    3180
tggacttaag ccactgatgc gggtttacac ggattcagag atgtcctcgg tggaatggaa    3240
gccgctcaga aagggtcaag ccgtgagaac gtgggaccgc gacatgttcc agcaggcaat    3300
tgagcggatg atgtcctggg agtcttggaa ccaaagggtc gggcaagaat atgcgaaact    3360
ggtggagcaa aaaaataggt ttgaacaaaa aaatttcgtt ggtcaagagc atctggttca    3420
tttggttaat caacttcaac aagatatgaa agaagcatca cctggcttgg aatctaaaga    3480
acaaacagca cactacgtta cgggtagggc gttgagggga tcggataaag ttttcgagaa    3540
gtggggtaag ttggccccccg acgccccttt cgatctgtat gacgccgaga taagaacgt    3600 tcagcggagg aacactcgcc gctttggttc gcacgatctg tttgcaaaac tggccgagcc    3660
tgagtaccag gccctttggc gggaggatgc gtcgttcctt acacgctacg cggtttataa    3720
ttcaattctc agaaagctca atcacgcgaa gatgtttgcg actttcactc ttccagatgc    3780
gacggcacac cctatatgga ctagattta taagttgggg ggcaacttgc accagtatac    3840
atttctgttc aacgaattcg gcgaacgcag gcatgcaatc aggttccata aacttttgaa    3900
agtcgagaat ggtgttgcca gggaggttga cgatgtcaca gtgcctatct cgatgtccga    3960
acaattggat aacttgctgc ccagagatcc gaacgaaccg attgcacttt atttcaggga    4020
ttatggtgcc gaacaacact ttacgggtga gttcggaggg gccaagattc agtgcagacg    4080
ggaccagctt gctcacatgc accgcaggag aggggctagg gatgtgtatt tgaacgtttc    4140
agttcgcgtg cagtcccaat ccgaggcgcg ggggagcgc agaccaccat acgcggctgt    4200
cttccggctg gttggcgata accatagagc gttcgtgcat ttcgataagc tgagcgatta    4260
cctcgccgaa catcctgatg acggaaagtt ggggtcagag gggcttctgt cgggcctgag    4320
ggtgatgtcc gtggccctgg gattgcgcac cagtgcctcg atcagcgttt ttagggtggc    4380
caggaaagat gagttgaaac ccaactcgaa ggggagggtt ccgttctttt tccctataaa    4440
gggcaacgat aacttggtcg cagtgcatga aggagccaa ctgctcaaac ttcccgggga    4500
gacagagtcc aaagatcttc gcgctataag ggaagagaga caagaactc tccggcagct    4560 gcgcacgcag ctcgcatacc tgcggttgct tgtccgctgc ggaagtgaag acgttggcag    4620
gcgcgagagg tcatgggcca aattgattga gcagccggtc gacgccgcaa atcacatgac    4680
tccggattgg agggaggctt tcgagaacga actgcagaag ttgaagagtc tgcatggcat    4740
atgctctgac aaagagtgga tggacgcggt ttacgagtcc gtccgccggg tctggcggca    4800
```

```
catgggaaa caagttcgcg attggagaaa ggatgttaga tccgggaaa ggccgaagat    4860
aagaggttat gccaaagacg tggttggtgg aaattctatc gaacagatcg aatatcttga    4920
gaggcagtac aagttcctca agagttggtc tttcttcggt aaagtctctg gacaagttat    4980
aagagcagaa aaggggagcc ggttcgctat caccttgcgg gaacacatag accacgcaaa    5040
agaagacaga ctgaagaagc tggcggacag aattatcatg gaagcgctgg ggtacgttta    5100
cgcgctggac gaaaggggga aaggtaaatg ggtggccaaa tacccgccat gccagttgat    5160
attgctggaa gaattgtccg aatatcaatt taataacgat agaccgccat ccgagaacaa    5220
ccaacttatg caatggtctc accggggagt tttccaggag ttgatcaacc aagctcaagt    5280
gcacgatctg cttgttggta caatgtacgc agcgttttcc tcacgcttcg acgctagaac    5340
aggagcgccg ggaattcggt gccggagggt gcctgcgagg tgtactcagg agcacaaccc    5400
ggagccattt ccctggtggt tgaataaatt cgttgtggaa catacgttgg atgcttgccc    5460
gcttcgggcg gacgacctca ttccgacggg tgagggcgag attttcgtgt cgccattctc    5520
ggctgaggaa ggggacttcc atcaaatcca tgctgacctc aatgcggcgc aaaatctgca    5580
gcagagattg tggagtgatt ttgacatctc tcagatcagg cttcggtgcg attggggaga    5640
agtcgatggt gaactcgttc tcattccgag actcaccggt aaaaggactg ctgattcata    5700
ttcgaacaaa gttttttaca ctaacacagg ggtcacttat tatgaaagag aacgcgtaa    5760
gaagcgccgc aaggtgttcg cgcaagagaa actttccgag gaagaggccg agttgctcgt    5820
tgaagctgac gaagctcgcg agaagtccgt cgttctgatg cgggatcctt ctggcataat    5880
aaacagggg aattggacac ggcagaagga attttggtcc atggtgaatc agcgcataga    5940
aggttatctg gtcaaacaga tcagaagcag ggttccctc caggattcag cgtgcgagaa    6000
cacgggcgat attaagcgtc ctgctgccac caaaaaggcc ggacaggcta agaaaaagaa    6060
gggagacggc tctggatcgg ggtcgggttc tggctcagtc gaccttgatc ttgacctcga    6120
actcagactt ggatttgctc tcgatctcga ccttgaactt agactcggat tgctctcttga    6180
cctcgatctt gagcttagac tcggattcgc ttaggacgtc ggcggccgcc gacgtccgat    6240
cgttcaaaca tttggcaata aagtttctta agattgaatc ctgttgccgg tcttgcgatg    6300
attatcatat aatttctgtt gaattacgtt aagcatgtaa taattaacat gtaatgcatg    6360
acgttattta tgagatgggt tttttatgatt agagtcccgc aattatacat ttaatacgcg    6420
atagaaaaca aaatatagcg cgcaaactag gataaattat cgcgcgcggt gtcatctatg    6480
ttactagatc gggaattgat cccccctcga cagcttccgg aaaggggcgaa ttcgcaactt    6540
tgtatacaaa agttgaacga gaaacgtaaa atgatataaa tatcaatata ttaaattaga    6600
ttttgcataa aaaacagact acataatact gtaaaacaca acatatccag tcactatgcc    6660
atccagctga tatcccctat agtgagtcgt attacatggt catagctgtt tcctggcagc    6720
tctgcccgt gtctcaaaat ctctgatgtt acattgcaca agataaaaat atatcatcat    6780
gcctcctc                                                              6788
```

<210> SEQ ID NO 41
<211> LENGTH: 6557
<212> TYPE: DNA
<213> ORGANISM: Artificial Sequence
<220> FEATURE:
<223> OTHER INFORMATION: Vector

<400> SEQUENCE: 41

```
acctacaccg aactgagata cctacagcgt gagctatgag aaagcgccac gcttcccgaa    60
gggagaaagg cggacaggta tccggtaagc ggcagggtcg gaacaggaga gcgcacgagg   120
gagcttccag ggggaaacgc ctggtatctt tatagtcctg tcgggtttcg ccacctctga   180
cttgagcgtc gattttgtgt atgctcgtca ggggggcgga gcctatggaa aaacgccagc   240
aacgcggcct ttttacggtt cctggccttt tgctggcctt ttgctcacat gttctttcct   300
gcgttatccc ctgattctgt ggataaccgt attaccgcct ttgagtgagc tgataccgct   360
cgccgcagcc gaacgaccga gcgcagcgag tcagtgagcg aggaagcgga agagcgccca   420
atacgcaaac cgcctctccc cgcgcgttgg ccgattcatt aatgcagctg gcacgacagg   480
tttcccgact ggaaagcggg cagtgagcgc aacgcaatta atacgcgtac cgcgagccag   540
gaagagtttg tagaaacgca aaaaggccat ccgtcaggat ggccttctgc ttagtttgat   600
gcctggcagt tccctactct cgcgttaacg cttgcatgga tgttttccca gtcacgacgt   660
tgtaaaacga cggccagtct taagctcggg ccccaaataa tgatttattt ttgactgata   720
gtgacctgtt cgttgcaaca aattgatgag caatgctttt ttataatgcc aactttgtac   780
aaaaaagcag gctccgaatt cgcccttcac catggctcct aagaagaagc ggaaggttgg   840
tattcacggg gtgcctgcgg ctgccacaag gtctttcata cttaagatag agccaaacga   900
agaggtcaaa aagggattgt ggaaaaccca tgaagtcctg aaccatggca ttgcctacta   960
catgaacatc ctgaaactta tacggcagga ggctatttat gagcaccacg agcaggatcc  1020
aaaaaacccc aaaaaggttt cgaaggctga atccaggcc gaactgtggg acttcgttct  1080
caaaatgcag aaatgtaatt cgttcactca tgaagttgac aaagacgtcg tgtttaacat  1140
tttgagggag ctttacgagg agttggttcc gagctccgtc gaaaagaagg gtgaagcaaa  1200
tcagctgtcg aataagttct tgtaccctt ggtggacccg aacagccaat ctggaaaagg  1260
gacagcatca tcagggcgga agcctcggtg gtataacttg aagattgctg gagacccttc  1320
gtgggaagag gaaaagaaaa agtgggagga agataagaag aaggacccac ttgccaaaat  1380
tctcggcaaa cttgccgaat atggattgat accgctgttc atccccttta cggattctaa  1440
cgaacccatc gttaaagaaa tcaagtggat ggaaaaatct cgcaatcagt ccgtccggag  1500
gctggacaaa gatatgttta acaagctttt ggaacgcttt ctctcgtggg agtcgtggaa  1560
tcttaaggtc aaagaagagt atgaaaaggt cgagaaggaa cacaagacac tggaggagag  1620
gattaaggaa gacattcaag cattcaagtc actggagcaa tacgaaaagg aacggcagga  1680
gcaattgctt cgcgacacgc tcaataccaa tgaatatagg ctttccaaga ggggcctgag  1740
aggatggcgg gaaataatcc agaaatggct caagatggac gagaatgaac cttcagaaaa  1800
atatctcgag gttttaaaag attaccaaag gaaacatcca cgcgaggcag gggattacag  1860
cgtgtacgag ttctctctcca agaaggaaaa ccattttatc tggcgcaatc atcccgaata  1920
cccgtacctc tatgcgacgt tctgcgaaat agacaaaaag aaaaagatg ctaagcaaca  1980 agcgactttc acacttgcag atcccataaa tcacccattg tgggtgcggt ttgaagaaag  2040
gtcgggctct aacctcaata agtacagaat tttgacggag cagttgcaca cagaaaagct  2100
gaagaagaag ttgacggttc agctggatcg ccttatctac ccaaccgagt ctggtggctg  2160
ggaagagaag gggaaagtcg acatagtgtt gctgccatct aggcagttct ataaccagat  2220
ttttctcgat atagaagaaa agggtaaaca tgcatttacg tataaagacg agtccataaa  2280 gtttccactag aaaggaacac ttggcggcgc aagggtgcag tttgatcggg accaccttcg  2340
caggtacccc cacaaggttg aaagtggaaa cgttggacgg atctatttta atatgaccgt  2400
```

```
caacatagaa cccacagaat cccctgtttc caaatccctg aaaatacacc gggacgattt   2460
tcctaaattt gtgaacttta aaccgaagga gttgaccgag tggataaagg acagtaaagg   2520
gaaaaagctg aagtccggta tcgaaagcct ggagattggg ctcagagtta tgtcgatagc   2580
gctgggtcaa aggcaggcag cagccgcctc tatatttgag gtcgtggacc agaagcccga   2640
cattgaaggt aaactgttct ttccgattaa ggggacggaa ctctacgcag tccatcgcgc   2700
ctccttcaat ataaagctgc cgggcgaaac actggtaaaa tcacgcgagg ttttgcgcaa   2760
agcgcgggaa gacaacctga aactcatgaa tcaaaagctc aatttcctgc gcaatgtgtt   2820
gcacttccag cagtttgagg atattaccga aagagagaaa agggttacaa aatggatatc   2880
ccggcaagaa aactctgatg ttccgctggt ttaccaggat gagcttatac agattaggga   2940
acttatgtat aaaccttaca aagattgggt tgcattcctc aagcagctgc ataagagact   3000
tgaagtcgag atcggcaaag aagtcaaaca ctggcgcaag agcctgagcg atggtcggaa   3060
agggttgtac ggaatcagtt tgaaaaatat cgacgaaata gatagaacca ggaaattttt   3120
gttgcgctgg tcactgagac caacggaacc gggagaagtc agaaggttgg agccaggcca   3180
gagatttgca attgaccagc tgaaccatct gaatgcactg aaagaggaca gattgaagaa   3240
gatggcgaat acgattatta tgcatgcttt gggttattgt tacgacgtta ggaagaagaa   3300
atggcaggcc aagaaccctg cgtgccaaat catcctgttc gaagatctga gtaactacaa   3360
tccgtatgaa gaaggagtc gcttcgagaa cagtaaactg atgaaatggt cccggcgcga   3420
gataccacgc caagttgcgc ttcaagggga aatatacggg cttcaagttg ggaagttgg   3480 agcgcagttt tctagccggt tccacgccaa gacagggtcc ccgggtataa ggtgcagtgt   3540
ggtgacgaaa gaaagttgc aggataatag attctttaaa aatcttcaac gggaagggcg   3600
cctgacgctt gacaagattg cagtgttgaa agaggggat ttgtaccccg ataaaggcgg   3660
ggagaagttc atttctttgt cgaaggaccg caagttggtt acgacgcatg cagacattaa   3720
cgcagcacaa aatctgcaaa aaagattctg gactcggacg catggttttt acaaggttta   3780
ctgtaaagca tatcaagtcg atggtcagac ggtttacatt cccgaatcta aagatcagaa   3840
acagaaaatc attgaggagt tcggtgaagg ttactttata ctcaaggacg gtgtttacga   3900
atggggtaat gctggtaaac tgaaaattaa gaaggggtcc tccaagcaat catcttctga   3960
gctcgtcgac agcgacatcc ttaaggatag cttcgatctt gcctctgagc tcaagggaga   4020
aaagttgatg ctgtatcgcg atcctagtgg aaatgtcttt ccctcagata aatggatggc   4080
agcaggtgtg ttcttcggga aattggaacg catactgata tcaaaactga ccaatcaata   4140
ctctatatct actattgaag acgattcaag taagcaatcg atgaagcgtc ctgctgccac   4200
caaaaaggcc ggacaggcta agaaaaagaa gggagacggc tctggatcgg ggtcgggttc   4260
tggctcagtc gaccttgatc ttgaccctcga actcagactt ggatttgctc tcgatctcga   4320
ccttgaactt agactcggat tgctcttga cctcgatctt gagcttagac tcggattcgc   4380
ttaggacgtc ggcggccgcc gacgtccgat cgttcaaaca tttggcaata agtttcttta   4440
agattgaatc ctgttgccgg tcttgcgatg attatcatat aatttctgtt gaattacgtt   4500
aagcatgtaa taattaacat gtaatgcatg acgttattta tgagatgggt ttttatgatt   4560
agagtcccgc aattatacat ttaatacgcg atagaaaaca aaatatagcg cgcaaactag   4620
gataaattat cgcgcgcggt gtcatctatg ttactagatc gggaattgat ccccctcga   4680 cagcttccgg aaagggcgaa ttcgcaactt tgtatacaaa agttgaacga gaaacgtaaa   4740
```

-continued

| | |
|---|---|
| atgatataaa tatcaatata ttaaattaga ttttgcataa aaaacagact acataatact | 4800 |
| gtaaaacaca acatatccag tcactatgcc atccagctga tatcccctat agtgagtcgt | 4860 |
| attacatggt catagctgtt tcctggcagc tctggcccgt gtctcaaaat ctctgatgtt | 4920 |
| acattgcaca agataaaaat atatcatcat gcctcctctg gaccagccag gacagaaatg | 4980 |
| cctcgacttc gctgctaccc aaggttgccg ggtgacgcac accgtggaaa cggatgaagg | 5040 |
| cacgaaccca gtggacataa gcctgttcgg ttcgtaagct gtaatgcaag tagcgtatgc | 5100 |
| gctcacgcaa ctggtccaga accttgaccg aacgcagcgg tggtaacggc gcagtggcgg | 5160 |
| ttttcatggc ttgttatgac tgttttttttg gggtacagtc tatgcctcgg gcatccaagc | 5220 |
| agcaagcgcg ttacgccgtg ggtcgatgtt tgatgttatg gagcagcaac gatgttacgc | 5280 |
| agcagggcag tcgccctaaa acaaagttaa acattatgag ggaagcggtg atcgccgaag | 5340 |
| tatcgactca actatcagag gtagttggcg tcatcgagcg ccatctcgaa ccgacgttgc | 5400 |
| tggccgtaca tttgtacggc tccgcagtgg atggcggcct gaagccacac agtgatattg | 5460 |
| atttgctggt tacggtgacc gtaaggcttg atgaaacaac gcggcgagct ttgatcaacg | 5520 |
| accttttgga aacttcggct tcccctggag agagcgagat tctccgcgct gtagaagtca | 5580 |
| ccattgttgt gcacgacgac atcattccgt ggcgttatcc agctaagcgc gaactgcaat | 5640 |
| ttggagaatg gcagcgcaat gacattcttg caggtatctt cgagccagcc acgatcgaca | 5700 |
| ttgatctggc tatcttgctg acaaaagcaa gagaacatag cgttgccttg gtaggtccag | 5760 |
| cggcggagga actctttgat ccggttcctg aacaggatct atttgaggcg ctaaatgaaa | 5820 |
| ccttaacgct atggaactcg ccgcccgact gggctggcga tgagcgaaat gtagtgctta | 5880 |
| cgttgtcccg catttggtac agcgcagtaa ccggcaaaat cgcgccgaag gatgtcgctg | 5940 |
| ccgactggga aatggagcgc ctgccggccc agtatcagcc cgtcatactt gaagctagac | 6000 |
| aggcttatct tggacaagaa gaagatcgct tggcctcgcg cgcagatcag ttggaagaat | 6060 |
| ttgtccacta cgtgaaaggc gagatcacca aggtagtcgg caaataaccc tcgagccacc | 6120 |
| catgaccaaa atcccttaac gtgagttacg cgtcgttcca ctgagcgtca gaccccgtag | 6180 |
| aaaagatcaa aggatcttct tgagatcctt ttttctgcg cgtaatctgc tgcttgcaaa | 6240 |
| caaaaaaacc accgctacca gcggtggttt gtttgccgga tcaagagcta ccaactcttt | 6300 |
| ttccgaaggt aactggcttc agcagagcgc agataccaaa tactgttctt ctagtgtagc | 6360 |
| cgtagttagg ccaccacttc aagaactctg tagcaccgcc tacatacctc gctctgctaa | 6420 |
| tcctgttacc agtggctgct gccagtggcg ataagtcgtg tcttaccggg ttggactcaa | 6480 |
| gacgatagtt accggataag gcgcagcggt cgggctgaac ggggggttcg tgcacacagc | 6540 |
| ccagcttgga gcgaacg | 6557 |

<210> SEQ ID NO 42
<211> LENGTH: 6788
<212> TYPE: DNA
<213> ORGANISM: Artificial Sequence
<220> FEATURE:
<223> OTHER INFORMATION: Vector

<400> SEQUENCE: 42

| | |
|---|---|
| tggaccagcc aggacagaaa tgcctcgact tcgctgctac ccaaggttgc cgggtgacgc | 60 |
| acaccgtgga aacggatgaa ggcacgaacc cagtggacat aagcctgttc ggttcgtaag | 120 |
| ctgtaatgca agtagcgtat gcgctcacgc aactggtcca gaaccttgac cgaacgcagc | 180 |
| ggtggtaacg gcgcagtggc ggttttcatg gcttgttatg actgtttttt tggggtacag | 240 |

| | |
|---|---|
| tctatgcctc gggcatccaa gcagcaagcg cgttacgccg tgggtcgatg tttgatgtta | 300 |
| tggagcagca acgatgttac gcagcagggc agtcgcccta aaacaaagtt aaacatcatg | 360 |
| agggaagcgg tgatcgccga agtatcgact caactatcag aggtagttgg cgtcatcgag | 420 |
| cgccatctcg aaccgacgtt gctggccgta catttgtacg gctccgcagt ggatggcggc | 480 |
| ctgaagccac acagtgatat tgatttgctg gttacggtga ccgtaaggct tgatgaaaca | 540 |
| acgcggcgag ctttgatcaa cgaccttttg gaaacttcgg cttcccctgg agagagcgag | 600 |
| attctccgcg ctgtagaagt caccattgtt gtgcacgacg acatcattcc gtggcgttat | 660 |
| ccagctaagc gcgaactgca atttggagaa tggcagcgca atgacattct tgcaggtatc | 720 |
| ttcgagccag ccacgatcga cattgatctg ctatcttgc tgacaaaagc aagagaacat | 780 |
| agcgttgcct tggtaggtcc agcggcgagg aactctttg atccggttcc tgaacaggat | 840 |
| ctatttgagg cgctaaatga aaccttaacg ctatggaact cgccgcccga ctgggctggc | 900 |
| gatgagcgaa atgtagtgct tacgttgtcc cgcatttggt acagcgcagt aaccggcaaa | 960 |
| atcgcgccga aggatgtcgc tgccgactgg gcaatggagc gcctgccggc ccagtatcag | 1020 |
| cccgtcatac ttgaagctag acaggcttat cttggacaag aagaagatcg cttggcctcg | 1080 |
| cgcgcagatc agttggaaga atttgtccac tacgtgaaag gcgagatcac caaggtagtc | 1140 |
| ggcaaataac cctcgagcca cccatgacca aaatccctta acgtgagtta cgcgtcgttc | 1200 |
| cactgagcgt cagaccccgt agaaaagatc aaaggatctt cttgagatcc ttttttctg | 1260 |
| cgcgtaatct gctgcttgca acaaaaaaa ccaccgctac cagcggtggt ttgtttgccg | 1320 |
| gatcaagagc taccaactct ttttccgaag gtaactggct tcagcagagc gcagatacca | 1380 |
| aatactgtcc ttctagtgta gccgtagtta ggccaccact tcaagaactc tgtagcaccg | 1440 |
| cctacatacc tcgctctgct aatcctgtta ccagtggctg ctgccagtgg cgataagtcg | 1500 |
| tgtcttaccg ggttggactc aagacgatag ttaccggata aggcgcagcg gtcgggctga | 1560 |
| acggggggtt cgtgcacaca gcccagcttg gagcgaacga cctacaccga actgagatac | 1620 |
| ctacagcgtg agctatgaga aagcgccacg cttcccgaag ggagaaaggc ggacaggtat | 1680 |
| ccggtaagcg gcagggtcgg aacaggagag cgcacgaggg agcttccagg gggaaacgcc | 1740 |
| tggtatcttt atagtcctgt cgggtttcgc cacctctgac ttgagcgtcg atttttgtga | 1800 |
| tgctcgtcag gggggcggag cctatggaaa aacgccagca acgcggcctt tttacggttc | 1860 |
| ctggcctttt gctggccttt tgctcacatg ttctttcctg cgttatcccc tgattctgtg | 1920 |
| gataaccgta ttaccgcctt tgagtgagct gataccgctc gccgcagccg aacgaccgag | 1980 |
| cgcagcgagt cagtgagcga ggaagcggaa gagcgcccaa tacgcaaacc gcctctcccc | 2040 |
| gcgcgttggc cgattcatta atgcagctgg cacgacaggt ttcccgactg gaaagcgggc | 2100 |
| agtgagcgca acgcaattaa tacgcgtacc gcgagccagg aagagtttgt agaaacgcaa | 2160 |
| aaaggccatc cgtcaggatg gccttctgct tagtttgatg cctggcagtt tatgcgggc | 2220 |
| gtcctgcccg ccaccctccg ggccgttgct tcacaacgtt caaatccgct cccggcggat | 2280 |
| ttgtcctact caggagagcg ttcaccgaca acaacagat aaaacgaaag gcccagtctt | 2340 |
| ccgactgagc cttcgttttt atttgatgcc tggcagttcc ctactctcgc gttaacgctt | 2400 |
| gcatggatgt tttcccagtc acgacgttgt aaaacgacgg ccagtcttaa gctcgggccc | 2460 |
| caaataatga ttttattttg actgatagtg acctgttcgt tgcaacaaat tgatgagcaa | 2520 |
| tgcttttta taatgccaac tttgtacaaa aaagcaggct ccgaattcgc ccttcaccat | 2580 |

```
ggctcctaag aagaagcgga aggttggtat tcacggggtg cctgcggctg ccgtcaagtc    2640
catgaaggtc aagttgcgcc tggataacat gccagagatc agagccggac tttggaaact    2700
tcacaccgag gttaatgcgg gtgtgcggta ctatacggaa tggcttagcc ttttgaggca    2760
agaaaatctt tatcggagga gtcccaatgg cgatggagaa caagaatgct ataaaactgc    2820
tgaggaatgc aaggctgaac tccttgagag actcagagcc cgccaagttg agaatgggca    2880
ctgcggccct gctgggagtg atgacgaact gctgcaattg gcacggcaac tttatgaact    2940
tctggtccca caagcaatcg ggctaaagg tgatgcgcag caaatcgcaa ggaagtttct    3000
tagtccccct tgccgacaagg atgccgtggg tggtttggga atagcaaaag caggaaataa    3060
gcctaggtgg gttcggatga gggaggctgg agagccaggt tgggaagagg aaaaggctaa    3120
agccgaggcg agaaagagta cggatagaac cgccgatgtt cttcgcgctc ttgcagactt    3180
cggtcttaaa cctcttatga gagtctacac agactcagac atgtccagcg tgcagtggaa    3240
accacttcgc aaaggacaag cggtcagaac ctgggataga gacatgttcc aacaagcgat    3300
cgaaagaatg atgagtttggg aatcgtggaa tcagcgcgtt ggagaagcgt acgcaaagct    3360
cgtggaacaa aagtcgaggt ttgaacagaa aaatttgtg ggacaagaac atcttgtcca    3420
acttgtcaat caacttcaac aagacatgaa ggaagcatca cacggcctgg agtcgaaaga    3480
acaaactgcg cattacttga ctgggagagc gctgagaggg agcgacaaag tttttgagaa    3540
gtgggaaaaa ctcgatcctg atgccccatt tgacctctat gataccgaaa tcaagaatgt    3600
tcaacggagg aatactcgca ggttcggatc tcatgatctg tttgcgaagc tcgcggaacc    3660
taaatatcag gcgctctgga gagaggacgc ttctttcctc acgaggtatg cggtttacaa    3720
tagcattgtc agaaaactga atcacgctaa aatgtttgcg acttttactc ttccggatgc    3780
taccgcccac ccgatctgga cgcggtttga caaactcggc ggcaacctgc accagtacac    3840
tttcttgttt aacgaatttg gcgagggcag gcacgccatt cggtttcaga agctgttgac    3900
ggttgaggat ggcgttgcta aagaggtcga cgacgtcacg gttccgattt ctatgtccgc    3960
gcagctggat gacctcttgc ctcgggaccc acacgagctc gttgcactct acttccagga    4020
ctacggtgca gaacaacatc tggctggaga gtttggcggc gcgaaaattc aataccgccg    4080
cgatcaattg aaccacctgc acgccagaag aggcgccaga gatgtctacc ttaatctgag    4140
cgtccgcgtt cagtcacaat ccgaagccag gggagaaagg cgccctccgt atgcagcggt    4200
cttcaggctt gttggcgata accaccgcgc gtttgttcac tttgataaat tgtcagatta    4260
cctcgcagaa cacccagacg atggtaagct gggtcggaa ggtttgctct ctgggctcag    4320
agtcatgtca gttgccttgg gtcttaggac ttccgcgagc atatctgtct tccgcgtcgc    4380
aagaaaggac gaattgaagc cgaacagtga aggccgggtc ccttttttgct tcccgatcga    4440 agggaacgaa aacctcgttg ctgtccacga gcggagccaa ctgttgaagc ttcccggtga    4500
aacgaatccg aaagatctga gagcgatcag agaagagcgc caaggacgc ttagacagct    4560 ccggacgcaa cttgcatact tgcgccttct ggttcgctgc ggtagtgaag acgttggaag    4620
aagagagagg tcatgggcta aactcataga gcaacctatg gatgctaatc aaatgacgcc    4680
tgattggaga gaagcattcg aagacgaact tcagaaactg aaatcccttt acgggatatg    4740
cggcgatcgc gagtggacag aagcagtgta tgagtctgtg aggcgcgtgt ggcggcatat    4800
gggtaaacag gtgcgcgatt ggagaaaaga cgttaggagc ggggaaagac ctaagatacg    4860
gggatatcag aaagacgttg tcgggggaaa tagcattgaa cagattgaat atttggagcg    4920
ccaatataag ttcctcaaat cctggtcttt cttcggcaaa gtgtcaggcc aggtgatacg    4980
```

```
cgcggaaaag ggatcgcgct ttgcaataac tctgagagaa catattgatc atgccaaaga    5040
agatcggttg aagaaactcg ccgatagaat catcatggag gcgcttggtt atgtctacgc    5100
cttggacgat gaacgggaa agggaaagtg ggtcgccaag tatccaccct tgccaactcat    5160 tctcctcgaa gaactttccg aataccagtt taacaacgat cggccgccat cagagaataa    5220
tcaactgatg cagtggtccc atcgcggtgt gtttcaagag ttgctcaatc aggcccaagt    5280
ccatgatctg cttgttggca caatgtatgc agccttttcc tcccggtttg atgcaagaac    5340
aggggctcct ggcatacgct gtagacgggt cccggcgagg tgcgcccgcg aacaaaaccc    5400
tgaaccgttc ccctggtggt tgaacaagtt cgttgcggag cacaagctgg acgggtgtcc    5460
tctgcgggcc gacgatctta ttcccaccgg ggaaggggaa ttctttgtga gcccttctc    5520 ggcggaggaa ggggattttc accaaataca tgcagatctt aatgccgcac aaaatttgca    5580
gaggagactg tggtcagact ttgatattag tcagatacgc ctccgctgtg actggggaga    5640
ggtcgatggc gagcctgtgt tgataccaag aacgaccgga aagaggacag ccgattcgta    5700
tggaaacaag gttttttaca cgaagacggg cgttacttac tacgaaagag aaagagggaa    5760
gaagagaagg aaagtctttg cccaagaaga attgagcgag gaagaagccg agctcttggt    5820
cgaagcggac gaggcacggg aaaagtctgt cgtcctcatg agggacccct ccggaattat    5880
taaccgggga gattggacgc ggcagaaaga gttttggtcc atggttaatc aacgcataga    5940
aggctacctt gtcaagcaaa taagaagtcg cgtgagattg caggagagtg catgtgagaa    6000
cactggggac ataaagcgtc ctgctgccac caaaaaggcc ggacaggcta agaaaaagaa    6060
gggagacggc tctggatcgg ggtcgggttc tggctcagtc gaccttgatc ttgacctcga    6120
actcagactt ggatttgctc tcgatctcga ccttgaactt agactcggat tgctcttga    6180 cctcgatctt gagcttagac tcggattcgc ttaggacgtc ggcggccgcc gacgtccgat    6240
cgttcaaaca tttggcaata aagtttctta agattgaatc ctgttgccgg tcttgcgatg    6300
attatcatat aatttctgtt gaattacgtt aagcatgtaa taattaacat gtaatgcatg    6360
acgttattta tgagatgggt ttttatgatt agagtcccgc aattatacat ttaatacgcg    6420
atagaaaaca aaatatagcg cgcaaactag gataaattat cgcgcgcggt gtcatctatg    6480
ttactagatc gggaattgat ccccccctcga cagcttccgg aaagggcgaa ttcgcaactt    6540
tgtatacaaa agttgaacga gaaacgtaaa atgatataaa tatcaatata ttaaattaga    6600
ttttgcataa aaaacagact acataatact gtaaaacaca acatatccag tcactatgcc    6660
atccagctga tatcccctat agtgagtcgt attacatggt catagctgtt tcctggcagc    6720
tctggcccgt gtctcaaaat ctctgatgtt acattgcaca agataaaaat atatcatcat    6780
gcctcctc                                                              6788
```

<210> SEQ ID NO 43
<211> LENGTH: 8542
<212> TYPE: DNA
<213> ORGANISM: Artificial Sequence
<220> FEATURE:
<223> OTHER INFORMATION: Vector

<400> SEQUENCE: 43

```
tggaccagcc aggacagaaa tgcctcgact tcgctgctac ccaaggttgc cgggtgacgc      60
acaccgtgga aacggatgaa ggcacgaacc cagtggacat aagcctgttc ggttcgtaag     120
ctgtaatgca agtagcgtat gcgctcacgc aactggtcca gaaccttgac cgaacgcagc     180
```

-continued

```
ggtggtaacg gcgcagtggc ggttttcatg gcttgttatg actgtttttt tggggtacag      240
tctatgcctc gggcatccaa gcagcaagcg cgttacgccg tgggtcgatg tttgatgtta      300
tggagcagca acgatgttac gcagcagggc agtcgcccta aaacaaagtt aaacatcatg      360
agggaagcgg tgatcgccga agtatcgact caactatcag aggtagttgg cgtcatcgag      420
cgccatctcg aaccgacgtt gctggccgta catttgtacg gctccgcagt ggatggcggc      480
ctgaagccac acagtgatat tgatttgctg gttacggtga ccgtaaggct tgatgaaaca      540
acgcggcgag ctttgatcaa cgaccttttg gaaacttcgg cttccctgg agagagcgag       600 attctccgcg ctgtagaagt caccattgtt gtgcacgacg acatcattcc gtggcgttat      660
ccagctaagc gcgaactgca atttggagaa tggcagcgca atgacattct tgcaggtatc      720
ttcgagccag ccacgatcga cattgatctg gctatcttgc tgacaaaagc aagagaacat      780
agcgttgcct tggtaggtcc agcggcggag gaactctttg atccggttcc tgaacaggat      840
ctatttgagg cgctaaatga aaccttaacg ctatggaact cgccgcccga ctgggctggc      900
gatgagcgaa atgtagtgct tacgttgtcc cgcatttggt acagcgcagt aaccggcaaa      960
atcgcgccga aggatgtcgc tgccgactgg gcaatggagc gcctgccggc ccagtatcag     1020
cccgtcatac ttgaagctag acaggcttat cttggacaag aagaagatcg cttggcctcg     1080
cgcgcagatc agttggaaga atttgtccac tacgtgaaag gcgagatcac caaggtagtc     1140
ggcaaataac cctcgagcca cccatgacca aaatccctta acgtgagtta cgcgtcgttc     1200
cactgagcgt cagacccccgt agaaaagatc aaaggatctt cttgagatcc ttttttttctg    1260 cgcgtaatct gctgcttgca acaaaaaaa ccaccgctac cagcggtggt ttgtttgccg      1320
gatcaagagc taccaactct tttccgaag gtaactggct tcagcagagc gcagatacca      1380
aatactgtcc ttctagtgta gccgtagtta ggccaccact tcaagaactc tgtagcaccg     1440
cctacatacc tcgctctgct aatcctgtta ccagtggctg ctgccagtgg cgataagtcg     1500
tgtcttaccg ggttggactc aagacgatag ttaccggata aggcgcagcg gtcgggctga     1560
acggggggtt cgtgcacaca gcccagcttg gagcgaacga cctacaccga actgagatac     1620
ctacagcgtg agctatgaga aagcgccacg cttcccgaag ggagaaaggc ggacaggtat     1680
ccggtaagcg gcagggtcgg aacaggagag cgcacgaggg agcttccagg gggaaacgcc     1740
tggtatcttt atagtcctgt cgggtttcgc cacctctgac ttgagcgtcg attttttgtga    1800 tgctcgtcag gggggcggag cctatggaaa aacgccagca acgcggcctt tttacggttc     1860 ctggccttt gctggccttt tgctcacatg ttctttcctg cgttatcccc tgattctgtg      1920
gataaccgta ttaccgcctt tgagtgagct gataccgctc gccgcagccg aacgaccgag     1980
cgcagcgagt cagtgagcga ggaagcggaa gagcgcccaa tacgcaaacc gcctctcccc     2040
gcgcgttggc cgattcatta atgcagctgg cacgacaggt ttcccgactg gaaagcgggc     2100
agtgagcgca acgcaattaa tacgcgtacc gcgagccagg aagagtttgt agaaacgcaa     2160
aaaggccatc cgtcaggatg gccttctgct tagtttgatg cctggcagtt tatggcgggc     2220
gtcctgcccg ccaccctccg ggccgttgct tcacaacgtt caaatccgct cccggcggat     2280
ttgtcctact caggagagcg ttcaccgaca acaacagat aaaacgaaag gcccagtctt      2340
ccgactgagc ctttcgtttt atttgatgcc tggcagttcc ctactctcgc gttaacgctt     2400
gcatggatgt tttcccagtc acgacgttgt aaaacgacgg ccagtcttaa gctcgggccc     2460
caaataatga ttttattttg actgatagtg acctgttcgt tgcaacaaat tgatgagcaa      2520 tgcttttttta taatgccaac tttgtacaaa aaagcaggct ccgaattcgc ccttcaccat    2580
```

```
ggctcctaag aagaagcgga aggttggtat tcacggggtg cctgcggctt cgatctatca    2640
agaattcgtt aataagtatt cgcttctaa aacactgaga ttcgaactca tacctcaagg     2700
aaagacactc gagaacataa aggctagggg cctcatattg gatgatgaaa agagagccaa    2760
ggactataaa aaagccaaac agataatcga caagtaccac caattcttca tagaagaaat    2820
cctttccagc gtctgcatta gcgaggattt gttgcaaaat tacagcgatg tctacttcaa    2880
gcttaagaag agcgatgacg acaatctcca gaaagacttc aaatcagcga aggacacaat    2940
taagaagcag atcagcgagt atatcaaaga tagtgaaaaa ttcaagaacc ttttcaatca    3000
gaacctgata gacgcaaaaa aaggacaaga aagcgacctc attctttggt tgaagcagtc    3060
taaggacaac gggattgagc tttttaaggc gaatagcgat ataaccgaca tcgacgaggc    3120
gcttgagatc ataaagtcgt ttaagggatg acaacatac ttcaaaggct tccatgagaa     3180
tcgcaaaaac gtctactcca gcaacgacat tccaacgtcg attatataca gaattgttga    3240
tgataacctc cctaaattcc tcgaaaataa ggcaaaatat gaaagcctta agataaagc     3300
gcctgaagca atcaattatg aacaaatcaa aaggatcttt gctgaagaat tgacgtttga    3360
tatagactac aagacgtcag aagttaacca gagggtgttt tcactcgacg aggtgtttga    3420
gattgctaat ttcaacaact acctcaatca gagtgggatc acgaagttca acactattat    3480
aggtggtaag ttcgtgaatg gtgagaacac taaaagaaaa gggattaacg aatatataaa    3540
cctttatagt caacagatca acgacaagac tttgaagaaa tataagatga gcgtcctctt    3600
caagcagata ctcagtgaca cggaatccaa gagctttgtg atcgacaagc tcgaagatga    3660
ctcggatgtg gtcactacca tgcaatcctt ctacgagcaa attgccgctt tcaaaactgt    3720
ggaggagaag agtataaagg agacactgtc tctgcttttt gacgatctta aggcccagaa    3780
attggatctt tccaaaatat atttcaagaa tgataagtca cttacggacc tttcccaaca    3840
agttttgac gattattcag ttattggtac ggcggttctt gagtacatta cgcagcagat    3900
agcccccaag aatctggaca cccctctaa gaaagaacag gagttgatag cgaagaagac    3960
agagaaggcg aaatacctct cgctggagac cataaaattg gcactggaag aatttaacaa    4020
gcatcgcgac atagataaac agtgccgctt cgaggaaatt ttggcaaatt ttgcagccat    4080
tccaatgatt ttcgacgaga tagcgcaaaa caaggataat ttggcacaaa tttcaataaa    4140
atatcaaaac cagggcaaga aggacctctt gcaggcttcg gcagaggatg atgttaaggc    4200
tattaaagac ttgttggacc aaacgaacaa tctgttgcac aagttgaaaa ttttccacat    4260
tagtcaaagc gaggataaag caaacatatt ggacaaagac gagcacttt atctggtgtt     4320
tgaggagtgc tacttcgagc ttgctaatat tgtcccactt tataataaaa taagaaacta    4380
cattacgcaa aagccatatt cagatgaaaa gtttaagctc aatttcgaaa atagtactct    4440
tgccaacggc tgggacaaga ataaggagcc agataatacc gccatacttt ttatcaaaga    4500
tgataaatat tatcttgggg tgatgaataa aagaataat aagatcttcg atgataaagc     4560
gataaaggaa aataagggtg aaggctataa aaaaattgtt tacaaactgt tgccgggagc    4620
aaataaaatg ctccccaagg ttttttttc ggcaaagagc attaaatttt acaatccttc     4680
agaagacatt ctgcgcataa gaaatcattc gacacacact aaaaatggtt cgccacaaaa    4740
gggctacgag aaatttgaat tcaacattga ggactgtcgg aagttcattg atttctacaa    4800
gcagtccatc tccaagcacc cggagtggaa agattttggg tttcggtttt ccgacacgca    4860
gagatacaac agcattgatg aatttttatag agaggtcgag aatcaaggtt ataagcttac    4920
```

```
ctttgaaaac atttctgaat catacattga ttcagtggtc aatcagggca aactctatct    4980
ttttcaaata tacaacaagg actttagtgc ttatagtaaa gggcggccca atttgcatac    5040
tctctattgg aaagcgctgt ttgatgagcg gaaccttcaa gacgtcgtgt ataagctcaa    5100
cggggaagcc gagctctttt accgcaagca gtccataccg aaaaaaataa cacaccctgc    5160
caaagaagcc atcgccaaca agaataaaga caatcctaaa aaagagtccg tcttcgaata    5220
tgatcttatt aaggacaaga ggtttacaga agataaattt ttcttccatt gtcccataac    5280
tatcaatttc aaaagctctg gcgcgaacaa atttaacgac gaaatcaatc tcttgttgaa    5340
agaaaaagcc aacgatgtgc acattctgtc gatcgccagg ggagagcgcc acttggcata    5400
ctacacccTT gttgatggga aggaaatat tattaaacag gacacattta atatcatcgg    5460
caacgatcgc atgaagacca actatcatga caaactggca gcaattgaaa aggaccgcga    5520
ctcagcgaga aaagactgga agaagatcaa taatatcaaa gaaatgaaag agggttattt    5580
gtctcaagtg gtccatgaga tcgcgaagtt ggtcattgaa tataatgcca tagtggtctt    5640
cgaagatctg aattttggat ttaagcgcgg caggttcaaa gtcgaaaaac aggtctacca    5700
aaagttggaa aagatgctca tcgaaaagct gaattacctt gtcttcaaag ataacgaatt    5760
cgataaaacc gggggggtct tgagggccta ccaactgact gcacccttTg agactttTaa    5820
aaagatgggt aaacagacag gaataattta ctatgttcct gccggtttca ctagcaagat    5880
ttgccccgtt accggattcg tgaatcaact ctatcccaaa tacgaatccg tgagcaagag    5940
tcaggaattc ttctccaaat ttgataaaat atgctataat ctcgacaaag gttatttcga    6000
gttctcgttc gactataaga acttcgggga taaggctgcc aagggaaagt ggactatagc    6060
aagctttggt agtcgcctta taaattttag gaacagcgac aagaatcaca actgggacac    6120
tcggaagtc tacccaacaa aagaactgga gaaactcttg aaggattata gtatcgagta    6180
tgggcatggg gagtgtatca aggcagcgat ttgtggagag tccgacaaaa agttttttgc    6240
taaactcacc tcggtgctca acactatcct ccagatgaga aattcaaaaa cagggacaga    6300
gctcgattac ctcattagcc ccgttgccga cgtcaatgga aacttttcg actcaagaca    6360
ggctccaaaa aacatgccgc aagatgcgga cgcgaatggg gcctatcaca taggcctgaa    6420
agggcttatg ctccttggga gaattaaaaa taaccaagaa ggcaaaaaac tcaacctcgt    6480
cattaagaac gaagaatact tcgaatttgt tcagaacagg aataacaagc gtcctgctgc    6540
caccaaaaag gccggacagg ctaagaaaaa gaagggagac ggctctggat cggggtcggg    6600
ttctggctca gtcgacttgc ttgatccggg gacaccaatg gacgcggacc tggtggcttc    6660
atcgaccgtg gtttgggaac aggacgccga tccattcgcc gggaccgccg atgactttcc    6720
tgcttttaat gaggaagagt tggcttggct gatggaactc ctgccgcagg gcggctcagg    6780
gggtctcctt gaccccggca cccccatgga cgctgacctc gttgcaagtt cgacggttgt    6840
ttgggagcaa gatgcagatc cgtttgcggg tacagctgat gactttccag ccttcaacga    6900
agaggagctg catggcttaa tggagcttct gcctcaggcc agaggaggt cgggtgggct    6960
cttggatcct gggacgccga tggatgccga ccttgtcgcg tcctctactg tggtttggga    7020
gcaggacgcc gacccgttcg ctggtactgc tgatgacttt ccggcctTta atgaggagga    7080
actcgcttgg ctcatggagt tgttgccaca agggggtagt ggcggtcttc tggacccggg    7140
aacgcctatg gatgctgact tggtggcatc gagcaccgtc gtctgggaac aggatgcgga    7200
cccgtttgct ggtaccgctg atgatttTcc ggcatttaac gaggaagaat tggcgtggct    7260
catggaattg cttccccagg cgagaggggg ttccggtggc ttgctggatc cgggaacgcc    7320
```

```
tatggatgcc gatctcgtgg cgtcgtcaac cgtggtctgg gagcaagacg ctgacccgtt    7380
tgccggcaca gcagatgatt ttccagcttt caatgaggaa gaactggcat ggttgatgga    7440
attgcttcca cagggaggga gcggaggcct cctcgatcct ggaacaccta tggacgcaga    7500
cctggttgcc tcttcaactg tcgtgtggga acaagatgca gacccgttcg caggtacagc    7560
tgatgacttc cctgccttta atgaggagga actcgcgtgg ctcatggaac ttttgcccca    7620
agcacgcggt ggctctgggg gtggcggatc gggaggagat cgcgctggacg atttcgactt    7680 ggacatgttg ggctcagacg ctttggacga ctttgatctc gacatgcttg ggtccgacgc    7740
attggatgat ttcgaccttg acatgcttgg ttccgacgca ctcgatgact tcgatcttga    7800
tatgctcgcc cgcggatctg acgctctcga cgacttcgat cttgacatgt gggctcaga    7860 tgcgctcgac gactttgatc tcgatatgtt gggtagcgac gcactcgatg actttgactt    7920
ggatatgctg gggagcgacg ccttggacga tttcgatctg gacatgctgt aaaagctttg    7980
ataggacgtc cgatcgttca acatttggc aataaagttt cttaagattg aatcctgttg    8040
ccggtcttgc gatgattatc atataatttc tgttgaatta cgttaagcat gtaataatta    8100
acatgtaatg catgacgtta tttatgagat gggtttttat gattagagtc ccgcaattat    8160
acatttaata cgcgatagaa aacaaaatat agcgcgcaaa ctaggataaa ttatcgcgcg    8220
cggtgtcatc tatgttacta gatcgggaat tgatcccccc tcgacagctt ccggaaaggg    8280
cgaattcgca actttgtata caaagttga acgagaaacg taaaatgata taaatatcaa    8340
tatattaaat tagattttgc ataaaaaaca gactacataa tactgtaaaa cacaacatat    8400
ccagtcacta tgccatccag ctgatatccc ctatagtgag tcgtattaca tggtcatagc    8460
tgtttcctgg cagctctggc ccgtgtctca aaatctctga tgttacattg cacaagataa    8520
aaatatatca tcatgcctcc tc                                             8542
```

<210> SEQ ID NO 44
<211> LENGTH: 8029
<212> TYPE: DNA
<213> ORGANISM: Artificial Sequence
<220> FEATURE:
<223> OTHER INFORMATION: Vector

<400> SEQUENCE: 44

```
tggaccagcc aggacagaaa tgcctcgact tcgctgctac ccaaggttgc cgggtgacgc      60
acaccgtgga aacggatgaa ggcacgaacc cagtggacat aagcctgttc ggttcgtaag    120
ctgtaatgca agtagcgtat gcgctcacgc aactggtcca gaaccttgac cgaacgcagc    180
ggtggtaacg gcgcagtggc ggttttcatg gcttgttatg actgtttttt tggggtacag    240
tctatgcctc gggcatccaa gcagcaagcg cgttacgccg tgggtcgatg tttgatgtta    300
tggagcagca acgatgttac gcagcagggc agtcgcccta aacaaagtt aaacatcatg    360 agggaagcgg tgatcgccga agtatcgact caactatcag aggtagttgg cgtcatcgag    420
cgccatctcg aaccgacgtt gctggccgta catttgtacg gctccgcagt ggatggcggc    480
ctgaagccac acagtgatat tgatttgctg gttacggtga ccgtaaggct tgatgaaaca    540
acgcggcgag ctttgatcaa cgaccttttg gaaacttcgg cttccctgg agagagcgag    600 attctccgcg ctgtagaagt caccattgtt gtgcacgacg acatcattcc gtggcgttat    660
ccagctaagc gcgaactgca atttggagaa tggcagcgca atgacattct tgcaggtatc    720
ttcgagccag ccacgatcga cattgatctg gctatcttgc tgacaaaagc aagagaacat    780
```

```
agcgttgcct tggtaggtcc agcggcggag gaactctttg atccggttcc tgaacaggat      840
ctatttgagg cgctaaatga aaccttaacg ctatggaact cgccgcccga ctgggctggc      900
gatgagcgaa atgtagtgct tacgttgtcc cgcatttggt acagcgcagt aaccggcaaa      960
atcgcgccga aggatgtcgc tgccgactgg gcaatgagc gcctgccggc ccagtatcag     1020
cccgtcatac ttgaagctag acaggcttat cttggacaag aagaagatcg cttggcctcg     1080
cgcgcagatc agttggaaga atttgtccac tacgtgaaag gcgagatcac caaggtagtc     1140
ggcaaataac cctcgagcca cccatgacca aaatccctta acgtgagtta cgcgtcgttc     1200
cactgagcgt cagaccccgt agaaaagatc aaaggatctt cttgagatcc ttttttttctg     1260 cgcgtaatct gctgcttgca acaaaaaaa ccaccgctac cagcggtggt ttgtttgccg     1320
gatcaagagc taccaactct ttttccgaag gtaactggct tcagcagagc gcagatacca     1380
aatactgtcc ttctagtgta gccgtagtta ggccaccact tcaagaactc tgtagcaccg     1440
cctacatacc tcgctctgct aatcctgtta ccagtggctg ctgccagtgg cgataagtcg     1500
tgtcttaccg ggttggactc aagacgatag ttaccggata aggcgcagcg gtcgggctga     1560
acggggggtt cgtgcacaca gcccagcttg gagcgaacga cctacaccga actgagatac     1620
ctacagcgtg agctatgaga aagcgccacg cttcccgaag ggagaaaggc ggacaggtat     1680
ccggtaagcg gcagggtcgg aacaggagag cgcacgaggg agcttccagg gggaaacgcc     1740
tggtatcttt atagtcctgt cgggtttcgc cacctctgac ttgagcgtcg attttttgtga     1800 tgctcgtcag gggggcggag cctatggaaa aacgccagca acgcggcctt tttacggttc     1860
ctggcctttt gctggccttt tgctcacatg ttctttcctg cgttatcccc tgattctgtg     1920
gataaccgta ttaccgcctt tgagtgagct gataccgctc gccgcagccg aacgaccgag     1980
cgcagcgagt cagtgagcga ggaagcggaa gagcgcccaa tacgcaaacc gcctctcccc     2040
gcgcgttggc cgattcatta atgcagctgg cacgacaggt ttcccgactg gaaagcgggc     2100
agtgagcgca acgcaattaa tacgcgtacc gcgagccagg aagagtttgt agaaacgcaa     2160
aaaggccatc cgtcaggatg gccttctgct tagtttgatg cctggcagtt tatggcgggc     2220
gtcctgcccg ccaccctccg ggccgttgct tcacaacgtt caaatccgct cccggcggat     2280
ttgtcctact caggagagcg ttcaccgaca acaacagat aaaacgaaag gcccagtctt     2340
ccgactgagc ctttcgtttt atttgatgcc tggcagttcc ctactctcgc gttaacgctt     2400
gcatggatgt tttcccagtc acgacgttgt aaaacgacgg ccagtcttaa gctcgggccc     2460
caaataatga ttttattttg actgatagtg acctgttcgt tgcaacaaat tgatgagcaa     2520 tgcttttta taatgccaac tttgtacaaa aaagcaggct ccgaattcgc ccttcaccat     2580
ggctcctaag aagaagcgga aggttggtat tcacggggtg cctgcggctg ccgtcaagtc     2640
catgaaggtc aagttgcgcc tggataacat gccagagatc agagccggac tttggaaact     2700
tcacaccgag gttaatgcgg gtgtgcggta ctatacggaa tggcttagcc ttttgaggca     2760
agaaaatctt tatcggagga gtcccaatgg cgatggagaa caagaatgct ataaaactgc     2820
tgaggaatgc aaggctgaac tccttgagag actcagagcc cgccaagttg agaatgggca     2880
ctgcggccct gctgggagtg atgacgaact gctgcaattg gcacggcaac tttatgaact     2940
tctggtccca caagcaatcg ggctaaagg tgatgcgcag caaatcgcaa ggaagtttct     3000 tagtccccctt gccgacaagg atgccgtggg tggtttggga atagcaaaag caggaaataa     3060
gcctaggtgg gttcggatga gggaggctgg agagccaggt tggaagagg aaaaggctaa     3120 agccgaggcg agaaagagta cggatagaac cgccgatgtt cttcgcgctc ttgcagactt     3180
```

```
cggtcttaaa cctcttatga gagtctacac agactcagac atgtccagcg tgcagtggaa   3240
accacttcgc aaaggacaag cggtcagaac ctgggataga gacatgttcc aacaagcgat   3300
cgaaagaatg atgagttggg aatcgtggaa tcagcgcgtt ggagaagcgt acgcaaagct   3360
cgtggaacaa aagtcgaggt ttgaacagaa aaattttgtg ggacaagaac atcttgtcca   3420
acttgtcaat caacttcaac aagacatgaa ggaagcatca cacggcctgg agtcgaaaga   3480
acaaactgcg cattacttga ctgggagagc gctgagaggg agcgacaaag tttttgagaa   3540
gtgggaaaaa ctcgatcctg atgccccatt tgacctctat gataccgaaa tcaagaatgt   3600
tcaacggagg aatactcgca ggttcggatc tcatgatctg tttgcgaagc tcgcggaacc   3660
taaatatcag gcgctctgga gagaggacgc ttctttcctc acgaggtatg cggtttacaa   3720
tagcattgtc agaaaactga atcacgctaa aatgtttgcg acttttactc ttccggatgc   3780
taccgcccac ccgatctgga cgcggtttga caaactcggc ggcaacctgc accagtacac   3840
tttcttgttt aacgaatttg gcgagggcag gcacgccatt cggttcaga agctgttgac   3900 ggttgaggat ggcgttgcta agaggtcga cgacgtcacg gttccgattt ctatgtccgc   3960
gcagctggat gacctcttgc ctcgggaccc acacgagctc gttgcactct acttccagga   4020
ctacggtgca gaacaacatc tggctggaga gtttggcggc gcgaaaattc aataccgccg   4080
cgatcaattg aaccacctgc acgccagaag aggcgccaga gatgtctacc ttaatctgag   4140
cgtccgcgtt cagtcacaat ccgaagccag gggagaaagg cgccctccgt atgcagcggt   4200
cttcaggctt gttggcgata accaccgcgc gtttgttcac tttgataaat tgtcagatta   4260
cctcgcagaa cacccagacg atggtaagct ggggtcggaa ggtttgctct ctgggctcag   4320
agtcatgtca gttgccttgg gtcttaggac ttccgcgagc atatctgtct ccgcgtcgc   4380 aagaaaggac gaattgaagc cgaacagtga aggccgggtc ccttttttgct tcccgatcga   4440 agggaacgaa aacctcgttg ctgtccacga gcggagccaa ctgttgaagc ttcccggtga   4500
aacggaatcg aaagatctga gagcgatcag agaagagcgc caaaggacgc ttagacagct   4560
ccggacgcaa cttgcatact tgcgccttct ggttcgctgc ggtagtgaag acgttggaag   4620
aagagagagg tcatgggcta aactcataga gcaacctatg gatgctaatc aaatgacgcc   4680
tgattggaga gaagcattcg aagacgaact tcagaaactg aaatccctt acgggatatg   4740 cggcgatcgc gagtggacag aagcagtgta tgagtctgtg aggcgcgtgt ggcggcatat   4800
gggtaaacag gtgcgcgatt ggagaaaaga cgttaggagc ggggaaagac ctaagatacg   4860
gggatatcag aaagacgttg tcgggggaaa tagcattgaa cagattgaat atttggagcg   4920
ccaatataag ttcctcaaat cctggtcttt cttcggcaaa gtgtcaggcc aggtgatacg   4980
cgcggaaaag ggatcgcgct ttgcaataac tctgagagaa catattgatc atgccaaaga   5040
agatcggttg aagaaactcg ccgatagaat catcatggag gcgcttggtt atgtctacgc   5100
cttggacgat gaacggggaa agggaaagtg ggtcgccaag tatccaccct tgccaactcat   5160 tctcctcgaa gaactttccg aataccagtt taacaacgat cggccgccat cagagaataa   5220
tcaactgatg cagtggtccc atcgcggtgt gtttcaagag ttgctcaatc aggcccaagt   5280
ccatgatctg cttgttggca caatgtatgc agccttttcc tcccggtttg atgcaagaac   5340
aggggctcct ggcatacgct gtagacgggt cccggcgagg tgcgcccgcg aacaaaaccc   5400
tgaaccgttc ccctggtggt tgaacaagtt cgttgcggag cacaagctgg acgggtgtcc   5460
tctgcgggcc gacgatctta ttcccaccgg ggaagggaa ttctttgtga gcccttctc   5520
```

```
ggcggaggaa ggggattttc accaaataca tgcagatctt aatgccgcac aaaatttgca      5580
gaggagactg tggtcagact ttgatattag tcagatacgc ctccgctgtg actggggaga      5640
ggtcgatggc gagcctgtgt tgataccaag aacgaccgga agaggacag ccgattcgta       5700 tggaaacaag gttttttaca cgaagacggg cgttacttac tacgaaagag aaagagggaa      5760
gaagagaagg aaagtctttg cccaagaaga attgagcgag gaagaagccg agctcttggt      5820
cgaagcggac gaggcacggg aaaagtctgt cgtcctcatg agggacccct ccggaattat      5880
taaccgggga gattggacgc ggcagaaaga gttttggtcc atggttaatc aacgcataga      5940
aggctacctt gtcaagcaaa taagaagtcg cgtgagattg caggagagtg catgtgagaa      6000 cactgggac ataaagcgtc ctgctgccac caaaaaggcc ggacaggcta agaaaaagaa       6060
gggagacggc tctggatcgg ggtcgggttc tggctcagtc gacttgcttg atccggggac      6120
accaatggac gcggacctgg tggcttcatc gaccgtggtt tgggaacagg acgccgatcc      6180
attcgccggg accgccgatg actttcctgc ttttaatgag gaagagttgg cttggctgat      6240
ggaactcctg ccgcagggcg gctcagggg tctccttgac cccggcaccc ccatggacgc       6300
tgacctcgtt gcaagttcga cggttgtttg ggagcaagat gcagatccgt ttgcgggtac      6360
agctgatgac tttccagcct tcaacgaaga ggagctggca tggcttatgg agcttctgcc      6420
tcaggccaga ggagggtcgg gtgggctctt ggatcctggg acgccgatgg atgccgacct      6480
tgtcgcgtcc tctactgtgg tttgggagca ggacgccgac ccgttcgctg gtactgctga      6540
tgactttccg gcctttaatg aggaggaact cgcttggctc atggagttgt tgccacaagg      6600
gggtagtggc ggtcttctgg acccgggaac gcctatggat gctgacttgg tggcatcgag      6660
caccgtcgtc tgggaacagg atgcggaccc gtttgctggt accgctgatg attttccggc      6720
atttaacgag gaagaattgg cgtggctcat ggaattgctt ccccaggcga gggggttc       6780 cggtggcttg ctggatccgg gaacgcctat ggatgccgat ctcgtggcgt cgtcaaccgt      6840
ggtctgggag caagacgctg acccgtttgc cggcacagca gatgattttc cagctttcaa      6900
tgaggaagaa ctggcatggt tgatggaatt gcttccacag ggagggagcg gaggcctcct      6960
cgatcctgga acacctatgg acgcagacct ggttgcctct tcaactgtcg tgtgggaaca      7020
agatgcagac ccgttcgcag gtacagctga tgacttccct gcctttaatg aggaggaact      7080
cgcgtggctc atggaacttt tgccccaagc acgcggtggc tctgggggtg gcggatcggg      7140
aggagatgcg ctgacgatt tcgacttgga catgttgggc tcagacgctt tggacgactt      7200
tgatctcgac atgcttgggt ccgacgcatt ggatgatttc gaccttgaca tgcttggttc      7260
cgacgcactc gatgacttcg atcttgatat gctcgcccgc ggatctgacg ctctcgacga      7320
cttcgatctt gacatgttgg gctcagatgc gctcgacgac tttgatctcg atatgttggg      7380
tagcgacgca ctcgatgact tgacttgga tatgctgggg agcgacgcct tggacgattt       7440
cgatctggac atgctgtaaa agctttgata ggacgtccga tcgttcaaac atttggcaat      7500
aaagtttctt aagattgaat cctgttgccg gtcttgcgat gattatcata taatttctgt      7560
tgaattacgt taagcatgta ataattaaca tgtaatgcat gacgttattt atgagatggg      7620
tttttatgat tagagtcccg caattataca tttaatacgc gatagaaaac aaaatatagc      7680
gcgcaaacta ggataaatta tcgcgcgcgg tgtcatctat gttactagat cgggaattga      7740
tcccccctcg acagcttccg gaagggcga attcgcaact ttgtatacaa agttgaacg       7800 agaaacgtaa aatgatataa atatcaatat attaaattag attttgcata aaaaacagac      7860
tacataatac tgtaaaacac aacatatcca gtcactatgc catccagctg atatccccta      7920
```

```
tagtgagtcg tattacatgg tcatagctgt ttcctggcag ctctggcccg tgtctcaaaa    7980
tctctgatgt tacattgcac aagataaaaa tatatcatca tgcctcctc               8029

<210> SEQ ID NO 45
<211> LENGTH: 9871
<212> TYPE: DNA
<213> ORGANISM: Artificial Sequence
<220> FEATURE:
<223> OTHER INFORMATION: Vector

<400> SEQUENCE: 45
tggaccagcc aggacagaaa tgcctcgact tcgctgctac ccaaggttgc cgggtgacgc      60
acaccgtgga aacggatgaa ggcacgaacc cagtggacat aagcctgttc ggttcgtaag    120
ctgtaatgca agtagcgtat gcgctcacgc aactggtcca gaaccttgac cgaacgcagc    180
ggtggtaacg gcgcagtggc ggttttcatg gcttgttatg actgtttttt tggggtacag    240
tctatgcctc gggcatccaa gcagcaagcg cgttacgccg tgggtcgatg tttgatgtta    300
tggagcagca acgatgttac gcagcagggc agtcgcccta aaacaaagtt aaacatcatg    360
agggaagcgg tgatcgccga agtatcgact caactatcag aggtagttgg cgtcatcgag    420
cgccatctcg aaccgacgtt gctggccgta catttgtacg gctccgcagt ggatggcggc    480
ctgaagccac acagtgatat tgatttgctg gttacggtga ccgtaaggct tgatgaaaca    540
acgcggcgag ctttgatcaa cgaccttttg gaaacttcgg cttcccctgg agagagcgag    600
attctccgcg ctgtagaagt caccattgtt gtgcacgacg acatcattcc gtggcgttat    660
ccagctaagc gcgaactgca atttggagaa tggcagcgca atgacattct tgcaggtatc    720
ttcgagccag ccacgatcga cattgatctg gctatcttgc tgacaaaagc aagagaacat    780
agcgttgcct tggtaggtcc agcggcggag gaactctttg atccggttcc tgaacaggat    840
ctatttgagg cgctaaatga aaccttaacg ctatggaact cgccgcccga ctgggctggc    900
gatgagcgaa atgtagtgct tacgttgtcc cgcatttggt acagcgcagt aaccggcaaa    960
atcgcgccga aggatgtcgc tgccgactgg gcaatggagc gcctgccggc ccagtatcag   1020
cccgtcatac ttgaagctag acaggcttat cttggacaag aagaagatcg cttggcctcg   1080
cgcgcagatc agttggaaga atttgtccac tacgtgaaag gcgagatcac caaggtagtc   1140
ggcaaataac cctcgagcca cccatgacca aaatccctta acgtgagtta cgcgtcgttc   1200
cactgagcgt cagaccccgt agaaaagatc aaaggatctt cttgagatcc ttttttttctg   1260 cgcgtaatct gctgcttgca acaaaaaaa ccaccgctac cagcggtggt ttgtttgccg   1320
gatcaagagc taccaactct ttttccgaag gtaactggct tcagcagagc gcagatacca   1380
aatactgtcc ttctagtgta gccgtagtta ggccaccact tcaagaactc tgtagcaccg   1440
cctacatacc tcgctctgct aatcctgtta ccagtggctg ctgccagtgg cgataagtcg   1500
tgtcttaccg ggttggactc aagacgatag ttaccggata aggcgcagcg gtcgggctga   1560
acggggggtt cgtgcacaca gcccagcttg gagcgaacga cctacaccga actgagatac   1620
ctacagcgtg agctatgaga aagcgccacg cttcccgaag ggagaaaggc ggacaggtat   1680
ccggtaagcg gcagggtcgg aacaggagag cgcacgaggg agcttccagg gggaaacgcc   1740
tggtatcttt atagtcctgt cgggtttcgc cacctctgac ttgagcgtcg attttttgtga   1800 tgctcgtcag gggggcggag cctatggaaa aacgccagca acgcggcctt tttacggttc   1860
ctggcctttt gctggccttt tgctcacatg ttctttcctg cgttatcccc tgattctgtg   1920
```

```
gataaccgta ttaccgcctt tgagtgagct gataccgctc gccgcagccg aacgaccgag   1980
cgcagcgagt cagtgagcga ggaagcggaa gagcgcccaa tacgcaaacc gcctctcccc   2040
gcgcgttggc cgattcatta atgcagctgg cacgacaggt ttcccgactg gaaagcgggc   2100
agtgagcgca acgcaattaa tacgcgtacc gcgagccagg aagagtttgt agaaacgcaa   2160
aaaggccatc cgtcaggatg gccttctgct tagtttgatg cctggcagtt tatggcgggc   2220
gtcctgcccg ccaccctccg ggccgttgct tcacaacgtt caaatccgct cccggcggat   2280
ttgtcctact caggagagcg ttcaccgaca acaacagat aaaacgaaag gcccagtctt   2340
ccgactgagc ctttcgtttt atttgatgcc tggcagttcc ctactctcgc gttaacgctt   2400
gcatggatgt tttcccagtc acgacgttgt aaaacgacgg ccagtcttaa gctcgggccc   2460
caaataatga ttttattttg actgatagtg acctgttcgt tgcaacaaat tgatgagcaa   2520 tgcttttttta taatgccaac tttgtacaaa aaagcaggct ccgaattcgc ccttcaccat   2580
ggctcctaag aagaagcgga aggttggtat tcacggggtg cctgcggctg ccgtcaagtc   2640
catgaaggtc aagttgcgcc tggataacat gccagagatc agagccggac tttgaaaact   2700
tcacaccgag gttaatgcgg gtgtgcggta ctatacggaa tggcttagcc ttttgaggca   2760
agaaaatctt tatcggagga gtcccaatgg cgatggagaa caagaatgct ataaaactgc   2820
tgaggaatgc aaggctgaac tccttgagag actcagagcc cgccaagttg agaatgggca   2880
ctgcggccct gctgggagtg atgacgaact gctgcaattg gcacggcaac tttatgaact   2940
tctggtccca caagcaatcg gggctaaagg tgatgcgcag caaatcgcaa ggaagtttct   3000 tagtccccctt gccgacaagg atgccgtggg tggtttggga atagcaaaag caggaaataa   3060
gcctaggtgg gttcggatga gggaggctgg agagccaggt tgggaagagg aaaaggctaa   3120
agccgaggcg agaaagagta cggatagaac cgccgatgtt cttcgcgctc ttgcagactt   3180
cggtcttaaa cctcttatga gagtctacac agactcagac atgtccagcg tgcagtggaa   3240
accacttcgc aaaggacaag cggtcagaac ctgggataga gacatgttcc aacaagcgat   3300
cgaaagaatg atgagttggg aatcgtggaa tcagcgcgtt ggagaagcgt acgcaaagct   3360
cgtggaacaa aagtcgaggt ttgaacagaa aaattttgtg ggacaagaac atcttgtcca   3420
acttgtcaat caacttcaac aagacatgaa ggaagcatca cacggcctgg agtcgaaaga   3480
acaaactgcg cattacttga ctgggagagc gctgagaggg agcgacaaag tttttgagaa   3540
gtgggaaaaa ctcgatcctg atgccccatt tgacctctat gataccgaaa tcaagaatgt   3600
tcaacggagg aatactcgca ggttcggatc tcatgatctg tttgcgaagc tcgcggaacc   3660
taaatatcag gcgctctgga gagaggacgc ttcttcctc acgaggtatg cggtttacaa   3720
tagcattgtc agaaaactga atcacgctaa aatgtttgcg acttttactc ttccggatgc   3780
taccgcccac ccgatctgga cgcggtttga caaactcggc ggcaacctgc accagtacac   3840
tttcttgttt aacgaatttg gcgagggcag gcacgccatt cggtttcaga agctgttgac   3900
ggttgaggat ggcgttgcta aagaggtcga cgacgtcacg gttccgattt ctatgtccgc   3960
gcagctggat gacctcttgc ctcgggaccc acacgagctc gttgcactct acttccagga   4020
ctacggtgca gaacaacatc tggctggaga gtttggcggc gcgaaaattc aataccgccg   4080
cgatcaattg aaccacctgc acgccagaag aggcgccaga gatgtctacc ttaatctgag   4140
cgtccgcgtt cagtcacaat ccgaagccag gggagaaagg cgcctccgt atgcagcggt   4200 cttcaggctt gttggcgata accaccgcgc gtttgttcac tttgataaat tgtcagatta   4260
cctcgcagaa cacccagacg atggtaagct ggggtcggaa ggtttgctct ctgggctcag   4320
```

```
agtcatgtca gttgccttgg gtcttaggac ttccgcgagc atatctgtct tccgcgtcgc    4380
aagaaaggac gaattgaagc cgaacagtga aggccgggtc cctttttgct tcccgatcga    4440
agggaacgaa aacctcgttg ctgtccacga gcggagccaa ctgttgaagc ttcccggtga    4500
aacggaatcg aaagatctga gagcgatcag agaagagcgc caaaggacgc ttagacagct    4560
ccggacgcaa cttgcatact tgcgccttct ggttcgctgc ggtagtgaag acgttggaag    4620
aagagagagg tcatgggcta aactcataga gcaacctatg gatgctaatc aaatgacgcc    4680
tgattggaga gaagcattcg aagacgaact tcagaaactg aaatccctt acgggatatg     4740 cggcgatcgc gagtggacag aagcagtgta tgagtctgtg aggcgcgtgt ggcggcatat    4800
gggtaaacag gtgcgcgatt ggagaaaaga cgttaggagc ggggaaagac ctaagatacg    4860
gggatatcag aaagacgttg tcggggggaaa tagcattgaa cagattgaat atttggagcg   4920
ccaatataag ttcctcaaat cctggtcttt cttcggcaaa gtgtcaggcc aggtgatacg    4980
cgcggaaaag ggatcgcgct ttgcaataac tctgagagaa catattgatc atgccaaaga    5040
agatcggttg aagaaactcg ccgatagaat catcatggag gcgcttggtt atgtctacgc    5100
cttggacgat gaacggggaa agggaaagtg ggtcgccaag tatccacctt gccaactcat    5160
tctcctcgaa gaactttccg aataccagtt taacaacgat cggccgccat cagagaataa    5220
tcaactgatg cagtggtccc atcgcggtgt gtttcaagag ttgctcaatc aggcccaagt    5280
ccatgatctg cttgttggca caatgtatgc agccttttcc tcccggtttg atgcaagaac    5340
aggggctcct ggcatacgct gtagacgggt cccggcgagg tgcgcccgcg aacaaaaccc    5400
tgaaccgttc ccctggtggt tgaacaagtt cgttgcggag cacaagctgg acgggtgtcc    5460
tctgcgggcc gacgatctta ttcccaccgg ggaaggggaa ttctttgtga gcccttctc    5520 ggcggaggaa ggggattttc accaaataca tgcagatctt aatgccgcac aaaatttgca    5580
gaggagactg tggtcagact ttgatattag tcagatacgc ctccgctgtg actgggagaa    5640
ggtcgatggc gagcctgtgt tgataccaag aacgaccgga aagaggacag ccgattcgta    5700
tggaaacaag gttttttaca cgaagacggg cgttacttac tacgaaagag aaagagggaa    5760
gaagagaagg aaagtctttg cccaagaaga attgagcgag gaagaagccg agctcttggt    5820
cgaagcggac gaggcacggg aaaagtctgt cgtcctcatg agggaccctt ccggaattat    5880
taaccgggga gattggacgc ggcagaaaga gttttggtcc atggttaatc aacgcataga    5940
aggctacctt gtcaagcaaa taagaagtcg cgtgagattg caggagagtg catgtgagaa    6000
cactggggac ataaagcgtc ctgctgccac caaaaaggcc ggacaggcta agaaaaagaa    6060
gggagacggc tctggatcgg ggtcgggttc tggctcagtc gacttgcttg atccggggac    6120
accaatggac gcggacctgg tggcttcatc gaccgtggtt tgggaacagg acgccgatcc    6180
attcgccggg accgccgatg actttcctgc ttttaatgag gaagagttgg cttggctgat    6240
ggaactcctg ccgcagggcg gctcagggg tctccttgac cccggcaccc ccatggacgc    6300
tgacctcgtt gcaagttcga cggttgtttg ggagcaagat gcagatccgt ttgcgggtac    6360
agctgatgac tttccagcct tcaacgaaga ggagctggca tggcttatgg agcttctgcc    6420
tcaggccaga ggagggtcgg gtgggctctt ggatcctggg acgccgatgg atgccgacct    6480
tgtcgcgtcc tctactgtgg tttgggagca ggacgccgac ccgttcgctg gtactgctga    6540
tgactttccg gcctttaatg aggaggaact cgcttggctc atggagttgt tgccacaagg    6600
gggtagtggc ggtcttctgg acccgggaac gcctatggat gctgacttgg tggcatcgag    6660
```

```
caccgtcgtc tgggaacagg atgcggaccc gtttgctggt accgctgatg attttccggc   6720
atttaacgag gaagaattgg cgtggctcat ggaattgctt ccccaggcga gagggggttc   6780
cggtggcttg ctggatccgg gaacgcctat ggatgccgat ctcgtggcgt cgtcaaccgt   6840
ggtctgggag caagacgctg acccgtttgc cggcacagca gatgattttc cagctttcaa   6900
tgaggaagaa ctggcatggt tgatggaatt gcttccacag ggagggagcg gaggcctcct   6960
cgatcctgga acacctatgg acgcagacct ggttgcctct tcaactgtcg tgtgggaaca   7020
agatgcagac ccgttcgcag gtacagctga tgacttccct gcctttaatg aggaggaact   7080
cgcgtggctc atggaacttt tgccccaagc acgcggtggc tctggggtg gcggatcggg   7140
aggagatgcg ctggacgatt tcgacttgga catgttgggc tcagacgctt tggacgactt   7200
tgatctcgac atgcttgggt ccgacgcatt ggatgatttc gaccttgaca tgcttggttc   7260
cgacgcactc gatgacttcg atcttgatat gctcgcccgc ggatctgacg ctctcgacga   7320
cttcgatctt gacatgttgg gctcagatgc gctcgacgac tttgatctcg atatgttggg   7380
tagcgacgca ctcgatgact tgacttgga tatgctgggg agcgacgcct ggacgatttt   7440
cgatctggac atgctggagg gcagaggaag tcttctaaca tgcggtgacg tggaggagaa   7500
tccccggccct atggcgtcaa atttcacgca gtttgttttg gttgataacg gcgggactgg   7560
cgacgttaca gtagctccat caaattttgc gaacggagtc gctgagtgga ttagctcaaa   7620
ttcaaggtcc caggcctaca aggttacctg ttctgttagg cagagttctg cgcaaaaaag   7680
aaaatatacc atcaaggttg aagtccctaa agttgcaaca caaacagtcg gtggtgttga   7740
gctcccgtgt gcagcctgga gatcttactt aaacatggag ctaacaattc caatattcgc   7800
tacaaactct gattgtgaac tgattgttaa ggcgatgcaa ggtctcttga agatggaaa   7860
ccctataccg tccgctatcg cagctaacag cggtatctat cctaagaaga agaggaaggt   7920
tggctctgga tcggggtcgg gttctggctc attgcttgat ccggggacac caatggacgc   7980
ggacctggtg gcttcatcga ccgtggtttg gaacaggac gccgatccat tcgccggac   8040
cgccgatgac tttcctgctt ttaatgagga agagttggct tggctgatgg aactcctgcc   8100
gcagggcggc tcagggggtc tccttgaccc cggcaccccc atggacgctg acctcgttgc   8160
aagttcgacg gttgtttggg agcaagatgc agatccgttt gcgggtacag ctgatgactt   8220
tccagccttc aacgaagagg agctggcatg gcttatggag cttctgcctc aggccagagg   8280
agggtcgggt gggctcttgg atcctgggac gccgatggat gccgaccttg tcgcgtcctc   8340
tactgtggtt tgggagcagg acgccgaccc gttcgctggt actgctgatg actttccggc   8400
ctttaatgag gaggaactcg cttggctcat ggagttgttg ccacaagggg gtagtggcgg   8460
tcttctggac ccgggaacgc ctatggatgc tgacttggtg gcatcgagca ccgtcgtctg   8520
ggaacaggat gcggacccgt ttgctggtac cgctgatgat tttccggcat ttaacgagga   8580
agaattggcg tggctcatgg aattgcttcc ccaggcgaga gggggttccg gtggcttgct   8640
ggatccggga acgcctatgg atgccgatct cgtggcgtcg tcaaccgtgg tctgggagca   8700
agacgctgac ccgtttgccg gcacagcaga tgattttcca gctttcaatg aggaagaact   8760
ggcatggttg atgaattgc ttccacaggg agggagcgga ggcctcctcg atcctggaac   8820
acctatggac gcagacctgg ttgcctcttc aactgtcgtg tgggaacaag atgcagaccc   8880
gttcgcaggt acagctgatg acttccctgc ctttaatgag gaggaactcg cgtggctcat   8940
ggaactttg ccccaagcac gcggtggctc tgggggtggc ggatcgggag agatgcgct   9000
ggacgatttc gacttggaca tgttgggctc agacgctttg gacgactttg atctcgacat   9060
```

```
gcttgggtcc gacgcattgg atgatttcga ccttgacatg cttggttccg acgcactcga    9120
tgacttcgat cttgatatgc tcgcccgcgg atctgacgct ctcgacgact tcgatcttga    9180
catgttgggc tcagatgcgc tcgacgactt tgatctcgat atgttgggta gcgacgcact    9240
cgatgacttt gacttggata tgctggggag cgacgccttg gacgatttcg atctggacat    9300
gctgtgatga taggacgtcc gatcgttcaa acatttggca ataaagtttc ttaagattga    9360
atcctgttgc cggtcttgcg atgattatca tataatttct gttgaattac gttaagcatg    9420
taataattaa catgtaatgc atgacgttat ttatgagatg gttttttatg attagagtcc    9480
cgcaattata catttaatac gcgatagaaa acaaaatata gcgcgcaaac taggataaat    9540
tatcgcgcgc ggtgtcatct atgttactag atcgggaatt gatcccccct cgacagcttc    9600
cggaaagggc gaattcgcaa ctttgtatac aaaagttgaa cgagaaacgt aaaatgatat    9660
aaatatcaat atattaaatt agattttgca taaaaaacag actacataat actgtaaaac    9720
acaacatatc cagtcactat gccatccagc tgatatcccc tatagtgagt cgtattacat    9780
ggtcatagct gtttcctggc agctctggcc cgtgtctcaa aatctctgat gttacattgc    9840
acaagataaa aatatatcat catgcctcct c                                   9871
```

<210> SEQ ID NO 46  
<211> LENGTH: 9748  
<212> TYPE: DNA  
<213> ORGANISM: Artificial Sequence  
<220> FEATURE:  
<223> OTHER INFORMATION: Vector

<400> SEQUENCE: 46

```
tggaccagcc aggacagaaa tgcctcgact tcgctgctac ccaaggttgc cgggtgacgc      60
acaccgtgga aacggatgaa ggcacgaacc cagtggacat aagcctgttc ggttcgtaag     120
ctgtaatgca agtagcgtat gcgctcacgc aactggtcca gaaccttgac cgaacgcagc     180
ggtggtaacg gcgcagtggc ggttttcatg gcttgttatg actgtttttt tggggtacag     240
tctatgcctc gggcatccaa gcagcaagcg cgttacgccg tgggtcgatg tttgatgtta     300
tggagcagca acgatgttac gcagcagggc agtcgcccta aaacaaagtt aaacatcatg     360
agggaagcgg tgatcgccga agtatcgact caactatcag aggtagttgg cgtcatcgag     420
cgccatctcg aaccgacgtt gctggccgta catttgtacg gctccgcagt ggatggcggc     480
ctgaagccac acagtgatat tgatttgctg gttacggtga ccgtaaggct tgatgaaaca     540
acgcggcgag ctttgatcaa cgaccttttg gaaacttcgg cttcccctgg agagagcgag     600
attctccgcg ctgtagaagt caccattgtt gtgcacgacg acatcattcc gtggcgttat     660
ccagctaagc gcgaactgca atttggagaa tggcagcgca atgacattct tgcaggtatc     720
ttcgagccag ccacgatcga cattgatctg gctatcttgc tgacaaaagc aagagaacat     780
agcgttgcct tggtaggtcc agcggcggag gaactctttg atccggttcc tgaacaggat     840
ctatttgagg cgctaaatga aaccttaacg ctatggaact cgccgcccga ctgggctggc     900
gatgagcgaa atgtagtgct tacgttgtcc cgcatttggt acagcgcagt aaccggcaaa     960
atcgcgccga aggatgtcgc tgccgactgg gcaatggagc gcctgccggc ccagtatcag    1020
cccgtcatac ttgaagctag acaggcttat cttggacaag aagaagatcg cttggcctcg    1080
cgcgcagatc agttggaaga atttgtccac tacgtgaaag gcgagatcac caaggtagtc    1140
ggcaaataac cctcgagcca cccatgacca aaatccctta acgtgagtta cgcgtcgttc    1200
```

```
cactgagcgt cagaccccgt agaaaagatc aaaggatctt cttgagatcc ttttttttctg    1260
cgcgtaatct gctgcttgca aacaaaaaaa ccaccgctac cagcggtggt ttgtttgccg    1320
gatcaagagc taccaactct ttttccgaag gtaactggct tcagcagagc gcagatacca    1380
aatactgtcc ttctagtgta gccgtagtta ggccaccact tcaagaactc tgtagcaccg    1440
cctacatacc tcgctctgct aatcctgtta ccagtggctg ctgccagtgg cgataagtcg    1500
tgtcttaccg ggttggactc aagacgatag ttaccggata aggcgcagcg gtcgggctga    1560
acggggggtt cgtgcacaca gcccagcttg gagcgaacga cctacaccga actgagatac    1620
ctacagcgtg agctatgaga aagcgccacg cttcccgaag ggagaaaggc ggacaggtat    1680
ccggtaagcg gcagggtcgg aacaggagag cgcacgaggg agcttccagg gggaaacgcc    1740
tggtatcttt atagtcctgt cgggtttcgc cacctctgac ttgagcgtcg attttttgtga    1800
tgctcgtcag gggggcggag cctatggaaa aacgccagca acgcggcctt tttacggttc    1860
ctggcctttt gctggccttt tgctcacatg ttctttcctg cgttatcccc tgattctgtg    1920
gataaccgta ttaccgcctt tgagtgagct gataccgctc gccgcagccg aacgaccgag    1980
cgcagcgagt cagtgagcga ggaagcggaa gagcgcccaa tacgcaaacc gcctctcccc    2040
gcgcgttggc cgattcatta atgcagctgg cacgacaggt ttcccgactg gaaagcgggc    2100
agtgagcgca acgcaattaa tacgcgtacc gcgagccagg aagagtttgt agaaacgcaa    2160
aaaggccatc cgtcaggatg gccttctgct tagtttgatg cctggcagtt tatggcgggc    2220
gtcctgcccg ccaccctccg ggccgttgct tcacaacgtt caaatccgct cccggcggat    2280
ttgtcctact caggagagcg ttcaccgaca acaacagat aaaacgaaag gcccagtctt    2340
ccgactgagc ctttcgtttt atttgatgcc tggcagttcc ctactctcgc gttaacgctt    2400
gcatggatgt tttcccagtc acgacgttgt aaaacgacgg ccagtcttaa gctcgggccc    2460
caaataatga ttttatttg actgatagtg acctgttcgt tgcaacaaat tgatgagcaa    2520
tgcttttttta taatgccaac tttgtacaaa aaagcaggct ccgaattcgc ccttcaccat    2580
ggctcctaag aagaagcgga aggttggtat tcacggggtg cctgcggctg ccgtcaagtc    2640
catgaaggtc aagttgcgcc tggataacat gccagagatc agagccggac tttggaaact    2700
tcacaccgag gttaatgcgg gtgtgcggta ctatacgaa tggcttagcc ttttgaggca    2760
agaaaatctt tatcggagga gtcccaatgg cgatggagaa caagaatgct ataaaactgc    2820
tgaggaatgc aaggctgaac tccttgagag actcagagcc cgccaagttg agaatgggca    2880
ctgcggccct gctgggagtg atgacgaact gctgcaattg gcacggcaac tttatgaact    2940
tctggtccca caagcaatcg gggctaaagg tgatgcgcag caaatcgcaa ggaagtttct    3000
tagtccccctt gccgacaagg atgccgtggg tggtttggga atagcaaaag caggaaataa    3060
gcctaggtgg gttcggatga gggaggctgg agagccaggt tgggaagagg aaaaggctaa    3120
agccgaggcg agaaagagta cggatagaac cgccgatgtt cttcgcgctc ttgcagactt    3180
cggtcttaaa cctcttatga gagtctacac agactcagac atgtccagcg tgcagtggaa    3240
accacttcgc aaaggacaag cggtcagaac ctgggatag acatgttcc aacaagcgat    3300
cgaaagaatg atgagttggg aatcgtggaa tcagcgcgtt ggagaagcgt acgcaaagct    3360
cgtggaacaa aagtcgaggt ttgaacagaa aaattttgtg ggacaagaac atcttgtcca    3420
acttgtcaat caacttccaac aagacatgaa ggaagcatca cacggcctgg agtcgaaaga    3480
acaaactgcg cattacttga ctgggagagc gctgagaggg agcgacaaag ttttttgagaa    3540
gtgggaaaaa ctcgatcctg atgccccatt tgacctctat gataccgaaa tcaagaatgt    3600
```

```
tcaacggagg aatactcgca ggttcggatc tcatgatctg tttgcgaagc tcgcggaacc    3660
taaatatcag gcgctctgga gagaggacgc ttctttcctc acgaggtatg cggtttacaa    3720
tagcattgtc agaaaactga atcacgctaa aatgtttgcg acttttactc ttccggatgc    3780
taccgcccac ccgatctgga cgcggtttga caaactcggc ggcaacctgc accagtacac    3840
tttcttgttt aacgaatttg gcgagggcag gcacgccatt cggtttcaga agctgttgac    3900
ggttgaggat ggcgttgcta agaggtcga cgacgtcacg gttccgattt ctatgtccgc     3960
gcagctggat gacctcttgc ctcgggaccc acacgagctc gttgcactct acttccagga    4020
ctacggtgca gaacaacatc tggctggaga gtttggcggc gcgaaaattc aataccgccg    4080
cgatcaattg aaccacctgc acgccagaag aggcgccaga gatgtctacc ttaatctgag    4140
cgtccgcgtt cagtcacaat ccgaagccag gggagaaagg cgcctccgt atgcagcggt     4200 cttcaggctt gttggcgata accaccgcgc gtttgttcac tttgataaat tgtcagatta    4260
cctcgcagaa cacccagacg atggtaagct ggggtcggaa ggtttgctct ctgggctcag    4320
agtcatgtca gttgccttgg gtcttaggac ttccgcgagc atatctgtct ccgcgtcgc     4380 aagaaaggac gaattgaagc cgaacagtga aggccgggtc ccttttttgct tcccgatcga    4440 agggaacgaa aacctcgttg ctgtccacga gcggagccaa ctgttgaagc ttcccggtga    4500 aacgaatcg aaagatctga gagcgatcag agaagagcgc caaggacgc ttagacagct      4560 ccggacgcaa cttgcatact gcgccttct ggttcgctgc ggtagtgaag acgttggaag     4620
aagagagagg tcatgggcta aactcataga gcaacctatg gatgctaatc aaatgacgcc    4680
tgattggaga gaagcattcg aagacgaact tcagaaactg aaatcccttt acgggatatg    4740
cggcgatcgc gagtggacag aagcagtgta tgagtctgtg aggcgcgtgt ggcggcatat    4800
gggtaaacag gtgcgcgatt ggagaaaaga cgttaggagc ggggaaagac ctaagatacg    4860
gggatatcag aaagacgttg tcgggggaaa tagcattgaa cagattgaat atttggagcg    4920
ccaatataag ttcctcaaat cctggtcttt cttcggcaaa gtgtcaggcc aggtgatacg    4980
cgcggaaaag ggatcgcgct ttgcaataac tctgagagaa catattgatc atgccaaaga    5040
agatcggttg aagaaactcg ccgatagaat catcatggag gcgcttggtt atgtctacgc    5100
cttggacgat gaacgggaa agggaaagtg ggtcgccaag tatccacctt gccaactcat     5160
tctcctcgaa gaactttccg aataccagtt taacaacgat cggccgccat cagagaataa    5220
tcaactgatg cagtggtccc atcgcggtgt gtttcaagag ttgctcaatc aggcccaagt    5280
ccatgatctg cttgttggca caatgtatgc agccttttcc tcccggtttg atgcaagaac    5340
aggggctcct ggcatacgct gtagacgggt cccggcgagg tgcgcccgcg aacaaaaccc    5400
tgaaccgttc ccctggtggt tgaacaagtt cgttgcggga cacaagctgg acgggtgtcc    5460
tctgcgggcc gacgatctta ttcccaccgg ggaaggggaa ttctttgtga gccctttctc    5520
ggcggaggaa gggggattttc accaaataca tgcagatctt aatgccgcac aaaatttgca    5580
gaggagactg tggtcagact ttgatattag tcagatacgc ctccgctgtg actggggaga    5640
ggtcgatggc gagcctgtgt tgataccaag aacgaccgga agaggacag ccgattcgta     5700 tggaaacaag gttttttaca cgaagacggg cgttacttac tacgaaagag aaagagggaa    5760
gaagagaagg aaagtctttg cccaagaaga attgagcgag gaagaagccg agctcttggt    5820
cgaagcggac gaggcacggg aaaagtctgt cgtcctcatg agggaccctt ccggaattat    5880
taaccgggga gattggacgc ggcagaaaga gttttggtcc atggttaatc aacgcataga    5940
```

```
aggctacctt gtcaagcaaa taagaagtcg cgtgagattg caggagagtg catgtgagaa     6000
cactggggac ataaagcgtc ctgctgccac caaaaaggcc ggacaggcta agaaaaagaa     6060
gggagacggc tctggatcgg ggtcgggttc tggctcagtc gacttgcttg atccggggac     6120
accaatggac gcggacctgg tggcttcatc gaccgtggtt tgggaacagg acgccgatcc     6180
attcgccggg accgccgatg actttcctgc ttttaatgag gaagagttgg cttggctgat     6240
ggaactcctg ccgcagggcg gctcaggggg tctccttgac cccggcaccc ccatggacgc     6300
tgacctcgtt gcaagttcga cggttgtttg ggagcaagat gcagatccgt ttgcgggtac     6360
agctgatgac tttccagcct tcaacgaaga ggagctggca tggcttatgg agcttctgcc     6420
tcaggccaga ggagggtcgg gtgggctctt ggatcctggg acgccgatgg atgccgacct     6480
tgtcgcgtcc tctactgtgg tttgggagca ggacgccgac ccgttcgctg gtactgctga     6540
tgactttccg gcctttaatg aggaggaact cgcttggctc atggagttgt tgccacaagg     6600
gggtagtggc ggtcttctgg acccgggaac gcctatggat gctgacttgg tggcatcgag     6660
caccgtcgtc tgggaacagg atgcggaccc gtttgctggt accgctgatg attttccggc     6720
atttaacgag gaagaattgg cgtggctcat ggaattgctt ccccaggcga gggggggttc     6780
cggtggcttg ctggatccgg gaacgccgat ggatgccgat ctcgtggcgt cgtcaaccgt     6840
ggtctgggag caagacgctg acccgttttgc cggcacagca gatgatttttc cagcctttcaa     6900 tgaggaagaa ctggcatggt tgatggaatt gcttccacag ggaggggagcg gaggcctcct     6960 cgatcctgga acacctatgg acgcagacct ggttgcctct tcaactgtcg tgtgggaaca     7020
agatgcagac ccgttcgcag gtacagctga tgacttccct gcctttaatg aggaggaact     7080
cgcgtggctc atggaacttt tgccccaagc acgcggtggc tctggggtg gcggatcggg     7140 aggagatgcg ctgacgatt tcgacttgga catgttgggc tcagacgctt tggacgactt     7200
tgatctcgac atgcttgggt ccgacgcatt ggatgatttc gaccttgaca tgcttggttc     7260
cgacgcactc gatgacttcg atcttgatat gctcgcccgc ggatctgacg ctctcgacga     7320
cttcgatctt gacatgttgg gctcagatgc gctcgacgac tttgatctcg atatgttggg     7380
tagcgacgca ctcgatgact ttgacttgga tatgctgggg agcgacgcct ggacgatttt     7440
cgatctggac atgctggagg gcagaggaag tcttctaaca tgcggtgacg tggaggagaa     7500
tcccggccct atggcgtcaa atttcacgca gtttgttttg gttgataacg gcgggactgg     7560
cgacgttaca gtagctccat caaattttgc gaacggagtc gctgagtgga ttagctcaaa     7620
ttcaaggtcc caggcctaca aggttacctg ttctgttagg cagagttctg cgcaaaaaag     7680
aaaatatacc atcaaggttg aagtccctaa agttgcaaca caaacagtcg gtggtgttga     7740
gctccctgtg gcagcctgga gatcttactt aaacatggag ctaacaattc caatattcgc     7800
tacaaactct gattgtgaac tgattgttaa ggcgatgcaa ggtctcttga agatggaaaa     7860
ccctataccg tccgctatcg cagctaacag cggtatctat cctaagaaga agaggaaggt     7920
tggctctgga tcgggtcgg gttctggctc aggatccggt accccaaaaa agaagagaaa     7980
ggtcgacccg aagaagaaaa ggaaagtcga ccctaaaaaa aaacgcaaag ttgatgcgct     8040
tgacgacttt gacttggaca tgttgggatc agatgccctc gacgactttg atctcgatat     8100
gcttggttcg gacgcgcttg acgatttcga tcttgacatg ctcggttctg atgcacttga     8160
tgacttcgat ttggacatgc tgcccaaaaa gaaaagaaag gtggatccaa agaagaaacg     8220
caaagtccct actcaggctg ggaagggac tctgagtgaa gctctcctgc aacttcagtt     8280
cgacgacgag gacttgggtg ccctttctcgg gaacagcacc gacccggctg ttttcactga     8340
```

```
cctcgcgtct gttgataatt ccgaattcca acagcttttg aatcaaggaa ttcctgttgc    8400
cccacatact actgaaccca tgctgatgga atatcccgaa gcaataacta gactggtgac    8460
cggtgcgcag cggccgccag acccagctcc agccccgctg ggtgcaccag gactgccgaa    8520
tggcttgctg tcaggcgatg aagactttag ttcgatcgct gatatggact tctctgcact    8580
gcttattaat tccaggtctt ctggtagtcg ggactctcgc gagggtatgt tcttgccaaa    8640
accagaggct ggatcggcaa tatctgatgt ttttgaggga cgggaggtct gccagccgaa    8700
acgcatccgc ccgtttcacc cgccaggtag cccctgggca aaccgcccat tgcccgcctc    8760
gcttgcccca accccaccg gtcctgttca cgaacccgtc ggatctctga ccccagcccc    8820
tgttccacag ccgttggacc cagccccagc agtcaccccg gaggccagtc atctcctgga    8880
ggacccagat gaagagacca gtcaggcagt taaggctttg cggaaatgg ctgacaccgt    8940 catacctcag aaagaagaag cagccatttg cggacagatg gatctgtctc atcccccctcc   9000 ccggggtcac cttgatgagc tgacaacaac gctggagagt atgacggaag atcttaactt    9060
ggactcacct ctgaccccgg aactcaacga atattggat acatttttga cgatgagtg    9120 tctgcttcat gcaatgcaca tcagtaccgg actgagtata tttgatacta gcttgtttaa    9180
gctttgatag gacgtccgat cgttcaaaca tttggcaata aagtttctta agattgaatc    9240
ctgttgccgg tcttgcgatg attatcatat aatttctgtt gaattacgtt aagcatgtaa    9300
taattaacat gtaatgcatg acgttatta tgagatgggt ttttatgatt agagtcccgc    9360
aattatacat ttaatacgcg atagaaaaca aaatatagcg cgcaaactag gataaattat    9420
cgcgcgcggt gtcatctatg ttactagatc gggaattgat ccccccctcga cagcttccgg    9480 aaagggcgaa ttcgcaactt tgtatacaaa agttgaacga gaacgtaaa atgatataaa    9540 tatcaatata ttaaattaga ttttgcataa aaaacagact acataatact gtaaaacaca    9600
acatatccag tcactatgcc atccagctga tatcccctat agtgagtcgt attacatggt    9660
catagctgtt tcctggcagc tctggcccgt gtctcaaaat ctctgatgtt acattgcaca    9720
agataaaaat atatcatcat gcctcctc                                       9748
```

<210> SEQ ID NO 47
<211> LENGTH: 5063
<212> TYPE: DNA
<213> ORGANISM: Artificial Sequence
<220> FEATURE:
<223> OTHER INFORMATION: Vector

<400> SEQUENCE: 47

```
agttagcaat cagaacgtgt ctgacgtaca ggtcgcatcc gtgtacgaac gctagcagca      60
cggatctaac acaaacacgg atctaacaca aacatgaaca gaagtagaac taccgggccc     120
taaccatgga ccggaacgcc gatctagaga aggtagagag ggggggggg gggaggacga     180 gcggcgtacc ttgaagcgga ggtgccgacg ggtggatttg ggggagatct ggttgtgtgt     240
gtgtgcgctc cgaacaacac gaggttgggg aaagagggtg tggaggggt gtctatttat      300 tacggcgggc gaggaaggga aagcgaagga gcggtgggaa aggaatcccc cgtagctgcc     360
ggtgccgtga gaggaggagg aggccgcctg ccgtgccggc tcacgtctgc cgctccgcca     420
cgcaatttct ggatgccgac agcggagcaa gtccaacggt ggagcggaac tctcgagagg     480
ggtccagagg cagcgacaga gatgccgtgc cgtctgcttc gcttggcccg acgcgacgct     540
gctggttcgc tggttggtgt ccgttagact cgtcgacggc gtttaacagg ctggcattat     600
```

-continued

```
ctactcgaaa caagaaaaat gtttccttag ttttttaat ttcttaaagg gtatttgttt       660
aatttttagt cactttattt tattctattt tatatctaaa ttattaaata aaaaaactaa      720
aatagagttt tagttttctt aatttagagg ctaaaataga ataaaataga tgtactaaaa      780
aaattagtct ataaaaacca ttaaccctaa accctaaatg gatgtactaa taaaatggat      840
gaagtattat ataggtgaag ctatttgcaa aaaaaaagga gaacacatgc acactaaaaa      900
gataaaactg tagagtcctg ttgtcaaaat actcaattgt cctttagacc atgtctaact     960
gttcatttat atgattctct aaaacactga tattattgta gtactataga ttatattatt    1020
cgtagagtaa agtttaaata tatgtataaa gatagataaa ctgcacttca acaagtgtg     1080 acaaaaaaaa tatgtggtaa ttttttataa cttagacatg caatgctcat tatctctcta   1140
gagggaacgc catggggcaa cttttgtata caaagttggc attataaaaa agcattgctc    1200
atcaatttgt tgcaacgaac aggtcactat cagtcaaaat aaaatcatta ttgggcccga    1260
gcttaagact ggccgtcgtt ttacaacgtc gtgactggga aacatccat gcaagcgtta     1320 acgcgagagt agggaactgc caggcatcaa ataaaacgaa aggctcagtc ggaagactgg    1380
gcctttcgtt ttatctgttg tttgtcggtg aacgctctcc tgagtaggac aaatccgccg    1440
ggagcggatt tgaacgttgt gaagcaacgg cccgagggt ggcgggcagg acgcccgcca     1500
taaactgcca ggcatcaaac taagcagaag gccatcctga cggatggcct ttttgcgttt    1560
ctacaaactc ttcctggctc gcggtacgcg tattaattgc gttgcgctca ctgcccgctt    1620
tccagtcggg aaacctgtcg tgccagctgc attaatgaat cggccaacgc gcggggagag    1680
gcggtttgcg tattgggcgc tcttccgctt cctcgctcac tgactcgctg cgctcggtcg    1740
ttcggctgcg gcgagcggta tcagctcact caaaggcggt aatacggtta ccacagaat     1800 caggggataa cgcaggaaag aacatgtgag caaaaggcca gcaaaaggcc aggaaccgta    1860
aaaaggccgc gttgctggcg ttttttccata ggctccgccc cctgacgag catcacaaaa     1920 atcgacgctc aagtcagagg tggcgaaacc cgacaggact ataaagatac caggcgtttc    1980
cccctggaag ctccctcgtg cgctctcctg ttccgaccct gccgcttacc ggatacctgt    2040
ccgcctttct cccttcggga agcgtggcgc tttctcatag ctcacgctgt aggtatctca    2100
gttcggtgta ggtcgttcgc tccaagctgg gctgtgtgca cgaaccccc gttcagcccg     2160 accgctgcgc cttatccggt aactatcgtc ttgagtccaa cccggtaaga cacgacttat    2220
cgccactggc agcagccact ggtaacagga ttagcagagc gaggtatgta ggcggtgcta    2280
cagagttctt gaagtggtgg cctaactacg gctacactag aagaacagta tttggtatct    2340
gcgctctgct gaagccagtt accttcggaa aaagagttgg tagctcttga tccggcaaac    2400
aaaccaccgc tggtagcggt ggtttttttg tttgcaagca gcagattacg cgcagaaaaa    2460
aaggatctca agaagatcct ttgatctttt ctacggggtc tgacgctcag tggaacgacg    2520
cgtaactcac gttaagggat tttggtcatg ggtggctcga gggttatttg ccgactacct    2580
tggtgatctc gcctttcacg tagtggacaa attcttccaa ctgatctgcg cgcgaggcca    2640
agcgatcttc ttcttgtcca agataagcct gtctagcttc aagtatgacg ggctgatact    2700
gggccggcag cgctccatt gcccagtcgg cagcgacatc cttcggcgcg attttgccgg     2760
ttactgcgct gtaccaaatg cgggacaacg taagcactac atttcgctca tcgccagccc    2820
agtcgggcgg cgagttccat agcgttaagg tttcatttag cgcctcaaat agatcctgtt    2880
caggaaccgg atcaaagagt tcctccgccg ctggacctac caaggcaacg ctatgttctc    2940
ttgcttttgt cagcaagata gccagatcaa tgtcgatcgt ggctggctcg aagatacctg    3000
```

```
caagaatgtc attgcgctgc cattctccaa attgcagttc gcgcttagct ggataacgcc    3060
acggaatgat gtcgtcgtgc acaacaatgg tgacttctac agcgcggaga atctcgctct    3120
ctccagggga agccgaagtt tccaaaaggt cgttgatcaa agctcgccgc gttgtttcat    3180
caagccttac ggtcaccgta accagcaaat caatatcact gtgtggcttc aggccgccat    3240
ccactgcgga gccgtacaaa tgtacggcca gcaacgtcgg ttcgagatgg cgctcgatga    3300
cgccaactac ctctgatagt tgagtcgata cttcggcgat caccgcttcc ctcataatgt    3360
ttaactttgt tttagggcga ctgccctgct gcgtaacatc gttgctgctc cataacatca    3420
aacatcgacc cacggcgtaa cgcgcttgct gcttggatgc ccgaggcata gactgtaccc    3480
caaaaaaaca gtcataacaa gccatgaaaa ccgccactgc gccgttacca ccgctgcgtt    3540
cggtcaaggt tctggaccag ttgcgtgagc gcatacgcta cttgcattac agcttacgaa    3600
ccgaacaggc ttatgtccac tgggttcgtg ccttcatccg tttccacggt gtgcgtcacc    3660
cggcaacctt gggtagcagc gaagtcgagg catttctgtc ctggctggtc cagaggaggc    3720
atgatgatat attttatct tgtgcaatgt aacatcagag attttgagac acgggccaga    3780
gctgccagga aacagctatg accatgtaat acgactcact ataggggatg ctatgaccat    3840
gtaatacgac tcactatagg ggatatcagc tggatggcaa ataatgattt tattttgact    3900
gatagtgacc tgttcgttgc aacaaattga tgagcaatta tttttataa tgccaacttt    3960 gtacaagaaa gctgggtcga attccggccg ggtaccgtcc cattcgccat gccgaagcat    4020
gttgcccagc cggcgccagc gaggaggctg ggaccatgcc ggccagagac gccgcggtca    4080
gactgagctc cgtctcgtgc cacttctcag atttgagaag ctcaacgggc tttgccacct    4140
ggaaagtggc cattggcaca cccgttgaaa aattctgtcc tctagaccga cgagcttact    4200
cgtttcgtcc tcacggactc atcagggtct aggatccctg cagaagtaac accaaacaac    4260
agggtgagca tcgacaaaag aaacagtacc aagcaaataa atagcgtatg aaggcagggc    4320
taaaaaaatc cacatatagc tgctgcatat gccatcatcc aagtatatca agatcaaaat    4380
aattataaaa catacttgtt tattataata gataggtact caaggttaga gcatatgaat    4440
agatgctgca tatgccatca tgtatatgca tcagtaaaac ccacatcaac atgtatacct    4500
atcctagatc gatatttcca tccatcttaa actcgtaact atgaagatgt atgacacaca    4560
catacagttc caaattaat aaatacacca ggtagtttga acagtattc tactccgatc    4620 tagaacgaat gaacgaccgc ccaaccacac cacatcatca caaccaagcg aacaaaaagc    4680
atctctgtat atgcatcagt aaaacccgca tcaacatgta tacctatcct agatcgatat    4740
ttccatccat catcttcaat tcgtaactat gaatatgtat ggcacacaca tacagatcca    4800
aaattaataa atccaccagg tagtttgaaa cagaattaat tctactccga tctagaacga    4860
ccgcccaacc agaccacatc atcacaacca agacaaaaaa aagcatgaaa agatgacccg    4920
acaaacaagt gcacggcata tattgaaata aggaaaagg gcaaaccaaa ccctatgcaa    4980
cgaaacaaaa aaaatcatga aatcgatccc gtctgcggaa cggctagagc catcccagga    5040
ttccccaaag agaaacactg gca                                            5063
```

```
<210> SEQ ID NO 48
<211> LENGTH: 5072
<212> TYPE: DNA
<213> ORGANISM: Artificial Sequence
<220> FEATURE:
<223> OTHER INFORMATION: Vector
```

<400> SEQUENCE: 48

```
tcctcccccc cccctctct accttctcta gatcggcgtt ccggtccatg gttagggccc      60
ggtagttcta cttctgttca tgtttgtgtt agatccgtgt ttgtgttaga tccgtgctgc     120
tagcgttcgt acacggatgc gacctgtacg tcagacacgt tctgattgct aacttgccag    180
tgtttctctt tggggaatcc tgggatggct ctagccgttc cgcagacggg atcgatttca    240
tgattttttt tgtttcgttg catagggttt ggtttgccct tttcctttat ttcaatatat    300
gccgtgcact tgtttgtcgg gtcatctttt catgctttt tttgtcttgg ttgtgatgat     360
gtggtctggt tgggcggtcg ttctagatcg gagtagaatt aattctgttt caaactacct    420
ggtggattta ttaattttgg atctgtatgt gtgtgccata catattcata gttacgaatt    480
gaagatgatg gatggaaata tcgatctagg ataggtatac atgttgatgc gggttttact    540
gatgcatata cagagatgct ttttgttcgc ttggttgtga tgatgtggtg tggttgggcg    600
gtcgttcatt cgttctagat cggagtagaa tactgtttca aactacctgg tgtatttatt    660
aattttggaa ctgtatgtgt gtgtcataca tcttcatagt tacgagttta agatggatgg    720
aaatatcgat ctaggatagg tatacatgtt gatgtgggtt ttactgatgc atatacatga    780
tggcatatgc agcatctatt catatgctct aaccttgagt acctatctat tataataaac    840
aagtatgttt tataattatt ttgatcttga tatacttgga tgatggcata tgcagcagct    900
atatgtggat ttttttagcc ctgccttcat acgctattta tttgcttggt actgtttctt    960
ttgtcgatgc tcaccctgtt gtttggtgtt acttctgcag ggatccctcg ccctgatgag   1020
tccgtgagga cgaaacgagt aagctcgtcg gcgaggttct gtcttttggt caggacaacc   1080
gtctagctat aagtgctgca ggggtgtgag aaactcctat tgctggacga tgtctctttc   1140
gaggcattag cacgagacgg agctcagtct gaccgcggcg tctctggccg gcatggtccc   1200
agcctcctcg ctggcgccgg ctgggcaaca tgcttcggca tggcgaatgg gacggtaccc   1260
ggccggaatt cgacccagct ttcttgtaca aagttggcat tataaaaaat aattgctcat   1320
caatttgttg caacgaacag gtcactatca gtcaaaataa aatcattatt tgccatccag   1380
ctgatatccc ctatagtgag tcgtattaca tggtcatagc atccctata gtgagtcgta    1440
ttacatggtc atagctgttt cctggcagct ctggcccgtg tctcaaaatc tctgatgtta   1500
cattgcacaa gataaaaata tatcatcatg cctcctctgg accagccagg acagaaatgc   1560
ctcgacttcg ctgctaccca aggttgccgg gtgacgcaca ccgtggaaac ggatgaaggc   1620
acgaacccag tggacataag cctgttcggt tcgtaagctg taatgcaagt agcgtatgcg   1680
ctcacgcaac tggtccagaa ccttgaccga acgcagcggt ggtaacggcg cagtggcggt   1740
tttcatggct tgttatgact gtttttttgg ggtacagtct atgcctcggg catccaagca   1800
gcaagcgcgt tacgccgtgg gtcgatgttt gatgttatgg agcagcaacg atgttacgca   1860
gcagggcagt cgccctaaaa caaagttaaa cattatgagg gaagcggtga tcgccgaagt   1920
atcgactcaa ctatcagagg tagttggcgt catcgagcgc catctcgaac cgacgttgct   1980
ggccgtacat ttgtacggct ccgcagtgga tggcggcctg aagccacaca gtgatattga   2040
tttgctggtt acggtgaccg taaggcttga tgaaacaacg cggcgagctt tgatcaacga   2100
ccttttggaa acttcggctt cccctggaga gagcgagatt ctccgcgctg tagaagtcac   2160
cattgttgtg cacgacgaca tcattccgtg gcgttatcca gctaagcgcg aactgcaatt   2220
tggagaatgg cagcgcaatg acattcttgc aggtatcttc gagccagcca cgatcgacat   2280
tgatctggct atcttgctga caaaagcaag agaacatagc gttgccttgg taggtccagc   2340
```

```
ggcggaggaa ctctttgatc cggttcctga acaggatcta tttgaggcgc taaatgaaac    2400
cttaacgcta tggaactcgc cgcccgactg ggctggcgat gagcgaaatg tagtgcttac    2460
gttgtcccgc atttggtaca gcgcagtaac cggcaaaatc gcgccgaagg atgtcgctgc    2520
cgactgggca atggagcgcc tgccggccca gtatcagccc gtcatacttg aagctagaca    2580
ggcttatctt ggacaagaag aagatcgctt ggcctcgcgc gcagatcagt tggaagaatt    2640
tgtccactac gtgaaaggcg agatcaccaa ggtagtcggc aaataaccct cgagccaccc    2700
atgaccaaaa tcccttaacg tgagttacgc gtcgttccac tgagcgtcag accccgtaga    2760
aaagatcaaa ggatcttctt gagatccttt ttttctgcgc gtaatctgct gcttgcaaac    2820
aaaaaaacca ccgctaccag cggtggtttg tttgccggat caagagctac caactctttt    2880
tccgaaggta actggcttca gcagagcgca gataccaaat actgttcttc tagtgtagcc    2940
gtagttaggc caccacttca agaactctgt agcaccgcct acatacctcg ctctgctaat    3000
cctgttacca gtggctgctg ccagtggcga taagtcgtgt cttaccgggt tggactcaag    3060
acgatagtta ccggataagg cgcagcggtc gggctgaacg gggggttcgt gcacacagcc    3120
cagcttggag cgaacgacct acaccgaact gagataccta cagcgtgagc tatgagaaag    3180
cgccacgctt cccgaaggga gaaaggcgga caggtatccg gtaagcggca gggtcggaac    3240
aggagagcgc acgagggagc ttccaggggg aaacgcctgg tatctttata gtcctgtcgg    3300
gtttcgccac ctctgacttg agcgtcgatt tttgtgatgc tcgtcagggg ggcggagcct    3360
atggaaaaac gccagcaacg cggcctttt acggttcctg gccttttgct ggccttttgc    3420
tcacatgttc tttcctgcgt tatcccctga ttctgtggat aaccgtatta ccgcctttga    3480
gtgagctgat accgctcgcc gcagccgaac gaccgagcgc agcgagtcag tgagcgagga    3540
agcggaagag cgcccaatac gcaaaccgcc tctccccgcg cgttggccga ttcattaatg    3600
cagctggcac gacaggtttc ccgactggaa agcgggcagt gagcgcaacg caattaatac    3660
gcgtaccgcg agccaggaag agtttgtaga aacgcaaaaa ggccatccgt caggatggcc    3720
ttctgcttag tttgatgcct ggcagtttat gcgggcgtc ctgcccgcca ccctccgggc    3780
cgttgcttca caacgttcaa atccgctccc ggcggatttg tcctactcag agagcgttc    3840 accgacaaac aacagataaa acgaaaggcc cagtcttccg actgagcctt tcgtttatt    3900 tgatgcctgg cagttcccta ctctcgcgtt aacgcttgca tggatgtttt cccagtcacg    3960
acgttgtaaa acgacggcca gtcttaagct cgggcccaat aatgatttta ttttgactga    4020
tagtgacctg ttcgttgcaa caaattgatg agcaatgctt ttttataatg ccaactttgt    4080
atacaaaagt tgccccatgg cgttccctct agagagataa tgagcattgc atgtctaagt    4140
tataaaaaat taccacatat ttttttgtc acacttgttt gaagtgcagt ttatctatct    4200
ttatacatat atttaaactt tactctacga ataatataat ctatagtact acaataatat    4260
cagtgtttta gagaatcata taaatgaaca gttagacatg gtctaaagga caattgagta    4320
ttttgacaac aggactctac agtttatct ttttagtgtg catgtgttct ccttttttt    4380 tgcaaatagc ttcacctata taatacttca tccattttat tagtcatcc atttagggtt    4440 tagggttaat ggttttata gactaatttt tttagtacat ctattttatt ctattttagc    4500
ctctaaatta agaaaactaa aactctattt tagtttttt atttaataat ttagatataa    4560
aatagaataa aataaagtga ctaaaaatta aacaaatacc ctttaagaaa ttaaaaaaac    4620
taaggaaaca tttttcttgt ttcgagtaga taatgccagc ctgttaaacg ccgtcgacga    4680
```

-continued

```
gtctaacgga caccaaccag cgaaccagca gcgtcgcgtc gggccaagcg aagcagacgg    4740
cacggcatct ctgtcgctgc ctctggaccc ctctcgagag ttccgctcca ccgttggact    4800
tgctccgctg tcggcatcca gaaattgcgt ggcggagcgg cagacgtgag ccggcacggc    4860
aggcggcctc ctcctcctct cacggcaccg gcagctacgg gggattcctt tcccaccgct    4920
ccttcgcttt cccttcctcg cccgccgtaa taaatagaca ccccctccac accctctttc    4980
cccaacctcg tgttgttcgg agcgcacaca cacacaacca gatctccccc aaatccaccc    5040
gtcggcacct ccgcttcaag gtacgccgct cg                                  5072
```

<210> SEQ ID NO 49
<211> LENGTH: 5069
<212> TYPE: DNA
<213> ORGANISM: Artificial Sequence
<220> FEATURE:
<223> OTHER INFORMATION: Vector

<400> SEQUENCE: 49

```
tttcccagtc acgacgttgt aaaacgacgg ccagtcttaa gctcgggccc aaataatgat      60
tttattttga ctgatagtga cctgttcgtt gcaacaaatt gatgagcaat gcttttttat     120
aatgccaact ttgtatacaa aagttgcccc atggcgttcc ctctagagag ataatgagca     180
ttgcatgtct aagttataaa aaattaccac atatttttt tgtcacactt gtttgaagtg     240
cagtttatct atctttatac atatatttaa actttactct acgaataata taatctatag     300
tactacaata atatcagtgt tttagagaat catataaatg aacagttaga catggtctaa     360
aggacaattg agtattttga acaggact ctacagtttt atctttttag tgtgcatgtg      420
ttctcctttt tttttgcaaa tagcttcacc tatataatac ttcatccatt ttattagtac     480
atccatttag ggtttagggt taatggtttt tatagactaa ttttttttagt acatctattt     540 tattctatt tagcctctaa attaagaaaa ctaaaactct attttagttt ttttatttaa      600
taatttagat ataaaataga ataaaataaa gtgactaaaa attaaacaaa taccctttaa     660
gaaattaaaa aaactaagga acatttttc ttgtttcgag tagataatgc cagcctgtta     720
aacgccgtcg acgagtctaa cggacaccaa ccagcgaacc agcagcgtcg cgtcgggcca     780
agcgaagcag acggcacggc atctctgtcg ctgcctctgg accctctcg agagttccgc     840 tccaccgttg gacttgctcc gctgtcggca tccagaaatt gcgtggcgga gcggcagacg     900
tgagccggca cggcaggcgg cctcctcctc ctctcacggc accggcagct acggggatt     960 cctttcccac cgctccttcg ctttcccttc ctcgcccgcc gtaataaata gacacccct    1020 ccacaccctc tttccccaac ctcgtgttgt tcggagcgca cacacacaca accagatctc    1080
ccccaaatcc accgtcggc acctccgctt caaggtacgc cgctcgtcct ccccccccc    1140 cccctctcta ccttctctag atcggcgttc cggtccatgg ttagggcccg gtagttctac    1200
ttctgttcat gtttgtgtta gatccgtgtt tgtgttagat ccgtgctgct agcgttcgta    1260
cacggatgcg acctgtacgt cagacacgtt ctgattgcta acttgccagt gtttctcttt    1320
ggggaatcct gggatggctc tagccgttcc gcagacggga tcgatttcat gatttttttt    1380
gtttcgttgc atagggtttg gtttgccctt ttcctttatt tcaatatatg ccgtgcactt    1440
gtttgtcggg tcatcttttc atgcttttt ttgtcttggt tgtgatgatg tggtctggtt    1500
gggcggtcgt tctagatcgg agtagaatta attctgtttc aaactacctg gtggatttat    1560
taattttgga tctgtatgtg tgtgccatac atattcatag ttacgaattg aagatgatgg    1620
atggaaatat cgatctagga taggtataca tgttgatgcg ggttttactg atgcatatac    1680
```

```
agagatgctt tttgttcgct tggttgtgat gatgtggtgt ggttgggcgg tcgttcattc   1740
gttctagatc ggagtagaat actgtttcaa actacctggt gtatttatta attttggaac   1800
tgtatgtgtg tgtcatacat cttcatagtt acgagtttaa gatggatgga aatatcgatc   1860
taggataggt atacatgttg atgtgggttt tactgatgca tatacatgat ggcatatgca   1920
gcatctattc atatgctcta accttgagta cctatctatt ataataaaca agtatgtttt   1980
ataattattt tgatcttgat atacttggat gatggcatat gcagcagcta tatgtggatt   2040 ttttagccc tgccttcata cgctatttat ttgcttggta ctgtttcttt tgtcgatgct   2100
caccctgttg tttggtgtta cttctgcagg gatcccagaa cctgatgagt ccgtgaggac   2160
gaaacgagta agctcgtcgt tctgtctttt ggtcaggaca accgtctagc tataagtgct   2220
gcagggtgtg agaaactcct attgctggac gatgtctctt acgaggcatt agcacgagac   2280
ggagctcagt ctgaccgcgg cgtctctggc cggcatggtc ccagcctcct cgctggcgcc   2340
ggctgggcaa catgcttcgg catggcgaat gggacggtac ccggccggaa ttcgacccag   2400
ctttcttgta caaagttggc attataaaaa ataattgctc atcaatttgt tgcaacgaac   2460
aggtcactat cagtcaaaat aaaatcatta tttgccatcc agctgatatc ccctatagtg   2520
agtcgtatta catggtcata gcatcccta tagtgagtcg tattacatgg tcatagctgt   2580
ttcctggcag ctctgcccg tgtctcaaaa tctctgatgt tacattgcac aagataaaaa   2640
tatatcatca tgcctcctct ggaccagcca ggacagaaat gcctcgactt cgctgctgcc   2700
caaggttgcc gggtgacgca caccgtggaa acggatgaag gcacgaaccc agtggacata   2760
agcctgttcg gttcgtaagc tgtaatgcaa gtagcgtatg cgctcacgca actggtccag   2820
aaccttgacc gaacgcagcg gtggtaacgg cgcagtggcg gttttcatgg cttgttatga   2880 ctgtttttt ggggtacagt ctatgcctcg ggcatccaag cagcaagcgc gttacgccgt   2940
gggtcgatgt ttgatgttat ggagcagcaa cgatgttacg cagcagggca gtcgccctaa   3000
aacaaagtta acatcatga gggaagcggt gatcgccgaa gtatcgactc aactatcaga   3060
ggtagttggc gtcatcgagc gccatctcga accgacgttg ctggccgtac atttgtacgg   3120
ctccgcagtg gatggcggcc tgaagccaca cagtgatatt gatttgctgg ttacggtgac   3180
cgtaaggctt gatgaaacaa cgcggcgagc tttgatcaac gaccttttgg aaacttcggc   3240
ttcccctgga gagagcgaga ttctccgcgc tgtagaagtc accattgttg tgcacgacga   3300
catcattccg tggcgttatc cagctaagcg cgaactgcaa tttggagaat ggcagcgcaa   3360
tgacattctt gcaggtatct tcgagccagc cacgatcgac attgatctgg ctatcttgct   3420
gacaaaagca agagaacata gcgttgcctt ggtaggtcca gcggcggagg aactctttga   3480
tccggttcct gaacaggatc tatttgaggc gctaaatgaa accttaacgc tatggaactc   3540
gccgcccgac tgggctggcg atgagcgaaa tgtagtgctt acgttgtccc gcatttggta   3600
cagcgcagta accggcaaaa tcgcgccgaa ggatgtcgct gccgactggg caatggagcg   3660
cctgccggcc cagtatcagc ccgtcatact tgaagctaga caggcttatc ttggacaaga   3720
agaagatcgc ttggcctcgc gcgcagatca gttggaagaa tttgtccact acgtgaaagg   3780
cgagatcacc aaggtagtcg gcaaataacc ctcgagccac ccatgaccaa atcccttaa   3840 cgtgagttac gcgtcgttcc actgagcgtc agaccccgta gaaaagatca aggatcttc   3900 ttgagatcct ttttttctgc gcgtaatctg ctgcttgcaa acaaaaaaac caccgctacc   3960
agcggtggtt tgtttgccgg atcaagagct accaactctt tttccgaagg taactggctt   4020
```

```
cagcagagcg cagataccaa atactgtcct tctagtgtag ccgtagttag gccaccactt    4080
caagaactct gtagcaccgc ctacatacct cgctctgcta atcctgttac cagtggctgc    4140
tgccagtggc gataagtcgt gtcttaccgg gttggactca agacgatagt taccggataa    4200
ggcgcagcgt cgggctgaa cgggggttc gtgcacacag cccagcttgg agcgaacgac     4260
ctacaccgaa ctgagatacc tacagcgtga gcattgagaa agcgccacgc ttcccgaagg    4320
gagaaaggcg gacaggtatc cggtaagcgg cagggtcgga acaggagagc gcacgaggga    4380
gcttccaggg ggaaacgcct ggtatcttta tagtcctgtc gggtttcgcc acctctgact    4440
tgagcgtcga ttttgtgat gctcgtcagg ggggcggagc ctatggaaaa acgccagcaa     4500
cgcggccttt ttacggttcc tggccttttg ctggcctttt gctcacatgt tctttcctgc    4560
gttatcccct gattctgtgg ataaccgtat taccgccttt gagtgagctg ataccgctcg    4620
ccgcagccga acgaccgagc gcagcgagtc agtgagcgag gaagcggaag agcgcccaat    4680
acgcaaaccg cctctccccg cgcgttggcc gattcattaa tgcagctggc acgacaggtt    4740
tcccgactgg aaagcgggca gtgagcgcaa cgcaattaat gcgcgtaccg ctcgccagga    4800
agagtttgta gaaacgcaaa aaggccatcc gtcaggatgg ccttctgctt agtttgatgc    4860
ctggcagttt atggcgggcg tcctgcccgc caccctccgg gccgttgctt cacaacgttc    4920
aaatccgctc ccggcggatt tgtcctactc aggagagcgt tcaccgacaa caacagata    4980 aaacgaaagg cccagtcttc cgactgagcc tttcgtttta tttgatgcct ggcagttccc    5040
tactctcgcg ttaacgcttg catggatgt                                      5069
```

<210> SEQ ID NO 50
<211> LENGTH: 5094
<212> TYPE: DNA
<213> ORGANISM: Artificial Sequence
<220> FEATURE:
<223> OTHER INFORMATION: Vector

<400> SEQUENCE: 50

```
tttcccagtc acgacgttgt aaaacgacgg ccagtcttaa gctcgggccc aaataatgat     60
tttattttga ctgatagtga cctgttcgtt gcaacaaatt gatgagcaat gcttttttat    120
aatgccaact ttgtatacaa aagttgcccc atggcgttcc ctctagagag ataatgagca    180
ttgcatgtct aagttataaa aaattaccac atattttttt tgtcacactt gtttgaagtg    240
cagtttatct atctttatac atatatttaa actttactct acgaataata taatctatag    300
tactacaata atatcagtgt tttagagaat catataaatg aacagttaga catggtctaa    360
aggacaattg agtattttga acacaggact ctacagtttt atcttttttag tgtgcatgtg    420 ttctcctttt tttttgcaaa tagcttcacc tatataatac ttcatccatt ttattagtac    480
atccatttag ggtttagggt taatggtttt tatagactaa ttttttttagt acatctattt    540 tattctattt tagcctctaa attaagaaaa ctaaaactct attttagttt ttttatttaa    600
taatttagat ataaaataga ataaaataaa gtgactaaaa attaaacaaa tacccttttaa   660 gaaattaaaa aaactaagga aacatttttc ttgtttcgag tagataatgc cagcctgtta    720
aacgccgtcg acgagtctaa cggacaccaa ccagcgaacc agcagcgtcg cgtcgggcca    780
agcgaagcag acggcacggc atctctgtcg ctgcctctgg acccctctcg agagttccgc    840
tccaccgttg gacttgctcc gctgtccggca tccagaaatt gcgtggcgga gcggcagacg    900
tgagccggca cggcaggcgg cctcctcctc ctctcacggc accggcagct acggggatt    960 cctttcccac cgctccttcg cttttccctcc ctcgcccgcc gtaataaata gacacccct   1020
```

```
ccacaccctc tttccccaac ctcgtgttgt tcggagcgca cacacacaca accagatctc    1080
ccccaaatcc acccgtcggc acctccgctt caaggtacgc cgctcgtcct ccccccccc     1140
cccctctcta ccttctctag atcggcgttc cggtccatgg ttagggcccg gtagttctac   1200
ttctgttcat gtttgtgtta gatccgtgtt tgtgttagat ccgtgctgct agcgttcgta   1260
cacggatgcg acctgtacgt cagacacgtt ctgattgcta acttgccagt gtttctcttt   1320
ggggaatcct gggatggctc tagccgttcc gcagacggga tcgatttcat gatttttttt   1380
gtttcgttgc atagggtttg gtttgcccct ttcctttatt tcaatatatg ccgtgcactt   1440
gtttgtcggg tcatcttttc atgcttttt ttgtcttggt tgtgatgatg tggtctggtt    1500
gggcggtcgt tctagatcgg agtagaatta attctgtttc aaactacctg gtggatttat   1560
taattttgga tctgtatgtg tgtgccatac atattcatag ttacgaattg aagatgatgg   1620
atggaaatat cgatctagga taggtataca tgttgatgcg ggttttactg atgcatatac   1680
agagatgctt tttgttcgct tggttgtgat gatgtggtgt ggttgggcgg tcgttcattc   1740
gttctagatc ggagtagaat actgtttcaa actacctggt gtatttatta attttggaac   1800
tgtatgtgtg tgtcatacat cttcatagtt acgagtttaa gatggatgga aatatcgatc   1860
taggataggt atacatgttg atgtgggttt tactgatgca tatacatgat ggcatatgca   1920
gcatctattc atatgctcta accttgagta cctatctatt ataataaaca agtatgtttt   1980
ataattattt tgatcttgat atacttggat gatggcatat gcagcagcta tatgtggatt   2040
tttttagccc tgccttcata cgctatttat ttgcttggta ctgtttcttt tgtcgatgct   2100
caccctgttg tttggtgtta cttctgcagg gatcctagac cctgatgagt ccgtgaggac   2160
gaaacgagta agctcgtcgg tctagaggac agaatttttc aacgggtgtg ccaatggcca   2220
cttttccaggt ggcaaagccc gttgagcttc tcaggccaac atgaggatca cccatgtctg   2280
cagggcctga gaagtggcac gagacggagc tcagtctgac cgcggcgtct ctggccggca   2340
tggtcccagc ctcctcgctg gcgccggctg ggcaacatgc ttcggcatgg cgaatgggac   2400
ggtacccggc cggaattcga cccagctttc ttgtacaaag ttggcattat aaaaaataat   2460
tgctcatcaa tttgttgcaa cgaacaggtc actatcagtc aaaataaaat cattatttgc   2520
catccagctg atatccccta tagtgagtcg tattacatgg tcatagcatc ccctatagtg   2580
agtcgtatta catggtcata gctgtttcct ggcagctctg gcccgtgtct caaaatctct   2640
gatgttacat tgcacaagat aaaaatatat catcatgcct cctctggacc agccaggaca   2700
gaaatgcctc gacttcgctg ctgcccaagg ttgccgggtg acgcacaccg tggaaacgga   2760
tgaaggcacg aacccagtgg acataagcct gttcggttcg taagctgtaa tgcaagtagc   2820
gtatgcgctc acgcaactgg tccagaacct tgaccgaacg cagcggtggt aacggcgcag   2880
tggcggtttt catggcttgt tatgactgtt tttttggggt acagtctatg cctcgggcat   2940
ccaagcagca agcgcgttac gccgtgggtc gatgtttgat gttatggagc agcaacgatg   3000
ttacgcagca gggcagtcgc cctaaaacaa agttaaacat catgagggaa gcggtgatcg   3060
ccgaagtatc gactcaacta tcagaggtag ttggcgtcat cgagcgccat ctcgaaccga   3120
cgttgctggc cgtacatttg tacggctccg cagtggatgg cggcctgaag ccacacagtg   3180
atattgattt gctggttacg gtgaccgtaa ggcttgatga acaacgcgg cgagctttga    3240
tcaacgacct tttggaaact tcggcttccc ctggagagag cgagattctc cgcgctgtag   3300
aagtcaccat tgttgtgcac gacgacatca ttccgtggcg ttatccagct aagcgcgaac   3360
```

```
tgcaatttgg agaatggcag cgcaatgaca ttcttgcagg tatcttcgag ccagccacga    3420
tcgacattga tctggctatc ttgctgacaa agcaagaga acatagcgtt gccttggtag    3480
gtccagcggc ggaggaactc tttgatccgg ttcctgaaca ggatctattt gaggcgctaa    3540
atgaaacctt aacgctatgg aactcgccgc ccgactgggc tggcgatgag cgaaatgtag    3600
tgcttacgtt gtcccgcatt tggtacagcg cagtaaccgg caaaatcgcg ccgaaggatg    3660
tcgctgccga ctgggcaatg gagcgcctgc cggcccagta tcagcccgtc atacttgaag    3720
ctagacaggc ttatcttgga caagaagaag atcgcttggc ctcgcgcgca gatcagttgg    3780
aagaatttgt ccactacgtg aaaggcgaga tcaccaaggt agtcggcaaa taaccctcga    3840
gccacccatg accaaaatcc cttaacgtga gttacgcgtc gttccactga gcgtcagacc    3900
ccgtagaaaa gatcaaagga tcttcttgag atcctttttt tctgcgcgta atctgctgct    3960
tgcaaacaaa aaaaccaccg ctaccagcgg tggtttgttt gccggatcaa gagctaccaa    4020 ctcttttcc gaaggtaact ggcttcagca gagcgcagat accaaatact gtccttctag    4080
tgtagccgta gttaggccac cacttcaaga actctgtagc accgcctaca tacctcgctc    4140
tgctaatcct gttaccagtg gctgctgcca gtggcgataa gtcgtgtctt accgggttgg    4200
actcaagacg atagttaccg gataaggcgc agcggtcggg ctgaacgggg ggttcgtgca    4260
cacagcccag cttggagcga acgacctaca ccgaactgag atacctacag cgtgagcatt    4320
gagaaagcgc cacgcttccc gaagggagaa aggcggacag gtatccggta agcggcaggg    4380
tcggaacagg agagcgcacg agggagcttc caggggggaaa cgcctggtat ctttatagtc    4440
ctgtcgggtt tcgccacctc tgacttgagc gtcgattttt gtgatgctcg tcaggggggc    4500
ggagcctatg gaaaaacgcc agcaacgcgg cctttttacg gttcctggcc ttttgctggc    4560
cttttgctca catgttcttt cctgcgttat cccctgattc tgtggataac cgtattaccg    4620
cctttgagtg agctgatacc gctcgccgca gccgaacgac cgagcgcagc gagtcagtga    4680
gcgaggaagc ggaagagcgc ccaatacgca aaccgcctct ccccgcgcgt tggccgattc    4740
attaatgcag ctggcacgac aggtttcccg actggaaagc gggcagtgag cgcaacgcaa    4800
ttaatacgcg taccgctcgc caggaagagt ttgtagaaac gcaaaaaggc catccgtcag    4860
gatggccttc tgcttagttt gatgcctggc agtttatggc gggcgtcctg cccgccaccc    4920
tccgggccgt tgcttcacaa cgttcaaatc cgctcccggc ggatttgtcc tactcaggag    4980
agcgttcacc gacaaacaac agataaaacg aaaggcccag tcttccgact gagcctttcg    5040
ttttatttga tgcctggcag ttccctactc tcgcgttaac gcttgcatgg atgt          5094
```

<210> SEQ ID NO 51
<211> LENGTH: 5117
<212> TYPE: DNA
<213> ORGANISM: Artificial Sequence
<220> FEATURE:
<223> OTHER INFORMATION: Vector

<400> SEQUENCE: 51

```
tttcccagtc acgacgttgt aaaacgacgg ccagtcttaa gctcgggccc aaataatgat      60
tttattttga ctgatagtga cctgttcgtt gcaacaaatt gatgagcaat gcttttttat     120
aatgccaact ttgtatacaa aagttgcccc atggcgttcc ctctagagag ataatgagca     180
ttgcatgtct aagttataaa aaattaccac atatttttt tgtcacactt gtttgaagtg     240
cagtttatct atctttatac atatatttaa actttactct acgaataata taatctatag     300
tactacaata atatcagtgt tttagagaat catataaatg aacagttaga catggtctaa     360
```

-continued

```
aggacaattg agtattttga caacaggact ctacagtttt atcttttag tgtgcatgtg    420
ttctcctttt ttttgcaaa tagcttcacc tatataatac ttcatccatt ttattagtac    480
atccatttag ggtttagggt taatggtttt tatagactaa ttttttagt acatctattt    540
tattctattt tagcctctaa attaagaaaa ctaaaactct attttagttt ttttatttaa    600
taatttagat ataaaataga ataaaataaa gtgactaaaa attaaacaaa tacccttaa     660
gaaattaaaa aaactaagga aacatttttc ttgtttcgag tagataatgc cagcctgtta    720
aacgccgtcg acgagtctaa cggacaccaa ccagcgaacc agcagcgtcg cgtcgggcca    780
agcgaagcag acggcacggc atctctgtcg ctgcctctgg accctctcg agagttccgc     840
tccaccgttg gacttgctcc gctgtcggca tccagaaatt gcgtggcgga gcggcagacg    900
tgagccggca cggcaggcgg cctcctcctc ctctcacggc accggcagct acggggatt     960
cctttcccac cgctccttcg cttccctc ctcgcccgcc gtaataaata gacaccccct      1020
ccacacccctc tttccccaac ctcgtgttgt tcggagcgca cacacacaca accagatctc   1080
ccccaaatcc acccgtcggc acctccgctt caaggtacgc cgctcgtcct cccccccccc    1140
cccctctcta ccttctctag atcggcgttc cggtccatgg ttagggcccg gtagttctac    1200
ttctgttcat gtttgtgtta gatccgtgtt tgtgttagat ccgtgctgct agcgttcgta    1260
cacggatgcg acctgtacgt cagacacgtt ctgattgcta acttccagt gtttctcttt     1320
ggggaatcct gggatggctc tagccgttcc gcagacggga tcgatttcat gattttttt     1380
gtttcgttgc atagggtttg gtttgcccctt ttcctttatt tcaatatatg ccgtgcactt   1440
gtttgtcggg tcatctttc atgcttttt tgtcttggt tgtgatgatg tggtctggtt       1500
gggcggtcgt tctagatcgg agtagaatta attctgtttc aaactacctg gtggattat     1560
taattttgga tctgtatgtg tgtgccatac atattcatag ttacgaattg aagatgatgg    1620
atggaaatat cgatctagga taggtataca tgttgatgcg ggttttactg atgcatatac    1680
agagatgctt tttgttcgct tggttgtgat gatgtggtgt ggttgggcgg tcgttcattc    1740
gttctagatc ggagtagaat actgttcaa actacctggt gtatttatta atttggaac     1800
tgtatgtgtg tgtcatacat cttcatagtt acgagttaa gatggatgga aatatcgatc    1860
taggataggt atacatgttg atgtggggttt tactgatgca tatacatgat ggcatatgca   1920
gcatctattc atatgctcta accttgagta cctatctatt ataataaaca agtatgttt     1980
ataattattt tgatcttgat atacttggat gatggcatat gcagcagcta tatgtggatt    2040
tttttagccc tgccttcata cgctatttat ttgcttggta ctgtttcttt tgtcgatgct    2100
caccctgttg tttggtgtta cttctgcagg gatccaaatc tctgatgagt ccgtgaggac    2160
gaaacgagta agctcgtcag atttctgtct aaaggacaga atttttcaac gggtgtgcca    2220
atggccactt tccaggtggc aaagcccgtt gaacttctca aaaagaacgc tcgctcagtg    2280
ttctgacgtc ggatcactga gcgagcgatc tgagaagtgg cacagacgg agctcagtct     2340
gaccgcggcg tctctggccg gcatggtccc agcctcctcg ctggcgccgg ctgggcaaca    2400
tgcttcggca tggcgaatgg gacggtaccc ggccggaatt cgacccagct ttcttgtaca    2460
aagttggcat tataaaaaat aattgctcat caatttgttg caacgaacag gtcactatca    2520
gtcaaaataa aatcattatt tgccatccag ctgatatccc ctatagtgag tcgtattaca    2580
tggtcatagc atccctata gtgagtcgta ttacatggtc atagctgttt cctggcagct     2640
ctggcccgtg tctcaaaatc tctgatgtta cattgcacaa gataaaaata tatcatcatg    2700
```

```
cctcctctgg accagccagg acagaaatgc ctcgacttcg ctgctgccca aggttgccgg    2760
gtgacgcaca ccgtggaaac ggatgaaggc acgaacccag tggacataag cctgttcggt    2820
tcgtaagctg taatgcaagt agcgtatgcg ctcacgcaac tggtccagaa ccttgaccga    2880
acgcagcggt ggtaacggcg cagtggcggt tttcatggct tgttatgact gttttttttgg   2940
ggtacagtct atgcctcggg catccaagca gcaagcgcgt tacgccgtgg gtcgatgttt    3000
gatgttatgg agcagcaacg atgttacgca gcagggcagt cgccctaaaa caaagttaaa    3060
catcatgagg gaagcggtga tcgccgaagt atcgactcaa ctatcagagg tagttggcgt    3120
catcgagcgc catctcgaac cgacgttgct ggccgtacat ttgtacggct ccgcagtgga    3180
tggcggcctg aagccacaca gtgatattga tttgctggtt acggtgaccg taaggcttga    3240
tgaaacaacg cggcgagctt tgatcaacga ccttttggaa acttcggctt ccctgagga    3300
gagcgagatt ctccgcgctg tagaagtcac cattgttgtg cacgacgaca tcattccgtg    3360
gcgttatcca gctaagcgcg aactgcaatt tggagaatgg cagcgcaatg acattcttgc    3420
aggtatcttc gagccagcca cgatcgacat tgatctggct atcttgctga caaaagcaag    3480
agaacatagc gttgccttgg taggtccagc ggcggaggaa ctctttgatc cggttcctga    3540
acaggatcta tttgaggcgc taaatgaaac cttaacgcta tggaactcgc cgcccgactg    3600
ggctggcgat gagcgaaatg tagtgcttac gttgtcccgc atttggtaca gcgcagtaac    3660
cggcaaaatc gcgccgaagg atgtcgctgc cgactgggca atggagcgcc tgccggccca    3720
gtatcagccc gtcatacttg aagctagaca ggcttatctt ggacaagaag aagatcgctt    3780
ggcctcgcgc gcagatcagt tggaagaatt tgtccactac gtgaaaggcg agatcaccaa    3840
ggtagtcggc aaataaccct cgagccaccc atgaccaaaa tcccttaacg tgagttacgc    3900
gtcgttccac tgagcgtcag accccgtaga aaagatcaaa ggatcttctt gagatccttt    3960
ttttctgcgc gtaatctgct gcttgcaaac aaaaaaacca ccgctaccag cggtggtttg    4020
tttgccggat caagagctac caactctttt tccgaaggta actggcttca gcagagcgca    4080
gataccaaat actgtccttc tagtgtagcc gtagttaggc caccacttca agaactctgt    4140
agcaccgcct acatacctcg ctctgctaat cctgttacca gtggctgctg ccagtggcga    4200
taagtcgtgt cttaccgggt tggactcaag acgatagtta ccggataagg cgcagcggtc    4260
gggctgaacg gggggttcgt gcacacagcc cagcttggag cgaacgacct acaccgaact    4320
gagataccta cagcgtgagc attgagaaag cgccacgctt cccgaaggga gaaaggcgga    4380
caggtatccg gtaagcggca gggtcggaac aggagagcgc acgagggagc ttccaggggg    4440
aaacgcctgg tatctttata gtcctgtcgg gtttcgccac ctctgacttg agcgtcgatt    4500
tttgtgatgc tcgtcagggg ggcggagcct atggaaaaac gccagcaacg cggccttttt    4560
acggttcctg gccttttgct ggccttttgc tcacatgttc tttcctgcgt tatcccctga    4620
ttctgtggat aaccgtatta ccgcctttga gtgagctgat accgctcgcc gcagccgaac    4680
gaccgagcgc agcgagtcag tgagcgagga agcggaagag cgcccaatac gcaaaccgcc    4740
tctccccgcg cgttggccga ttcattaatg cagctggcac gacaggtttc ccgactggaa    4800
agcgggcagt gagcgcaacg caattaatac gcgtaccgct cgccaggaag agtttgtaga    4860
aacgcaaaaa ggccatccgt caggatggcc ttctgcttag tttgatgcct ggcagtttat    4920
ggcgggcgtc ctgcccgcca ccctccgggc cgttgcttca caacgttcaa atccgctccc    4980
ggcggatttg tcctactcag gagagcgttc accgacaaac aacagataaa acgaaaggcc    5040
cagtcttccg actgagcctt tcgttttatt tgatgcctgg cagttcccta ctctcgcgtt    5100
```
aacgcttgca tggatgt                                                    5117

<210> SEQ ID NO 52
<211> LENGTH: 1791
<212> TYPE: DNA
<213> ORGANISM: Artificial Sequence
<220> FEATURE:
<223> OTHER INFORMATION: Vector

<400> SEQUENCE: 52
tcaccattgt tgtgcacgac gacatcattc cgtggcgtta tccagctaag cgcgaactgc      60
aatttggaga atggcagcgc aatgacattc ttgcaggtat cttcgagcca gccacgatcg     120
acattgatct ggctatcttg ctgacaaaag caagagaaca tagcgttgcc ttggtaggtc     180
cagcggcgga ggaactcttt gatccggttc ctgaacagga tctatttgag cgctaaatg      240
aaaccttaac gctatggaac tcgccgcccg actgggctgg cgatgagcga atgtagtgc      300
ttacgttgtc ccgcatttgg tacagcgcag taaccgcaa atcgcgccg aaggatgtcg      360
ctgccgactg ggcaatggag cgcctgccgg cccagtatca gcccgtcata cttgaagcta     420
gacaggctta tcttggacaa gaagaagatc gcttggcctc gcgcgcagat cagttggaag     480
aatttgtcca ctacgtgaaa ggcgagatca ccaaggtagt cggcaaataa ccctcgagcc     540
acccatgacc aaaatccctt aacgtgagtt acgcgtcgtt ccactgagcg tcagacccg      600
tagaaaagat caaaggatct tcttgagatc ctttttttct gcgcgtaatc tgctgcttgc     660
aaacaaaaaa accaccgcta ccagcggtgg tttgtttgcc ggatcaagag ctaccaactc     720
tttttccgaa ggtaactggc ttcagcagag cgcagatacc aaatactgtc cttctagtgt     780
agccgtagtt aggccaccac ttcaagaact ctgtagcacc gcctacatac ctcgctctgc     840
taatcctgtt accagtggct gctgccagtg gcgataagtc gtgtcttacc gggttggact     900
caagacgata gttaccggat aaggcgcagc ggtcgggctg aacggggggt tcgtgcacac     960
agcccagctt ggagcgaacg acctacaccg aactgagata cctacagcgt gagcattgag    1020
aaagcgccac gcttcccgaa gggagaaagg cggacaggta tccggtaagc ggcagggtcg    1080
gaacaggaga gcgcacgagg gagcttccag ggggaaacgc ctggtatctt tatagtcctg    1140
tcgggtttcg ccacctctga cttgagcgtc gatttttgtg atgctcgtca gggggcgga     1200
gcctatggaa aaacgccagc aacgcggcct ttttacggtt cctggccttt tgctggcctt    1260
ttgctcacat gttctttcct gcgttatccc ctgattctgt ggataaccgt attaccgcct    1320
ttgagtgagc tgataccgct cgccgcagcc gaacgaccga gcgcagcgag tcagtgagcg    1380
aggaagcgga agagcgccca atacgcaaac cgcctctccc cgcgcgttgg ccgattcatt    1440
aatgcagctg gcacgacagg tttcccgact ggaaagcggg cagtgagcgc aacgcaatta    1500
atacgcgtac cgctcgccag gaagagtttg tagaaacgca aaaggccat ccgtcaggat     1560
ggccttctgc ttagtttgat gcctggcagt ttatggcggg cgtcctgccc gccaccctcc    1620
gggccgttgc ttcacaacgt tcaaatccgc tcccggcgga tttgtcctac tcaggagagc    1680
gttcaccgac aaacaacaga taaaacgaaa ggcccagtct tccgactgag cctttcgttt    1740
tatttgatgc ctggcagttc cctactctcg cgttaacgct gcatggatg t              1791

<210> SEQ ID NO 53
<211> LENGTH: 5057
<212> TYPE: DNA
<213> ORGANISM: Artificial Sequence
<220> FEATURE:

<223> OTHER INFORMATION: Vector

<400> SEQUENCE: 53

```
tttcccagtc acgacgttgt aaaacgacgg ccagtcttaa gctcgggccc aaataatgat    60
tttattttga ctgatagtga cctgttcgtt gcaacaaatt gatgagcaat gcttttttat   120
aatgccaact ttgtatacaa aagttgcccc atggcgttcc ctctagagag ataatgagca   180
ttgcatgtct aagttataaa aaattaccac atattttttt tgtcacactt gtttgaagtg   240
cagtttatct atctttatac atatatttaa actttactct acgaataata taatctatag   300
tactacaata atatcagtgt tttagagaat catataaatg aacagttaga catggtctaa   360
aggacaattg agtattttga caacaggact ctacagtttt atcttttttag tgtgcatgtg   420
ttctcctttt tttttgcaaa tagcttcacc tatataatac ttcatccatt ttattagtac   480
atccatttag ggtttagggt taatggtttt tatagactaa ttttttttagt acatctattt   540
tattctattt tagcctctaa attaagaaaa ctaaaactct attttagttt ttttatttaa   600
taatttagat ataaaataga ataaaataaa gtgactaaaa attaaacaaa taccctttaa   660
gaaattaaaa aaactaagga aacattttc ttgtttcgag tagataatgc cagcctgtta   720
aacgccgtcg acgagtctaa cggacaccaa ccagcgaacc agcagcgtcg cgtcgggcca   780
agcgaagcag acggcacggc atctctgtcg ctgcctctgg acccctctcg agagttccgc   840
tccaccgttg gacttgctcc gctgtcggca tccagaaatt gcgtggcgga gcggcagacg   900
tgagccggca cggcaggcgg cctcctcctc ctctcacggc accggcagct acggggggatt   960
cctttcccac cgctccttcg ctttcccttc ctcgcccgcc gtaataaata gacacccccct  1020
ccacaccctc tttccccaac ctcgtgttgt tcggagcgca cacacacaca accagatctc  1080
ccccaaatcc acccgtcggc acctccgctt caaggtacgc cgctcgtcct cccccccccc  1140
cccctctcta ccttctctag atcggcgttc cggtccatgg ttagggcccg gtagttctac  1200
ttctgttcat gtttgtgtta gatccgtgtt tgtgttagat ccgtgctgct agcgttcgta  1260
cacggatgcg acctgtacgt cagacacgtt ctgattgcta acttgccagt gtttctcttt  1320
ggggaatcct gggatggctc tagccgttcc gcagacggga tcgatttcat gattttttt    1380
gtttcgttgc atagggtttg gtttgccctt ttcctttatt tcaatatatg ccgtgcactt  1440
gtttgtcggg tcatcttttc atgctttttt tgtcttggt tgtgatgatg tggtctggtt   1500
gggcggtcgt tctagatcgg agtagaatta attctgtttc aaactacctg gtggatttat  1560
taattttgga tctgtatgtg tgtgccatac atattcatag ttacgaattg aagatgatgg  1620
atggaaatat cgatctagga taggtataca tgttgatgcg ggttttactg atgcatatac  1680
agagatgctt tttgttcgct tggttgtgat gatgtggtgt ggttgggcgg tcgttcattc  1740
gttctagatc ggagtagaat actgtttcaa actacctggt gtatttatta attttggaac  1800
tgtatgtgtg tgtcatacat cttcatagtt acgagtttaa gatggatgga aatatcgatc  1860
taggataggt atacatgttg atgtgggttt tactgatgca tatacatgat ggcatatgca  1920
gcatctattc atatgctcta accttgagta cctatctatt ataataaaca agtatgtttt  1980
ataattattt tgatcttgat atacttggat gatggcatat gcagcagcta tatgtggatt  2040
tttttagccc tgccttcata cgctatttat ttgcttggta ctgtttcttt tgtcgatgct  2100
caccctgttg tttggtgtta cttctgcagg gatccttaga cctgatgagt ccgtgaggac  2160
gaaacgagta agctcgtcgt ctaaaggaca gaattttttca acgggtgtgc caatggccac  2220
tttccaggtg gcaaagcccg ttgaacttca agcgaagtgg cacgagacgg agctcagtct  2280
```

```
gaccgcggcg tctctggccg gcatggtccc agcctcctcg ctggcgccgg ctgggcaaca   2340
tgcttcggca tggcgaatgg gacggtaccc ggccggaatt cgacccagct ttcttgtaca   2400
aagttggcat tataaaaaat aattgctcat caatttgttg caacgaacag gtcactatca   2460
gtcaaaataa aatcattatt tgccatccag ctgatatccc ctatagtgag tcgtattaca   2520
tggtcatagc atccctata gtgagtcgta ttacatggtc atagctgttt cctggcagct   2580
ctggcccgtg tctcaaaatc tctgatgtta cattgcacaa gataaaaata tatcatcatg   2640
cctcctctgg accagccagg acagaaatgc ctcgacttcg ctgctgccca aggttgccgg   2700
gtgacgcaca ccgtggaaac ggatgaaggc acgaacccag tggacataag cctgttcggt   2760
tcgtaagctg taatgcaagt agcgtatgcg ctcacgcaac tggtccagaa ccttgaccga   2820
acgcagcggt ggtaacggcg cagtggcggt tttcatggct tgttatgact gttttttttgg   2880
ggtacagtct atgcctcggg catccaagca gcaagcgcgt tacgccgtgg gtcgatgttt   2940
gatgttatgg agcagcaacg atgttacgca gcagggcagt cgccctaaaa caaagttaaa   3000
catcatgagg gaagcggtga tcgccgaagt atcgactcaa ctatcagagg tagttggcgt   3060
catcgagcgc catctcgaac cgacgttgct ggccgtacat ttgtacggct ccgcagtgga   3120
tggcggcctg aagccacaca gtgatattga tttgctggtt acggtgaccg taaggcttga   3180
tgaaacaacg cggcgagctt tgatcaacga cctttggaa acttcggctt ccctgagga   3240
gagcgagatt ctccgcgctg tagaagtcac cattgttgtg cacgacgaca tcattccgtg   3300
gcgttatcca gctaagcgcg aactgcaatt tggagaatgg cagcgcaatg acattcttgc   3360
aggtatcttc gagccagcca cgatcgacat tgatctggct atcttgctga caaaagcaag   3420
agaacatagc gttgccttgg taggtccagc ggcggaggaa ctctttgatc cggttcctga   3480
acaggatcta tttgaggcgc taaatgaaac cttaacgcta tggaactcgc cgcccgactg   3540
ggctggcgat gagcgaaatg tagtgcttac gttgtcccgc atttggtaca gcgcagtaac   3600
cggcaaaatc gcgccgaagg atgtcgctgc cgactgggca atggagcgcc tgccggccca   3660
gtatcagccc gtcatacttg aagctagaca ggcttatctt ggacaagaag aagatcgctt   3720
ggcctcgcgc gcagatcagt tggaagaatt tgtccactac gtgaaaggcg agatcaccaa   3780
ggtagtcggc aaataaccct cgagccaccc atgaccaaaa tcccttaacg tgagttacgc   3840
gtcgttccac tgagcgtcag accccgtaga aagatcaaa ggatcttctt gagatccttt   3900
ttttctgcgc gtaatctgct gcttgcaaac aaaaaaacca ccgctaccag cggtggtttg   3960
tttgccggat caagagctac caactctttt tccgaaggta actggcttca gcagagcgca   4020
gataccaaat actgtccttc tagtgtagcc gtagttaggc caccacttca gaactctgt   4080
agcaccgcct acatacctcg ctctgctaat cctgttacca gtggctgctg ccagtggcga   4140
taagtcgtgt cttaccgggt tggactcaag acgatagtta ccggataagg cgcagcggtc   4200
gggctgaacg gggggttcgt gcacacagcc cagcttggag cgaacgacct acaccgaact   4260
gagataccta cagcgtgagc attgagaaag cgccacgctt cccgaaggga gaaaggcgga   4320
caggtatccg gtaagcggca gggtcggaac aggagagcgc acgagggagc ttccaggggg   4380
aaacgcctgg tatctttata gtcctgtcgg gtttcgccac ctctgacttg agcgtcgatt   4440
tttgtgatgc tcgtcagggg ggcggagcct atggaaaaac gccagcaacg cggccttttt   4500
acggttcctg gccttttgct ggccttttgc tcacatgttc tttcctgcgt tatcccctga   4560
ttctgtggat aaccgtatta ccgcctttga gtgagctgat accgctcgcc gcagccgaac   4620
```

| | |
|---|---|
| gaccgagcgc agcgagtcag tgagcgagga agcggaagag cgcccaatac gcaaaccgcc | 4680 |
| tctccccgcg cgttggccga ttcattaatg cagctggcac gacaggtttc ccgactggaa | 4740 |
| agcgggcagt gagcgcaacg caattaatac gcgtaccgct cgccaggaag agtttgtaga | 4800 |
| aacgcaaaaa ggccatccgt caggatggcc ttctgcttag tttgatgcct ggcagtttat | 4860 |
| ggcgggcgtc ctgcccgcca ccctccgggc cgttgcttca caacgttcaa atccgctccc | 4920 |
| ggcggatttg tcctactcag gagagcgttc accgacaaac aacagataaa acgaaaggcc | 4980 |
| cagtcttccg actgagcctt tcgttttatt tgatgcctgg cagttcccta ctctcgcgtt | 5040 |
| aacgcttgca tggatgt | 5057 |

<210> SEQ ID NO 54
<211> LENGTH: 5087
<212> TYPE: DNA
<213> ORGANISM: Artificial Sequence
<220> FEATURE:
<223> OTHER INFORMATION: Vector

<400> SEQUENCE: 54

| | |
|---|---|
| tttcccagtc acgacgttgt aaaacgacgg ccagtcttaa gctcgggccc aaataatgat | 60 |
| tttattttga ctgatagtga cctgttcgtt gcaacaaatt gatgagcaat gcttttttat | 120 |
| aatgccaact ttgtatacaa aagttgcccc atggcgttcc ctctagagag ataatgagca | 180 |
| ttgcatgtct aagttataaa aaattaccac atatttttt tgtcacactt gtttgaagtg | 240 |
| cagtttatct atctttatac atatatttaa acttactct acgaataata taatctatag | 300 |
| tactacaata atatcagtgt tttagagaat catataaatg aacagttaga catggtctaa | 360 |
| aggacaattg agtattttga caacaggact ctacagtttt atcttttttag tgtgcatgtg | 420 |
| ttctcctttt tttttgcaaa tagcttcacc tatataatac ttcatccatt ttattagtac | 480 |
| atccatttag ggtttagggt taatggtttt tatagactaa ttttttagt acatctattt | 540 |
| tattctattt tagcctctaa attaagaaaa ctaaaactct attttagttt ttttatttaa | 600 |
| taatttagat ataaaataga ataaaataaa gtgactaaaa attaaacaaa taccctttaa | 660 |
| gaaattaaaa aaactaagga acattttttc ttgtttcgag tagataatgc cagcctgtta | 720 |
| aacgccgtcg acgagtctaa cggacaccaa ccagcgaacc agcagcgtcg cgtcgggcca | 780 |
| agcgaagcag acggcacggc atctctgtcg ctgcctctgg accctctcg agagttccgc | 840 |
| tccaccgttg gacttgctcc gctgtcggca tccagaaatt gcgtggcgga gcggcagacg | 900 |
| tgagccggca cggcaggcgg cctcctcctc ctctcacggc accggcagct acggggatt | 960 |
| cctttcccac cgctccttcg ctttcccttc ctcgcccgcc gtaataaata gacacccct | 1020 |
| ccacaccctc tttccccaac ctcgtgttgt tcggagcgca cacacacaca accagatctc | 1080 |
| ccccaaatcc accgtcggc acctccgctt caaggtacgc cgctcgtcct cccccccccc | 1140 |
| cccctctcta ccttctctag atcggcgttc cggtccatgg ttagggcccg gtagttctac | 1200 |
| ttctgttcat gtttgtgtta gatccgtgtt tgtgttagat ccgtgctgct agcgttcgta | 1260 |
| cacggatgcg acctgtacgt cagacacgtt ctgattgcta acttgccagt gtttctcttt | 1320 |
| ggggaatcct gggatggctc tagccgttcc gcagacggga tcgatttcat gattttttt | 1380 |
| gtttcgttgc atagggtttg gtttgccctt ttcctttatt tcaatatatg ccgtgcactt | 1440 |
| gtttgtcggg tcatctttc atgctttttt ttgtcttggt tgtgatgatg tggtctggtt | 1500 |
| gggcggtcgt tctagatcgg agtagaatta attctgtttc aaactacctg gtggattat | 1560 |
| taattttgga tctgtatgtg tgtgccatac atattcatag ttacgaattg aagatgatgg | 1620 |

```
atggaaatat cgatctagga taggtataca tgttgatgcg ggtttactg atgcatatac    1680 agagatgctt tttgttcgct tggttgtgat gatgtggtgt ggttgggcgg tcgttcattc    1740
gttctagatc ggagtagaat actgtttcaa actacctggt gtatttatta attttggaac    1800
tgtatgtgtg tgtcatacat cttcatagtt acgagtttaa gatggatgga aatatcgatc    1860
taggataggt atacatgttg atgtgggttt tactgatgca tatacatgat ggcatatgca    1920
gcatctattc atatgctcta accttgagta cctatctatt ataataaaca agtatgtttt    1980
ataattattt tgatcttgat atacttggat gatggcatat gcagcagcta tatgtggatt    2040
tttttagccc tgccttcata cgctatttat ttgcttggta ctgtttcttt tgtcgatgct    2100
caccctgttg tttggtgtta cttctgcagg gatccttaga cctgatgagt ccgtgaggac    2160
gaaacgagta agctcgtcgt ctaaaggaca gaatttttca acgggtgtgc caatggccac    2220
tttccaggtg gcaaagcccg ttgaacttcg gccgacgtct gtacccacta ggagtacaag    2280
gccgaagtgg cacgagacgg agctcagtct gaccgcggcg tctctggccg gcatggtccc    2340
agcctcctcg ctggcgccgg ctgggcaaca tgcttcggca tggcgaatgg acggtaccc    2400 ggccggaatt cgacccagct ttcttgtaca aagttggcat tataaaaaat aattgctcat    2460
caatttgttg caacgaacag gtcactatca gtcaaaataa aatcattatt tgccatccag    2520
ctgatatccc ctatagtgag tcgtattaca tggtcatagc atccctata gtgagtcgta    2580 ttacatggtc atagctgttt cctggcagct ctggcccgtg tctcaaaatc tctgatgtta    2640
cattgcacaa gataaaaata tatcatcatg cctcctctgg accagccagg acagaaatgc    2700
ctcgacttcg ctgctgccca aggttgccgg gtgacgcaca ccgtggaaac ggatgaaggc    2760
acgaacccag tggacataag cctgttcggt tcgtaagctg taatgcaagt agcgtatgcg    2820
ctcacgcaac tggtccagaa ccttgaccga acgcagcggg gtaacggcg cagtggcggt    2880 tttcatggct tgtttatgact gttttttttgg ggtacagtct atgcctcggg catccaagca    2940
gcaagcgcgt tacgccgtgg gtcgatgttt gatgttatgg agcagcaacg atgttacgca    3000
gcagggcagt cgccctaaaa caaagttaaa catcatgagg gaagcggtga tcgccgaagt    3060
atcgactcaa ctatcagagg tagttggcgt catcgagcgc catctcgaac cgacgttgct    3120
ggccgtacat ttgtacggct ccgcagtgga tggcggcctg aagccacaca gtgatattga    3180
tttgctggtt acggtgaccg taaggcttga tgaaacaacg cggcgagctt tgatcaacga    3240
ccttttggaa acttcggctt cccctggaga gagcgagatt ctccgcgctg tagaagtcac    3300
cattgttgtg cacgacgaca tcattccgtg gcgttatcca gctaagcgcg aactgcaatt    3360
tggagaatgg cagcgcaatg acattcttgc aggtatcttc gagccagcca cgatcgacat    3420
tgatctggct atcttgctga caaaagcaag agaacatagc gttgccttgg taggtccagc    3480
ggcggaggaa ctctttgatc cggttcctga acaggatcta tttgaggcgc taaatgaaac    3540
cttaacgcta tggaactcgc cgcccgactg gctggcgat gagcgaaatg tagtgcttac    3600
gttgtcccgc atttggtaca gcgcagtaac cggcaaaatc gcgccgaagg atgtcgctgc    3660
cgactgggca atggagcgcc tgccggccca gtatcagccc gtcatacttg aagctagaca    3720
ggcttatctt ggacaagaag aagatcgctt ggcctcgcgc gcagatcagt tggaagaatt    3780
tgtccactac gtgaaaggcg agatcaccaa ggtagtcggc aaataaccct cgagccaccc    3840
atgaccaaaa tcccttaacg tgagttacgc gtcgttccac tgagcgtcag accccgtaga    3900
aaagatcaaa ggatcttctt gagatccttt ttttctgcgc gtaatctgct gcttgcaaac    3960
```

| | |
|---|---:|
| aaaaaaacca ccgctaccag cggtggtttg tttgccggat caagagctac caactctttt | 4020 |
| tccgaaggta actggcttca gcagagcgca gataccaaat actgtccttc tagtgtagcc | 4080 |
| gtagttaggc caccacttca agaactctgt agcaccgcct acatacctcg ctctgctaat | 4140 |
| cctgttacca gtggctgctg ccagtggcga taagtcgtgt cttaccgggt tggactcaag | 4200 |
| acgatagtta ccggataagg cgcagcggtc gggctgaacg gggggttcgt gcacacagcc | 4260 |
| cagcttggag cgaacgacct acaccgaact gagataccta cagcgtgagc attgagaaag | 4320 |
| cgccacgctt cccgaaggga gaaaggcgga caggtatccg gtaagcggca gggtcggaac | 4380 |
| aggagagcgc acgagggagc ttccaggggg aaacgcctgg tatctttata gtcctgtcgg | 4440 |
| gtttcgccac ctctgacttg agcgtcgatt tttgtgatgc tcgtcagggg ggcggagcct | 4500 |
| atggaaaaac gccagcaacg cggcctttt acgttcctg gccttttgct ggccttttgc | 4560 |
| tcacatgttc tttcctgcgt tatcccctga ttctgtggat aaccgtatta ccgcctttga | 4620 |
| gtgagctgat accgctcgcc gcagccgaac gaccgagcgc agcgagtcag tgagcgagga | 4680 |
| agcggaagag cgcccaatac gcaaaccgcc tctccccgcg cgttggccga ttcattaatg | 4740 |
| cagctggcac gacaggtttc ccgactggaa agcgggcagt gagcgcaacg caattaatac | 4800 |
| gcgtaccgct cgccaggaag agtttgtaga acgcaaaaa ggccatccgt caggatggcc | 4860 |
| ttctgcttag tttgatgcct ggcagtttat ggcgggcgtc ctgcccgcca ccctccgggc | 4920 |
| cgttgcttca caacgttcaa atccgctccc ggcggatttg tcctactcag gagagcgttc | 4980 |
| accgacaaac aacagataaa acgaaaggcc cagtcttccg actgagcctt tcgttttatt | 5040 |
| tgatgcctgg cagttcccta ctctcgcgtt aacgcttgca tggatgt | 5087 |

<210> SEQ ID NO 55
<211> LENGTH: 5087
<212> TYPE: DNA
<213> ORGANISM: Artificial Sequence
<220> FEATURE:
<223> OTHER INFORMATION: Vector

<400> SEQUENCE: 55

| | |
|---|---:|
| tttcccagtc acgacgttgt aaaacgacgg ccagtcttaa gctcgggccc aaataatgat | 60 |
| tttattttga ctgatagtga cctgttcgtt gcaacaaatt gatgagcaat gcttttttat | 120 |
| aatgccaact ttgtatacaa aagttgcccc atggcgttcc ctctagagag ataatgagca | 180 |
| ttgcatgtct aagttataaa aaattaccac atattttttt tgtcacactt gtttgaagtg | 240 |
| cagtttatct atctttatac atatatttaa actttactct acgaataata taatctatag | 300 |
| tactacaata atatcagtgt tttagagaat catataaatg aacagttaga catggtctaa | 360 |
| aggacaattg agtattttga caacaggact ctacagtttt atcttttag tgtgcatgtg | 420 |
| ttctcctttt tttttgcaaa tagcttcacc tatataatac ttcatccatt ttattagtac | 480 |
| atccatttag ggtttagggt taatggtttt tatagactaa tttttttagt acatctattt | 540 |
| tattctattt tagcctctaa attaagaaaa ctaaaactct attttagttt tttatttaa | 600 |
| taatttagat ataaaataga ataaaataaa gtgactaaaa attaaacaaa taccctttaa | 660 |
| gaaattaaaa aaactaagga aacatttttc ttgtttcgag tagataatgc cagcctgtta | 720 |
| aacgccgtcg acgagtctaa cggacaccaa ccagcgaacc agcagcgtcg cgtcgggcca | 780 |
| agcgaagcag acggcacggc atctctgtcg ctgcctctgg acccctctcg agagttccgc | 840 |
| tccaccgttg gacttgctcc gctgtcggca tccagaaatt gcgtggcgga gcggcagacg | 900 |
| tgagccggca cggcaggcgg cctcctcctc ctctcacggc accggcagct acggggatt | 960 |

```
cctttcccac cgctccttcg ctttcccttc ctcgcccgcc gtaataaata gacaccccct   1020
ccacaccctc tttccccaac ctcgtgttgt tcggagcgca cacacacaca accagatctc   1080
ccccaaatcc acccgtcggc acctccgctt caaggtacgc cgctcgtcct cccccccccc   1140 ccctctcta ccttctctag atcggcgttc cggtccatgg ttagggcccg gtagttctac   1200
ttctgttcat gtttgtgtta gatccgtgtt tgtgttagat ccgtgctgct agcgttcgta   1260
cacggatgcg acctgtacgt cagacacgtt ctgattgcta acttgccagt gtttctcttt   1320
ggggaatcct gggatggctc tagccgttcc gcagacggga tcgatttcat gattttttt   1380 gtttcgttgc atagggtttg gtttgcccctt ttcctttatt tcaatatatg ccgtgcactt   1440
gtttgtcggg tcatcttttc atgctttttt ttgtcttggt tgtgatgatg tggtctggtt   1500
gggcggtcgt tctagatcgg agtagaatta attctgtttc aaactacctg gtggatttat   1560
taattttgga tctgtatgtg tgtgccatac atattcatag ttacgaattg aagatgatgg   1620
atggaaatat cgatctagga taggtataca tgttgatgcg ggttttactg atgcatatac   1680
agagatgctt tttgttcgct tggttgtgat gatgtggtgt ggttgggcgg tcgttcattc   1740
gttctagatc ggagtagaat actgtttcaa actacctggt gtatttatta attttggaac   1800
tgtatgtgtg tgtcatacat cttcatagtt acgagtttaa gatggatgga aatatcgatc   1860
taggataggt acatgttg atgtgggttt tactgatgca tatacatgat ggcatatgca   1920
gcatctattc atatgctcta accttgagta cctatctatt ataataaaca agtatgtttt   1980
ataattattt tgatcttgat atacttggat gatggcatat gcagcagcta tatgtggatt   2040
tttttagccc tgccttcata cgctatttat ttgcttggta ctgtttcttt tgtcgatgct   2100
caccctgttg tttggtgtta cttctgcagg gatccttaga cctgatgagt ccgtgaggac   2160
gaaacgagta agctcgtcgt ctaaaggaca gaattttca acgggtgtgc caatggccac   2220
tttccaggtg gcaaagcccg ttgaacttcg gccaacatga ggatcaccca tgtctgcagg   2280
gccgaagtgg cacgagacgg agctcagtct gaccgcggcg tctctggccg gcatggtccc   2340
agcctcctcg ctggcgccgg ctgggcaaca tgcttcggca tggcgaatgg gacggtaccc   2400
ggccggaatt cgacccagct ttcttgtaca agttggcat tataaaaaat aattgctcat   2460
caatttgttg caacgaacag gtcactatca gtcaaaataa aatcattatt tgccatccag   2520
ctgatatccc ctatagtgag tcgtattaca tggtcatagc atccctata gtgagtcgta   2580 ttacatggtc atagctgttt cctggcagct ctggcccgtg tctcaaaatc tctgatgtta   2640
cattgcacaa gataaaaata tatcatcatg cctcctctgg accagccagg acagaaatgc   2700
ctcgacttcg ctgctgccca aggttgccgg gtgacgcaca ccgtggaaac ggatgaaggc   2760
acgaacccag tggacataag cctgttcggt tcgtaagctg taatgcaagt agcgtatgcg   2820
ctcacgcaac tggtccagaa ccttgaccga acgcagcggt ggtaacggcg cagtggcggt   2880
tttcatggct tgttatgact gttttttgg ggtacagtct atgcctcggg catccaagca   2940
gcaagcgcgt tacgccgtgg gtcgatgttt gatgttatgg agcagcaacg atgttacgca   3000
gcagggcagt cgccctaaaa caaagttaaa catcatgagg gaagcggtga tcgccgaagt   3060
atcgactcaa ctatcagagg tagttggcgt catcgagcgc catctcgaac cgacgttgct   3120
ggccgtacat ttgtacggct ccgcagtgga tggcggcctg aagccacaca gtgatattga   3180
tttgctggtt acggtgaccg taaggcttga tgaaacaacg cggcgagctt tgatcaacga   3240
ccttttggaa acttcggctt cccctggaga gagcgagatt ctccgcgctg tagaagtcac   3300
```

```
cattgttgtg cacgacgaca tcattccgtg gcgttatcca gctaagcgcg aactgcaatt    3360
tggagaatgg cagcgcaatg acattcttgc aggtatcttc gagccagcca cgatcgacat    3420
tgatctggct atcttgctga caaaagcaag agaacatagc gttgccttgg taggtccagc    3480
ggcggaggaa ctctttgatc cggttcctga acaggatcta tttgaggcgc taaatgaaac    3540
cttaacgcta tggaactcgc cgcccgactg ggctggcgat gagcgaaatg tagtgcttac    3600
gttgtcccgc atttggtaca gcgcagtaac cggcaaaatc gcgccgaagg atgtcgctgc    3660
cgactgggca atggagcgcc tgccggccca gtatcagccc gtcatacttg aagctagaca    3720
ggcttatctt ggacaagaag aagatcgctt ggcctcgcgc gcagatcagt tggaagaatt    3780
tgtccactac gtgaaaggcg agatcaccaa ggtagtcggc aaataaccct cgagccaccc    3840
atgaccaaaa tcccttaacg tgagttacgc gtcgttccac tgagcgtcag accccgtaga    3900
aaagatcaaa ggatcttctt gagatccttt ttttctgcgc gtaatctgct gcttgcaaac    3960
aaaaaaacca ccgctaccag cggtggtttg tttgccggat caagagctac caactctttt    4020
tccgaaggta actggcttca gcagagcgca gataccaaat actgtccttc tagtgtagcc    4080
gtagttaggc caccacttca agaactctgt agcaccgcct acatacctcg ctctgctaat    4140
cctgttacca gtggctgctg ccagtggcga taagtcgtgt cttaccgggt tggactcaag    4200
acgatagtta ccggataagg cgcagcggtc gggctgaacg gggggttcgt gcacacagcc    4260
cagcttggag cgaacgacct acaccgaact gagatacct a cagcgtgagc attgagaaag    4320
cgccacgctt cccgaaggga gaaaggcgga caggtatccg gtaagcggca gggtcggaac    4380
aggagagcgc acgagggagc ttccagggggg aaacgcctgg tatctttata gtcctgtcgg    4440
gtttcgccac ctctgacttg agcgtcgatt tttgtgatgc tcgtcagggg gcggagcct    4500
atggaaaaac gccagcaacg cggcctttt t acggttcctg gccttttgct ggccttttgc    4560
tcacatgttc tttcctgcgt tatccctga ttctgtggat aaccgtatta ccgcctttga    4620
gtgagctgat accgctcgcc gcagccgaac gaccgagcgc agcgagtcag tgagcgagga    4680
agcggaagag cgcccaatac gcaaaccgcc tctccccgcg cgttggccga ttcattaatg    4740
cagctggcac gacaggtttc ccgactggaa agcgggcagt gagcgcaacg caattaatac    4800
gcgtaccgct cgccaggaag agtttgtaga aacgcaaaaa ggccatccgt caggatggcc    4860
ttctgcttag tttgatgcct ggcagtttat ggcgggcgtc ctgcccgcca ccctccgggc    4920
cgttgcttca caacgttcaa atccgctccc ggcggatttg tcctactcag gagagcgttc    4980
accgacaaac aacagataaa acgaaaggcc cagtcttccg actgagcctt tcgttttatt    5040
tgatgcctgg cagttcccta ctctcgcgtt aacgcttgca tggatgt                 5087

<210> SEQ ID NO 56
<211> LENGTH: 41
<212> TYPE: DNA
<213> ORGANISM: Oryza sativa

<400> SEQUENCE: 56
gttgcaatca agggcaccat ggcagcatct caggtacccc t                       41

<210> SEQ ID NO 57
<211> LENGTH: 42
<212> TYPE: DNA
<213> ORGANISM: Oryza sativa

<400> SEQUENCE: 57
attcatcgga agaactcctg atccattcat aacgatgtat gg                      42
```

```
<210> SEQ ID NO 58
<211> LENGTH: 20
<212> TYPE: DNA
<213> ORGANISM: Artificial Sequence
<220> FEATURE:
<223> OTHER INFORMATION: protospacer sequence

<400> SEQUENCE: 58
caatcaaggg caccatggtc                                                     20

<210> SEQ ID NO 59
<211> LENGTH: 20
<212> TYPE: DNA
<213> ORGANISM: Artificial Sequence
<220> FEATURE:
<223> OTHER INFORMATION: protospacer sequence

<400> SEQUENCE: 59
caatcaaggg caccatatca                                                     20

<210> SEQ ID NO 60
<211> LENGTH: 20
<212> TYPE: DNA
<213> ORGANISM: Artificial Sequence
<220> FEATURE:
<223> OTHER INFORMATION: protospacer sequence

<400> SEQUENCE: 60
caatcaaggg cattatggca                                                     20

<210> SEQ ID NO 61
<211> LENGTH: 20
<212> TYPE: DNA
<213> ORGANISM: Artificial Sequence
<220> FEATURE:
<223> OTHER INFORMATION: protospacer sequence

<400> SEQUENCE: 61
caatcaagta caccatggca                                                     20

<210> SEQ ID NO 62
<211> LENGTH: 20
<212> TYPE: DNA
<213> ORGANISM: Artificial Sequence
<220> FEATURE:
<223> OTHER INFORMATION: protospacer sequence

<400> SEQUENCE: 62
caattgaggg caccatggca                                                     20

<210> SEQ ID NO 63
<211> LENGTH: 20
<212> TYPE: DNA
<213> ORGANISM: Artificial Sequence
<220> FEATURE:
<223> OTHER INFORMATION: protospacer sequence

<400> SEQUENCE: 63
tgatcaaggg caccatggca                                                     20

<210> SEQ ID NO 64
<211> LENGTH: 20
<212> TYPE: DNA
<213> ORGANISM: Artificial Sequence
<220> FEATURE:
```

```
<223> OTHER INFORMATION: protospacer sequence

<400> SEQUENCE: 64
caatcaaggg caccatggca                                               20

<210> SEQ ID NO 65
<211> LENGTH: 20
<212> TYPE: DNA
<213> ORGANISM: Artificial Sequence
<220> FEATURE:
<223> OTHER INFORMATION: protospacer sequence

<400> SEQUENCE: 65
agcatatggt tgtaactttg                                               20

<210> SEQ ID NO 66
<211> LENGTH: 20
<212> TYPE: DNA
<213> ORGANISM: Artificial Sequence
<220> FEATURE:
<223> OTHER INFORMATION: protospacer sequence

<400> SEQUENCE: 66
agcatatggt tgtaacgaca                                               20

<210> SEQ ID NO 67
<211> LENGTH: 20
<212> TYPE: DNA
<213> ORGANISM: Artificial Sequence
<220> FEATURE:
<223> OTHER INFORMATION: protospacer sequence

<400> SEQUENCE: 67
agcatatggt tgcgacttca                                               20

<210> SEQ ID NO 68
<211> LENGTH: 20
<212> TYPE: DNA
<213> ORGANISM: Artificial Sequence
<220> FEATURE:
<223> OTHER INFORMATION: protospacer sequence

<400> SEQUENCE: 68
agcatatgtc tgtaacttca                                               20

<210> SEQ ID NO 69
<211> LENGTH: 20
<212> TYPE: DNA
<213> ORGANISM: Artificial Sequence
<220> FEATURE:
<223> OTHER INFORMATION: protospacer sequence

<400> SEQUENCE: 69
agcacgtggt tgtaacttca                                               20

<210> SEQ ID NO 70
<211> LENGTH: 20
<212> TYPE: DNA
<213> ORGANISM: Artificial Sequence
<220> FEATURE:
<223> OTHER INFORMATION: protospacer sequence

<400> SEQUENCE: 70
tacatatggt tgtaacttca                                               20
```

```
<210> SEQ ID NO 71
<211> LENGTH: 20
<212> TYPE: DNA
<213> ORGANISM: Artificial Sequence
<220> FEATURE:
<223> OTHER INFORMATION: protospacer sequence

<400> SEQUENCE: 71
agcatatggt tgtaacttca                                              20

<210> SEQ ID NO 72
<211> LENGTH: 15
<212> TYPE: DNA
<213> ORGANISM: Artificial Sequence
<220> FEATURE:
<223> OTHER INFORMATION: protospacer sequence

<400> SEQUENCE: 72
caatcaaggg cacca                                                   15

<210> SEQ ID NO 73
<211> LENGTH: 16
<212> TYPE: DNA
<213> ORGANISM: Artificial Sequence
<220> FEATURE:
<223> OTHER INFORMATION: protospacer sequence

<400> SEQUENCE: 73
caatcaaggg caccat                                                  16

<210> SEQ ID NO 74
<211> LENGTH: 17
<212> TYPE: DNA
<213> ORGANISM: Artificial Sequence
<220> FEATURE:
<223> OTHER INFORMATION: protospacer sequence

<400> SEQUENCE: 74
caatcaaggg caccatg                                                 17

<210> SEQ ID NO 75
<211> LENGTH: 18
<212> TYPE: DNA
<213> ORGANISM: Artificial Sequence
<220> FEATURE:
<223> OTHER INFORMATION: protospacer sequence

<400> SEQUENCE: 75
caatcaaggg caccatgg                                                18

<210> SEQ ID NO 76
<211> LENGTH: 19
<212> TYPE: DNA
<213> ORGANISM: Artificial Sequence
<220> FEATURE:
<223> OTHER INFORMATION: protospacer sequence

<400> SEQUENCE: 76
caatcaaggg caccatggc                                               19

<210> SEQ ID NO 77
<211> LENGTH: 45
<212> TYPE: DNA
<213> ORGANISM: Oryza sativa

<400> SEQUENCE: 77
```

```
gctcgttgca atcaagggca ccatggcagc atctcaggta ccccct                45
```

<210> SEQ ID NO 78
<211> LENGTH: 37
<212> TYPE: DNA
<213> ORGANISM: Artificial Sequence
<220> FEATURE:
<223> OTHER INFORMATION: mutant Oryza sativa sequence

<400> SEQUENCE: 78

```
gctcgttgca atcaagggca ccatctcagg taccccct                         37
```

<210> SEQ ID NO 79
<211> LENGTH: 35
<212> TYPE: DNA
<213> ORGANISM: Artificial Sequence
<220> FEATURE:
<223> OTHER INFORMATION: mutant Oryza sativa sequence

<400> SEQUENCE: 79

```
gctcgttgca atcaagggca ccatcaggta ccccct                           35
```

<210> SEQ ID NO 80
<211> LENGTH: 26
<212> TYPE: DNA
<213> ORGANISM: Artificial Sequence
<220> FEATURE:
<223> OTHER INFORMATION: mutant Oryza sativa sequence

<400> SEQUENCE: 80

```
gctcgttgca atcctcaggt acccct                                      26
```

<210> SEQ ID NO 81
<211> LENGTH: 39
<212> TYPE: DNA
<213> ORGANISM: Artificial Sequence
<220> FEATURE:
<223> OTHER INFORMATION: mutant Oryza sativa sequence

<400> SEQUENCE: 81

```
gctcgttgca atcaagggca ccagcagcat ctcaggtac                        39
```

<210> SEQ ID NO 82
<211> LENGTH: 33
<212> TYPE: DNA
<213> ORGANISM: Artificial Sequence
<220> FEATURE:
<223> OTHER INFORMATION: mutant Oryza sativa sequence

<400> SEQUENCE: 82

```
gctcgttgca atcaagggca ctcaggtacc cct                              33
```

<210> SEQ ID NO 83
<211> LENGTH: 33
<212> TYPE: DNA
<213> ORGANISM: Artificial Sequence
<220> FEATURE:
<223> OTHER INFORMATION: mutant Oryza sativa sequence

<400> SEQUENCE: 83

```
gctcgttgca atcaagggca ccatggtacc cct                              33
```

<210> SEQ ID NO 84
<211> LENGTH: 25
<212> TYPE: DNA
<213> ORGANISM: Artificial Sequence

```
<220> FEATURE:
<223> OTHER INFORMATION: mutant Oryza sativa sequence

<400> SEQUENCE: 84
gctcgttgca atctcaggta ccccct                                              25

<210> SEQ ID NO 85
<211> LENGTH: 37
<212> TYPE: DNA
<213> ORGANISM: Artificial Sequence
<220> FEATURE:
<223> OTHER INFORMATION: mutant Oryza sativa sequence

<400> SEQUENCE: 85
gctcgttgca atcaagggca ccatctcagg tacccct                                  37

<210> SEQ ID NO 86
<211> LENGTH: 32
<212> TYPE: DNA
<213> ORGANISM: Artificial Sequence
<220> FEATURE:
<223> OTHER INFORMATION: mutant Oryza sativa sequence

<400> SEQUENCE: 86
gctcgttgca atcaagggcc tcaggtaccc ct                                       32

<210> SEQ ID NO 87
<211> LENGTH: 38
<212> TYPE: DNA
<213> ORGANISM: Artificial Sequence
<220> FEATURE:
<223> OTHER INFORMATION: mutant Oryza sativa sequence

<400> SEQUENCE: 87
gctcgttgca atcaagggca cccatctcag gtacccct                                 38

<210> SEQ ID NO 88
<211> LENGTH: 33
<212> TYPE: DNA
<213> ORGANISM: Artificial Sequence
<220> FEATURE:
<223> OTHER INFORMATION: mutant Oryza sativa sequence

<400> SEQUENCE: 88
gctcgttgca atcaagggct ctcaggtacc cct                                      33

<210> SEQ ID NO 89
<211> LENGTH: 34
<212> TYPE: DNA
<213> ORGANISM: Artificial Sequence
<220> FEATURE:
<223> OTHER INFORMATION: mutant Oryza sativa sequence

<400> SEQUENCE: 89
gctcgttgca atcaagggca ccatggcagc agca                                     34

<210> SEQ ID NO 90
<211> LENGTH: 41
<212> TYPE: DNA
<213> ORGANISM: Oryza sativa

<400> SEQUENCE: 90
cttgcatcac acagccggaa ggtaccctcc tacacttcac a                             41

<210> SEQ ID NO 91
```

```
<211> LENGTH: 41
<212> TYPE: DNA
<213> ORGANISM: Oryza sativa

<400> SEQUENCE: 91
gttcctcaag gtgagcgccc cgcggcggcg gcggctgcgt t                          41

<210> SEQ ID NO 92
<211> LENGTH: 41
<212> TYPE: DNA
<213> ORGANISM: Oryza sativa

<400> SEQUENCE: 92
ttttgcctct ctctcctgtg cttgcctctt ccattcctgc t                          41
```